US010844052B2

(12) United States Patent
Lam et al.

(10) Patent No.: US 10,844,052 B2
(45) Date of Patent: Nov. 24, 2020

(54) LLS COMPOUNDS FOR TREATMENT OF CANCER

(71) Applicant: THE REGENTS OF THE UNIVERSITY OF CALIFORNIA, Oakland, CA (US)

(72) Inventors: Kit S. Lam, Davis, CA (US); Ruiwu Liu, Sacramento, CA (US); Tsung-Chieh Shih, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/091,098

(22) PCT Filed: Apr. 4, 2017

(86) PCT No.: PCT/US2017/025959
§ 371 (c)(1),
(2) Date: Oct. 3, 2018

(87) PCT Pub. No.: WO2017/176767
PCT Pub. Date: Oct. 12, 2017

(65) Prior Publication Data
US 2019/0256503 A1 Aug. 22, 2019

Related U.S. Application Data

(60) Provisional application No. 62/318,085, filed on Apr. 4, 2016, provisional application No. 62/359,604, filed on Jul. 7, 2016.

(51) Int. Cl.
| C07D 401/04 | (2006.01) |
| C07D 401/14 | (2006.01) |
| C07D 403/12 | (2006.01) |
| C07D 409/14 | (2006.01) |
| C07D 235/18 | (2006.01) |
| C07D 413/10 | (2006.01) |
| A61P 35/00 | (2006.01) |
| C08G 73/18 | (2006.01) |
| C08L 79/04 | (2006.01) |
| C07D 235/14 | (2006.01) |
| C07D 403/10 | (2006.01) |

(52) U.S. Cl.
CPC ............ *C07D 413/10* (2013.01); *A61P 35/00* (2018.01); *C07D 235/18* (2013.01); *C07D 401/04* (2013.01); *C07D 401/14* (2013.01); *C07D 403/12* (2013.01); *C07D 409/14* (2013.01); *C08G 73/18* (2013.01); *C08L 79/04* (2013.01); *C07D 235/14* (2013.01); *C07D 403/10* (2013.01)

(58) Field of Classification Search
CPC .. C07D 401/04; C07D 401/14; C07D 403/12; C07D 409/14; C07D 235/18
See application file for complete search history.

(56) References Cited

U.S. PATENT DOCUMENTS

2006/0281784 A1    12/2006  Poitout et al.
2014/0243324 A1     8/2014  Bissonnette et al.

FOREIGN PATENT DOCUMENTS

WO    2010039668 A2    4/2010

OTHER PUBLICATIONS

Chemical Abstracts Registry No. 1491588-44-3, indexed in the Registry file on STN CAS Online Dec. 10, 2013. (Year: 2013).*
Chemical Abstracts Registry No. 1482844-88-1, indexed in the Registry file on STN CAS Online Nov. 28, 2013 (Year: 2013).*
Takeuchi et al., Bioorganic & Medicinal Chemistry Letters, 2000, 10(20), pp. 2347-2351. (Year: 2000).*
Grant, R., Grant, C. (1987). Grant & Hackh's Chemical Dictionary (5th ed.). New York, NY: McGraw-Hill, p. 313. (Year: 1987).*
Consitutional versus Stereoisomers, http://butane.chem.uiuc.edu/jsmoore/chem232/notes_current/Stereochemistry/NOTES-Stereoisomers.pdf, Dec. 2009. (Year: 2009).*
Golub et al., Science, vol. 286, Oct. 15, 1999, pp. 531-537. (Year: 1999).*
Chemical Abstracts Registry No. 1539662-98-0, indexed in the Registry file on STN CAS Online Feb. 9, 2014. (Year: 2014).*
Chemical Abstracts Registry No. 1902189-77-8, indexed in the Registry file on STN CAS Online May 2, 2016. (Year: 2016).*
PUBMED CID 65037625, 'AKOS014369943', U.S. National Library of Medicine, Oct. 23, 2012 (Oct. 23, 2012), retrieved on Jun. 1, 2017 from https://pubchem.ncbi.nim.nih.gov/compound/65037625; p. 3.
International Searching Authority at the U.S. Patent and Trademark Office, International Search Report and Written Opinion for International Application No. PCT/US2017/025959, dated Sep. 5, 2017, 10 pages.
Extended European Search Report in European Patent Application No. 17770667.9 dated Oct. 28, 2019.

* cited by examiner

*Primary Examiner* — Laura L Stockton
(74) *Attorney, Agent, or Firm* — Mintz, Levin, Cohn, Ferris, Glovsky & Popeo, P.C.

(57) ABSTRACT

The present invention provides benzamidazole compounds and methods of using the compounds as galectin-1 inhibitors.

16 Claims, 17 Drawing Sheets

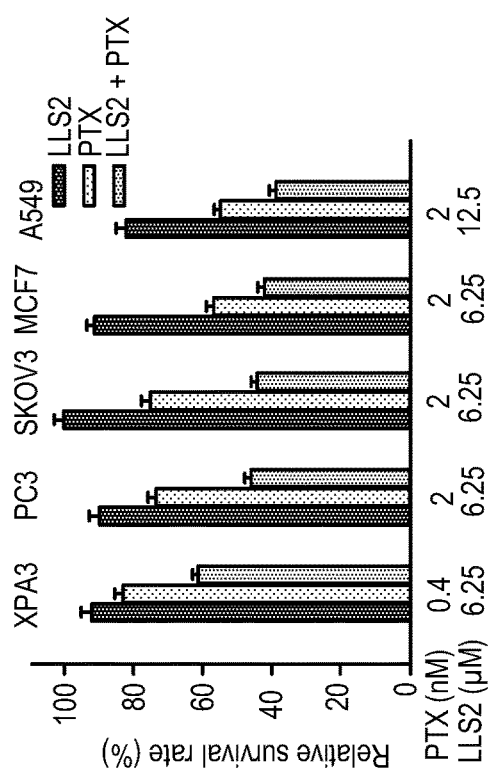
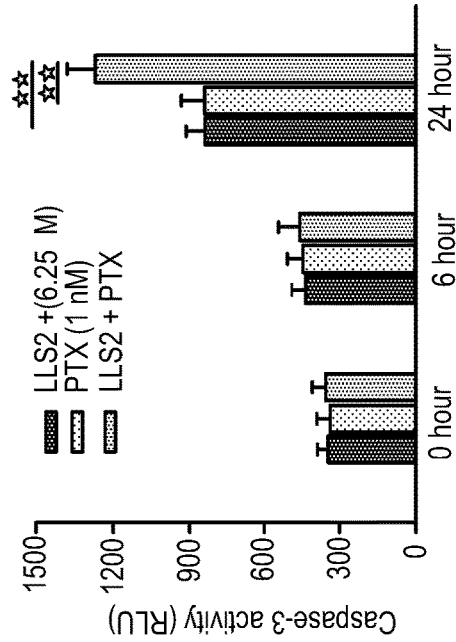
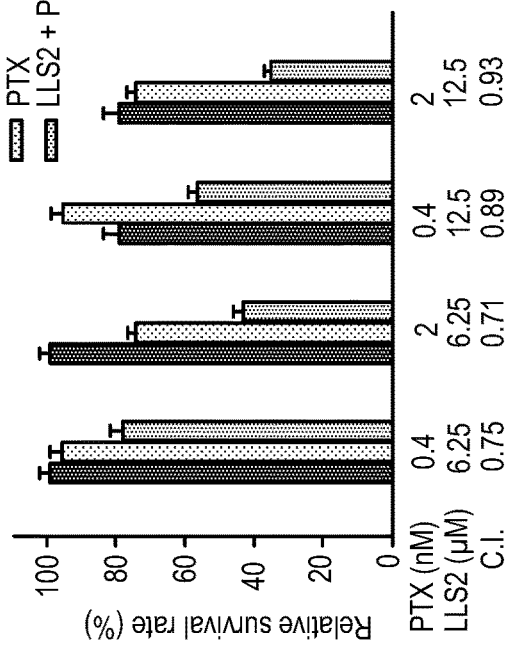
FIG. 6A
FIG. 6B
FIG. 6C
FIG. 6D sp|P09382|LEG1_HUMAN (99%), 14,715.8 Da
Galectin-1 OS=Homo sapiens GN=LGALS1 PE=1 SV=2
1 unique peptides, 2 unique spectra, 5 total spectra, 18/135 amino acids (13% coverage)

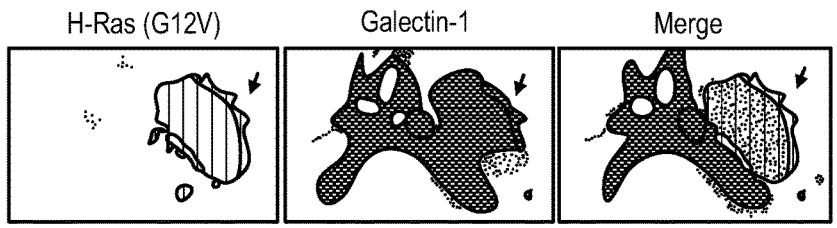
FIG. 9A
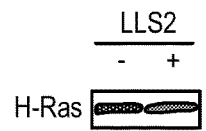
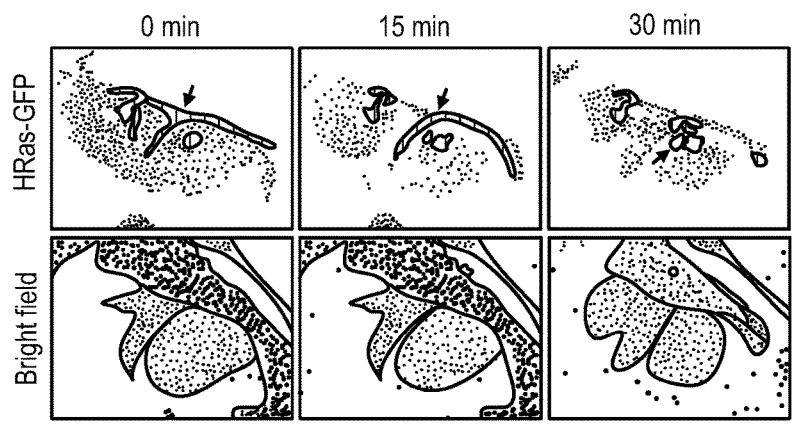
FIG. 9B
FIG. 9C
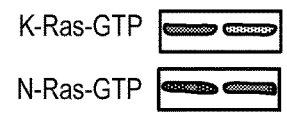
FIG. 9E
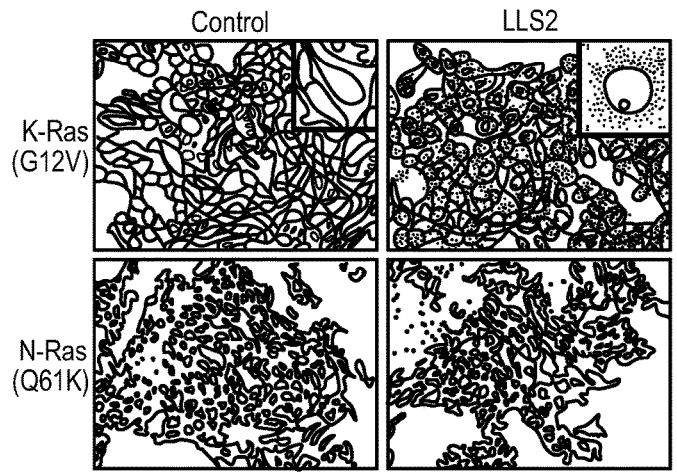
FIG. 9D
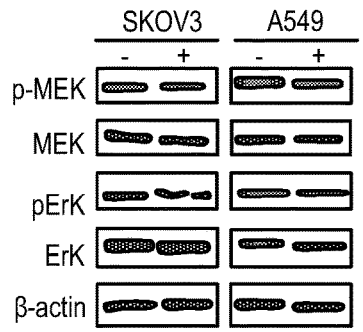
FIG. 9F LLS30 & Enzalutamide LLS30 & Docetaxel

| 4-(2-Aminoethyl) morpholine | 1-(2-Aminoethyl) pyrrolidine | 1-(3-Aminopropyl)-2-pyrrolidinone | Histamine |
|---|---|---|---|
| 2-(Aminomethyl) pyridine | (Aminomethyl) cyclopropane | (R)-(-)-1-Cyclohexyl ethylamine | 3-Methoxybenzylamine |
| 4-Methoxyphenethyl amine | 2,5-Difluoro benzylamine | 2-Phenoxyethylamine | 1-(3-Aminopropyl) imidazole |
| 1-(3- Aminopropyl)-2-pipecoline | 3,5-Dimethoxybenzyl amine | β-Alanine tert-butyl ester | 1-Boc-4-(aminomethyl) piperidine |
| N-(3-Aminopropyl) carbamic acid tert-butyl ester | H-Beta-Ala-NH2 | Tert-butyl N-(2-aminoethyl)carbamate | 1-(3-Aminopropyl) piperidine |
| Boc-N-methylethylene diamine | 1-(3-aminopropyl)-4-methylpiperazine | N,N-Dimethyl-1,3-propanediamine | 4-Methoxybenzylamine |
| 1-(2-Aminoethyl) piperidine | 3-(Trifluoromethoxyl) Benzylamine | 4-(Trifluoromethoxyl) Benzylamine | 4-(Dimethylamino) Benzylamine |
| 2-Methoxyethylamine | Isopropylamine | 2,2-Difluoroethylamine | 3-Chlorobenzylamine |
| 3-(4-Morpholinyl) propylamine | 3-(2,3-dihydro-indol-1-yl)-propylamine | 3,4-Difluorobenzylamine | 1-(3-Aminopropyl) pyrrolidine |
| (S)-(+)-1-Cyclohexylethylamine | 2-(2-Aminoethyl)-pyridine | 2-(2-Aminoethyl)-1-methylpyrrolidine | (3-Pyrrolidin-1-ylphenyl) methylamine |
| (2-Piperidinopyrid-4-yl)methylamine | (4-Piperidinophenyl) methylamine | | |

FIG. 16

| 5-Acetoxymethyl-2-furaldehyde | 2,4-Dimethoxy benzaldehyde | 4-Dimethylamino benzaldehyde | 2-Methoxycinnam aldehyde |
|---|---|---|---|
| 4-Dimethylamino cinnamaldehyde | 1-Methyl-1H-indole-5-carbaldehyde | 3-(4-tert-Butylphenoxy) benzaldehyde | 4-[(2-Cyanoethyl)methyl amino] benzaldehyde |
| 2-Methyl-6-quinolinecarbaldehyde | 3-Pyrid-3-yl benzaldehyde | N-Boc-piperidinyl-4-acetaldehyde | 6-Thiophen-3-yl-pyridine-3-carbaldehyde |
| 6-Furan-2-yl-pyridine-3-carbaldehyde | N-Boc-7-Azaindole-3-carboxaldehyde | N-(3-Formylphenyl) benzenesulfonamide | 6-(3-Trifluoromethoxy-phenyl)pyridine-3-carbaldehyde |
| 4-[4-tert-Butyl)-1,3-thiazol-2-yl] benzaldehyde | 4-(5-Methyl-1,2,4-oxadiazol-3-yl) benzaldehyde | 4-[Bis[2-(acetyloxy) ethyl]amino] benzaldehyde | 1-Methylindol-3-carboxaldehyde |
| 5-(Furan-2-yl)thiophene-2-carbaldehyde | 4-Metyl-3,4-dihydro-2h-1,4-benzoxazine-7-carbaldehyde | 4-(1H-Imidazol-1-ylmethyl) benzaldehyde | 4-(4-Pyridyl) benzaldehyde |
| 3-(2-Morpholin-4-ylethoxy) benzaldehyde | 1-Phenylpiperidine-4-carbaldehyde | 4-[(4-Methylpiperazin-1-yl)methyl] benzaldehyde | 3-(1H-Imidazol-1-ylmethyl) benzaldehyde |
| 2-Thiazolecarbox aldehyde | P-Anisaldehyde | 4-[(3-Dimethylamino)propoxy] benzaldehyde | 1-Methyl-2-pyrrolecarboxaldehyde |
| 3-Pyridinecarbox aldehyde | α,α,α-Trifluoro-m-tolualdehyde | o-Tolualdehyde | 1,2,3,6-Tetrahydro benzaldehyde |
| Hydrocinnamaldehyde | 4-[(Pyridin-3-yloxy) benzaldehyde | 3-(Methylthio) propionaldehyde | isobutyladehyde |
| 5-pyrid-4-ylthiophene-2-carbaldehyde | All trans-retinal | | |

FIG. 17

LLS COMPOUNDS FOR TREATMENT OF CANCER

CROSS-REFERENCES TO RELATED APPLICATIONS

This application is a U.S. National Phase Application of PCT International Application No. PCT/US2017/025959, filed Apr. 14, 2017, which claims priority to U.S. Provisional Application Nos. 62/359,604, filed Jul. 7, 2016, and 62/318,085, filed Apr. 4, 2016, each of which is incorporated herein in their entirety for all purposes.

STATEMENT AS TO RIGHTS TO INVENTIONS MADE UNDER FEDERALLY SPONSORED RESEARCH AND DEVELOPMENT

This work was supported by Grant 5R33CA160132-03 from the National Cancer Institute. The Federal Government has certain rights in this invention.

BACKGROUND OF THE INVENTION

Galectin-1 (gal-1) is a rather ubiquitous carbohydrate-binding protein that binds to β-galactoside groups on various cell surface receptors. It can be intracellularly located or secreted into the extracellular space. Gal-1 is often found to be highly elevated in tumor stroma in several cancers including prostate cancer. Increased gal-1 expression by tumor and connective tissue supporting the tumor is regarded as a definite sign of malignant progression, often correlating with the aggressiveness of the tumor and the acquisition of a metastatic phenotype (Ingrassia (2006) *Curr. Med. Chem.* 13:3513; Rorive (2001) *Glia* 33:241; van den Brule (2001) *J. Pathol.* 193:80). Gal-1 has been shown to play an important role in tumor transformation, tumor cell proliferation, cell aggregation, adhesion, migration, apoptosis, and immunoregulation. In addition, it is associated with poor prognosis for the patient and is frequently related to the dissemination of tumor cells at either long-range (metastasis), or into the surrounding normal tissue. Studies from the Castronovo group suggest gal-1 accumulating around the cells might act as an immunological shield by inducing activated T-cell apoptosis (van den Brule (2003) *Lab. Investigation* 83:377), modulating the survival or polarization of effector T cells (Rubinstein (2004) *Cancer Cell* 5:241). Thus, in addition to its direct involvement in cancer cell biology, gal-1 is also directly involved in the process of tumor immune escape. Gal-1 prolongs cell-surface retention of VEGF receptor 2 (VEGFR2) and stimulates VEGF-independent tumor angiogenesis (Croci (2014) *Cell* 156:744). Gal-1 promotes tumor progression through mechanisms leading to tumor-immune escape and metastasis (Rubinstein, op. cit.; Banh (2011) *Cancer Res.* 71:4423; Dalotto-Moreno (2013) *Cancer Res.* 73: 1107). Interestingly, gal-1 is regulated by hypoxia (Bahn, op. cit.) and controls EC signaling (Hsieh (2008) *Oncogene* 27:3746), VEGFR trafficking (D'Haene (2013) *PloS One* 8:e67029), and tumor angiogenesis (Thijssen (2006) *PNAS USA* 103:15975; Laderach (2013) *Cancer Res.* 73:86; Mathieu (2012) *J. Investigat. Dermat.* 132:2245). Gal-1 could therefore offer an important therapeutic target in the fight against a number of different types of cancer.

As the tumorigenic role of gal-1 has been established, researchers have turned their efforts to identifying molecules to block its function. Most of the compounds reported to date are β-galactoside-analogs, glycomimetics, peptides, or carbohydrates modified with organic moiety that target the canonical carbohydrate binding site. Most compounds bind gal-1 rather weakly (Kd>100 μM) and non-specifically due primarily to conserved structural homology of β-galactoside binding sites among all galectins. In addition, few of these compounds have been tested in vivo due to poor bioavailability. Small molecules should have better in vivo exposure because they are resistant to plasma proteases and glycosidases.

BRIEF SUMMARY OF THE INVENTION

In one embodiment, the present invention provides compounds having the structure of formula J:

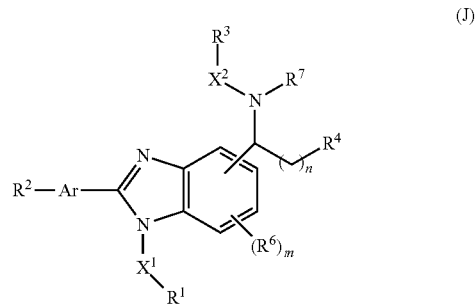

(J)

wherein Ar of formula J can be $C_{6-12}$ aryl or $C_{5-12}$ heteroaryl, wherein Ar can be substituted with 0 to 4 $R^5$ groups. $R^1$ can be $C_{1-6}$ alkyl, $-NR^{1a}R^{1b}$, $C_{3-10}$ cycloalkyl, $C_{3-8}$ heterocycloalkyl, $C_{6-12}$ aryl, or $C_{5-12}$ heteroaryl, wherein the aryl is optionally substituted with 1-4 $R^{1c}$ groups. $R^{1a}$ and $R^{1b}$ can each independently be hydrogen or $C_{1-6}$ alkyl. $R^2$ of formula I can be $N^{2a}R^{2b}$, $C_{5-12}$ heteroaryl or $C_{1-6}$ alkyl-$C_{5-12}$ heteroaryl, wherein the heteroaryl is optionally substituted with $C_{1-6}$ hydroxyalkyl. $R^{2a}$ and $R^{2b}$ can each independently be $C_{1-6}$ alkyl, $C_{1-6}$ hydroxyalkyl, or $C_{1-6}$ alkyl-OC(O)CH$_3$. Alternatively, $R^{2a}$ and $R^{2b}$ can be combined with the nitrogen to which they are attached to form a $C_{3-8}$ heterocycloalkyl having 0 to 2 additional heteroatoms which can be N, O, or S, wherein the $C_{3-8}$ heterocycloalkyl is optionally substituted with 1 to 4 $R^{2c}$ groups. Each $R^{1c}$ and $R^{2c}$ can independently be $C_{1-6}$ alkyl, halogen, $C_{1-6}$ haloalkyl, hydroxy, $C_{1-6}$ alkoxy, $C_{1-6}$ haloalkoxy, or $C_{6-12}$ aryl. $R^3$ of formula I can be hydrogen, $C_{1-6}$ alkyl, $C_{3-8}$ cycloalkyl, $C_{3-8}$ heterocycloalkyl, $C_{6-12}$ aryl, or $C_{5-12}$ heteroaryl, wherein the heterocycloalkyl, aryl, and heteroaryl are optionally substituted with 0 to 4 $R^{3a}$ groups. Each $R^{3a}$ can independently be $C_{1-6}$ alkyl, halogen, $C_{1-6}$ haloalkyl, hydroxy, $C_{1-6}$ alkoxy, $C_{1-6}$ haloalkoxy, $C_{3-8}$ cycloalkyl, $C_{3-8}$ heterocycloalkyl, $C_{6-12}$ aryl, $C_{5-12}$ heteroaryl, or $-SO_2-C_{6-12}$ aryl. $R^4$ of formula I can be hydrogen, $C_{1-6}$ alkyl, $-C(O)R^{4a}$, $-C(O)OR^{4a}$ or $-C(O)NR^{4a}R^{4b}$. Each $R^{4a}$ and $R^{4b}$ can independently be hydrogen or $C_{1-6}$ alkyl. Each $R^5$ and $R^6$ of formula I can independently be hydrogen or $C_{1-6}$ alkyl. $R^7$ of formula I can be hydrogen or $C_{1-6}$ alkyl-$C_{6-12}$ aryl, optionally substituted with 1-4 $R^{7a}$ groups. Each $R^{7a}$ can independently be $C_{1-6}$ alkyl, halogen, $C_{1-6}$ haloalkyl, $C_{1-6}$ alkoxy, or $C_{1-6}$ haloalkoxy. $X^1$ of formula I can be $C_{1-6}$ alkylene. $X^2$ of formula I can be absent or $C_{1-6}$ alkylene, $-C(O)NH-$, $-C(O)CH(NH_2)CH_2-$ or $-C(O)CH(NH_2)CH(OH)-$. Subscripts n and m of formula I can independently be integers from 0 to 3. The compounds of formula I can also be the pharmaceutically acceptable salts and isomers thereof.

In another embodiment, the present invention provides compounds having the structure of formula I:

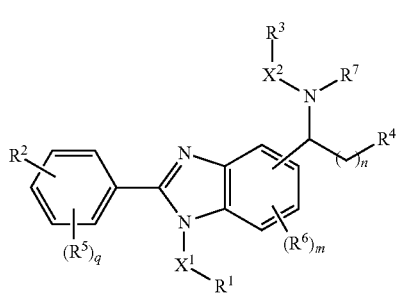

(I)

wherein $R^1$ of formula I can be $C_{1-6}$ alkyl, $-NR^{1a}R^{1b}$, $C_{3-10}$ cycloalkyl, $C_{3-8}$ heterocycloalkyl, $C_{6-12}$ aryl, or $C_{5-12}$ heteroaryl, wherein the aryl is optionally substituted with 1-4 $R^{1c}$ groups. $R^{1a}$ and $R^{1b}$ can each independently be hydrogen or $C_{1-6}$ alkyl. $R^2$ of formula I can be $NR^{2a}R^{2b}$, $C_{5-12}$ heteroaryl or $C_{1-6}$ alkyl-$C_{5-12}$ heteroaryl, wherein the heteroaryl is optionally substituted with $C_{1-6}$ hydroxyalkyl. $R^{2a}$ and $R^{2b}$ can each independently be $C_{1-6}$ alkyl, $C_{1-6}$ hydroxyalkyl, or $C_{1-6}$ alkyl-OC(O)CH$_3$. Alternatively, $R^{2a}$ and $R^{2b}$ can be combined with the nitrogen to which they are attached to form a $C_{3-8}$ heterocycloalkyl having 0 to 2 additional heteroatoms which can be N, O, or S, wherein the $C_{3-8}$ heterocycloalkyl is optionally substituted with 1 to 4 $R^{2c}$ groups. Each $R^{1c}$ and $R^{2c}$ can independently be $C_{1-6}$ alkyl, halogen, $C_{1-6}$ haloalkyl, hydroxy, $C_{1-6}$ alkoxy, $C_{1-6}$ haloalkoxy, or $C_{6-12}$ aryl. $R^3$ of formula I can be hydrogen, $C_{1-6}$ alkyl, $C_{3-8}$ cycloalkyl, $C_{3-8}$ heterocycloalkyl, $C_{6-12}$ aryl, or $C_{5-12}$ heteroaryl, wherein the heterocycloalkyl, aryl, and heteroaryl are optionally substituted with 0 to 4 $R^{3a}$ groups. Each $R^{3a}$ can independently be $C_{1-6}$ alkyl, halogen, $C_{1-6}$ haloalkyl, hydroxy, $C_{1-6}$ alkoxy, $C_{1-6}$ haloalkoxy, $C_{3-8}$ cycloalkyl, $C_{3-8}$ heterocycloalkyl, $C_{6-12}$ aryl, $C_{5-12}$ heteroaryl, or $-SO_2-C_{6-12}$ aryl. $R^4$ of formula I can be hydrogen, $C_{1-6}$ alkyl, $-C(O)R^{4a}$, $-C(O)OR^{4a}$ or $-C(O)NR^{4a}R^{4b}$. Each $R^{4a}$ and $R^{4b}$ can independently be hydrogen or $C_{1-6}$ alkyl. Each $R^5$ and $R^6$ of formula I can independently be hydrogen or $C_{1-6}$ alkyl. $R^7$ of formula I can be hydrogen or $C_{1-6}$ alkyl-$C_{6-12}$ aryl, optionally substituted with 1-4 $R^{7a}$ groups. Each $R^{7a}$ can independently be $C_{1-6}$ alkyl, halogen, $C_{1-6}$ haloalkyl, $C_{1-6}$ alkoxy, or $C_{1-6}$ haloalkoxy. $X^1$ of formula I can be $C_{1-6}$ alkylene. $X^2$ of formula I can be absent or $C_{1-6}$ alkylene, $-C(O)NH-$, $-C(O)CH(NH_2)CH_2-$ or $-C(O)CH(NH_2)CH(OH)-$. Subscripts n and m of formula I can independently be integers from 0 to 3. Subscript q can be an integer from 0 to 4. The compounds of formula I can also be the pharmaceutically acceptable salts and isomers thereof.

In another embodiment, the present invention provides a pharmaceutical composition including a compound of formula I and a pharmaceutically acceptable excipient.

In another embodiment, the present invention provides a method of treating a disorder, the method including administering to a subject in need of such treatment, a therapeutically effective amount of a compound of formula I.

BRIEF DESCRIPTION OF THE DRAWINGS

FIG. 6 shows (a) the cytotoxicity of LLS2 alone, PTX alone, and the combination of LLS2 and PTX. (b) the combination index (C.I.) of the treatment of combination of LLS2 and PTX. C.I.<0.9 indicates synergism, C.I.=0.9-1.10 indicates additive interaction, and C.I.>1.1 indicates antagonism. (c) the potentiation of the anticancer effects of PTX by LLS2 at various concentrations and (d) increased apoptosis after combination treatment in SKOV3 cells.

Then, mice were randomly divided into control and treatment groups (n=5). Mice were given a daily I.V. administration for 5 successive days.

FIG. 8 shows (a) identification of eluted protein from a pull-down assay as galectin-1 by LC MS/MS, (b) validation of the LC MS/MS result using immunoblot analysis with anti-galectin-1 Ab (1: blank bead, 2: LLS2-beads, 3: small molecule-bead control), (c) immunostaining results revealing that LLS2 co-localizes with galectin-1 (SKOV3, A549, PC3 and XPA3 cells were stained by biotinylated LLS2 (green), Gal-1 antibody (red), and nuclei were stained with DAPI (blue), and (d) computer modeling showing that LLS2 binds the interface of the galectin-1 dimer. (Residues that are within 3.5 angstroms from LLS2 are shown. Scale bars: 50 m.)

FIG. 9 shows (a) Co-localization of galectin-1 and H-Ras. (b) Once activated by EGF, H-Ras will be partially trafficked to the plasma membrane leading to the activation of Erk pathway. After 15 mins treatment with LLS2 (25 μM), there was a loss of membrane-localized H-Ras. Notably, intracellular H-Ras was augmented 30 mins after LLS2 treatment. (c) Quantification of membrane associated H-Ras (active form) by immunoblot analysis after treatment with buffer (−) or LLS2 (+), showing that LLS2 was able to lower the level of membrane-associated H-Ras. (d) LLS2 also miscolocalized the EGF-stimulated K-Ras(G12V) but not N-Ras (Q61D). (f) phospho-Mek and phospho-Erk were downregulated after treatment with LLS2 for 2 hours.

Figures 10A, 10B:
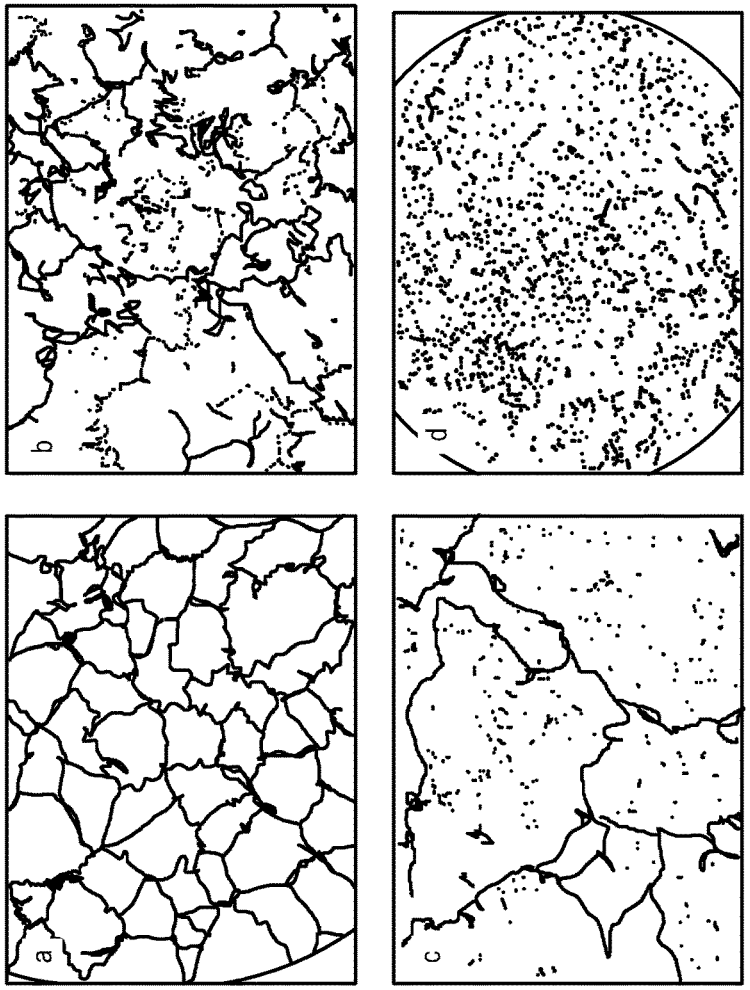

FIG. 10 shows (A) HUVECs cultured on Matrigel-coated plates with (a) PC3-conditioned medium (CM), (b) PC3 CM+LLS2 (10 μM), (c) Galectin-1 (1 μM) and (d) Galectin-1 (1 μM)+LLS2 (10 μM); (B) tube formation as determined by assaying the numbers of branch nodes after 24 h of culture under a phase contrast microscope.

Figure 11:
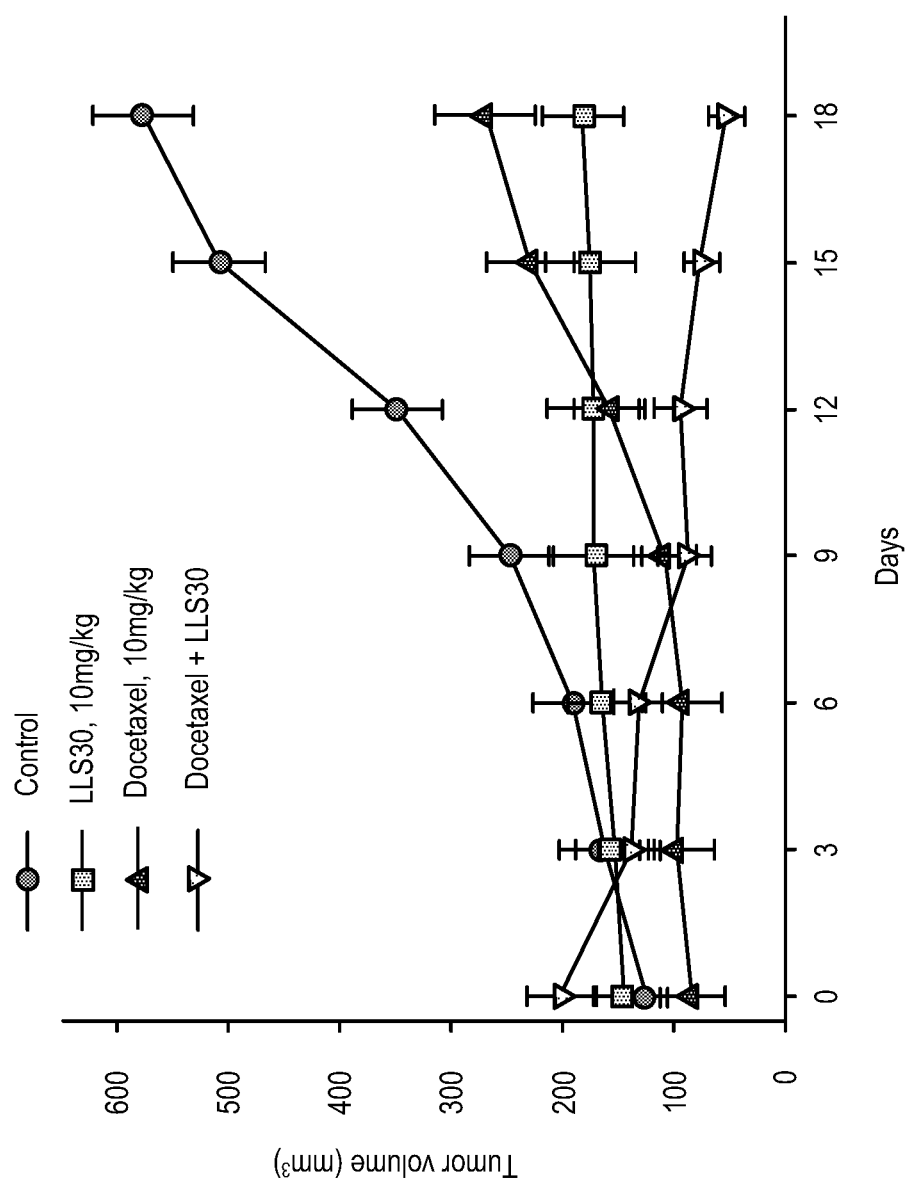

FIG. 11 shows the inhibition of xenograft tumor growth in response to treatment with compounds of the present invention.

FIG. 12 shows (a) LLS30 (2 μM) suppresses MEK/ERK pathway on MPNST cells. (b) LLS30 exerts death on MPNST cells.

Figure 13:
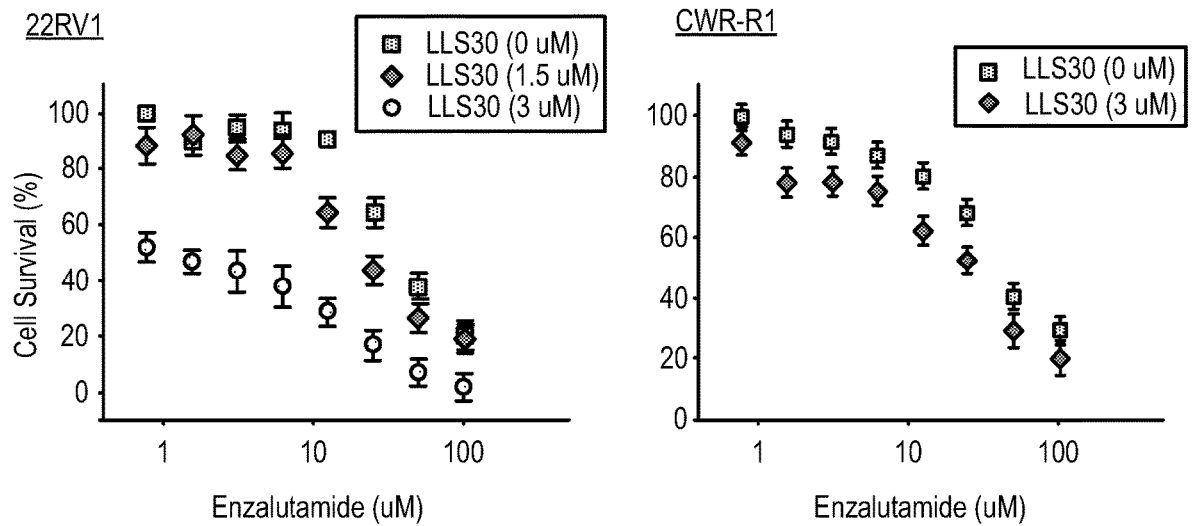
Figure 13:
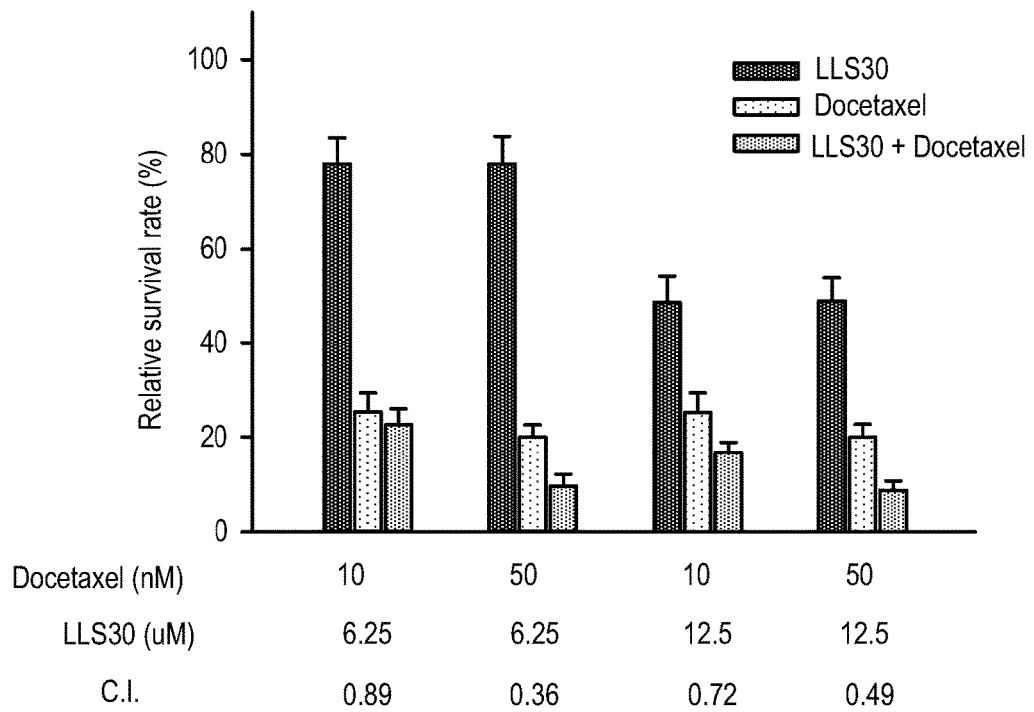

FIG. 13 shows the synergistic anti-cancer effect of LLS30 with Enzalutamide (top panels) or Docetaxel (PC3, bottom panel).

Figure 14:
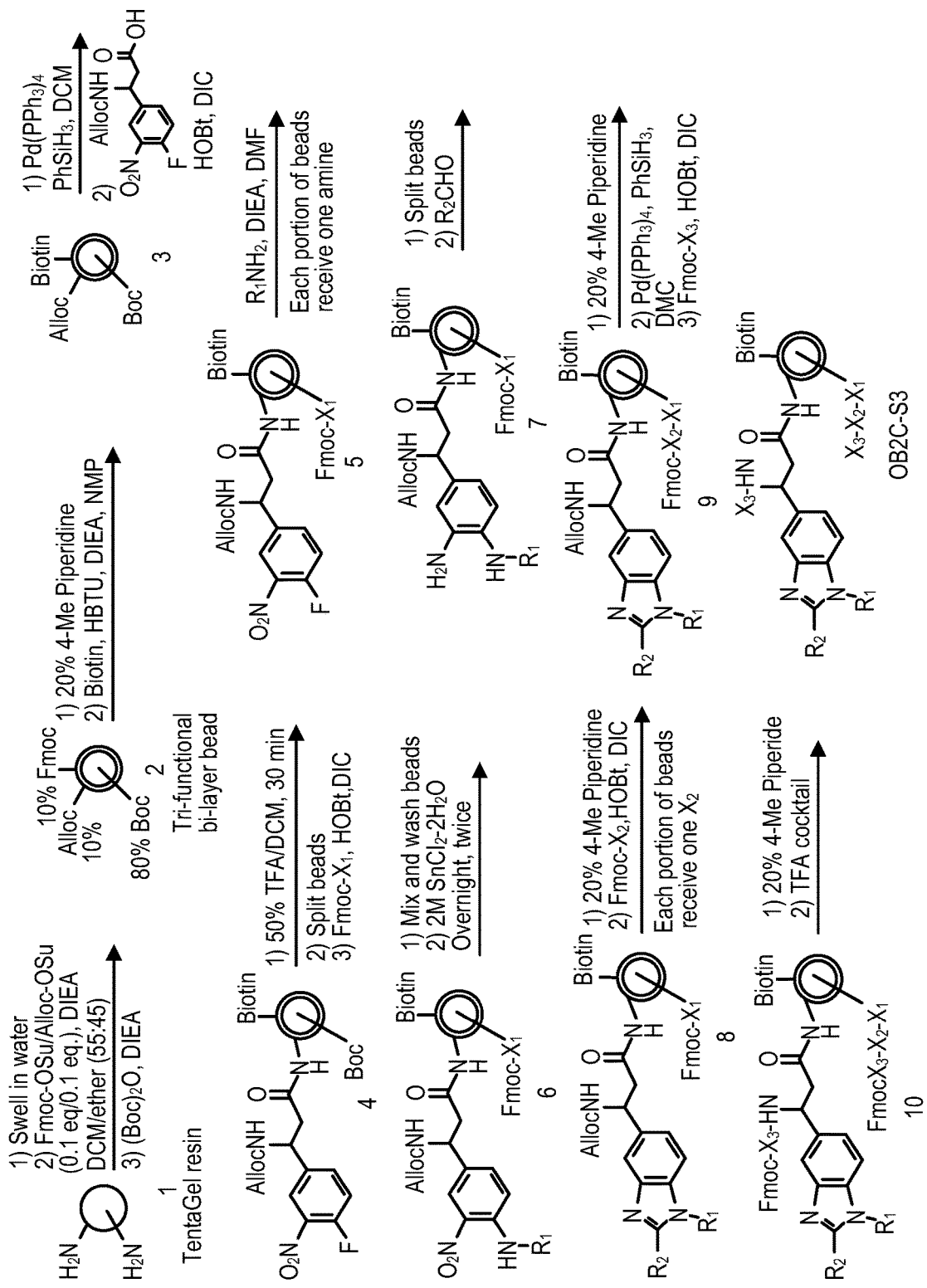

FIG. 14 shows a synthetic scheme for a library of bead-bound benzimidazole-based small molecules of the present invention.

Figure 15:
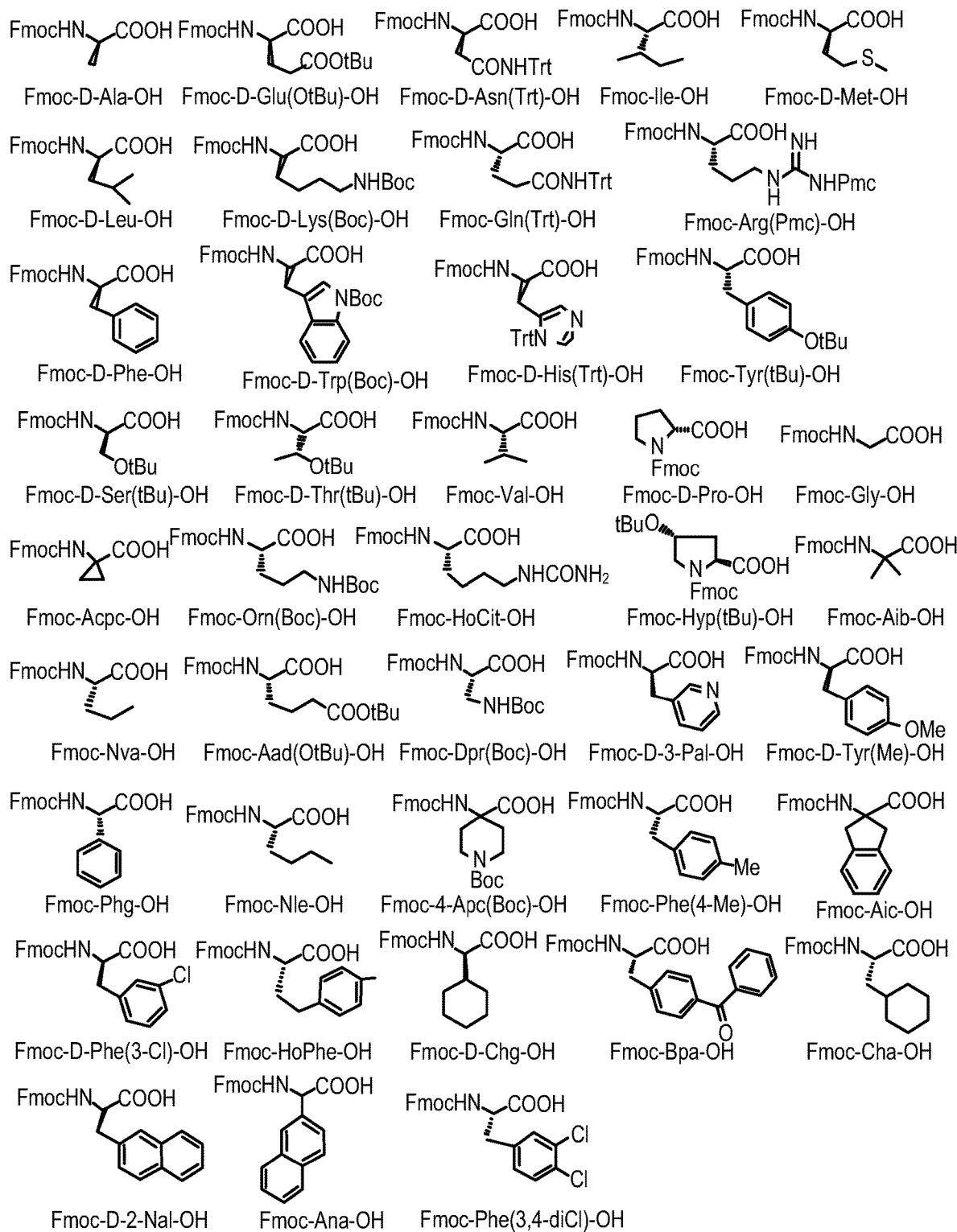

FIG. 15 shows structures of amino acids for use with the synthetic scheme of FIG. 13.

FIG. 16 shows structures of primary amines for use with the synthetic scheme of FIG. 13.

FIG. 17 shows structures of aldehydes for use with the synthetic scheme of FIG. 13.

DETAILED DESCRIPTION OF THE INVENTION

I. General

The present invention provides compounds capable of inhibiting the carbohydrate-binding protein galectin-1 and thereby providing beneficial therapeutic effects. The present invention also provides methods of treating diseases and disorders by inhibiting galectin-1 with the compounds of the present invention.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Hydroxyalkyl" or "alkylhydroxy" refer to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxy-ethyl (where the hydroxy is in the 1- or 2-position), hydroxy-propyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Hydrate" refers to a compound that is complexed to at least one water molecule. The compounds of the present invention can be complexed with from 1 to 10 water molecules.

"Isomers" refers to compounds with the same chemical formula but which are structurally distinguishable. Certain compounds of the present invention possess asymmetric carbon atoms (optical centers) or double bonds; the racemates, diastereomers, geometric isomers and individual isomers are all intended to be encompassed within the scope of the present invention.

"Tautomer" refers to one of two or more structural isomers which exist in equilibrium and which are readily converted from one form to another. The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Contacting" refers to the process of bringing into contact at least two distinct species such that they can react with one another or interact such that one has an effect on the other. It should be appreciated, however, the resulting reaction product can be produced directly from a reaction between the added reagents or from an intermediate from one or more of the added reagents which can be produced in the reaction mixture.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject in need thereof" refers to a living organism suffering from or prone to a condition that can be treated by administration of a pharmaceutical composition as provided herein. Non-limiting examples include humans, other mammals and other non-mammalian animals.

"Disorder" or "condition" refer to a state of being or health status of a patient or subject capable of being treated with the galectin-1 (gal-1) inhibitors of the present invention. Examples of disorders or conditions include, but are not limited to, ovarian cancer, prostate cancer, lung cancer, breast cancer, kidney cancer, pancreatic cancer, colon cancer, and non-small cell lung cancer.

"Chemotherapeutic agent" refers to a compound or pharmaceutical composition useful for treating or ameliorating cancer. The agent can be given with a curative intent, with an aim to prolong life, or for the purpose of reducing symptoms.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

The present invention provides many galectin-1 (gal-1) inhibitors of Formulas I and J. In some embodiments, the present invention provides compounds having the structure

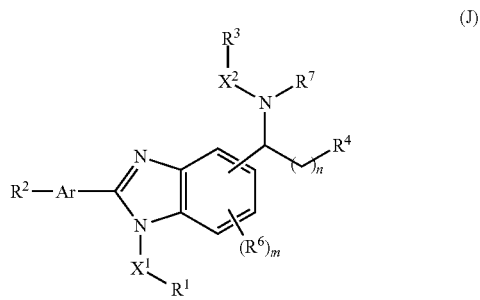

(J)

wherein Ar of formula J can be $C_{6-12}$ aryl or $C_{5-12}$ heteroaryl, wherein Ar can be substituted with 0 to 4 $R^5$ groups. $R^1$ can be $C_{1-6}$ alkyl, $-NR^{1a}R^{1b}$, $C_{3-10}$ cycloalkyl, $C_{3-8}$ heterocycloalkyl, $C_{6-12}$ aryl, or $C_{5-12}$ heteroaryl, wherein the aryl is optionally substituted with 1-4 $R^{1c}$ groups. $R^{1a}$ and $R^{1b}$ can each independently be hydrogen or $C_{1-6}$ alkyl. $R^2$ of formula I can be $NR^{2a}R^{2b}$, $C_{5-12}$ heteroaryl or $C_{1-6}$ alkyl-$C_{5-12}$ heteroaryl, wherein the heteroaryl is optionally substituted with $C_{1-6}$ hydroxyalkyl. $R^{2a}$ and $R^{2b}$ can each independently be $C_{1-6}$ alkyl, $C_{1-6}$ hydroxyalkyl, or $C_{1-6}$ alkyl-OC(O)CH$_3$. Alternatively, $R^{2a}$ and $R^{2b}$ can be combined with the nitrogen to which they are attached to form a $C_{3-8}$ heterocycloalkyl having 0 to 2 additional heteroatoms which can be N, O, or S, wherein the $C_{3-8}$ heterocycloalkyl is optionally substituted with 1 to 4 $R^{2c}$ groups. Each $R^{1c}$ and $R^{2c}$ can independently be $C_{1-6}$ alkyl, halogen, $C_{1-6}$ haloalkyl, hydroxy, $C_{1-6}$ alkoxy, $C_{1-6}$ haloalkoxy, or $C_{6-12}$ aryl. $R^3$ of formula I can be hydrogen, $C_{1-6}$ alkyl, $C_{3-8}$ cycloalkyl, $C_{3-8}$ heterocycloalkyl, $C_{6-12}$ aryl, or $C_{5-12}$ heteroaryl, wherein the heterocycloalkyl, aryl, and heteroaryl are optionally substituted with 0 to 4 $R^{3a}$ groups. Each $R^{3a}$ can independently be $C_{1-6}$ alkyl, halogen, $C_{1-6}$ haloalkyl, hydroxy, $C_{1-6}$ alkoxy, $C_{1-6}$ haloalkoxy, $C_{3-8}$ cycloalkyl, $C_{3-8}$ heterocycloalkyl, $C_{6-12}$ aryl, $C_{5-12}$ heteroaryl, or $-SO_2-C_{6-12}$ aryl. $R^4$ of formula I can be hydrogen, $C_{1-6}$ alkyl, $-C(O)R^{4a}$, $-C(O)OR^{4a}$ or $-C(O)NR^{4a}R^{4b}$. Each $R^{4a}$ and $R^{4b}$ can independently be hydrogen or $C_{1-6}$ alkyl. Each $R^5$ and $R^6$ of formula I can independently be hydrogen or $C_{1-6}$ alkyl. $R^7$ of formula I can be hydrogen or $C_{1-6}$ alkyl-$C_{6-12}$ aryl, optionally substituted with 1-4 $R^{7a}$ groups. Each $R^{7a}$ can independently be $C_{1-6}$ alkyl, halogen, $C_{1-6}$ haloalkyl, $C_{1-6}$ alkoxy, or $C_{1-6}$ haloalkoxy. $X^1$ of formula I can be $C_{1-6}$ alkylene. $X^2$ of formula I can be absent or $C_{1-6}$ alkylene, $-C(O)NH-$, $-C(O)CH(NH_2)CH_2-$ or $-C(O)CH(NH_2)CH(OH)-$. Subscripts n and m of formula I can independently be integers from 0 to 3. The compounds of formula I can also be the pharmaceutically acceptable salts and isomers thereof.

In some embodiments, Ar can be $C_{6-12}$ aryl or $C_{5-12}$ heteroaryl, wherein Ar can be substituted with 0 to 4 $R^5$ groups. Representative aryl and heteroaryl groups include, but are not limited to, phenyl, pyrrole, pyridine, imidazole, pyrazole, triazole, pyrazine, pyrimidine, pyridazine, triazine, thiophene, furan, thiazole, isothiazole, oxazole, isoxazole, indole, isoindole, quinoline, isoquinoline, quinoxaline, quinazoline, phthalazine, cinnoline, benzothiophene, and benzofuran. In some embodiments, Ar can be phenyl or pyridyl. In some embodiments, Ar can be phenyl. In some embodiments, Ar can be pyridyl.

In some embodiments, the present invention provides compounds having the structure

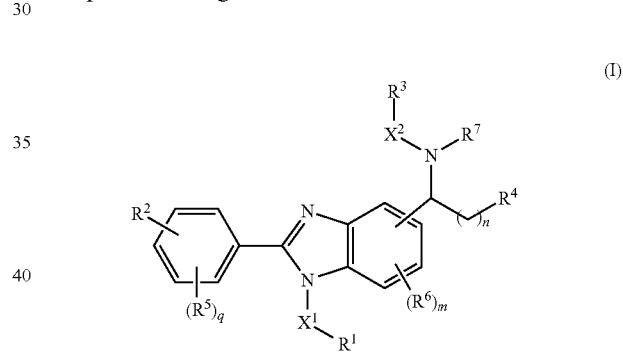

(I)

wherein $R^1$ of formula I can be $C_{1-6}$ alkyl, $-NR^{1a}R^{1b}$, $C_{3-10}$ cycloalkyl, $C_{3-8}$ heterocycloalkyl, $C_{6-12}$ aryl, or $C_{5-12}$ heteroaryl, wherein the aryl is optionally substituted with 1-4 $R^{1c}$ groups. $R^{1a}$ and $R^{1b}$ can each independently be hydrogen or $C_{1-6}$ alkyl. $R^2$ of formula I can be $NR^{2a}R^{2b}$, $C_{5-12}$ heteroaryl or $C_{1-6}$ alkyl-$C_{5-12}$ heteroaryl, wherein the heteroaryl is optionally substituted with $C_{1-6}$ hydroxyalkyl. $R^{2a}$ and $R^{2b}$ can each independently be $C_{1-6}$ alkyl, $C_{1-6}$ hydroxyalkyl, or $C_{1-6}$ alkyl-OC(O)CH$_3$. Alternatively, $R^{2a}$ and $R^{2b}$ can be combined with the nitrogen to which they are attached to form a $C_{3-8}$ heterocycloalkyl having 0 to 2 additional heteroatoms which can be N, O, or S, wherein the $C_{3-8}$ heterocycloalkyl is optionally substituted with 1 to 4 $R^{2c}$ groups. Each $R^{1c}$ and $R^{2c}$ can independently be $C_{1-6}$ alkyl, halogen, $C_{1-6}$ haloalkyl, hydroxy, $C_{1-6}$ alkoxy, $C_{1-6}$ haloalkoxy, or $C_{6-12}$ aryl. $R^3$ of formula I can be hydrogen, $C_{1-6}$ alkyl, $C_{3-8}$ cycloalkyl, $C_{3-8}$ heterocycloalkyl, $C_{6-12}$ aryl, or $C_{5-12}$ heteroaryl, wherein the heterocycloalkyl, aryl, and heteroaryl are optionally substituted with 0 to 4 $R^{3a}$ groups. Each $R^{3a}$ can independently be $C_{1-6}$ alkyl, halogen, $C_{1-6}$ haloalkyl, hydroxy, $C_{1-6}$ alkoxy, $C_{1-6}$ haloalkoxy, $C_{3-8}$ cycloalkyl, $C_{3-8}$ heterocycloalkyl, $C_{6-12}$ aryl, $C_{5-12}$ heteroaryl, or $-SO_2-C_{6-12}$ aryl. $R^4$ of formula I can be hydrogen, $C_{1-6}$ alkyl, —C(O)$R^{4a}$, —C(O)O$R^{4a}$ or —C(O)N$R^{4a}R^{4b}$. Each $R^{4a}$ and $R^{4b}$ can independently be hydrogen or $C_{1-6}$ alkyl. Each $R^5$ and $R^6$ of formula I can independently be hydrogen or $C_{1-6}$ alkyl. $R^7$ of formula I can be hydrogen or $C_{1-6}$ alkyl-$C_{6-12}$ aryl, optionally substituted with 1-4 $R^{7a}$ groups. Each $R^{7a}$ can independently be $C_{1-6}$ alkyl, halogen, $C_{1-6}$ haloalkyl, $C_{1-6}$ alkoxy, or $C_{1-6}$ haloalkoxy. $X^1$ of formula I can be $C_{1-6}$ alkylene. $X^2$ of formula I can be absent or $C_{1-6}$ alkylene, —C(O)NH—, —C(O)CH(NH$_2$)CH$_2$— or —C(O)CH(NH$_2$)CH(OH)—. Subscripts n and m of formula I can independently be integers from 0 to 3. Subscript q can be an integer from 0 to 4. The compounds of formula I can also be the pharmaceutically acceptable salts and isomers thereof.

In some embodiments, $R^1$ of formula I can be $C_{1-6}$ alkyl, —N$R^{1a}R^{1b}$, $C_{3-10}$ cycloalkyl, $C_{3-8}$ heterocycloalkyl, $C_{6-12}$ aryl, or $C_{5-12}$ heteroaryl, wherein the aryl is optionally substituted with 1-4 $R^{1c}$ groups. In some embodiments, $R^1$ can be $C_{1-6}$ alkyl, —NH$_2$, $C_{3-10}$ cycloalkyl, $C_{3-8}$ heterocycloalkyl, $C_{6-12}$ aryl, or $C_{5-12}$ heteroaryl, wherein the aryl is optionally substituted with 1-4 $R^{1c}$ groups. In some embodiments, $R^1$ can be $C_{1-6}$ alkyl, —NH$_2$, $C_{3-10}$ cycloalkyl, $C_{5-6}$ heterocycloalkyl, or $C_{5-6}$ heteroaryl, wherein the heterocycloalkyl or heteroaryl has 1, 2, or 3 N atoms. In some embodiments, $R^1$ can be $C_{1-6}$ alkyl, —NH$_2$, adamantyl, piperidinyl, phenyl, pyridinyl, and imidazolyl, wherein the phenyl is optionally substituted with 1-4 $R^{1c}$ groups. In some embodiments, $R^{1a}$ and $R^{1b}$ can each independently be hydrogen or $C_{1-6}$ alkyl. The alkyl of $R^{1a}$ or $R^{1b}$ can independently be any suitable alkyl group, such as methyl, ethyl, propyl, butyl, pentyl, and hexyl, among others.

In some embodiments, $R^1$ of formula I is an aryl that is optionally substituted with 1-4 $R^{1c}$ groups. In some embodiments, each $R^{1c}$ can independently be $C_{1-6}$ alkyl, halogen, $C_{1-6}$ haloalkyl, hydroxy, $C_{1-6}$ alkoxy, $C_{1-6}$ haloalkoxy, or $C_{6-12}$ aryl In some embodiments, each $R^{1c}$ can independently be halogen, $C_{1-6}$ haloalkyl, $C_{1-6}$ alkoxy, or $C_{1-6}$ haloalkoxy. In some embodiments, each $R^{1c}$ can independently be fluoro, chloro, —CF$_3$, —OCH$_3$, or —OCF$_3$.

In some embodiments, $R^2$ of formula I can be N$R^{2a}R^{2b}$, $C_{5-12}$ heteroaryl or $C_{1-6}$ alkyl-$C_{5-12}$ heteroaryl, wherein the heteroaryl is optionally substituted with $C_{1-6}$ hydroxyalkyl. In some embodiments, $R^2$ of formula I can be N$R^{2a}R^{2b}$. In some embodiments, $R^{2a}$ and $R^{2b}$ can each independently be $C_{1-6}$ alkyl, $C_{1-6}$ hydroxyalkyl, or $C_{1-6}$ alkyl-OC(O)CH$_3$. In some embodiments, $R^{2a}$ and $R^{2b}$ can be combined with the nitrogen to which they are attached to form a $C_{3-8}$ heterocycloalkyl having 0 to 2 additional heteroatoms which can be N, O, or S, wherein the $C_{3-8}$ heterocycloalkyl is optionally substituted with 1 to 4 $R^{2c}$ groups. In some embodiments, $R^{2a}$ and $R^{2b}$ can each independently be —CH$_2$CH$_2$OH or —CH$_2$CH$_2$OC(O)CH$_3$. In some embodiments, $R^{2a}$ and $R^{2b}$ are combined with the nitrogen to which they are attached to form 4-morpholino or 4-methylpiperazin-1-yl.

In some embodiments, each $R^{2c}$ can independently be $C_{1-6}$ alkyl, halogen, $C_{1-6}$ haloalkyl, hydroxy, $C_{1-6}$ alkoxy, $C_{1-6}$ haloalkoxy, or $C_{6-12}$ aryl. In some embodiments, each $R^{2c}$ is independently $C_{1-6}$ alkyl. The alkyl of each $R^{2c}$ can independently be any suitable alkyl group, such as methyl, ethyl, propyl, butyl, pentyl, and hexyl, among others.

In some embodiments, $R^3$ of formula I can be hydrogen, $C_{1-6}$ alkyl, $C_{3-8}$ cycloalkyl, $C_{3-8}$ heterocycloalkyl, $C_{6-12}$ aryl, or $C_{5-12}$ heteroaryl, wherein the heterocycloalkyl, aryl, and heteroaryl are optionally substituted with 0 to 4 $R^{3a}$ groups.

In some embodiments, $R^3$ can be hydrogen, $C_{3-8}$ cycloalkyl, $C_{6-12}$ aryl, or $C_{5-12}$ heteroaryl, wherein the aryl and heteroaryl are optionally substituted with 1 to 4 $R^{3a}$ groups. In some embodiments, $R^3$ can be hydrogen, $C_{3-8}$ cycloalkyl, $C_{6-12}$ aryl, or $C_{5-6}$ heteroaryl, wherein the aryl and heteroaryl are optionally substituted with 1 to 4 $R^{3a}$ groups. In some embodiments, $R^3$ can be hydrogen, cyclohexyl, phenyl, naphthalenyl, pyrrolyl, indazolyl, indolyl, and thiophenyl, wherein the phenyl, pyrrolyl, and thiophenyl is optionally substituted with 1 to 4 $R^{3a}$ groups.

In some embodiments, each $R^{3a}$ can independently be $C_{1-6}$ alkyl, halogen, $C_{1-6}$ haloalkyl, hydroxy, $C_{1-6}$ alkoxy, $C_{1-6}$ haloalkoxy, $C_{3-8}$ cycloalkyl, $C_{3-8}$ heterocycloalkyl, $C_{6-12}$ aryl, $C_{5-12}$ heteroaryl, or —SO$_2$—$C_{6-12}$ aryl. In some embodiments, each $R^{3a}$ can independently be halogen, $C_{1-6}$ haloalkyl, $C_{1-6}$ alkoxy, $C_{5-12}$ heteroaryl, or —SO$_2$—$C_{6-12}$ aryl. In some embodiments, each $R^{3a}$ can independently be halogen, $C_{1-6}$ haloalkyl, $C_{1-6}$ alkoxy, $C_{5-6}$ heteroaryl, or —SO$_2$—$C_{6-12}$ aryl, wherein the heteroaryl has 1, 2, or 3 N atoms. In some embodiments, each $R^{3a}$ can independently be bromo, chloro, —CF$_3$, —OCH$_3$, pyridine, pyrimidine, pyrazole, or —SO$_2$-phenyl.

In some embodiments, $R^4$ of formula I can be hydrogen, $C_{1-6}$ alkyl, —C(O)$R^{4a}$, —C(O)O$R^{4a}$ or —C(O)N$R^{4a}R^{4b}$. In some embodiments, each $R^{4a}$ and $R^{4b}$ can independently be hydrogen or $C_{1-6}$ alkyl. The alkyl of each $R^{4a}$ and $R^{4b}$ can independently be any suitable alkyl group, such as methyl, ethyl, propyl, butyl, pentyl, and hexyl, among others. In some embodiments, $R^4$ is —C(O)NH$_2$.

In some embodiments, $R^7$ of formula I can be hydrogen or $C_{1-6}$ alkyl-$C_{6-12}$ aryl, optionally substituted with 1-4 $R^{7a}$ groups. In some embodiments, each $R^{7a}$ can independently be $C_{1-6}$ alkyl, halogen, $C_{1-6}$ haloalkyl, $C_{1-6}$ alkoxy, or $C_{1-6}$ haloalkoxy. In some embodiments, $R^7$ is hydrogen.

In some embodiments, $X^1$ of formula I can be $C_{1-6}$ alkylene. The alkylene of $X^1$ can be any suitable alkylene group, such as methylene, ethylene, propylene, butylene, pentylene, and hexylene, among others. In some embodiments, $X^1$ can be methylene, ethylene, or propylene. In some embodiments, $X^2$ of formula I can be absent. In some embodiments, $X^2$ can be $C_{1-6}$ alkylene, —C(O)NH—, —C(O)CH(NH$_2$)CH$_2$— or —C(O)CH(NH$_2$)CH(OH)—. In some embodiments, $X^2$ can be methylene, —C(O)NH—, —C(O)CH(NH$_2$)CH$_2$— or —C(O)CH(NH$_2$)CH(OH)—.

In some embodiments, subscripts n and m of formula I can independently be integers from 0 to 3. In some embodiments, subscript n can be 0, 1, 2, or 3. In some embodiments, subscript n can be 0 or 1. In some embodiments, subscript n is 0. In some embodiments, subscript n is 1. In some embodiments, subscript m can be 0, 1, 2, or 3. In some embodiments, subscript m can be 0 or 1. In some embodiments, subscript m is 0. In some embodiments, subscript m is 1. In some embodiments, subscript q can be an integer from 0 to 4. In some embodiments, subscript q can be 0, 1, 2, 3, or 4. In some embodiments, subscript q can be 0, 1, 2, or 3. In some embodiments, subscript q can be 0 or 1. In some embodiments, subscript q is 0. In some embodiments, subscript q is 1.

In some embodiments, the compounds of formula I can have the following structure:

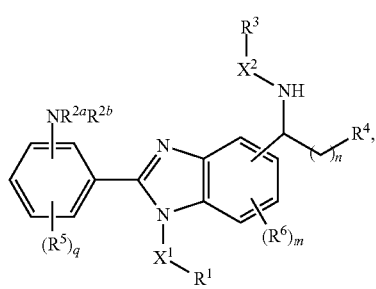
(Ia)
wherein R[1], R[2a], R[2b], R[3], R[4], R[5], R[6], X[1], X[2], m, n, and q are as defined above.
In some embodiments, the compounds of formula I can have the following structure:
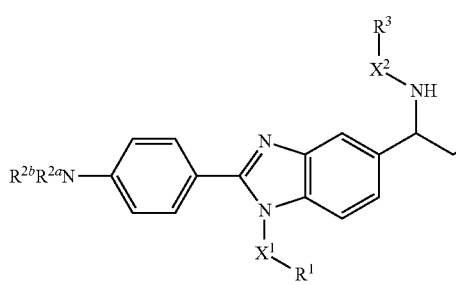
(Ib)
wherein R[1], R[2a], R[2b], R[3], X[1], X[2], m, n, and q are as defined above.
In some embodiments, the compounds of formula I can be:
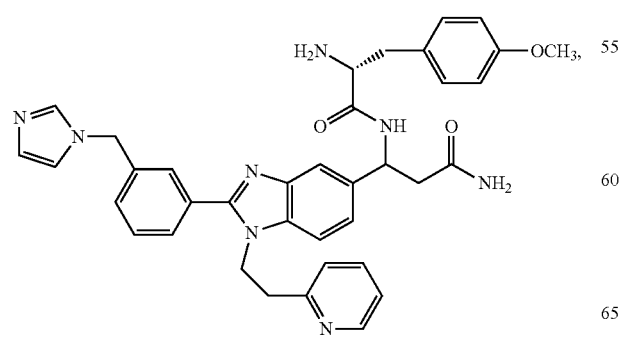
LLS1
-continued
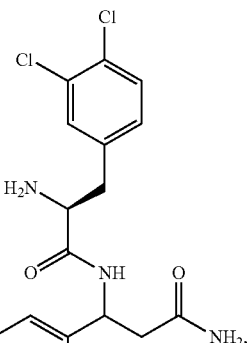
LLS2
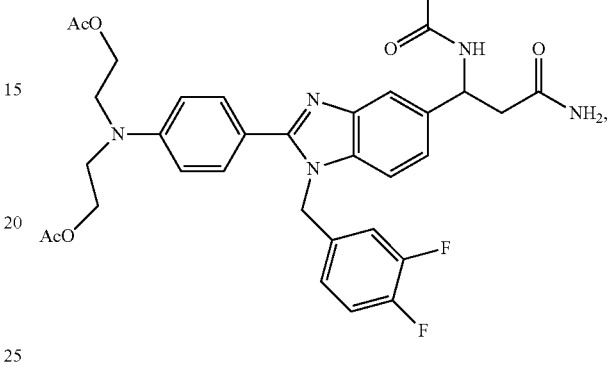
LLS3
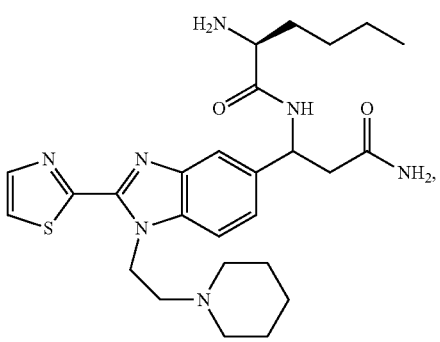
LLS4

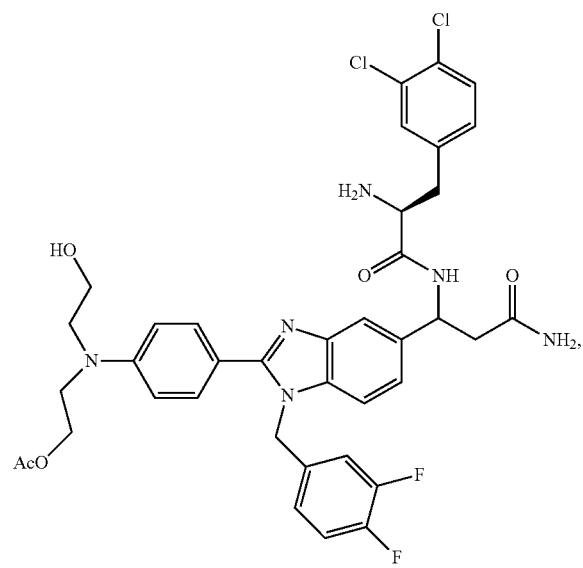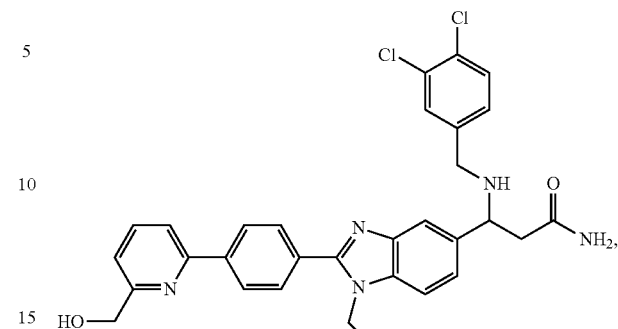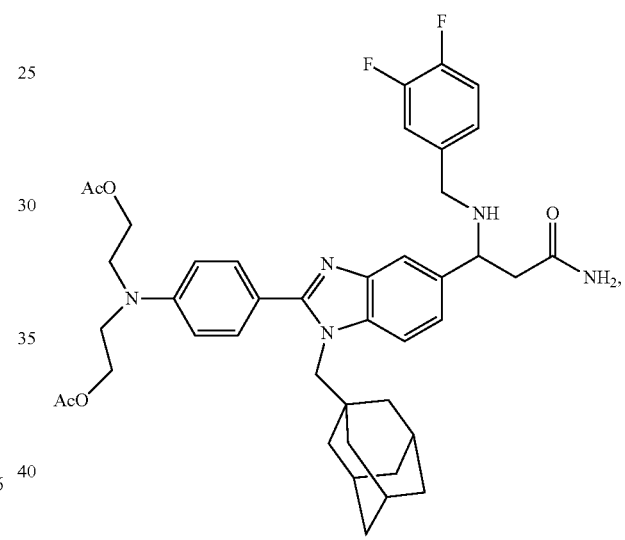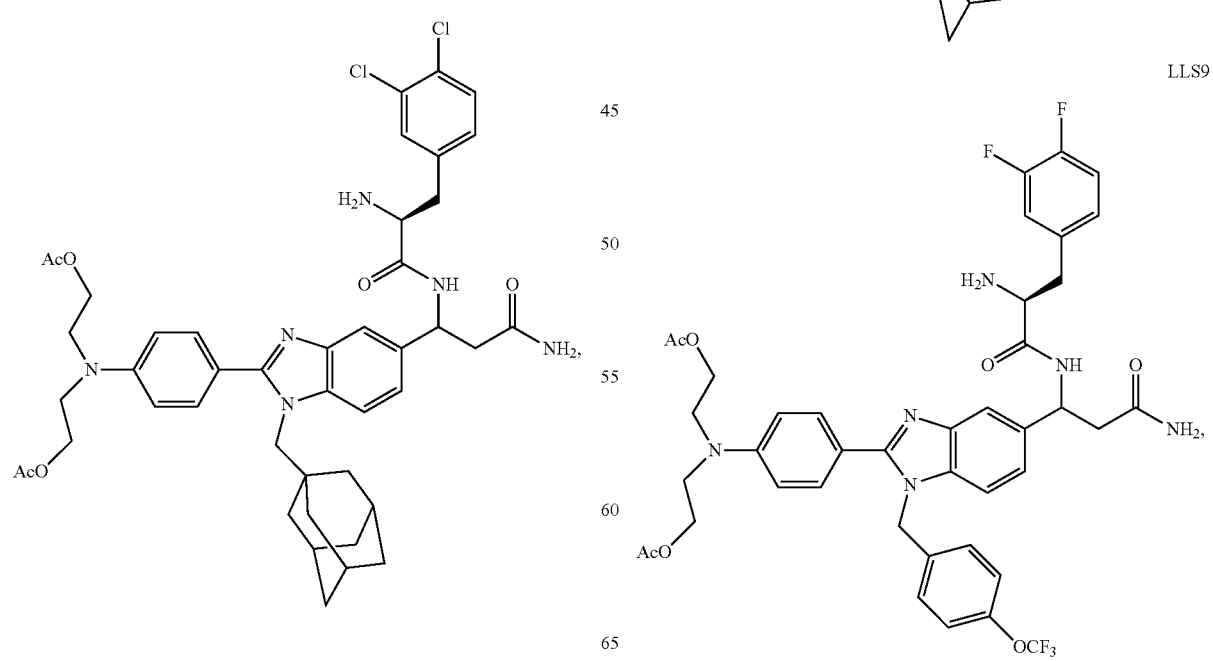

-continued

LLS10

LLS11

LLS12

LLS13

LLS14

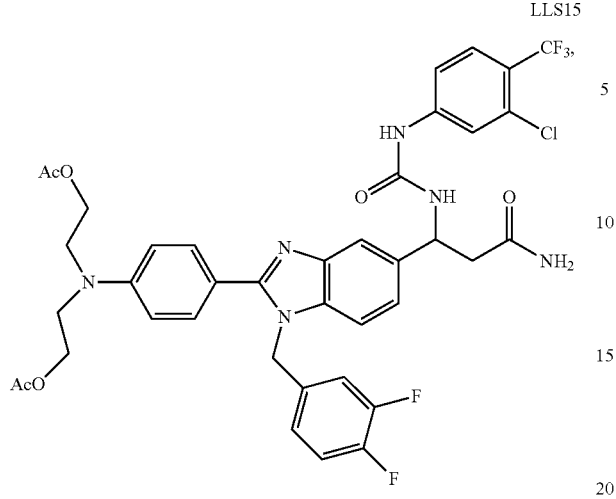
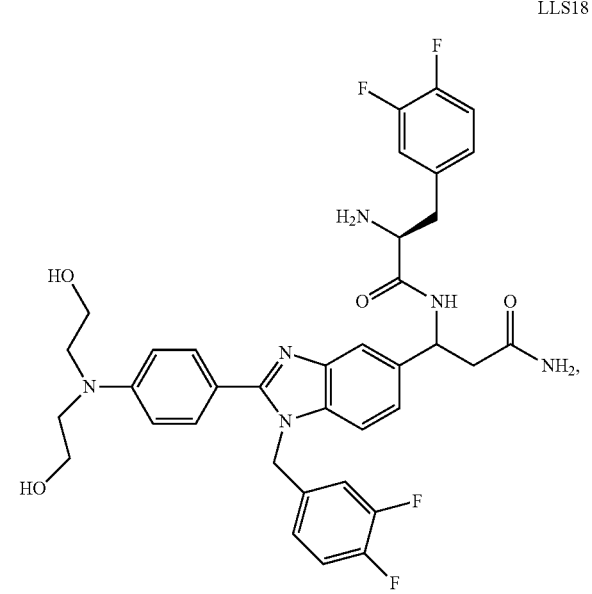

LLS21
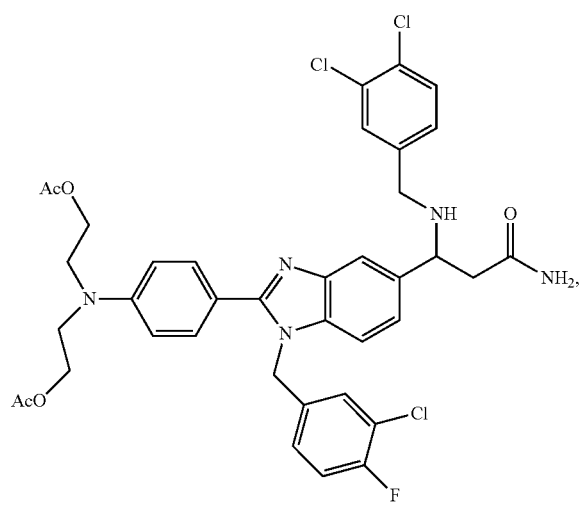
LLS22
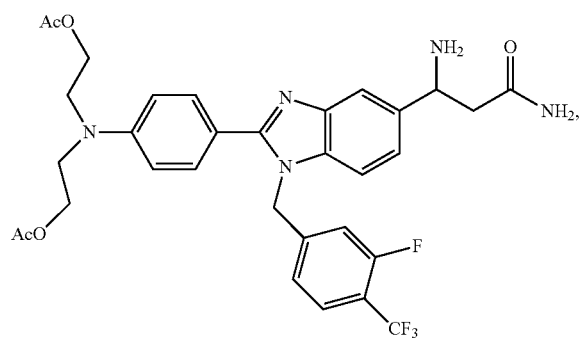
LLS23
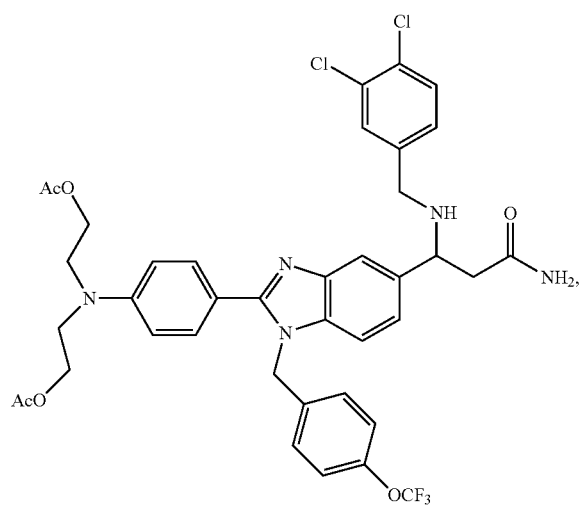
LLS24
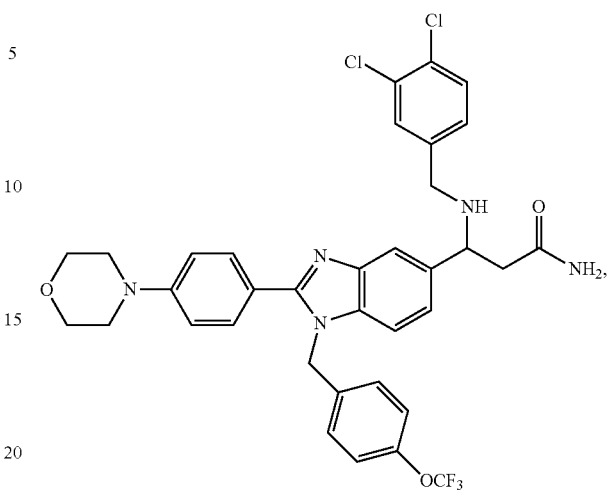
LLS25
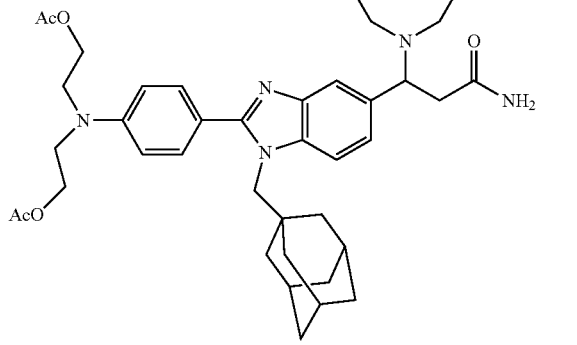
LLS26
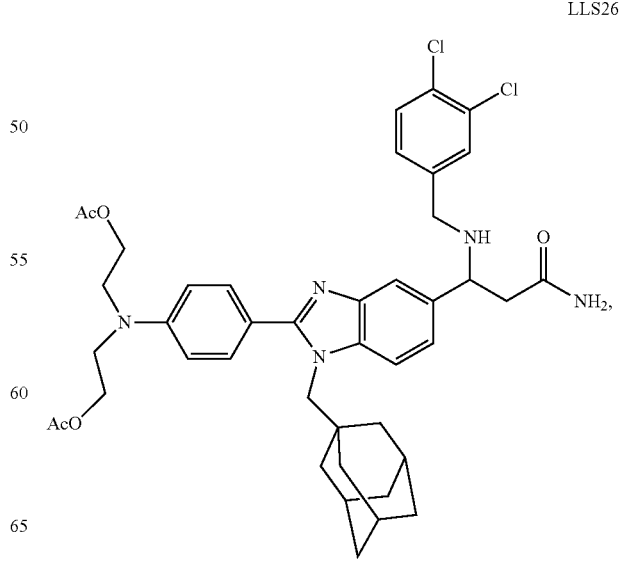

-continued

LLS27

LLS28

LLS29

LLS30

LLS31

LLS32

LLS33
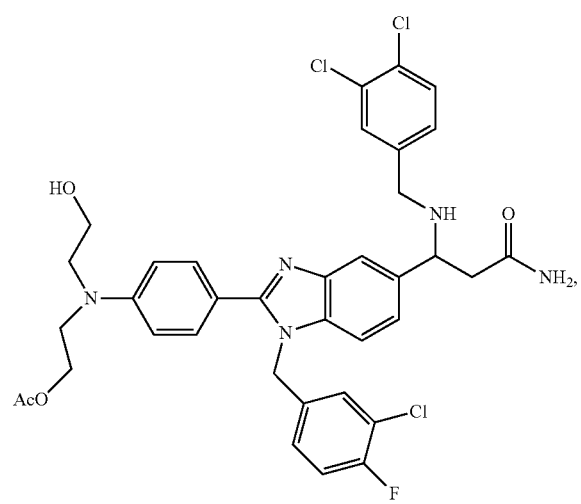
LLS34
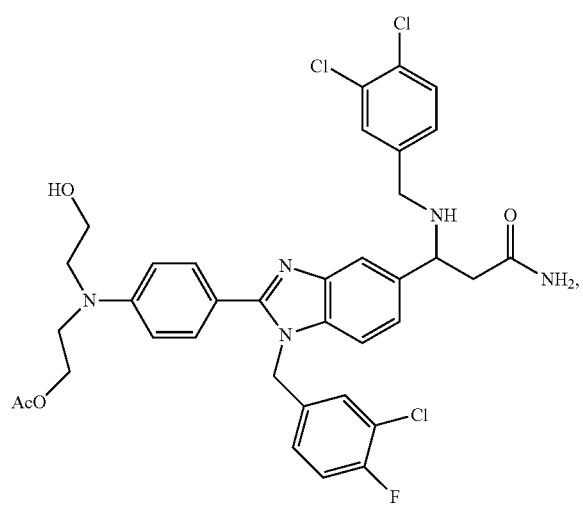
LLS35
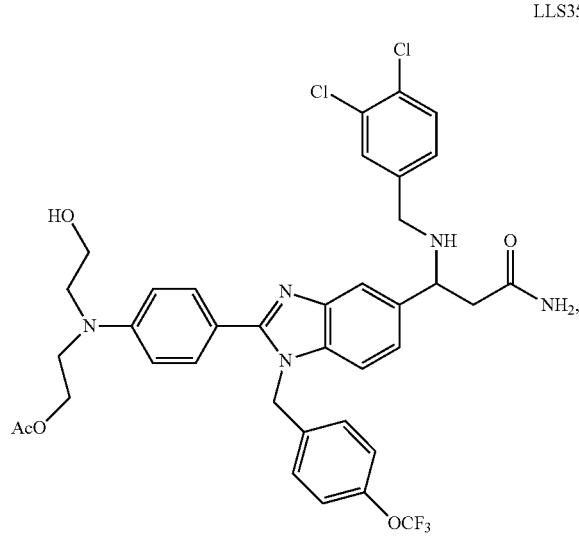
LLS36
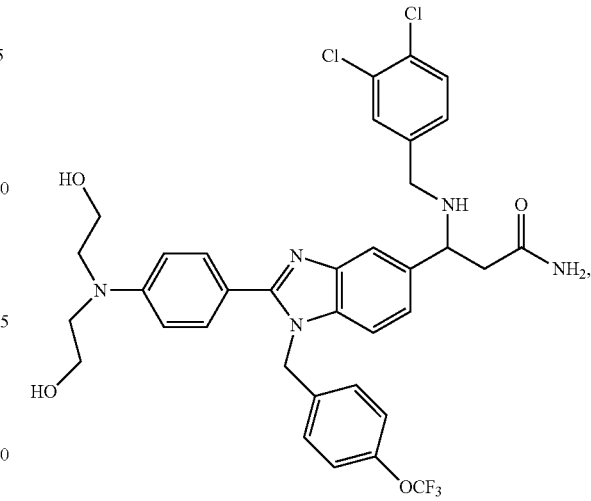
LLS37
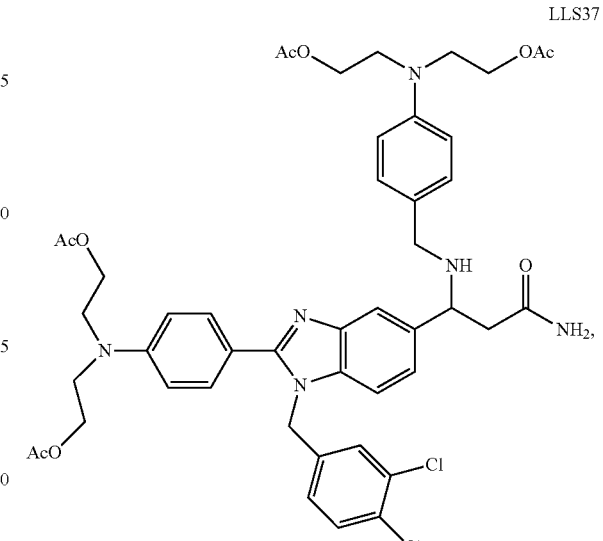
LLS38
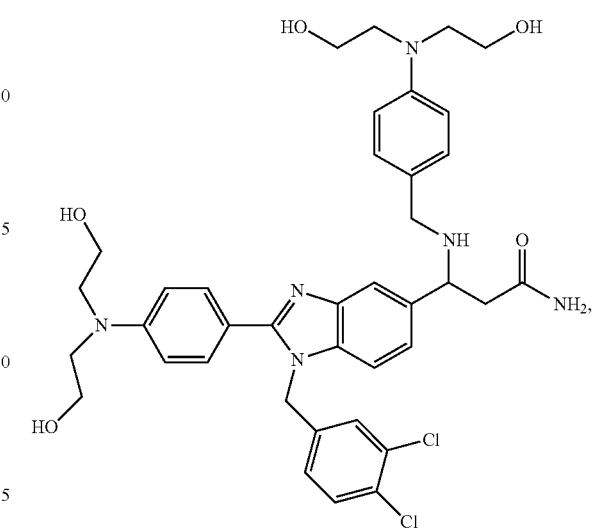

LLS39
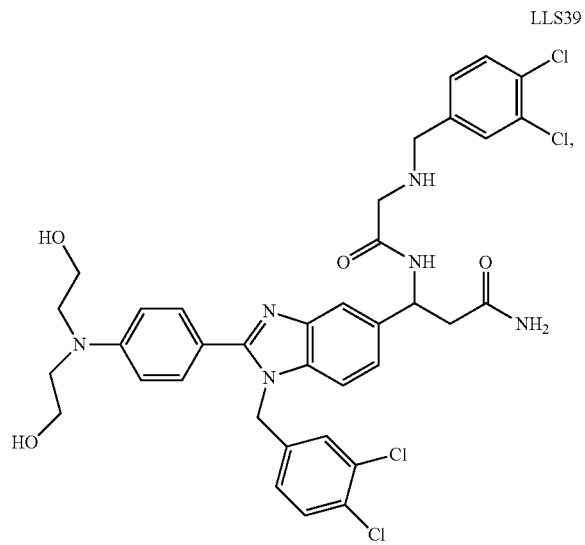
LLS40
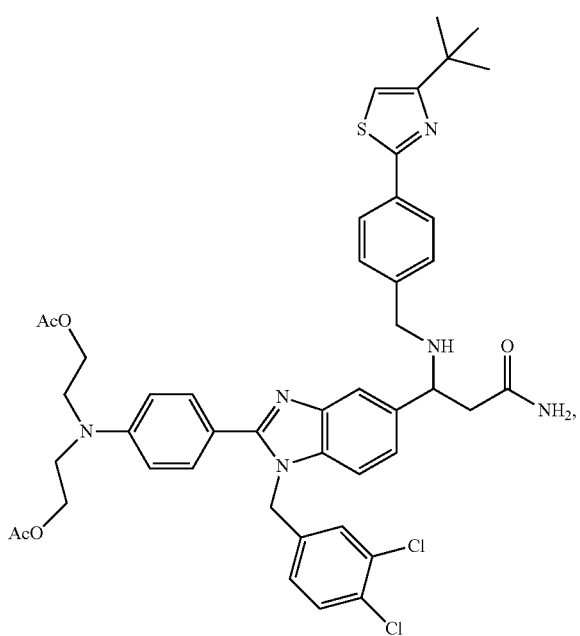
LLS41
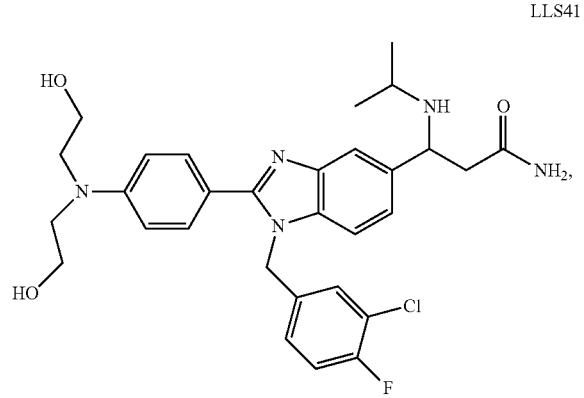
LLS42
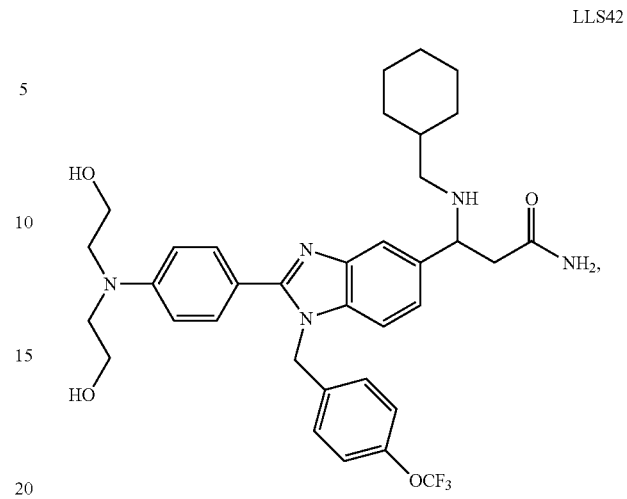
LLS43
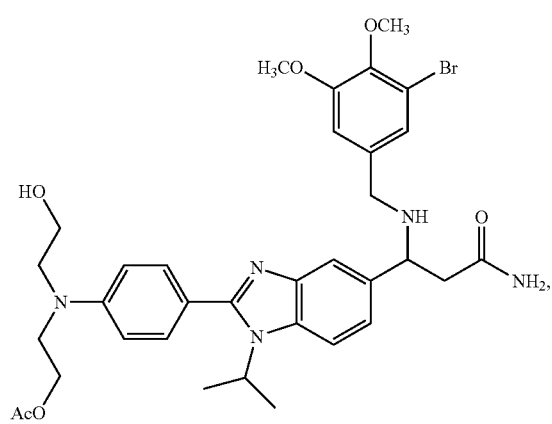
LLS43Ac
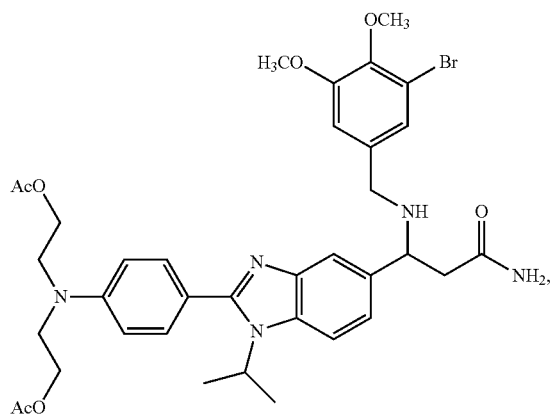

LLS44
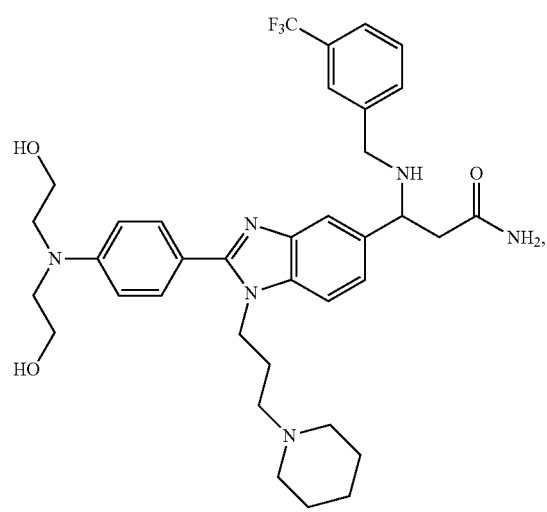
LLS45
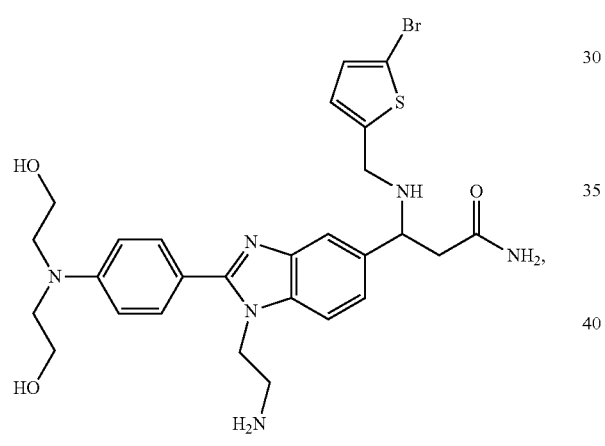
LLS45Ac
LLS46
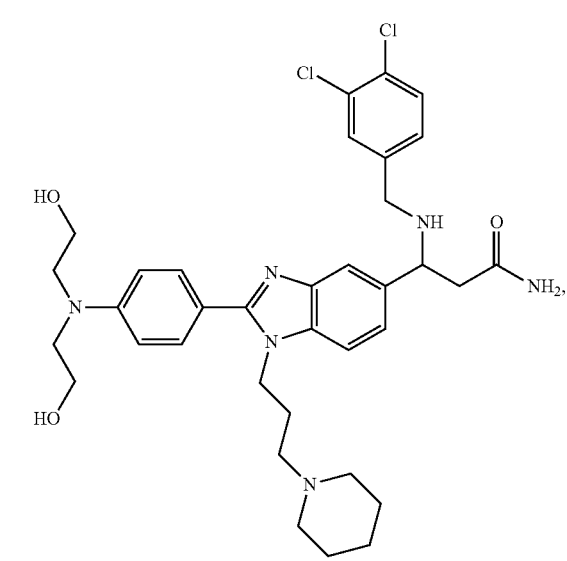
LLS51
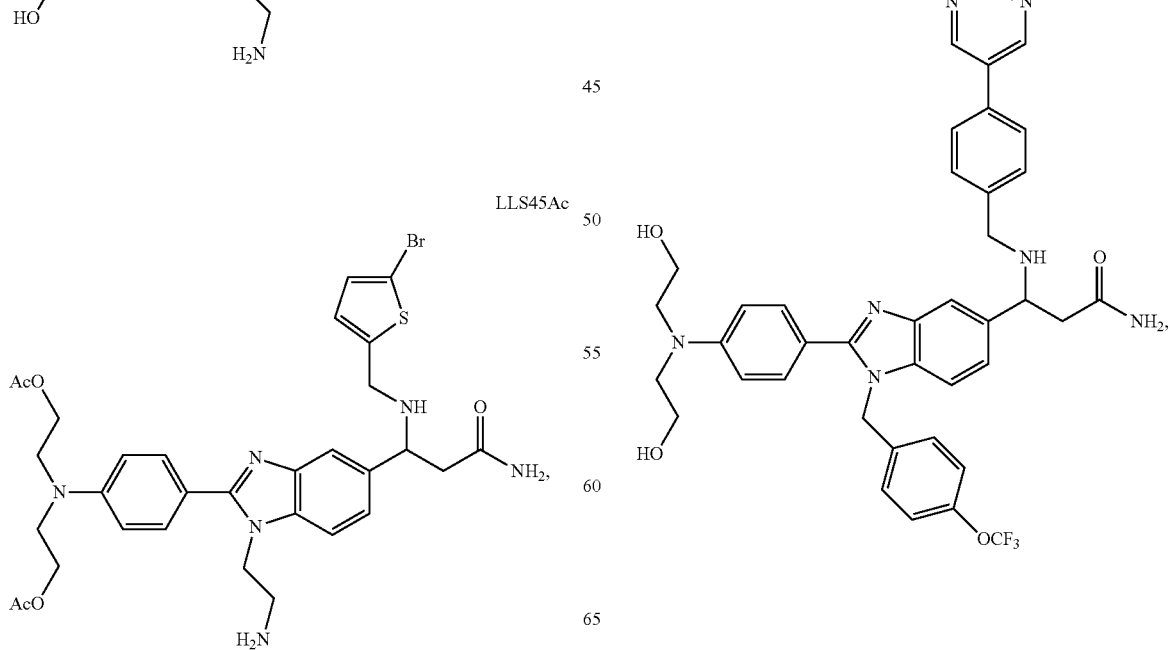

-continued
LLS52
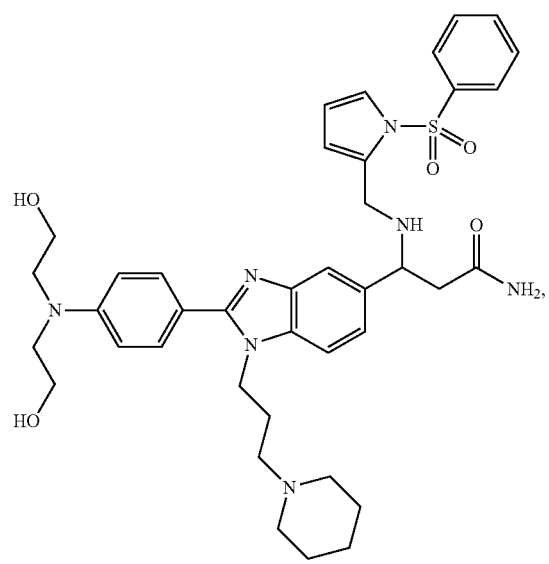
LLS53
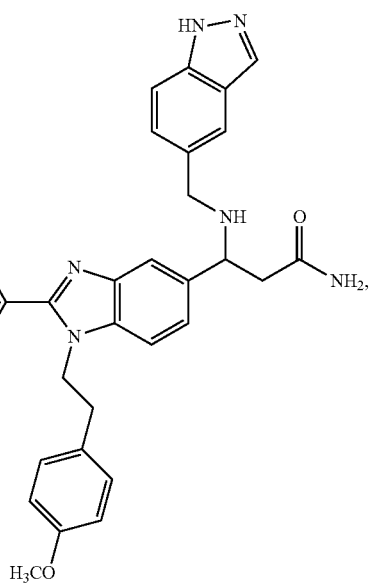
LLS52Ac
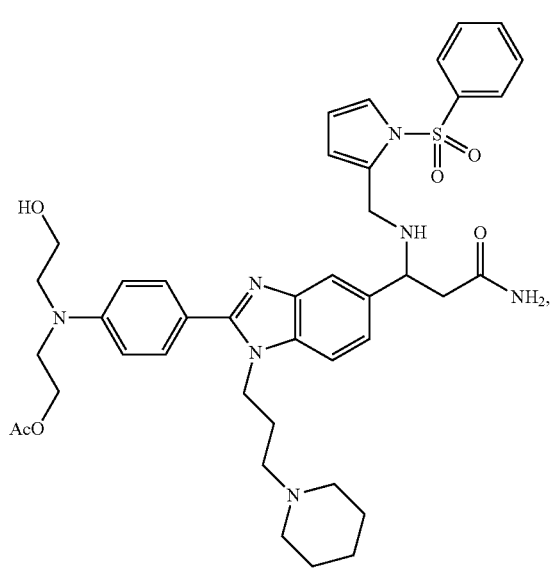
LLS53Ac
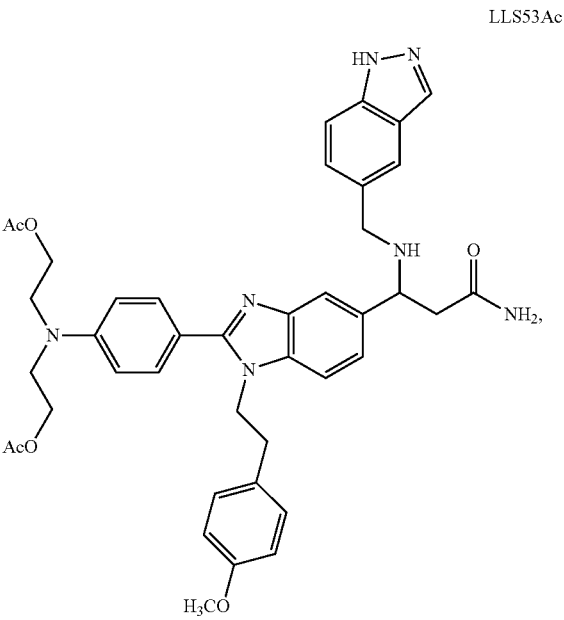

-continued
LLS54
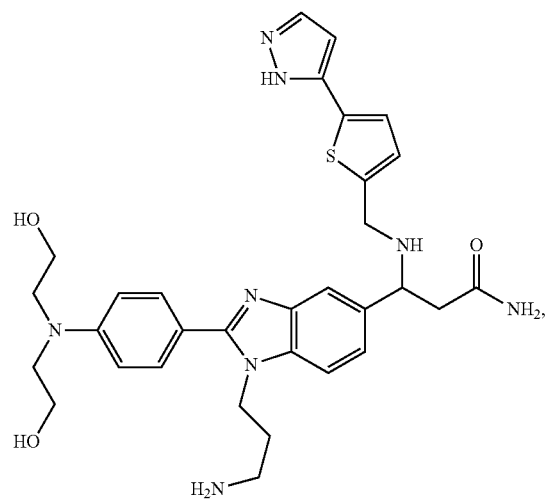
LLS55
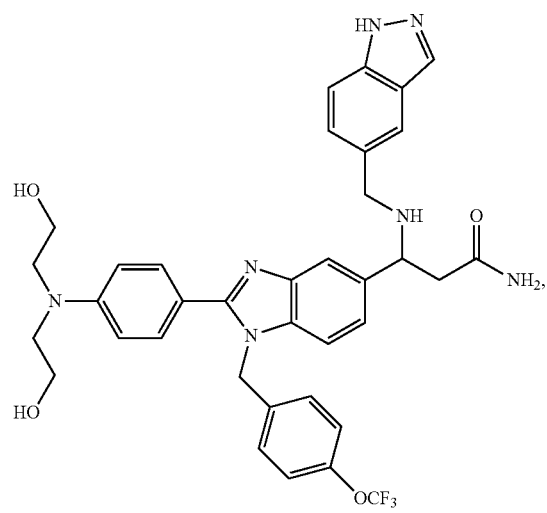
LLS56
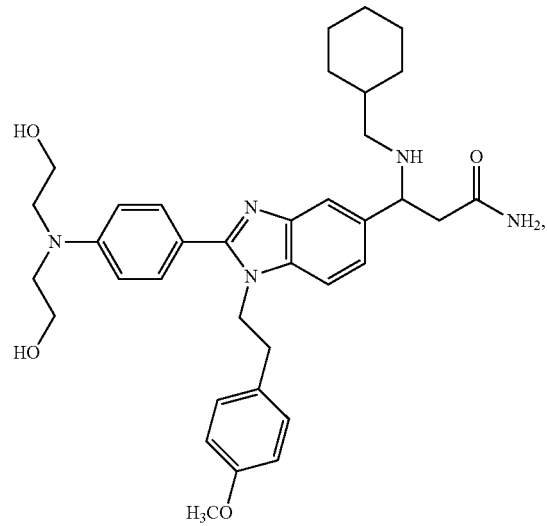
-continued
LLS56Ac
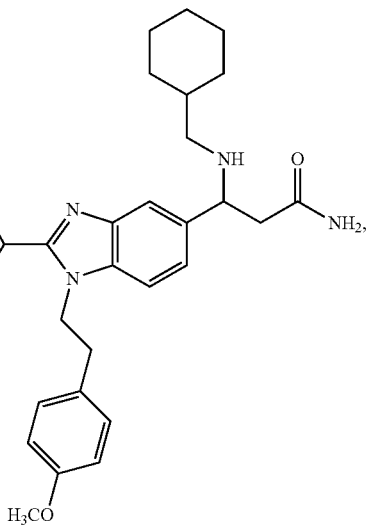
LLS58
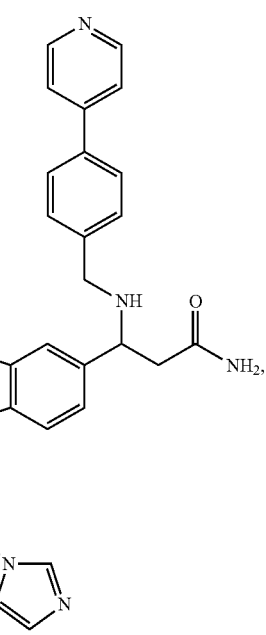

37
-continued
LLS58Ac
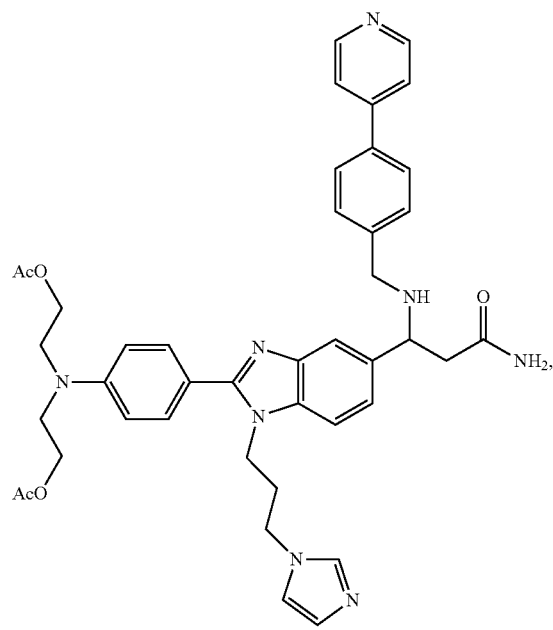
LLS59
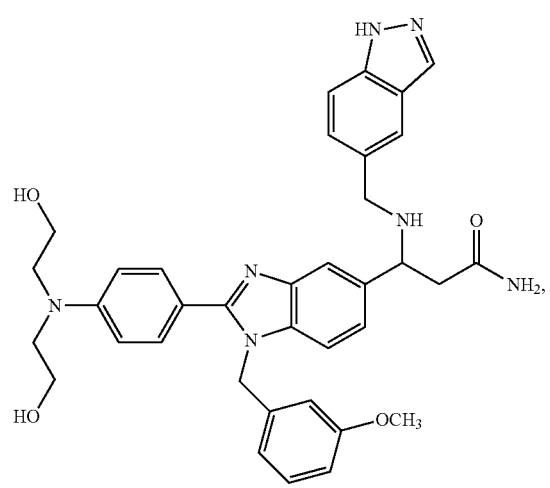
LLS63
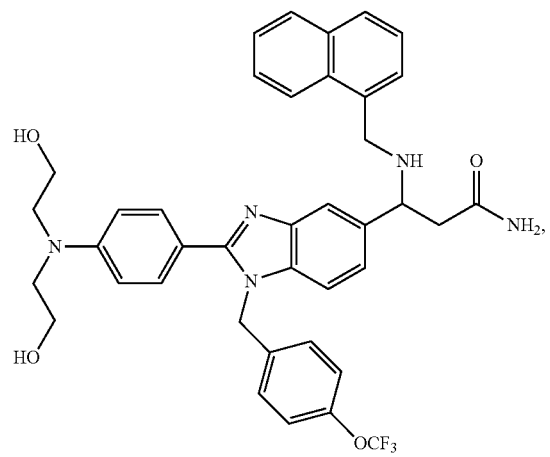
38
-continued
LLS64
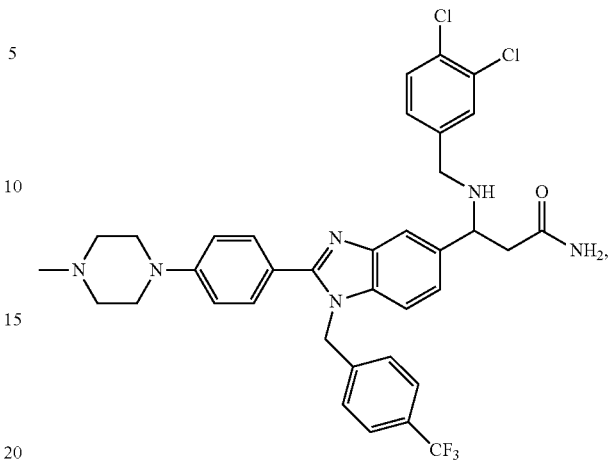
LLS65
LLS66
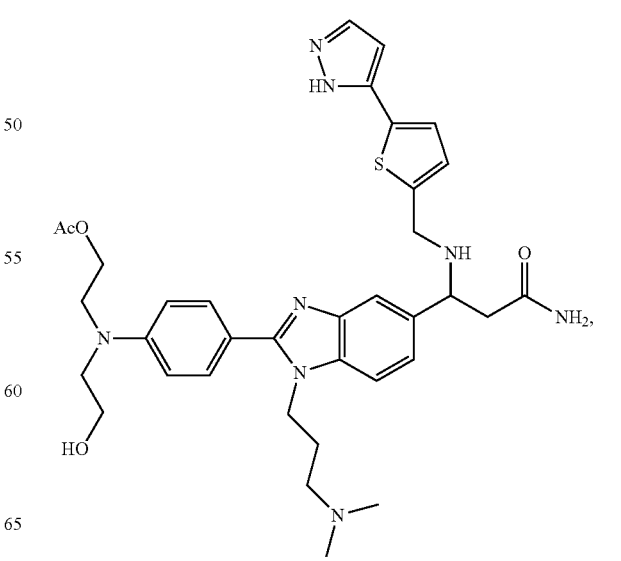

-continued

LLS67

LLS69Ac

-continued

LLS71

LLS73

LLS76

LLS77
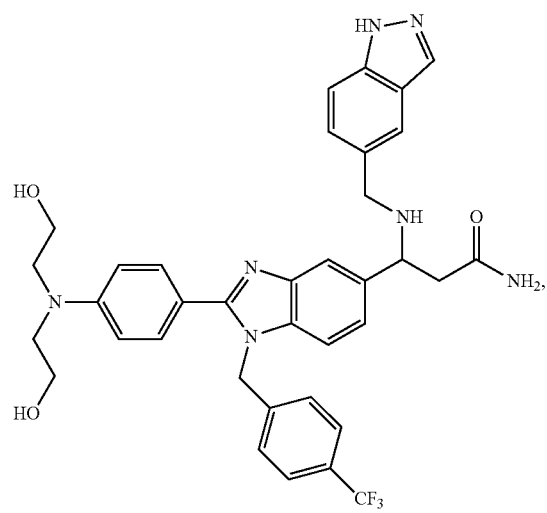
LLS78
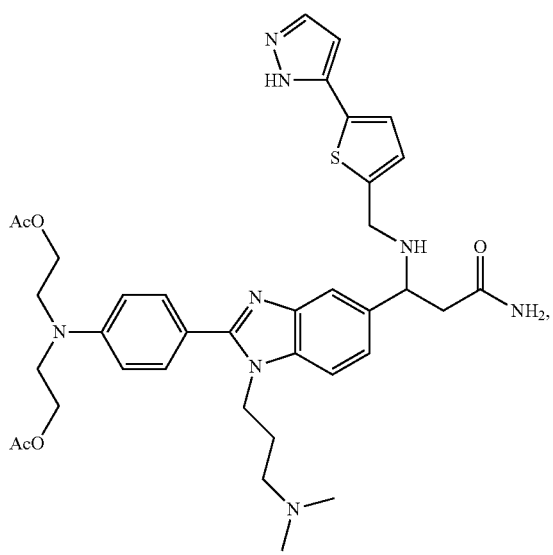
LLS80
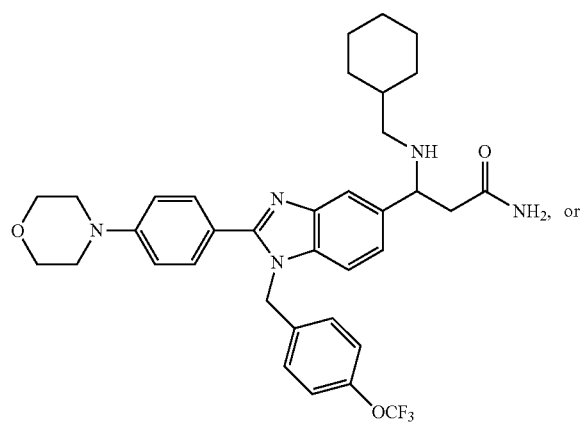
LLS82
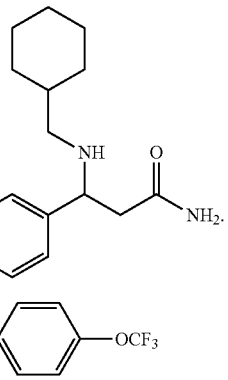
In some embodiments, the compound of formula I can be:
LLS30
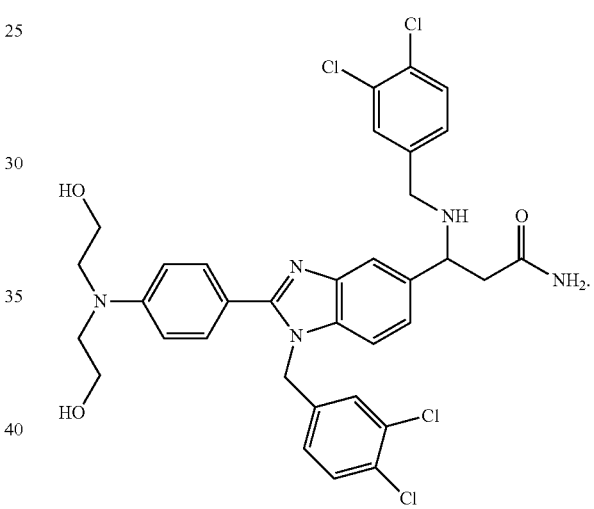
In some embodiments, the compound of formula I can be:
LLS80
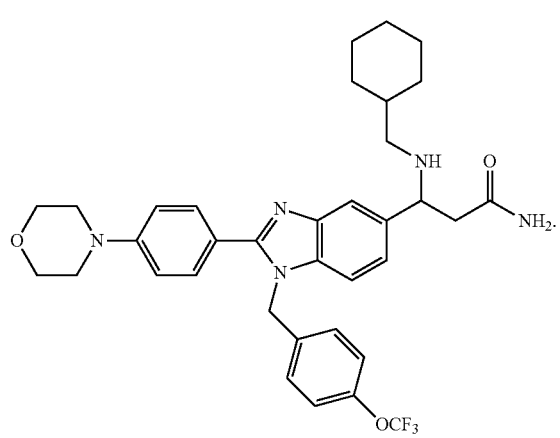

In some embodiments, the compound can be:
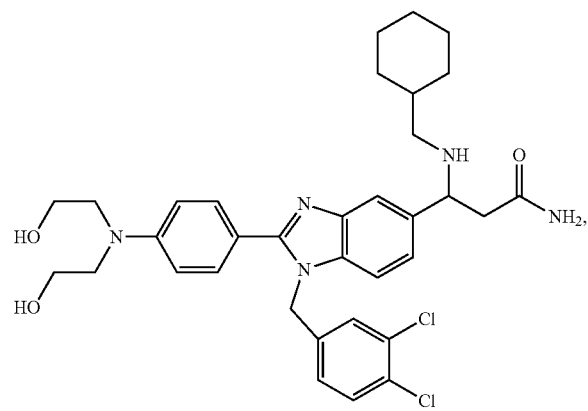
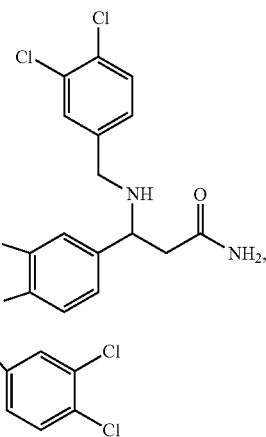
-continued
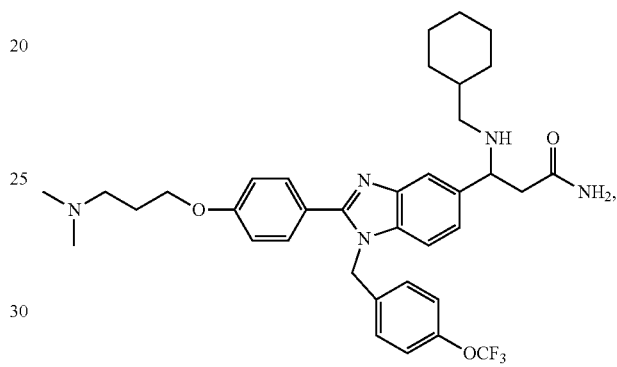
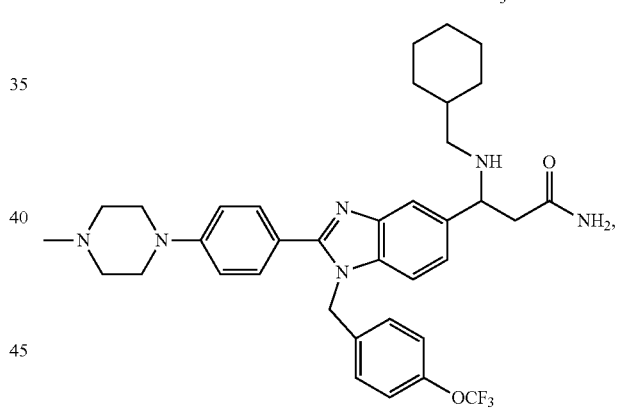
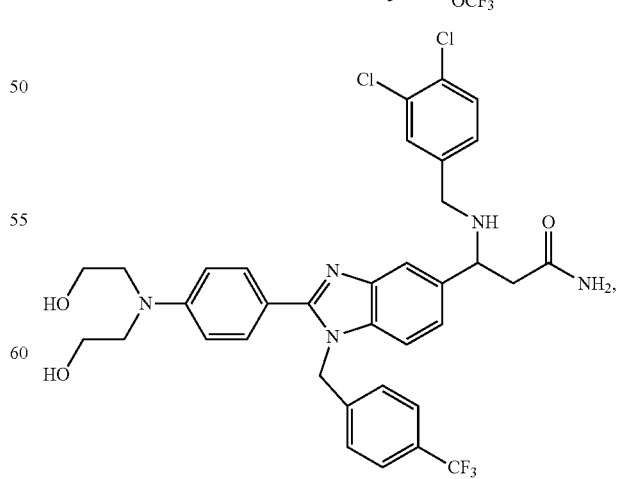

45
-continued
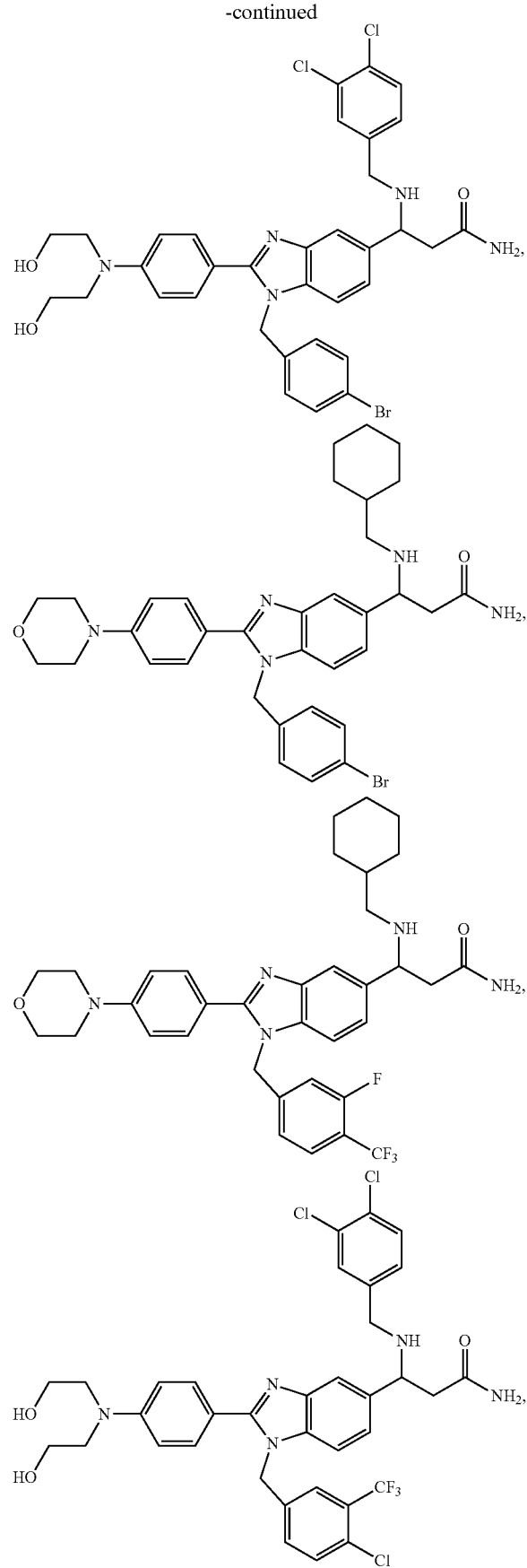
46
-continued
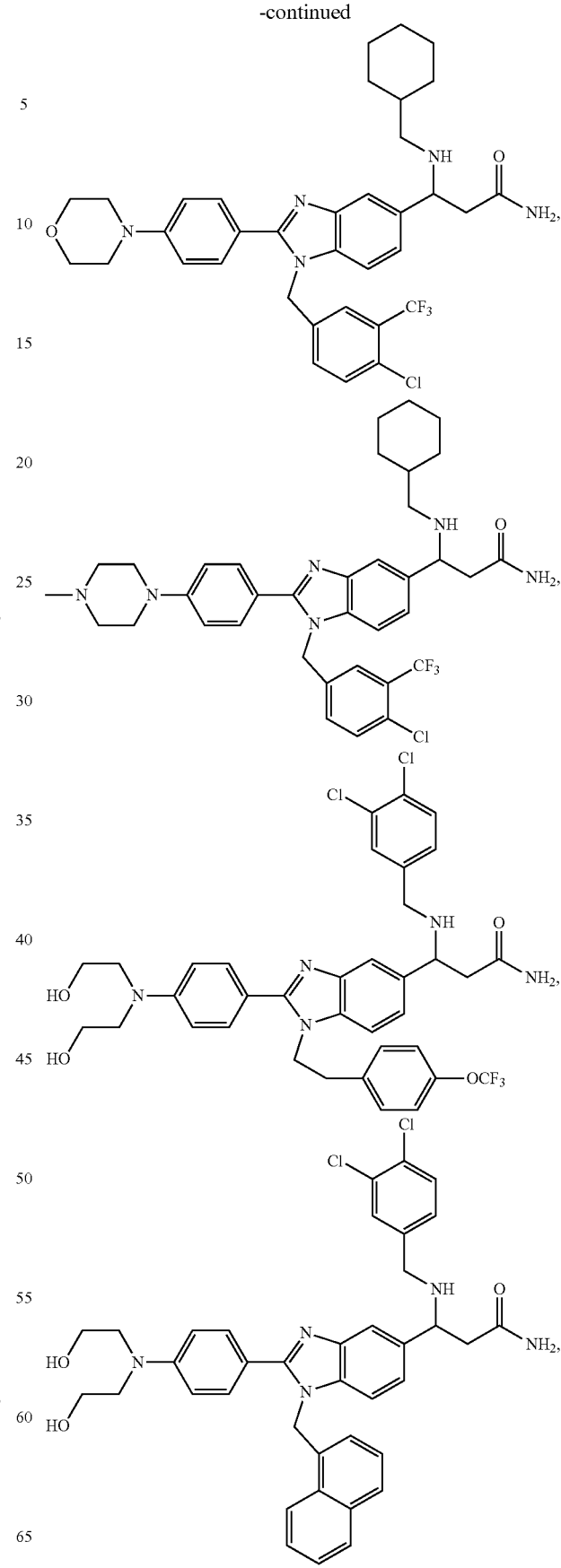

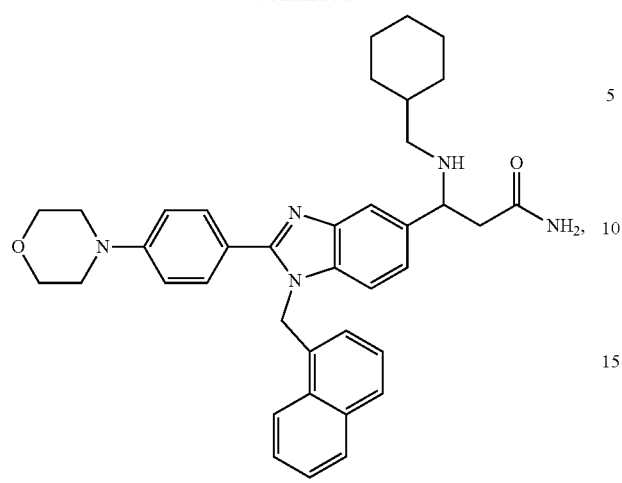
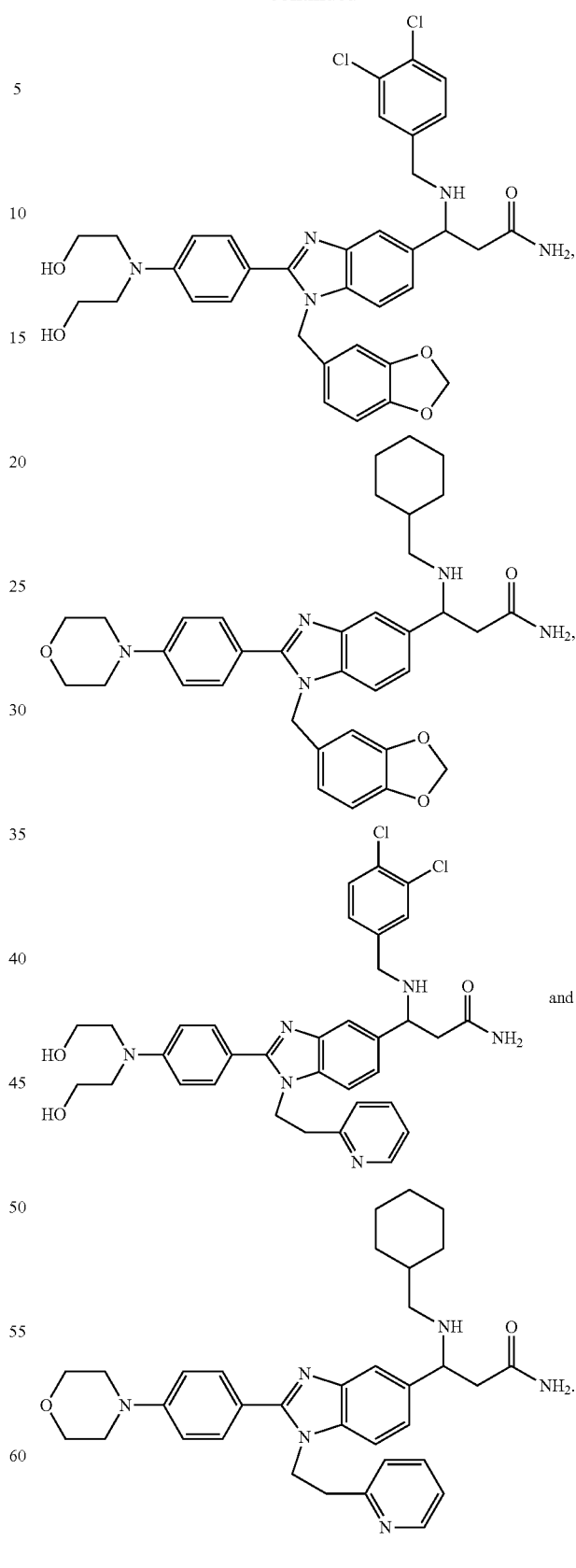

49

In some embodiments, the compound can be:

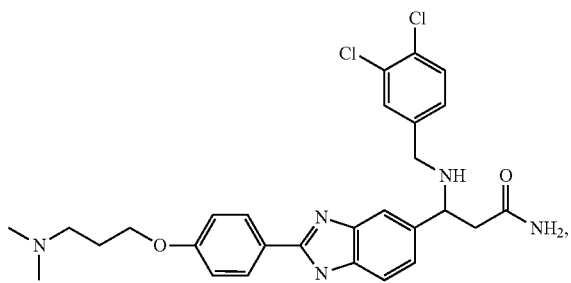

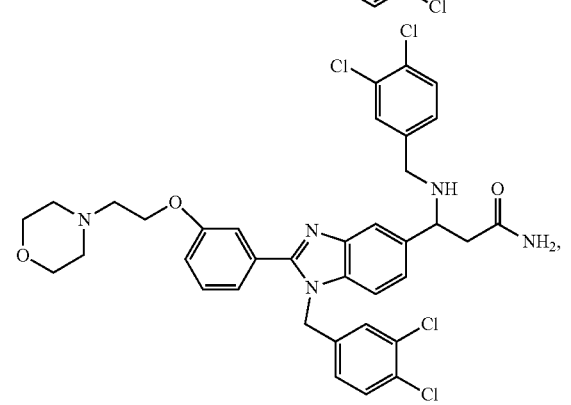

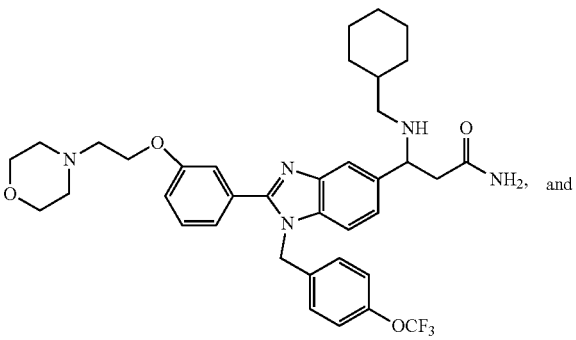

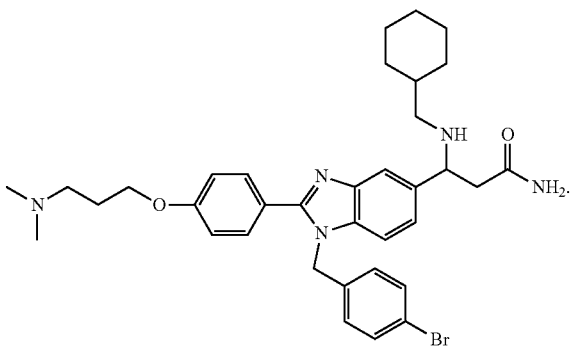 [SMILES: CN(C)CCCOc1ccc(-c2nc3cc(C(CC(N)=O)NCC4CCCCC4)ccc3n2Cc2ccc(Br)cc2)cc1]

50

In some embodiments, the compound can be:

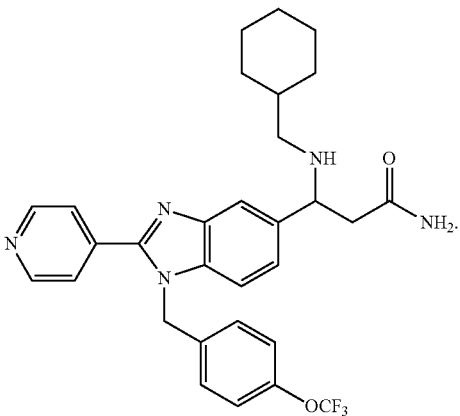 [SMILES: NC(=O)CC(NCC1CCCCC1)c1ccc2c(c1)nc(-c1ccncc1)n2Cc1ccc(OC(F)(F)F)cc1]

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds described may indicate relative stereochemistry, the compounds may exist as a racemic mixture or as either enantiomer.

IV. Pharmaceutical Compositions

In some embodiments, the present invention provides a pharmaceutical composition including a pharmaceutically acceptable excipient and a compound of the present invention. In some embodiments, the composition also includes an additional chemotherapeutic agent.

Chemotherapeutic Agents

Chemotherapeutic agents suitable for use with the present invention include those agents that are useful for treating or ameliorating cancer and include, but are not limited to, aldesleukin, alectinib anaplastic lymphoma kinase, cabozantinib, elotuzumab, fluoxymesterone, iobenguane, imiquimod, interferon, ixazomib, lanreotide, lentinan, mitotane, nab-paclitaxel, necitumumab, octreotide, somatostatin, omacetaxine, sipuleucel-T, tegafur/gimeracil/oteracil and tegafur/uracil.

Additional chemotherapeutic agents suitable for use with the present invention include, but are not limited to, azacitidine, capecitabine, carmofur, cladribine, clofarabine, cytarabine, decitabine, floxuridine, fludarabine, fluorouracil, gemcitabine, mercaptopurine, nelarabine, pentostatin, tegafur, tioguanine, trifluridine/tipiracil, methotrexate, pemetrexed, pralatrexate, raltitrexed, hydroxycarbamide, irinotecan, topotecan, daunorubicin, doxorubicin, epirubicin, idarubicin, mitoxantrone, valrubicin, etoposide, teniposide, cabazitaxel, docetaxel, paclitaxel, vinblastine, vincristine, vindesine, vinflunine, vinorelbine, bendamustine, busulfan, carmustine, chlorambucil, chlormethine, cyclophosphamide, dacarbazine, fotemustine, ifosfamide, lomustine, melphalan, streptozotocin, temozolomide, trabectedin, carboplatin, cisplatin, nedaplatin, oxaliplatin, altretamine, bleomycin, bortezomib, carfilzomib, dactinomycin, eribulin, estramustine, ixabepilone, mitomycin, procarbazine, abarelix, abiraterone, anastrozole, bicalutamide, cyproterone, degarelix, enzalutamide, exemestane, flutamide, fulvestrant, goserelin, histrelin, letrozole, leuprolide, mifepristone, nilutamide, tamoxifen, toremifene, triptorelin, ibritumomab tiuxetan, radium Ra 223 dichloride, strontium-89, samarium (153Sm) lexidronam, tositumomab, ado-trastuzumab emtansine, alemtuzumab, bevacizumab, blinatumomab, brentuximab vedotin, cetuximab, daratumumab, denosumab, dinutuximab, gemtuzumab ozogamicin, ibritumomab tiuxetan, ipilimumab, nivolumab, obinutuzumab, ofatumumab, panitumumab, pembrolizumab, pertuzumab, ramucirumab, rituximab, tositumomab, trastuzumab, afatinib, aflibercept, axitinib, bosutinib, cobimetinib, crizotinib, dasatinib, erlotinib, gefitinib, imatinibl, lapatinibl, lenvatinibl, nilotinib, osimertinib, pazopanib, ponatinib, regorafenib, ruxolitinib, sorafenib, sunitinib, trametinib, vandetanib, everolimus, temsirolimus, alitretinoin, bexarotene, isotretinoin, tamibarotene, tretinoin, lenalidomide, pomalidomide, thalidomide, belinostat, panobinostat, romidepsin, valproate, vorinostat, anagrelide, arsenic trioxide, asparaginase, Bacillus Calmete-Guérin vaccine, ceritinib, dabrafenib, denileukin diftitox, idelalisib, ibrutinib, olaparib, palbociclib, sonidegib, talimogene laherparepvec, vemurafenib, and vismodegib The chemotherapeutic agents of the present invention also include the salts, hydrates, solvates and prodrug forms. The compounds of the present invention also include the isomers and metabolites of those described above.

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine.

The neutral forms of the chemotherapeutic agents can be regenerated by contacting the salt with a base or acid and isolating the parent anti-inflammatory glucocorticosteroid in the conventional manner. The parent form of the anti-inflammatory glucocorticosteroid differs from the various salt forms in certain physical properties, such as solubility in polar solvents, but otherwise the salts are equivalent to the parent form of the compound for the purposes of the present invention.

Certain chemotherapeutic agents of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain chemotherapeutic agents of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides chemotherapeutic agents which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

V. Formulations

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

VI. Administration

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds and compositions of the present invention can be co-administered with other agents. Co-administration includes administering the compound or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

The compounds and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

VII. Methods of Treating a Disorder

In some embodiments, the present invention provides a method of treating a disorder, the method including administering to a subject in need of such treatment, a therapeutically effective amount of a compound of the present invention, thereby treating the disorder.

In some embodiments, a compound of the present invention is a galectin-1 (gal-1) inhibitor that is a chemotherapeutic agent. A chemotherapeutic agent, as used herein, refers to any compound or pharmaceutical composition useful for treating or ameliorating cancer. The agent can be given with a curative intent, with an aim to prolong life, or for the purpose of reducing symptoms.

In some embodiments, treatment with an effective amount of a gal-1 inhibitor of the present invention can cause the mutated proto-oncogene H-Ras (G12V) to mis-localize to intracellular compartments rather than at the plasma membrane. In some embodiments, treatment with an effective amount of a gal-1 inhibitor of the present invention can down-regulate expression of H-Ras. In some embodiments, treatment with an effective amount of a gal-1 inhibitor of the present invention can cause the mutated proto-oncogene K-Ras (G12V) to mis-localize to intracellular compartments rather than at the plasma membrane. In some embodiments, treatment with an effective amount of a gal-1 inhibitor of the present invention can down-regulate expression of K-Ras. In some embodiments, treatment with an effective amount of a gal-1 inhibitor of the present invention can down-regulate expression of phosphorylated extracellular signal-regulated kinases (ERK) or phosphorylated MEK kinase.

Examples of disorders or conditions suitable for use with the present invention include, but are not limited to, acute lymphoblastic leukemia, acute myeloid leukemia, adrenocortical carcinoma, anal cancer, appendix cancer, astrocytoma, basal-cell carcinoma, bile duct cancer, bladder cancer, bone tumor, brainstem glioma, brain cancer, cerebellar astrocytoma, cerebral astrocytoma, ependymoma, medulloblastoma, supratentorial primitive neuroectodermal tumors, visual pathway and hypothalamic glioma, breast cancer, bronchial adenomas, Burkitt's lymphoma, central nervous system lymphoma, cerebellar astrocytoma, cervical cancer, chondrosarcoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, epitheliod hemangioendothelioma (EHE), esophageal cancer, Ewing's sarcoma, extracranial germ cell tumor, extragonadal germ cell tumor, extrahepatic bile duct cancer, eye cancer, intraocular melanoma, retinoblastoma, gallbladder cancer, gastric cancer, gastrointestinal carcinoid tumor, gastrointestinal stromal tumor (GIST), germ cell tumor, gestational trophoblastic tumor, gastric carcinoid, hairy cell leukemia, head and neck cancer, heart cancer, hepatocellular cancer, Hodgkin lymphoma, hypopharyngeal cancer, hypothalamic and visual pathway glioma, childhood, intraocular melanoma, islet cell carcinoma, Kaposi sarcoma, kidney cancer, laryngeal cancer, leukaemias, lip and oral cavity cancer, liposarcoma, liver cancer, non-small cell lung cancer, small-cell lung cancer, lymphomas, macroglobulinemia, male breast cancer, malignant fibrous histiocytoma of bone, medulloblastoma, melanoma, Merkel cell cancer, mesothelioma, metastatic squamous neck cancer, mouth cancer, multiple endocrine neoplasia syndrome, multiple myeloma, mycosis fungoides, myelodysplastic syndromes, myelogenous leukemia, myeloid leukemia, adult acute, myeloproliferative disorders, chronic, myxoma, nasal cavity and paranasal sinus cancer, nasopharyngeal carcinoma, neuroblastoma, non-Hodgkin lymphoma, oligodendroglioma, oral cancer, oropharyngeal cancer, osteosarcoma, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma, supratentorial primitive neuroectodermal tumors, pituitary adenoma. plasma cell neoplasia, pleuropulmonary blastoma, primary central nervous system lymphoma, prostate cancer, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sézary syndrome, non-melanoma skin cancer, melanoma Merkel cell skin carcinoma, small intestine cancer, squamous cell carcinoma, squamous neck cancer, stomach cancer, cutaneous T-Cell lymphoma, testicular cancer, throat cancer, thymoma, thyroid cancer, transitional cell cancer of the renal pelvis and ureter, trophoblastic tumor, gestational, urethral cancer, uterine cancer, vaginal cancer, vulvar cancer, Waldenström macroglobulinemia, and Wilms tumor.

Gal-1 inhibitors of this invention can be tested for their ability to induce cancer cell death in a variety of assays. For example, in some embodiments, benzimidazole compounds of this invention are synthesized on beads that also display cell adhesion ligands. Living cells are incubated with the beads under conditions in which cells are captured by the beads and the cell membranes of the captured cells are exposed to the galectin-1 inhibitors. A colorimetric assay is used to detect cleaved caspase-3 in the fixed cells and identify the compounds inducing apoptosis. In some embodiments, propidium iodide is used to stain late apoptotic cells.

Gal-1 inhibitors of this invention can be tested for their ability to inhibit in vivo tumor growth in a variety of assays. For example, in some embodiments, cancer cells are subcutaneously injected into congenital athymic mice. The injection can be in the dorsal flanks of the mice. The tumors are allowed to grow to a predetermined size. The predetermined size can be approximately 100 mm$^3$. Treatment mice are then given doses of a compound of this invention, as the tumor size and body weight are measured. The doses of gal-1 inhibitor can also have one or more other chemotherapeutic agents to allow for studies of synergistic effects. In some embodiments, the doses are administered daily. In some embodiments, the doses are administered for 5 successive days.

VIII. Examples

Figure 1:
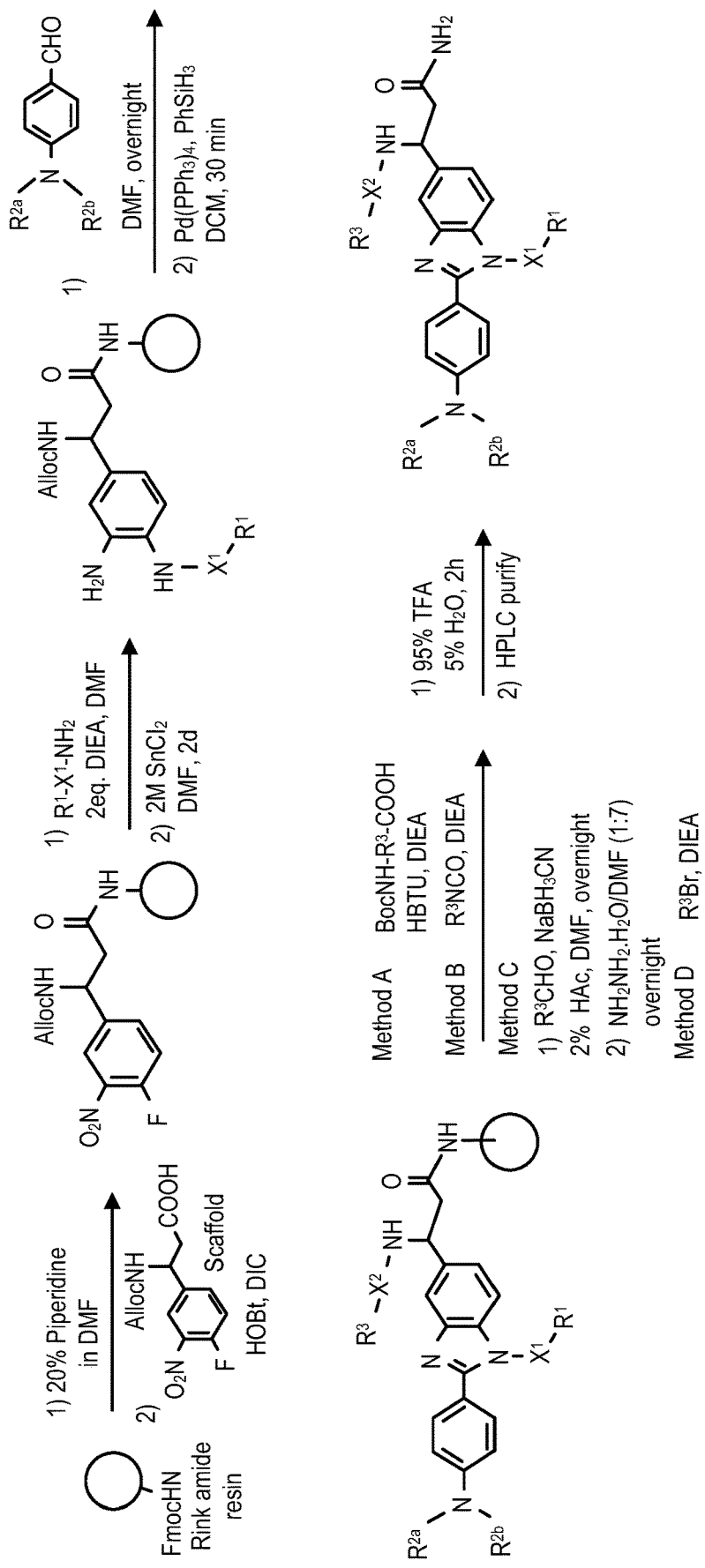
FIG. 1 shows a synthetic scheme for making the compounds of the present invention.

FIG. 1 shows a general synthetic procedure that can be used to prepare compounds of the present invention. Starting materials can be obtained from commercial sources and by employing known synthetic methods. Fluoroenylmethyloxycarbonyl (Fmoc)-protected Rink-amide resin at 0.5 mmol/g loading is swollen in dimethylformamide (DMF) for 2 hours. Fmoc is then removed with 20% 4-methylpiperidine/DMF in a 5-minute incubation followed by a 15-minute incubation. After filtration, the beads are washed with DMF three times, with methanol (MeOH) three times, and again with DMF three times. Three equivalents of Alloc-scaffold is added to a solution of three equivalents each of 6-chloro-1-hydroxybenzotriazole (6-Cl-HOBt) and 1,3-diisopropylcarbodiimide (DIC), mixed for 5 minutes, added to the beads, and rotated for approximately 2 hours until a Kaiser test is negative. The beads are washed five times with DMF. A solution of 3 equivalents of $R_1NH_2$ and 6 equivalents of N,N-diisopropylethylamine (DIEA) in DMF is added to the beads and rotated overnight. The $NO_2$ reduction is achieved with 2 M $SnCl_2 \cdot 2H_2O$ solution in DMF overnight, repeated two to three times. A solution of 4 equivalents of aldehyde $R_2CHO$ in DMF is added to the beads and rotated overnight. The Alloc group on the scaffold is deprotected by $Pd(PPh_3)_4/PhSiH_3$ solution in dichloromethane (DCM) for 30 minutes, twice. The beads are coupled with $R_3$ using one of the following methods:

Method A: Four equivalents of Boc-amino acids in the presence of HOBt/DIC are added to the beads and rotated for 2-4 hours. The side chain protecting group is removed and the product is cleaved by a mixture of 95% trifluoroacetic acid (TFA), 2.5% triisopropylsilane (TIS), and 2.5% water.

Method B: Five equivalents of isocyanate in the presence of 10 equivalents of DIEA in DMF are added to the beads and rotated for 2-4 hours. The compound is cleaved by a mixture of 95% TFA, 2.5% TIS, and 2.5% water.

Method C: Five equivalents of aldehyde in DMF or a 7:3 mixture of tetrahydrofuran (THF) and MeOH containing 2% acetic acid is added to the beads. Sodium cyanoborohydride in THF/MeOH containing 2% acetic acid is then added to the beads. The mixture is rotated at room temperature for 2-12 hours. The compound is cleaved by a mixture of 95% TFA, 2.5% TIS, and 2.5% water.

Method D: One and a half equivalents of alkyl halide and three equivalents of DIEA in DMF are added to the beads. The mixture is rotated at room temperature for 1-2 days. The compound is cleaved by a mixture of 95% TFA, 2.5% TIS, and 2.5% water.

Compounds LLS22 and LLS76 are synthesized without coupling of $R^3$ and are cleaved off the beads after Allocdeprotection by a mixture of 95% TFA, 2.5% TIS, and 2.5% water.

The cleavage liquid is collected. After evaporation of TFA and solvents, the concentrated cleavage product is precipitated with cold tert-butyl methyl ether and purified by semipreparative reverse-phase high-performance liquid chromatography. For those compounds with a hydroxyethyl group at one or both of the $R^{2a}$ and $R^{2b}$ positions, the acetyl group is removed with a 1:7 mixture of hydrazine and DMF for 12-16 hours prior to cleavage, or with aqueous potassium hydroxide for 5-12 hours after TFA cleavage and product precipitation.

Example structures below are named according to standard IUPAC nomenclature using the CambridgeSoft ChemDraw naming package.

Example 1. LLS1. (2R)—N-(1-(2-(3-((1H-imidazol-1-yl)methyl)phenyl)-1-(2-(pyridin-2-yl)ethyl)-1H-benzo[d]imidazol-5-yl)-3-amino-3-oxopropyl)-2-amino-3-(4-methoxyphenyl)propanamide

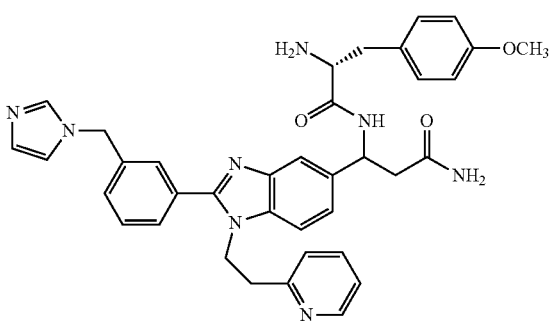 [SMILES: COc1ccc(C[C@@H](N)C(=O)NC(CC(N)=O)c2ccc3c(c2)nc(-c2cccc(Cn4ccnc4)c2)n3CCc2ccccn2)cc1]

(2R)—N-(1-(2-(3-((1H-imidazol-1-yl)methyl)phenyl)-1-(2-(pyridin-2-yl)ethyl)-1H-benzo[d]imidazol-5-yl)-3-amino-3-oxopropyl)-2-amino-3-(4-methoxyphenyl)propanamide was prepared using the procedure detailed above with Method A. MALDI-TOF MS: m+H=643.35.

Example 2. LLS2. ((4-(5-(3-amino-1-((S)-2-amino-3-(3,4-dichlorophenyl)propanamido)-3-oxopropyl)-1-(3,4-difluorobenzyl)-1H-benzo[d]imidazol-2-yl)phenyl)azanediyl)bis(ethane-2,1-diyl) Diacetate

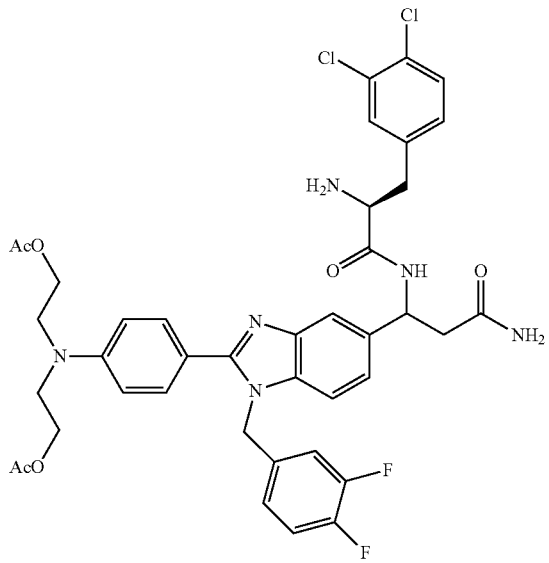

((4-(5-(3-amino-1-((S)-2-amino-3-(3,4-dichlorophenyl)propanamido)-3-oxopropyl)-1-(3,4-difluorobenzyl)-1H-benzo[d]imidazol-2-yl)phenyl)azanediyl)bis(ethane-2,1-diyl) diacetate was prepared using the procedure detailed above with Method A. MALDI-TOF MS: m+H=809.28. 1H NMR (DMSO-d6, 600 MHz) δ 9.23 (br. s, 1H), 8.28 (br. s, 1H), 8.18 (br. s, 1H), 7.77 (s, 1H), 7.67 (s, 1H), 7.63 (d, 1H), 7.61 (d, 1H), 7.58 (d, 1H), 7.56 (d, 1H), 7.31 (d, 2H), 7.29 (2, 1H), 7.25 (two signals, d, 1H each), 7.03 (d, 2H), 6.91 (br. s, 1H), 6.85 (br. s, 1H), 5.69 (d, 2H), 5.38 (app. quin, 1H), 4.20 (app. q, 4H), 4.07 (m, 1H), 3.72 (app q, 4H), 3.16 (dd, 1H, 3JHH=14.2 Hz, 2JHH=6.6 Hz), 3.02 (dd, 1H, 3JHH=14.2 Hz, 2JHH=6.6 Hz), 2.61-2.67 (m, 1H), 2.54 (m, 1H), 1.98 (s, 6H). 13C (DMSO-d6, 150 MHz) δ 171.0, 170.2, 166.5, 158.2, 152.3, 150.4, 150.2, 149.8, 148.7, 148.1, 135.8, 131.7, 131.4, 130.8, 130.6, 130.2, 129.9, 123.7, 123.4, 118.1, 118.0, 115.9, 111.9, 60.9, 53.1, 50.2, 49.0, 41.7, 36.1, 20.7.

Example 3. LLS3. ((4-(5-(3-amino-1-((2S,3S)-2-amino-3-hydroxybutanamido)-3-oxopropyl)-1-(3,4-difluorobenzyl)-1H-benzo[d]imidazol-2-yl)phenyl)azanediyl)bis(ethane-2,1-diyl) Diacetate

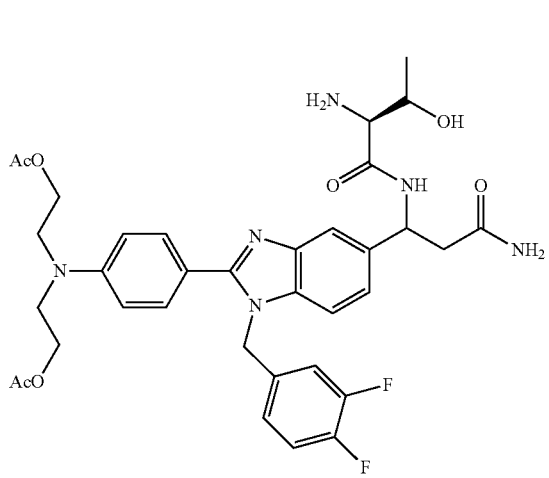 [SMILES: CC(=O)OCCN(CCOC(C)=O)c1ccc(-c2nc3cc(C(CC(N)=O)NC(=O)[C@@H](N)C(C)O)ccc3n2Cc2ccc(F)c(F)c2)cc1]

((4-(5-(3-amino-1-((2S,3S)-2-amino-3-hydroxybutanamido)-3-oxopropyl)-1-(3,4-difluorobenzyl)-1H-benzo[d]imidazol-2-yl)phenyl)azanediyl)bis(ethane-2,1-diyl) diacetate was prepared using the procedure detailed above with Method A. MALDI-TOF MS: m+H=695.32.

Example 4. LLS4. (2S)-2-amino-N-(3-amino-3-oxo-1-(1-(2-(piperidin-1-yl)ethyl)-2-(thiazol-2-yl)-1H-benzo[d]imidazol-5-yl)propyl)hexanamide

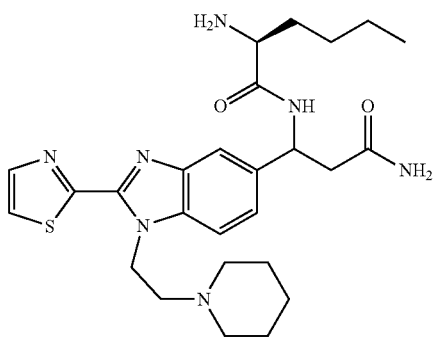 [SMILES: CCCC[C@H](N)C(=O)NC(CC(N)=O)c1ccc2c(c1)nc(-c1nccs1)n2CCN1CCCCC1]

(2S)-2-amino-N-(3-amino-3-oxo-1-(1-(2-(piperidin-1-yl)ethyl)-2-(thiazol-2-yl)-1H-benzo[d]imidazol-5-yl)propyl)hexanamide was prepared using the procedure detailed above with Method A. MALDI-TOF MS: m+H=512.39.

Example 5. LLS5. 2-((4-(5-(3-amino-1-((S)-2-amino-3-(3,4-dichlorophenyl)propanamido)-3-oxopropyl)-1-(3,4-difluorobenzyl)-1H-benzo[d]imidazol-2-yl)phenyl)(2-hydroxyethyl)amino)ethyl Acetate

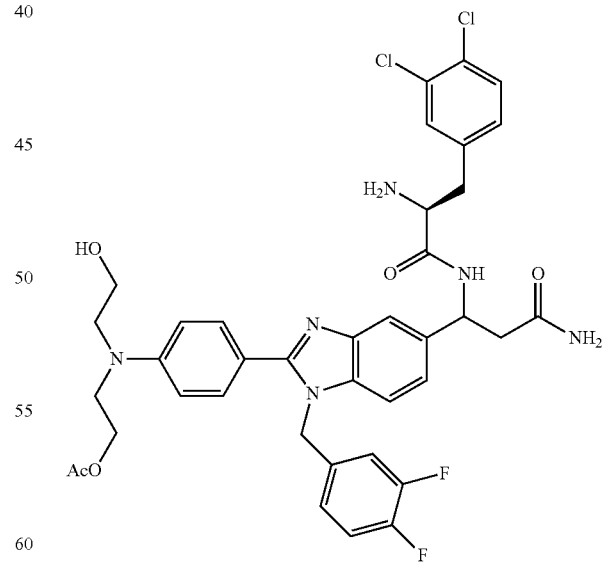

2-((4-(5-(3-amino-1-((S)-2-amino-3-(3,4-dichlorophenyl)propanamido)-3-oxopropyl)-1-(3,4-difluorobenzyl)-1H-benzo[d]imidazol-2-yl)phenyl)(2-hydroxyethyl)amino)ethyl acetate was prepared using the procedure detailed above with Method A. MALDI-TOF MS: m+H=767.35.

Example 6. LLS6. ((4-(1-(((1s,3R)-adamantan-1-yl)methyl)-5-(3-amino-1-((S)-2-amino-3-(3,4-dichlorophenyl)propanamido)-3-oxopropyl)-1H-benzo[d]imidazol-2-yl)phenyl)azanediyl)bis(ethane-2,1-diyl) Diacetate

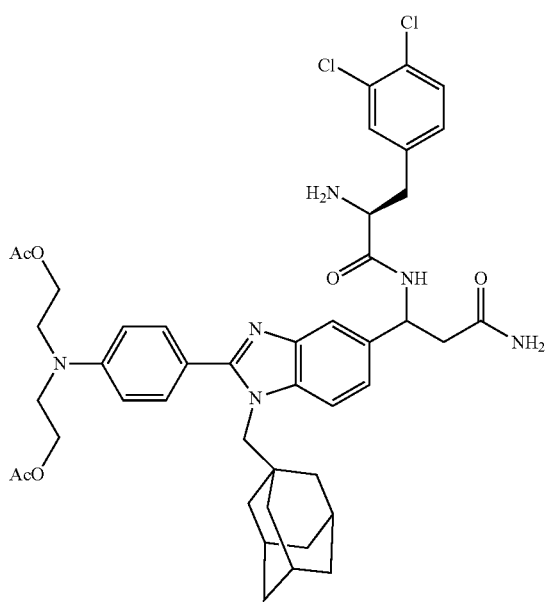 [SMILES: CC(=O)OCCN(CCOC(C)=O)c1ccc(-c2nc3cc(C(CC(N)=O)NC(=O)[C@@H](N)Cc4ccc(Cl)c(Cl)c4)ccc3n2CC23CC4CC(CC(C4)C2)C3)cc1]

((4-(1-(((1s,3R)-adamantan-1-yl)methyl)-5-(3-amino-1-((S)-2-amino-3-(3,4-dichlorophenyl)propanamido)-3-oxopropyl)-1H-benzo[d]imidazol-2-yl)phenyl)azanediyl)bis(ethane-2,1-diyl) diacetate was prepared using the procedure as detailed above with Method A. MALDI-TOF MS: m+H=831.38.

Example 7. LLS7. 3-(1-(((1s,3s)-adamantan-1-yl)methyl)-2-(4-(6-(hydroxymethyl)pyridin-2-yl)phenyl)-1H-benzo[d]imidazol-5-yl)-3-((3,4-dichlorobenzyl)amino)propanamide

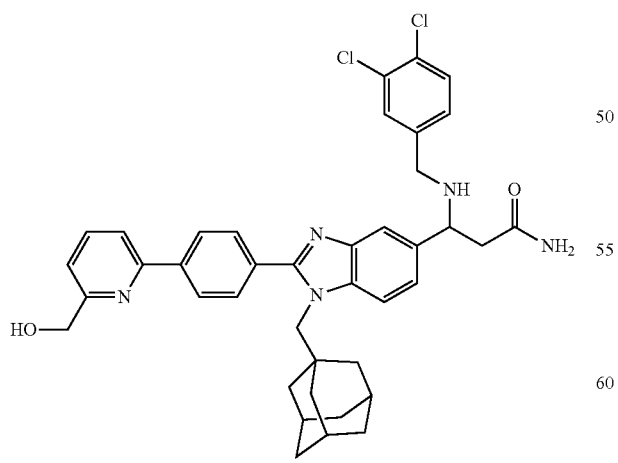

3-(1-(((1s,3s)-adamantan-1-yl)methyl)-2-(4-(6-(hydroxymethyl)pyridin-2-yl)phenyl)-1H-benzo[d]imidazol-5-yl)-3-((3,4-dichlorobenzyl)amino)propanamide was pre- pared using the procedure detailed above with Method C. MALDI-TOF MS: m+H=694.29.

Example 8. LLS8. ((4-(1-(((1s,3s)-adamantan-1-yl)methyl)-5-(3-amino-1-((3,4-difluorobenzyl)amino)-3-oxopropyl)-1H-benzo[d]imidazol-2-yl)phenyl)azanediyl)bis(ethane-2,1-diyl) Diacetate

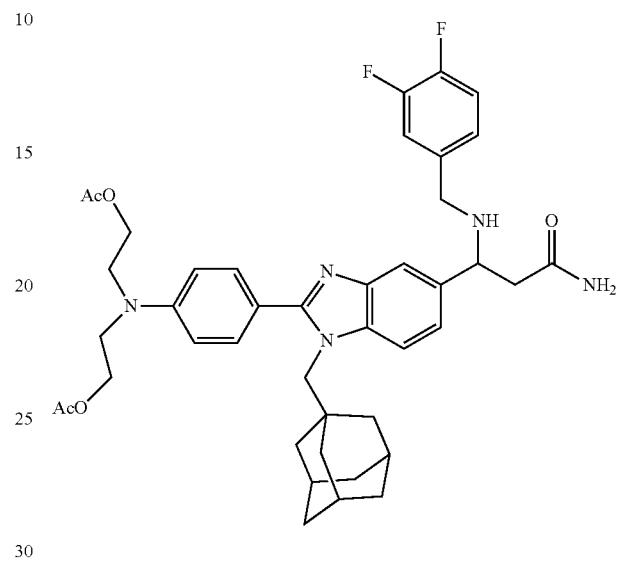

((4-(1-(((1s,3 s)-adamantan-1-yl)methyl)-5-(3-amino-1-((3,4-difluorobenzyl)amino)-3-oxopropyl)-1H-benzo[d]imidazol-2-yl)phenyl)azanediyl)bis(ethane-2,1-diyl) diacetate was prepared using the procedure detailed above with Method C. MALDI-TOF MS: m+H=742.43.

Example 9. LLS9. ((4-(5-(3-amino-1-((S)-2-amino-3-(3,4-difluorophenyl)propanamido)-3-oxopropyl)-1-(4-(trifluoromethoxy)benzyl)-1H-benzo[d]imidazol-2-yl)phenyl)azanediyl)bis(ethane-2,1-diyl) Diacetate

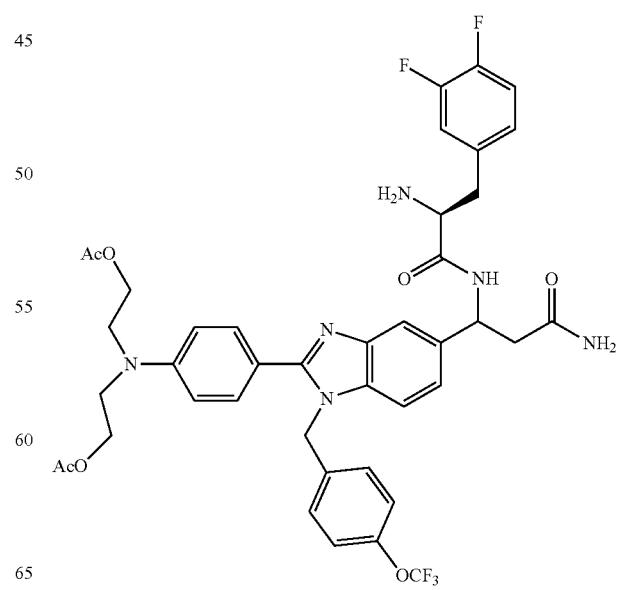

((4-(5-(3-amino-1-((S)-2-amino-3-(3,4-difluorophenyl) propanamido)-3-oxopropyl)-1-(4-(trifluoromethoxy)benzyl)-1H-benzo[d]imidazol-2-yl)phenyl)azanediyl)bis(ethane-2,1-diyl) diacetate was prepared using the procedure detailed above with Method A. MALDI-TOF MS: m+H=825.39.

Example 10. LLS10. ((4-(5-(3-amino-1-((S)-2-amino-3-(3,4-dichlorophenyl)propanamido)-3-oxopropyl)-1-(2,5-difluorobenzyl)-1H-benzo[d]imidazol-2-yl)phenyl)azanediyl)bis(ethane-2,1-diyl) Diacetate

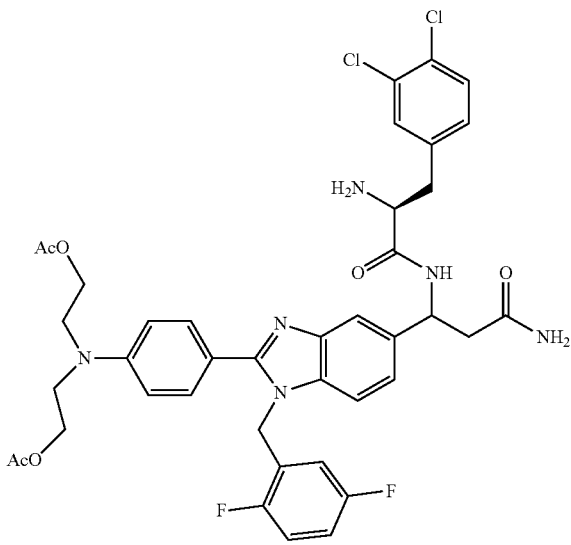 [SMILES: CC(=O)OCCN(CCOC(C)=O)c1ccc(-c2nc3cc(C(CC(N)=O)NC(=O)[C@@H](N)Cc4ccc(Cl)c(Cl)c4)ccc3n2Cc2cc(F)ccc2F)cc1]

((4-(5-(3-amino-1-((S)-2-amino-3-(3,4-dichlorophenyl) propanamido)-3-oxopropyl)-1-(2,5-difluorobenzyl)-1H-benzo[d]imidazol-2-yl)phenyl)azanediyl)bis(ethane-2,1-diyl) diacetate was prepared using the procedure detailed above with Method A. MALDI-TOF MS: m+H=809.30.

Example 11. LLS11. ((4-(5-(3-amino-1-((S)-2-amino-3-(3,4-difluorophenyl)propanamido)-3-oxopropyl)-1-(3,4-difluorobenzyl)-1H-benzo[d]imidazol-2-yl)phenyl)azanediyl)bis(ethane-2,1-diyl) Diacetate

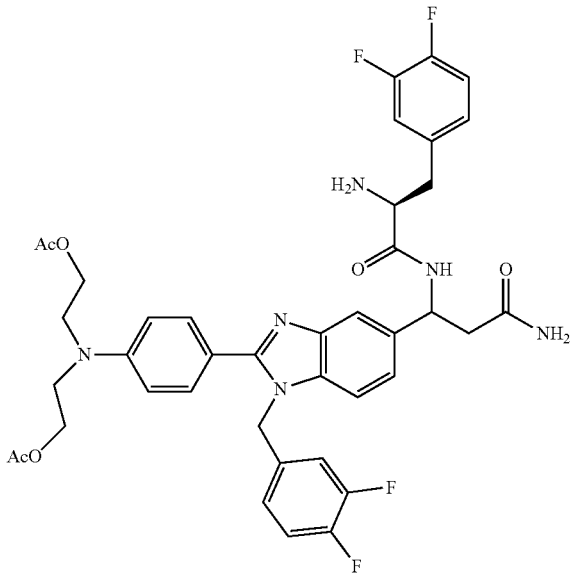 [SMILES: CC(=O)OCCN(CCOC(C)=O)c1ccc(-c2nc3cc(C(CC(N)=O)NC(=O)[C@@H](N)Cc4ccc(F)c(F)c4)ccc3n2Cc2ccc(F)c(F)c2)cc1]

((4-(5-(3-amino-1-((S)-2-amino-3-(3,4-difluorophenyl) propanamido)-3-oxopropyl)-1-(3,4-difluorobenzyl)-1H-benzo[d]imidazol-2-yl)phenyl)azanediyl)bis(ethane-2,1-diyl) diacetate was prepared using the procedure detailed above with Method A. MALDI-TOF MS: m+H=776.78.

Example 12. LLS12. (2S)-2-amino-N-(3-amino-1-(2-(4-(bis(2-hydroxyethyl)amino)phenyl)-1-(3,4-difluorobenzyl)-1H-benzo[d]imidazol-5-yl)-3-oxopropyl)-3-(3,4-dichlorophenyl)propanamide

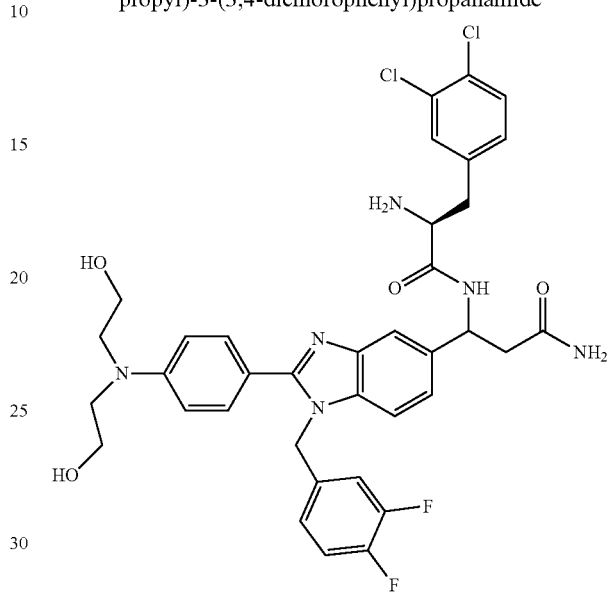

(2S)-2-amino-N-(3-amino-1-(2-(4-(bis(2-hydroxyethyl) amino)phenyl)-1-(3,4-difluorobenzyl)-1H-benzo[d]imidazol-5-yl)-3-oxopropyl)-3-(3,4-dichlorophenyl)propanamide was prepared using the procedure detailed above with Method A. MALDI-TOF MS: m+H=725.29.

Example 13. LLS13. (2S)-2-amino-N-(3-amino-1-(2-(4-(bis(2-hydroxyethyl)amino)phenyl)-1-(2,5-difluorobenzyl)-1H-benzo[d]imidazol-5-yl)-3-oxopropyl)-3-(3,4-dichlorophenyl)propanamide

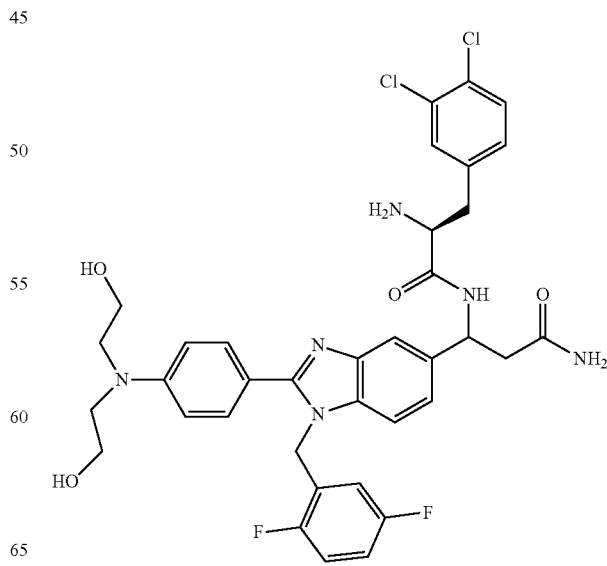

(2S)-2-amino-N-(3-amino-1-(2-(4-(bis(2-hydroxyethyl) amino)phenyl)-1-(2,5-difluorobenzyl)-1H-benzo[d]imidazol-5-yl)-3-oxopropyl)-3-(3,4-dichlorophenyl)propanamide was prepared using the procedure detailed above with Method A. MALDI-TOF MS: m+H=725.35.

Example 14. LLS14. 3-(2-(4-(bis(2-hydroxyethyl) amino)phenyl)-1-(3,4-difluorobenzyl)-1H-benzo[d] imidazol-5-yl)-3-((2,6-dichlorobenzyl)amino)propanamide

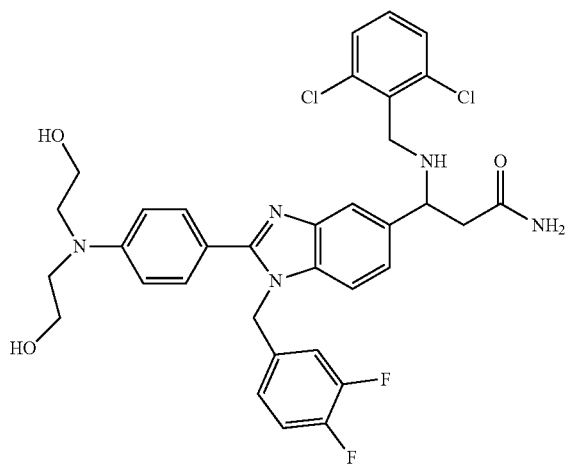 [SMILES: NC(=O)CC(NCc1c(Cl)cccc1Cl)c1ccc2c(c1)nc(-c1ccc(N(CCO)CCO)cc1)n2Cc1ccc(F)c(F)c1]

3-(2-(4-(bis(2-hydroxyethyl)amino)phenyl)-1-(3,4-difluorobenzyl)-1H-benzo[d]imidazol-5-yl)-3-((2,6-dichlorobenzyl)amino)propanamide was prepared using the procedure detailed above with Method C. MALDI-TOF MS: m+H=668.20.

Example 15. LLS15. ((4-(5-(3-amino-1-(3-(3-chloro-4-(trifluoromethyl)phenyl)ureido)-3-oxopropyl)-1-(3,4-difluorobenzyl)-1H-benzo[d]imidazol-2-yl)phenyl)azanediyl)bis(ethane-2,1-diyl) Diacetate

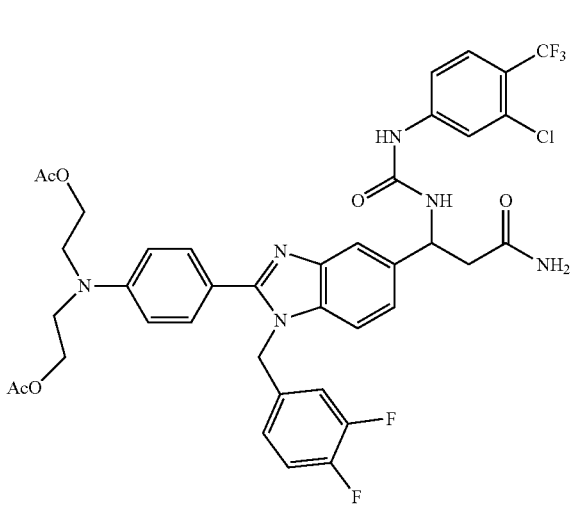 [SMILES: CC(=O)OCCN(CCOC(C)=O)c1ccc(-c2nc3cc(C(CC(N)=O)NC(=O)Nc4ccc(C(F)(F)F)c(Cl)c4)ccc3n2Cc2ccc(F)c(F)c2)cc1]

((4-(5-(3-amino-1-(3-(3-chloro-4-(trifluoromethyl)phenyl)ureido)-3-oxopropyl)-1-(3,4-difluorobenzyl)-1H-benzo[d]imidazol-2-yl)phenyl)azanediyl)bis(ethane-2,1-diyl) diacetate was prepared using the procedure detailed above with Method B. MALDI-TOF MS: m+H=815.32.

Example 16. LLS16. ((4-(5-(3-amino-1-(3-(3,4-dichlorophenyl)ureido)-3-oxopropyl)-1-(3,4-difluorobenzyl)-1H-benzo[d]imidazol-2-yl)phenyl) azanediyl)bis(ethane-2,1-diyl) Diacetate

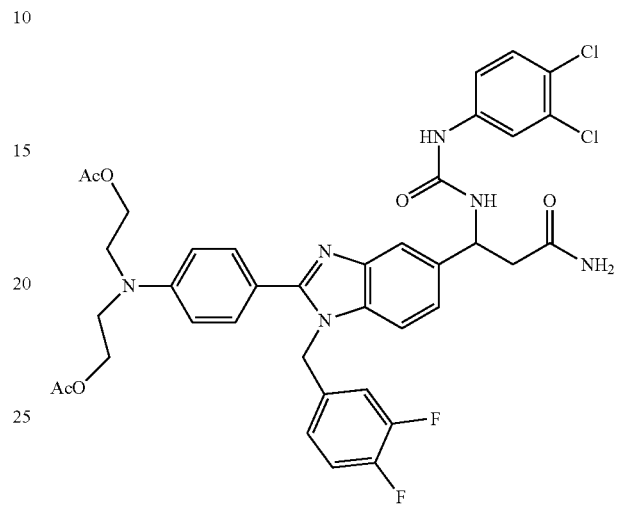

((4-(5-(3-amino-1-(3-(3,4-dichlorophenyl)ureido)-3-oxopropyl)-1-(3,4-difluorobenzyl)-1H-benzo[d]imidazol-2-yl)phenyl)azanediyl)bis(ethane-2,1-diyl) diacetate was prepared using the procedure detailed above with Method B. MALDI-TOF MS: m+H=781.29

Example 17. LLS17. ((4-(5-(3-amino-1-((3,4-dichlorobenzyl)amino)-3-oxopropyl)-1-(3,4-difluorobenzyl)-1H-benzo[d]imidazol-2-yl)phenyl) azanediyl)bis(ethane-2,1-diyl) Diacetate

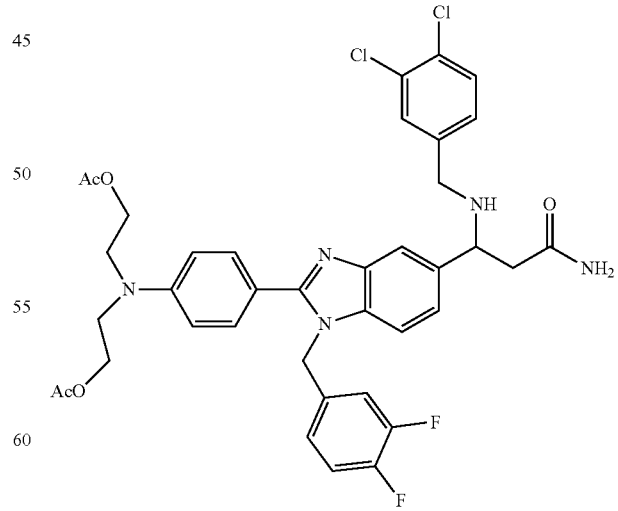

((4-(5-(3-amino-1-((3,4-dichlorobenzyl)amino)-3-oxopropyl)-1-(3,4-difluorobenzyl)-1H-benzo[d]imidazol-2-yl)phenyl)azanediyl)bis(ethane-2,1-diyl) diacetate was prepared using the procedure detailed above with Method C. MALDI-TOF MS: m+H=7752.31.

Example 18. LLS18. (2S)-2-amino-N-(3-amino-1-(2-(4-(bis(2-hydroxyethyl)amino)phenyl)-1-(3,4-difluorobenzyl)-1H-benzo[d]imidazol-5-yl)-3-oxopropyl)-3-(3,4-difluorophenyl)propanamide

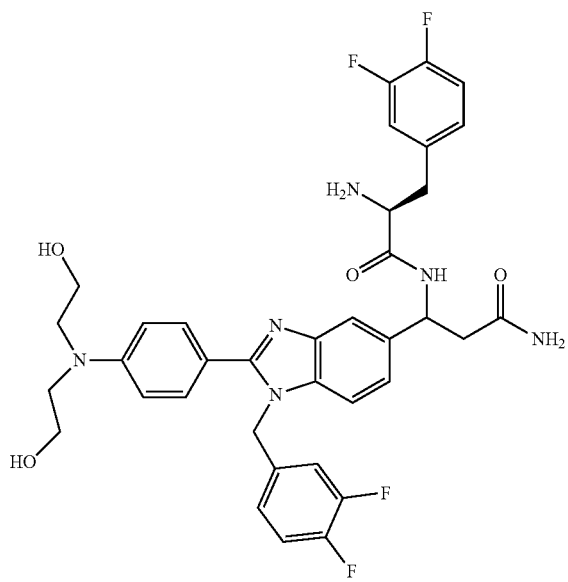 [SMILES: NC(=O)CC(NC(=O)[C@@H](N)Cc1ccc(F)c(F)c1)c1ccc2c(c1)nc(-c1ccc(N(CCO)CCO)cc1)n2Cc1ccc(F)c(F)c1]

(2S)-2-amino-N-(3-amino-1-(2-(4-(bis(2-hydroxyethyl)amino)phenyl)-1-(3,4-difluorobenzyl)-1H-benzo[d]imidazol-5-yl)-3-oxopropyl)-3-(3,4-difluorophenyl)propanamide was prepared using the procedure detailed above with Method A. MALDI-TOF MS: m+H=693.36.

Example 19. LLS19.3-(2-(4-(bis(2-hydroxyethyl)amino)phenyl)-1-(3,4-difluorobenzyl)-1H-benzo[d]imidazol-5-yl)-3-((3,4-dichlorobenzyl)amino)propanamide

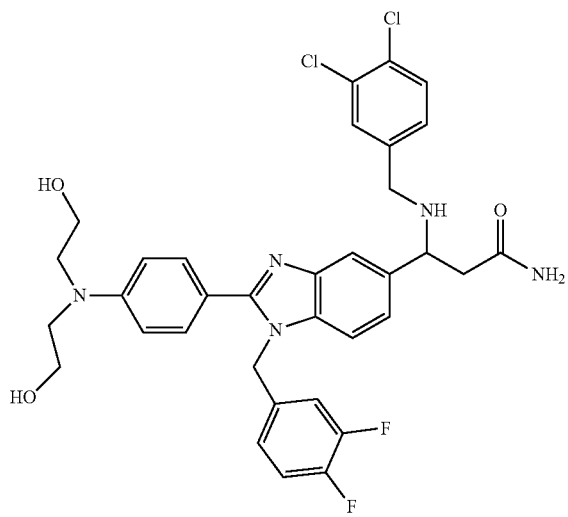 [SMILES: NC(=O)CC(NCc1ccc(Cl)c(Cl)c1)c1ccc2c(c1)nc(-c1ccc(N(CCO)CCO)cc1)n2Cc1ccc(F)c(F)c1]

3-(2-(4-(bis(2-hydroxyethyl)amino)phenyl)-1-(3,4-difluorobenzyl)-1H-benzo[d]imidazol-5-yl)-3-((3,4-dichlorobenzyl)amino)propanamide was prepared using the procedure detailed above with Method C. MALDI-TOF MS: m+H=668.27.

Example 20. LLS20. ((4-(5-(3-amino-1-((3,4-dichlorobenzyl)amino)-3-oxopropyl)-1-(3,4-dichlorobenzyl)-1H-benzo[d]imidazol-2-yl)phenyl)azanediyl)bis(ethane-2,1-diyl) Diacetate

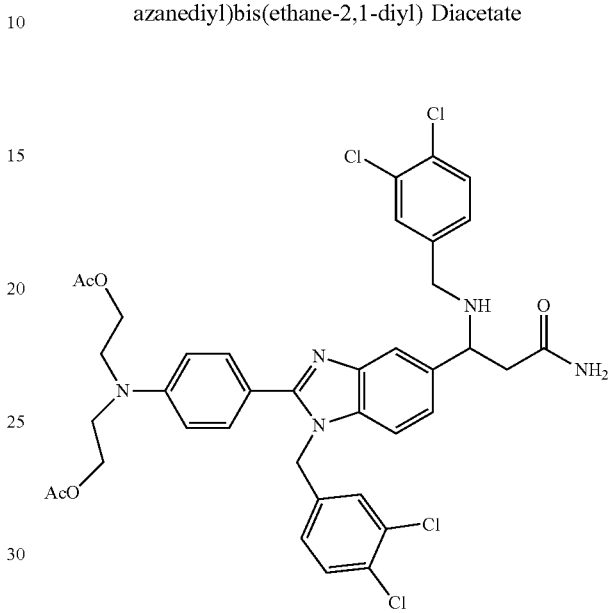

((4-(5-(3-amino-1-((3,4-dichlorobenzyl)amino)-3-oxopropyl)-1-(3,4-dichlorobenzyl)-1H-benzo[d]imidazol-2-yl)phenyl)azanediyl)bis(ethane-2,1-diyl) diacetate was prepared using the procedure detailed above with Method C. MALDI-TOF MS: m+H=784.22.

Example 21. LLS21. ((4-(5-(3-amino-1-((3,4-dichlorobenzyl)amino)-3-oxopropyl)-1-(3-chloro-4-fluorobenzyl)-1H-benzo[d]imidazol-2-yl)phenyl)azanediyl)bis(ethane-2,1-diyl) Diacetate

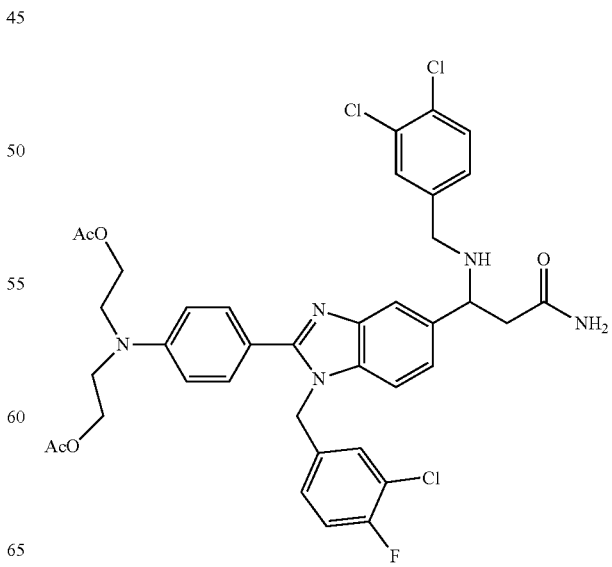

((4-(5-(3-amino-1-((3,4-dichlorobenzyl)amino)-3-oxopropyl)-1-(3-chloro-4-fluorobenzyl)-1H-benzo[d]imidazol-2-yl)phenyl)azanediyl)bis(ethane-2,1-diyl) diacetate was prepared using the procedure detailed above with Method C. MALDI-TOF MS: m+H=768.30.

Example 22. LLS22. ((4-(5-(1,3-diamino-3-oxopropyl)-1-(3-fluoro-4-(trifluoromethyl)benzyl)-1H-benzo[d]imidazol-2-yl)phenyl)azanediyl)bis(ethane-2,1-diyl) Diacetate

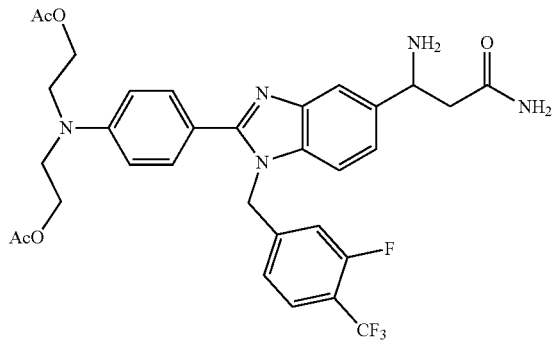 [SMILES: CC(=O)OCCN(CCOC(C)=O)c1ccc(-c2nc3cc(C(N)CC(N)=O)ccc3n2Cc2ccc(C(F)(F)F)c(F)c2)cc1]

((4-(5-(1,3-diamino-3-oxopropyl)-1-(3-fluoro-4-(trifluoromethyl)benzyl)-1H-benzo[d]imidazol-2-yl)phenyl)azanediyl)bis(ethane-2,1-diyl) diacetate was prepared using the procedure detailed above without coupling of $R^3$ and with cleaving off the beads by a mixture of 95% TFA, 2.5% TIS, and 2.5% water. MALDI-TOF MS: m+H=644.37.

Example 23. LLS23. ((4-(5-(3-amino-1-((3,4-dichlorobenzyl)amino)-3-oxopropyl)-1-(4-(trifluoromethoxy)benzyl)-1H-benzo[d]imidazol-2-yl)phenyl)azanediyl)bis(ethane-2,1-diyl) Diacetate

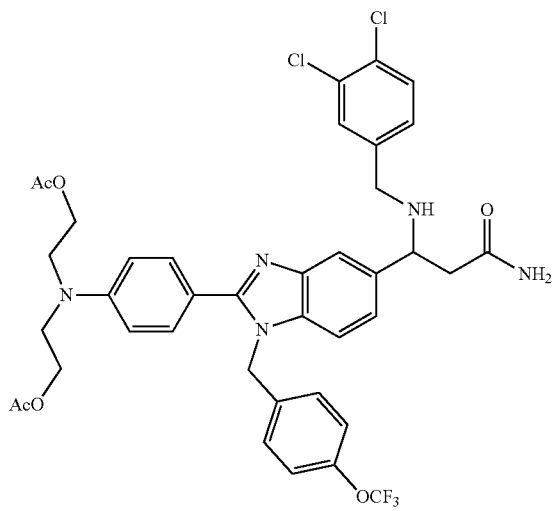 [SMILES: CC(=O)OCCN(CCOC(C)=O)c1ccc(-c2nc3cc(C(CC(N)=O)NCc4ccc(Cl)c(Cl)c4)ccc3n2Cc2ccc(OC(F)(F)F)cc2)cc1]

((4-(5-(3-amino-1-((3,4-dichlorobenzyl)amino)-3-oxopropyl)-1-(4-(trifluoromethoxy)benzyl)-1H-benzo[d]imidazol-2-yl)phenyl)azanediyl)bis(ethane-2,1-diyl) diacetate was prepared using the procedure detailed above with Method C. MALDI-TOF MS: m+H=800.37.

Example 24. LLS24. 3-((3,4-dichlorobenzyl)amino)-3-(2-(4-morpholinophenyl)-1-(4-(trifluoromethoxy)benzyl)-1H-benzo[d]imidazol-5-yl)propanamide

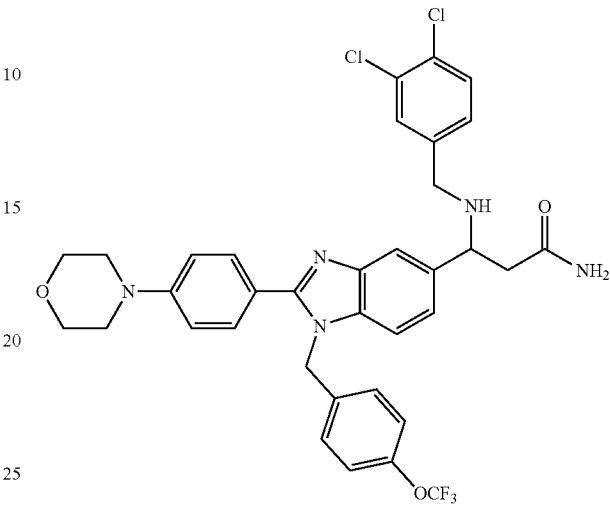

3-((3,4-dichlorobenzyl)amino)-3-(2-(4-morpholinophenyl)-1-(4-(trifluoromethoxy)benzyl)-1H-benzo[d]imidazol-5-yl)propanamide was prepared using the procedure detailed above with Method C. MALDI-TOF MS: m+H=698.29.

Example 25. LLS25. ((4-(1-(((1s,3s)-adamantan-1-yl)methyl)-5-(3-amino-1-(bis(3,4-dichlorobenzyl)amino)-3-oxopropyl)-1H-benzo[d]imidazol-2-yl)phenyl)azanediyl)bis(ethane-2,1-diyl) Diacetate

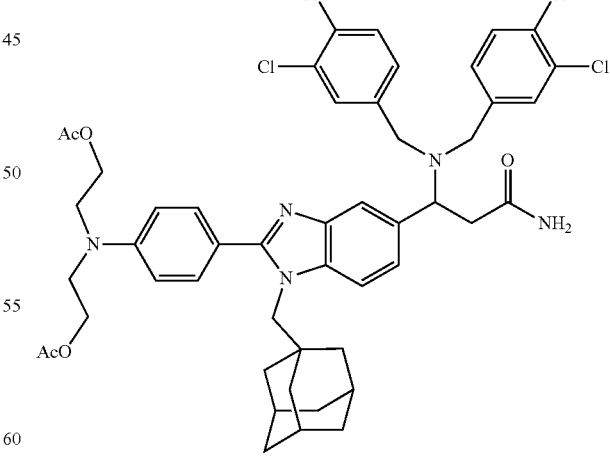

((4-(1-(((1s,3s)-adamantan-1-yl)methyl)-5-(3-amino-1-(bis(3,4-dichlorobenzyl)amino)-3-oxopropyl)-1H-benzo[d]imidazol-2-yl)phenyl)azanediyl)bis(ethane-2,1-diyl) diacetate was prepared using the procedure detailed above with Method D. MALDI-TOF MS: m+H=932.37.

Example 26. LLS26. ((4-(1-(((1s,3s)-adamantan-1-yl)methyl)-5-(3-amino-1-((3,4-dichlorobenzyl)amino)-3-oxopropyl)-1H-benzo[d]imidazol-2-yl)phenyl)azanediyl)bis(ethane-2,1-diyl) Diacetate

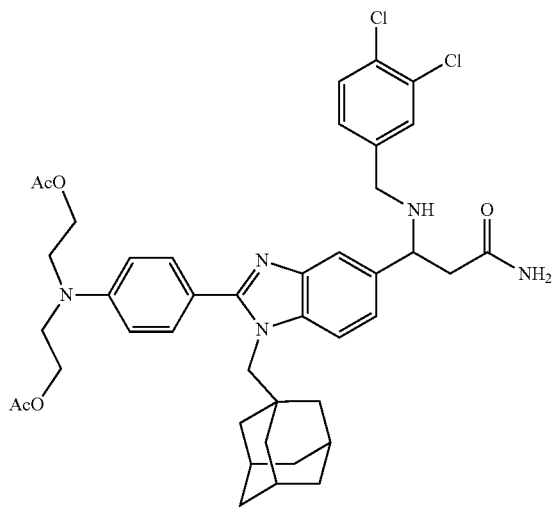 [SMILES: CC(=O)OCCN(CCOC(C)=O)c1ccc(-c2nc3cc(C(CC(N)=O)NCc4ccc(Cl)c(Cl)c4)ccc3n2CC23CC4CC(CC(C4)C2)C3)cc1]

((4-(1-(((1s,3s)-adamantan-1-yl)methyl)-5-(3-amino-1-((3,4-dichlorobenzyl)amino)-3-oxopropyl)-1H-benzo[d]imidazol-2-yl)phenyl)azanediyl)bis(ethane-2,1-diyl) diacetate was prepared using the procedure detailed above with Method C. MALDI-TOF MS: m+H=774.43.

Example 27. LLS27. 3-(2-(4-(bis(2-hydroxyethyl)amino)phenyl)-1-(3-fluoro-4-(trifluoromethyl)benzyl)-1H-benzo[d]imidazol-5-yl)-3-((3,4-dichlorobenzyl)amino)propanamide

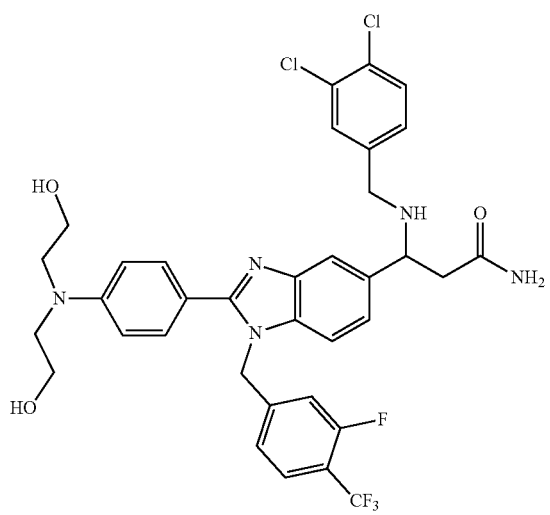 [SMILES: NC(=O)CC(NCc1ccc(Cl)c(Cl)c1)c1ccc2c(c1)nc(-c1ccc(N(CCO)CCO)cc1)n2Cc1ccc(C(F)(F)F)c(F)c1]

3-(2-(4-(bis(2-hydroxyethyl)amino)phenyl)-1-(3-fluoro-4-(trifluoromethyl)benzyl)-1H-benzo[d]imidazol-5-yl)-3-((3,4-dichlorobenzyl)amino)propanamide was prepared using the procedure detailed above with Method C. MALDI-TOF MS: m+H=718.32.

Example 28. LLS28. 3-(1-(((1s,3s)-adamantan-1-yl)methyl)-2-(4-(bis(2-hydroxyethyl)amino)phenyl)-1H-benzo[d]imidazol-5-yl)-3-((3,4-dichlorobenzyl)amino)propanamide

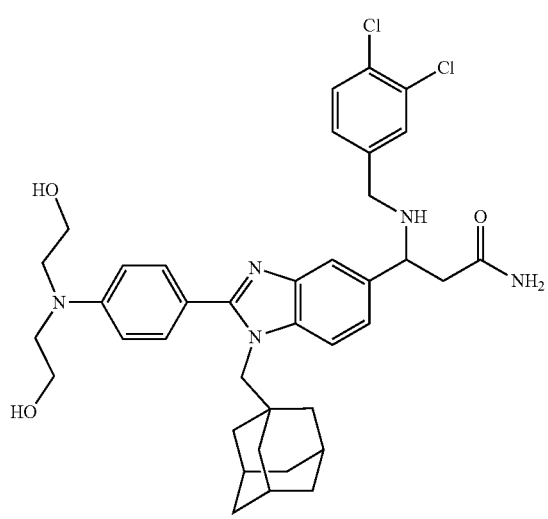 [SMILES: NC(=O)CC(NCc1ccc(Cl)c(Cl)c1)c1ccc2c(c1)nc(-c1ccc(N(CCO)CCO)cc1)n2CC12CC3CC(CC(C3)C1)C2]

3-(1-(((1s,3s)-adamantan-1-yl)methyl)-2-(4-(bis(2-hydroxyethyl)amino)phenyl)-1H-benzo[d]imidazol-5-yl)-3-((3,4-dichlorobenzyl)amino)propanamide was prepared using the procedure detailed above with Method C. MALDI-TOF MS: m+H=690.40.

Example 29. LLS29. 3-(1-(((1s,3s)-adamantan-1-yl)methyl)-2-(4-(bis(2-hydroxyethyl)amino)phenyl)-1H-benzo[d]imidazol-5-yl)-3-(bis(3,4-dichlorobenzyl)amino)propanamide

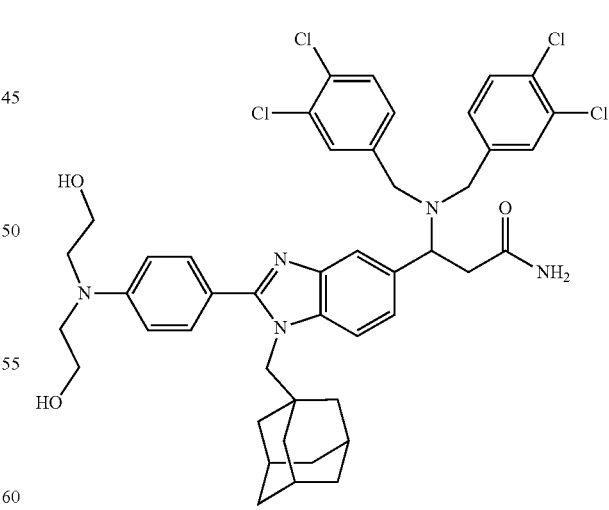

3-(1-(((1s,3s)-adamantan-1-yl)methyl)-2-(4-(bis(2-hydroxyethyl)amino)phenyl)-1H-benzo[d]imidazol-5-yl)-3-(bis(3,4-dichlorobenzyl)amino)propanamide was prepared using the procedure detailed above with Method D. MALDI-TOF MS: m+H=849.71.

Example 30. LLS30. 3-(2-(4-(bis(2-hydroxyethyl)amino)phenyl)-1-(3,4-dichlorobenzyl)-1H-benzo[d]imidazol-5-yl)-3-((3,4-dichlorobenzyl)amino)propanamide

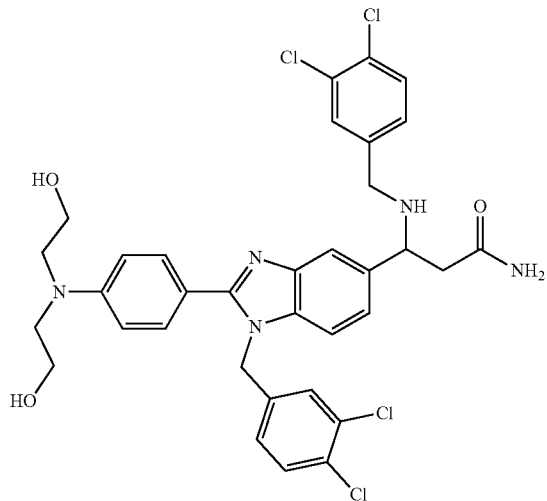

3-(2-(4-(bis(2-hydroxyethyl)amino)phenyl)-1-(3,4-dichlorobenzyl)-1H-benzo[d]imidazol-5-yl)-3-((3,4-dichlorobenzyl)amino)propanamide was prepared using the procedure detailed above with Method C. MALDI-TOF MS: m+H=700.25.

Example 31. LLS31. 3-(2-(4-(bis(2-hydroxyethyl)amino)phenyl)-1-(3-chloro-4-fluorobenzyl)-1H-benzo[d]imidazol-5-yl)-3-((3,4-dichlorobenzyl)amino)propanamide

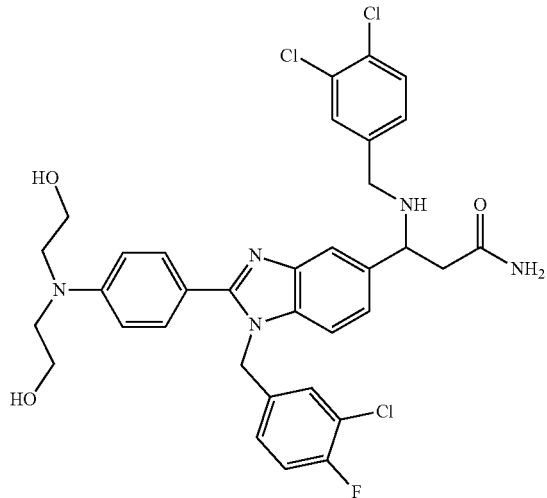 [SMILES: NC(=O)CC(NCc1ccc(Cl)c(Cl)c1)c1ccc2c(c1)nc(-c1ccc(N(CCO)CCO)cc1)n2Cc1ccc(F)c(Cl)c1]

3-(2-(4-(bis(2-hydroxyethyl)amino)phenyl)-1-(3-chloro-4-fluorobenzyl)-1H-benzo[d]imidazol-5-yl)-3-((3,4-dichlorobenzyl)amino)propanamide was prepared using the procedure detailed above with Method C. MALDI-TOF MS: m+H=684.27.

Example 32. LLS32. 2-((4-(1-(((1s,3s)-adamantan-1-yl)methyl)-5-(3-amino-1-((3,4-dichlorobenzyl)amino)-3-oxopropyl)-1H-benzo[d]imidazol-2-yl)phenyl)(2-hydroxyethyl)amino)ethyl Acetate

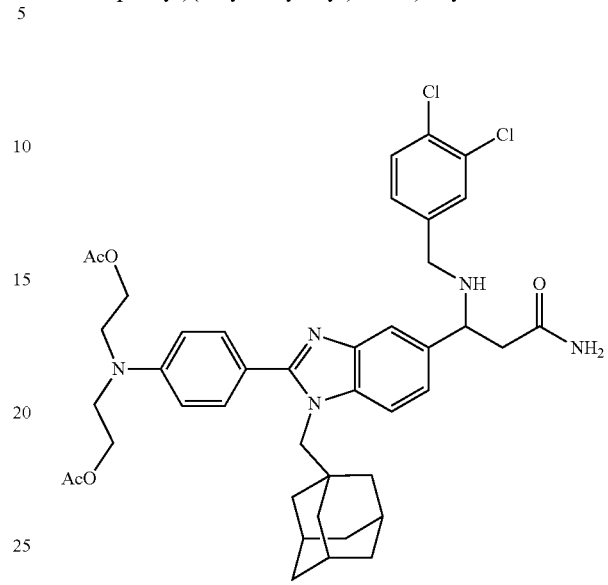

2-((4-(1-(((1s,3s)-adamantan-1-yl)methyl)-5-(3-amino-1-((3,4-dichlorobenzyl)amino)-3-oxopropyl)-1H-benzo[d]imidazol-2-yl)phenyl)(2-hydroxyethyl)amino)ethyl acetate was prepared using the procedure detailed above with Method C. MALDI-TOF MS: m+H=732.44.

Example 33. LLS33. 2-((4-(5-(3-amino-1-((3,4-dichlorobenzyl)amino)-3-oxopropyl)-1-(3,4-dichlorobenzyl)-1H-benzo[d]imidazol-2-yl)phenyl)(2-hydroxyethyl)amino)ethyl Acetate

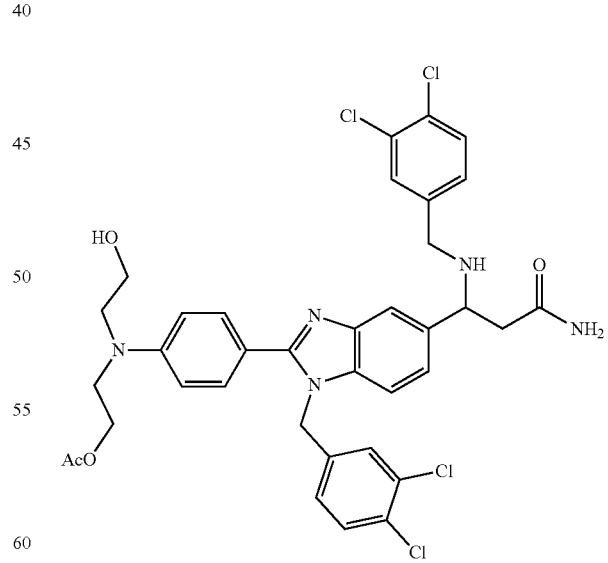

2-((4-(5-(3-amino-1-((3,4-dichlorobenzyl)amino)-3-oxopropyl)-1-(3,4-dichlorobenzyl)-1H-benzo[d]imidazol-2-yl)phenyl)(2-hydroxyethyl)amino)ethyl acetate was prepared using the procedure detailed above with Method C. MALDI-TOF MS: m+H=742.23.

Example 34. LLS34. 2-((4-(5-(3-amino-1-((3,4-dichlorobenzyl)amino)-3-oxopropyl)-1-(3-chloro-4-fluorobenzyl)-1H-benzo[d]imidazol-2-yl)phenyl)(2-hydroxyethyl)amino)ethyl Acetate

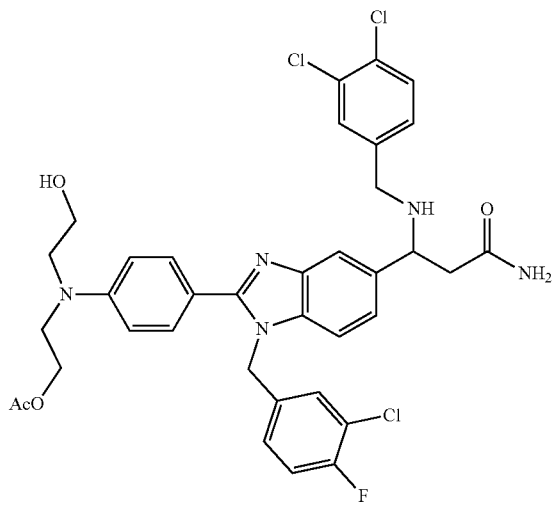 [SMILES: CC(=O)OCCN(CCO)c1ccc(-c2nc3cc(C(CC(N)=O)NCc4ccc(Cl)c(Cl)c4)ccc3n2Cc2ccc(F)c(Cl)c2)cc1]

2-((4-(5-(3-amino-1-((3,4-dichlorobenzyl)amino)-3-oxopropyl)-1-(3-chloro-4-fluorobenzyl)-1H-benzo[d]imidazol-2-yl)phenyl)(2-hydroxyethyl)amino)ethyl acetate was prepared using the procedure detailed above with Method C. MALDI-TOF MS: m+H=726.33.

Example 35. LLS35. 2-((4-(5-(3-amino-1-((3,4-dichlorobenzyl)amino)-3-oxopropyl)-1-(4-(trifluoromethoxy)benzyl)-1H-benzo[d]imidazol-2-yl)phenyl)(2-hydroxyethyl)amino)ethyl Acetate

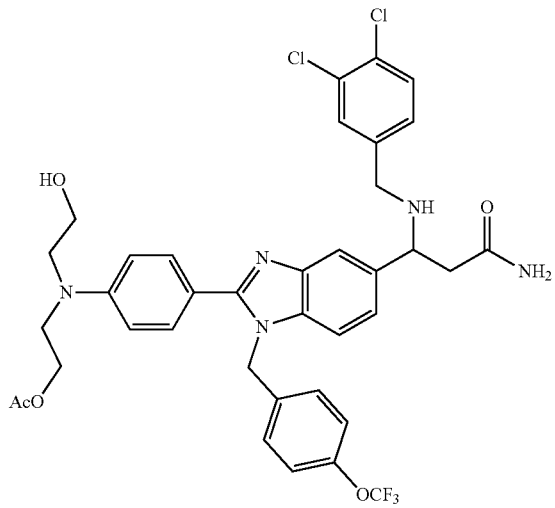

2-((4-(5-(3-amino-1-((3,4-dichlorobenzyl)amino)-3-oxopropyl)-1-(4-(trifluoromethoxy)benzyl)-1H-benzo[d]imidazol-2-yl)phenyl)(2-hydroxyethyl)amino)ethyl acetate was prepared using the procedure detailed above with Method C. MALDI-TOF MS: m+H=758.30.

Example 36. LLS36. 3-(2-(4-(bis(2-hydroxyethyl)amino)phenyl)-1-(4-(trifluoromethoxy)benzyl)-1H-benzo[d]imidazol-5-yl)-3-((3,4-dichlorobenzyl)amino)propanamide

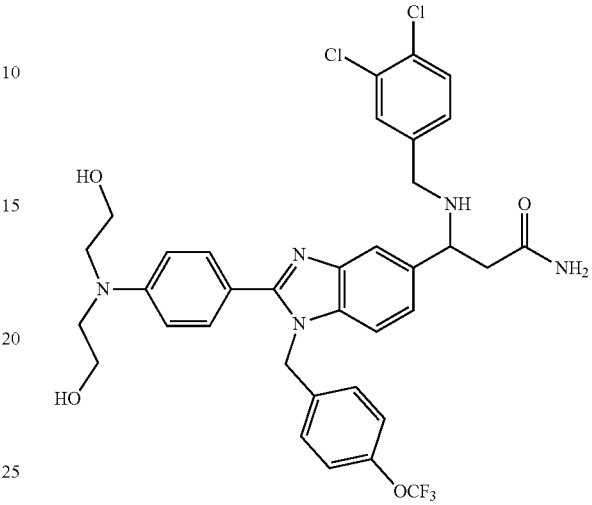

3-(2-(4-(bis(2-hydroxyethyl)amino)phenyl)-1-(4-(trifluoromethoxy)benzyl)-1H-benzo[d]imidazol-5-yl)-3-((3,4-dichlorobenzyl)amino)propanamide was prepared using the procedure detailed above with Method C. MALDI-TOF MS: m+H=716.32.

Example 37. LLS37. ((4-(5-(3-amino-1-((4-(bis(2-acetoxyethyl)amino)benzyl)amino)-3-oxopropyl)-1-(3,4-dichlorobenzyl)-1H-benzo[d]imidazol-2-yl)phenyl)azanediyl)bis(ethane-2,1-diyl) Diacetate

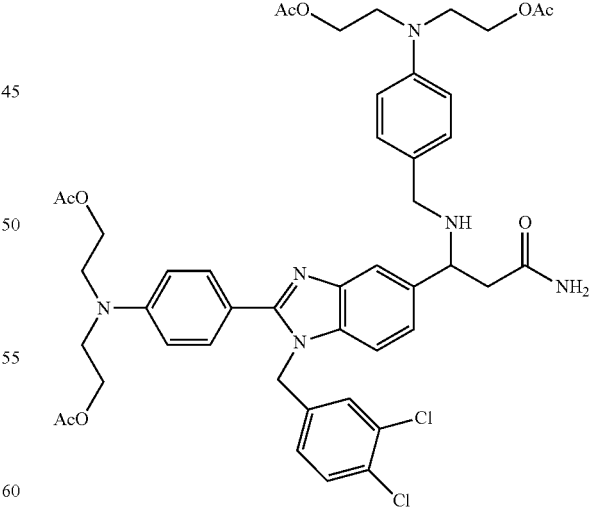

((4-(5-(3-amino-1-((4-(bis(2-acetoxyethyl)amino)benzyl)amino)-3-oxopropyl)-1-(3,4-dichlorobenzyl)-1H-benzo[d]imidazol-2-yl)phenyl)azanediyl)bis(ethane-2,1-diyl) diacetate was prepared using the procedure detailed above with Method C. MALDI-TOF MS: m+H=903.44.

Example 38. LLS38. 3-((4-(bis(2-hydroxyethyl)amino)benzyl)amino)-3-(2-(4-(bis(2-hydroxyethyl)amino)phenyl)-1-(3,4-dichlorobenzyl)-1H-benzo[d]imidazol-5-yl)propanamide

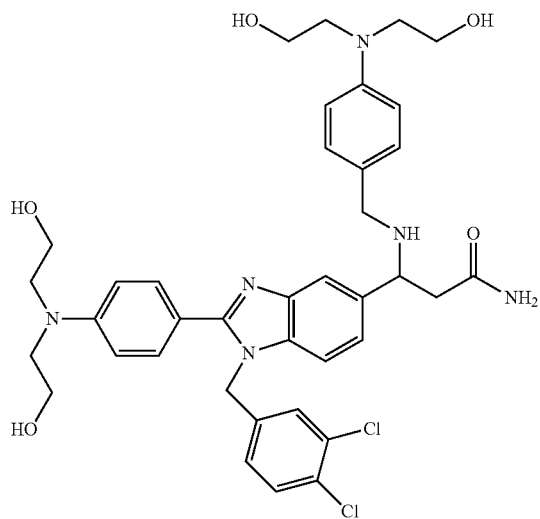 [SMILES: NC(=O)CC(NCc1ccc(N(CCO)CCO)cc1)c1ccc2c(c1)nc(-c1ccc(N(CCO)CCO)cc1)n2Cc1ccc(Cl)c(Cl)c1]

3-((4-(bis(2-hydroxyethyl)amino)benzyl)amino)-3-(2-(4-(bis(2-hydroxyethyl)amino)phenyl)-1-(3,4-dichlorobenzyl)-1H-benzo[d]imidazol-5-yl)propanamide was prepared using the procedure detailed above with Method C. MALDI-TOF MS: m+H=735.34.

Example 39. LLS39. 3-(2-(4-(bis(2-hydroxyethyl)amino)phenyl)-1-(3,4-dichlorobenzyl)-1H-benzo[d]imidazol-5-yl)-3-(2-((3,4-dichlorobenzyl)amino)acetamido)propanamide

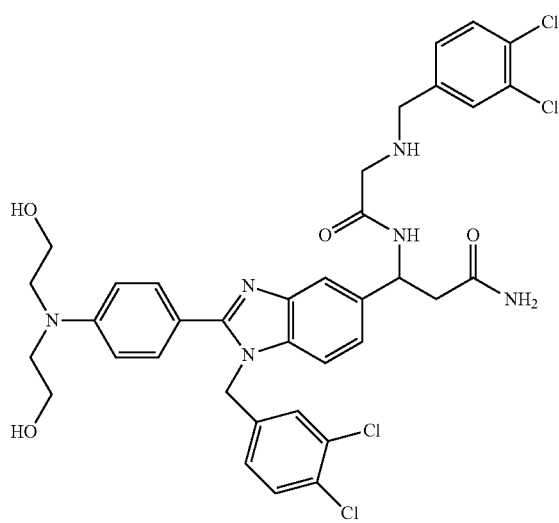 [SMILES: NC(=O)CC(NC(=O)CNCc1ccc(Cl)c(Cl)c1)c1ccc2c(c1)nc(-c1ccc(N(CCO)CCO)cc1)n2Cc1ccc(Cl)c(Cl)c1]

3-(2-(4-(bis(2-hydroxyethyl)amino)phenyl)-1-(3,4-dichlorobenzyl)-1H-benzo[d]imidazol-5-yl)-3-(2-((3,4-dichlorobenzyl)amino)acetamido)propanamide was prepared using the procedure detailed above, but with Fmoc-Glycine coupled to the amino group after Alloc-deprotection, followed by Fmoc-deprotection and coupling of aldehyde using Method C. MALDI-TOF MS: m+H=757.23.

Example 40. LLS40. ((4-(5-(3-amino-1-((4-(4-(tert-butyl)thiazol-2-yl)benzyl)amino)-3-oxopropyl)-1-(3,4-dichlorobenzyl)-1H-benzo[d]imidazol-2-yl)phenyl)azanediyl)bis(ethane-2,1-diyl) Diacetate

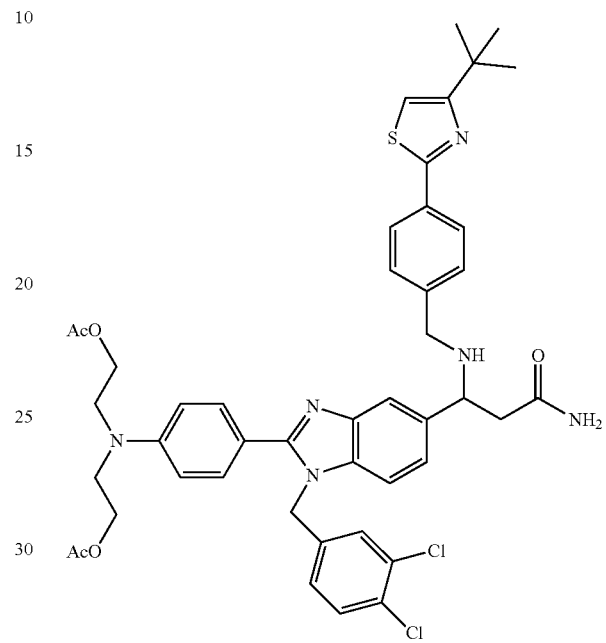

((4-(5-(3-amino-1-((4-(4-(tert-butyl)thiazol-2-yl)benzyl)amino)-3-oxopropyl)-1-(3,4-dichlorobenzyl)-1H-benzo[d]imidazol-2-yl)phenyl)azanediyl)bis(ethane-2,1-diyl) diacetate was prepared using the procedure detailed above with Method C. MALDI-TOF MS: m+H=771.38.

Example 41. LLS41. 3-(2-(4-(bis(2-hydroxyethyl)amino)phenyl)-1-(3-chloro-4-fluorobenzyl)-1H-benzo[d]imidazol-5-yl)-3-(isopropylamino)propanamide

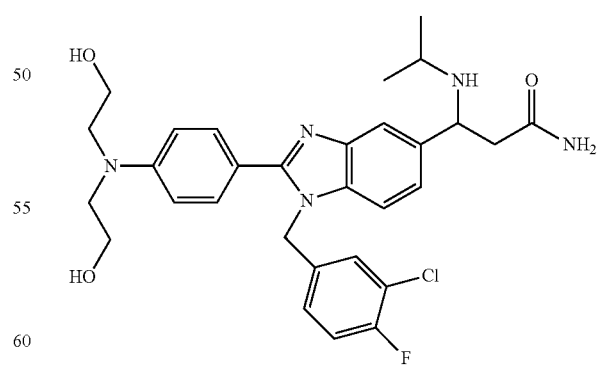

3-(2-(4-(bis(2-hydroxyethyl)amino)phenyl)-1-(3-chloro-4-fluorobenzyl)-1H-benzo[d]imidazol-5-yl)-3-(isopropylamino)propanamide was prepared using the procedure detailed above with Method D. MALDI-TOF MS: m+H=568.40.

Example 42. LLS42. 3-(2-(4-(bis(2-hydroxyethyl)amino)phenyl)-1-(4-(trifluoromethoxy)benzyl)-1H-benzo[d]imidazol-5-yl)-3-((cyclohexylmethyl)amino)propanamide

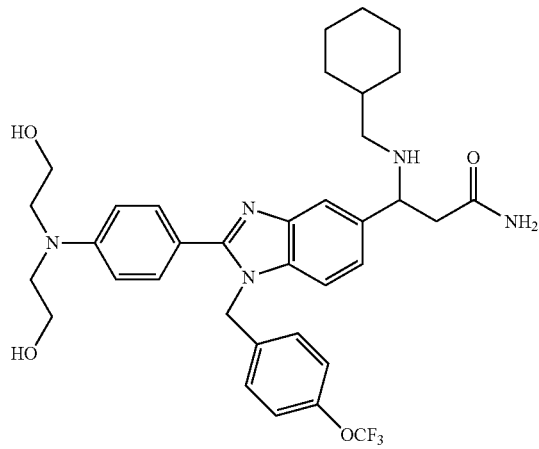 [SMILES: NC(=O)CC(NCC1CCCCC1)c1ccc2c(c1)nc(-c1ccc(N(CCO)CCO)cc1)n2Cc1ccc(OC(F)(F)F)cc1]

3-(2-(4-(bis(2-hydroxyethyl)amino)phenyl)-1-(4-(trifluoromethoxy)benzyl)-1H-benzo[d]imidazol-5-yl)-3-((cyclohexylmethyl)amino)propanamide was prepared using the procedure detailed above with Method C. MALDI-TOF MS: m+H=654.18.

Example 43. LLS43. 2-((4-(5-(3-amino-1-((3-bromo-4,5-dimethoxybenzyl)amino)-3-oxopropyl)-1-isopropyl-1H-benzo[d]imidazol-2-yl)phenyl)(2-hydroxyethyl)amino)ethyl Acetate

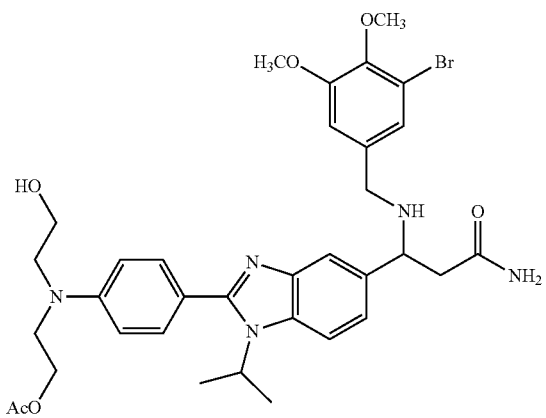 [SMILES: COc1cc(CNC(CC(N)=O)c2ccc3c(c2)nc(-c2ccc(N(CCO)CCOC(C)=O)cc2)n3C(C)C)cc(Br)c1OC]

2-((4-(5-(3-amino-1-((3-bromo-4,5-dimethoxybenzyl)amino)-3-oxopropyl)-1-isopropyl-1H-benzo[d]imidazol-2-yl)phenyl)(2-hydroxyethyl)amino)ethyl acetate was prepared using the procedure detailed above with Method C. MALDI-TOF MS: m+H=696.18, 698.18.

Example 44. LLS43Ac. ((4-(5-(3-amino-1-((3-bromo-4,5-dimethoxybenzyl)amino)-3-oxopropyl)-1-isopropyl-1H-benzo[d]imidazol-2-yl)phenyl)azanediyl)bis(ethane-2,1-diyl) Diacetate

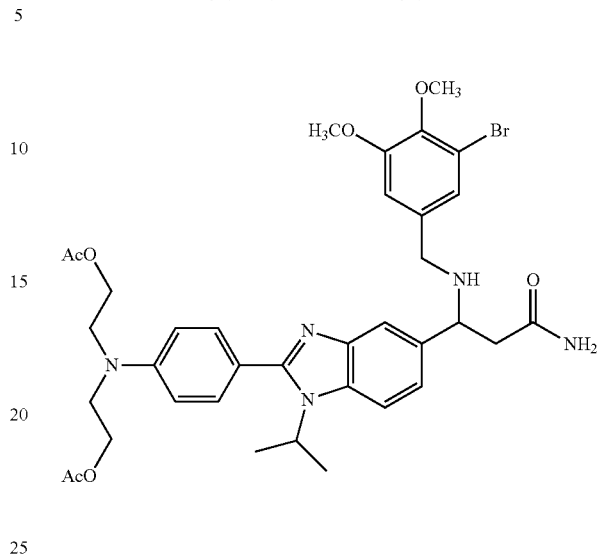

((4-(5-(3-amino-1-((3-bromo-4,5-dimethoxybenzyl)amino)-3-oxopropyl)-1-isopropyl-1H-benzo[d]imidazol-2-yl)phenyl)azanediyl)bis(ethane-2,1-diyl) diacetate was prepared using the procedure detailed above with Method C. MALDI-TOF MS: m+H=738.15, 740.15.

Example 45. LLS44. 3-(2-(4-(bis(2-hydroxyethyl)amino)phenyl)-1-(3-(piperidin-1-yl)propyl)-1H-benzo[d]imidazol-5-yl)-3-((3-(trifluoromethyl)benzyl)amino)propanamide

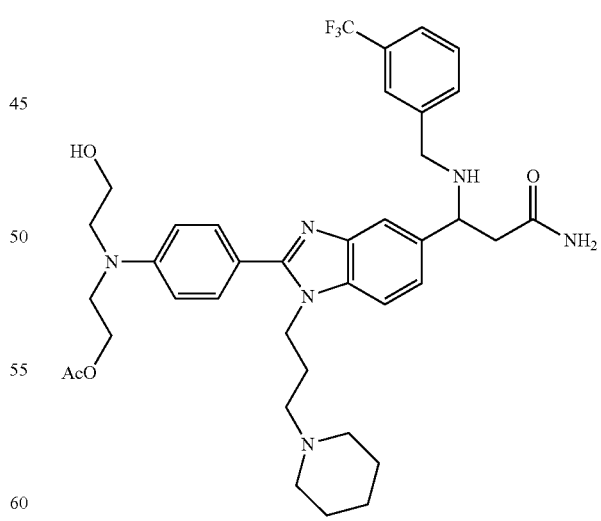

3-(2-(4-(bis(2-hydroxyethyl)amino)phenyl)-1-(3-(piperidin-1-yl)propyl)-1H-benzo[d]imidazol-5-yl)-3-((3-(trifluoromethyl)benzyl)amino)propanamide was prepared using the procedure detailed above with Method C. MALDI-TOF MS: m+H=667.57.

Example 46. LLS45. 3-(1-(2-aminoethyl)-2-(4-(bis (2-hydroxyethyl)amino)phenyl)-1H-benzo[d]imidazol-5-yl)-3-(((5-bromothiophen-2-yl)methyl)amino)propanamide

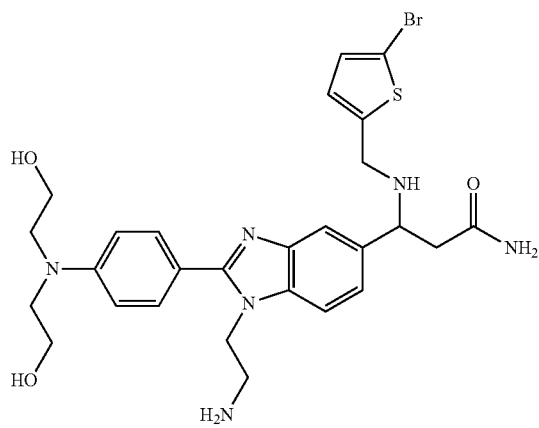 [SMILES: NCCn1c(-c2ccc(N(CCO)CCO)cc2)nc2cc(C(CC(N)=O)NCc3ccc(Br)s3)ccc21]

3-(1-(2-aminoethyl)-2-(4-(bis(2-hydroxyethyl)amino)phenyl)-1H-benzo[d]imidazol-5-yl)-3-(((5-bromothiophen-2-yl)methyl)amino)propanamide was prepared using the procedure detailed above with Method C. MALDI-TOF MS: m+H=623.18, 625.18 (M+Na).

Example 47. LLS45Ac. ((4-(5-(3-amino-1-(((5-bromothiophen-2-yl)methyl)amino)-3-oxopropyl)-1-(2-aminoethyl)-1H-benzo[d]imidazol-2-yl)phenyl)azanediyl)bis(ethane-2,1-diyl) Diacetate

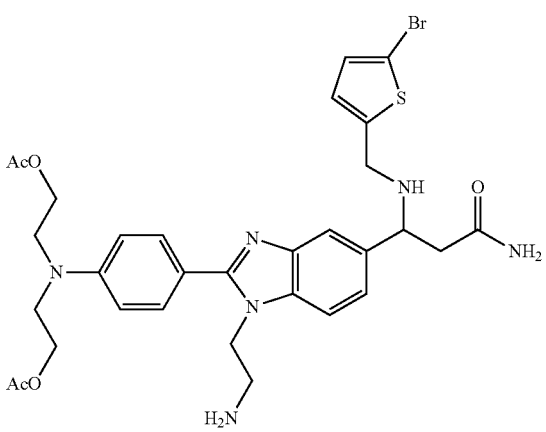 [SMILES: CC(=O)OCCN(CCOC(C)=O)c1ccc(-c2nc3cc(C(CC(N)=O)NCc4ccc(Br)s4)ccc3n2CCN)cc1]

((4-(5-(3-amino-1-(((5-bromothiophen-2-yl)methyl)amino)-3-oxopropyl)-1-(2-aminoethyl)-1H-benzo[d]imidazol-2-yl)phenyl)azanediyl)bis(ethane-2,1-diyl) diacetate was prepared using the procedure detailed above with Method C. MALDI-TOF MS: m+H=685.23, 687.23.

Example 48. LLS46. 3-(2-(4-(bis(2-hydroxyethyl)amino)phenyl)-1-(3-(piperidin-1-yl)propyl)-1H-benzo[d]imidazol-5-yl)-3-((3,4-dichlorobenzyl)amino)propanamide 3-(2-(4-(bis(2-hydroxyethyl)amino)phenyl)-1-(3-(piperidin-1-yl)propyl)-1H-benzo[d]imidazol-5-yl)-3-((3,4-dichlorobenzyl)amino)propanamide was prepared using the procedure detailed above with Method C. MALDI-TOF MS: m+H=667.42.

Example 49. LLS51. 3-(2-(4-(bis(2-hydroxyethyl)amino)phenyl)-1-(4-(trifluoromethoxy)benzyl)-1H-benzo[d]imidazol-5-yl)-3-((4-(pyrimidin-5-yl)benzyl)amino)propanamide 3-(2-(4-(bis(2-hydroxyethyl)amino)phenyl)-1-(4-(trifluoromethoxy)benzyl)-1H-benzo[d]imidazol-5-yl)-3-((4-(pyrimidin-5-yl)benzyl)amino)propanamide was prepared using the procedure detailed above with Method C. MALDI-TOF MS: m+H=726.41.

Example 50. LLS52. 3-(2-(4-(bis(2-hydroxyethyl)amino)phenyl)-1-(3-(piperidin-1-yl)propyl)-1H-benzo[d]imidazol-5-yl)-3-(((1-(phenylsulfonyl)-1H-pyrrol-2-yl)methyl)amino)propanamide

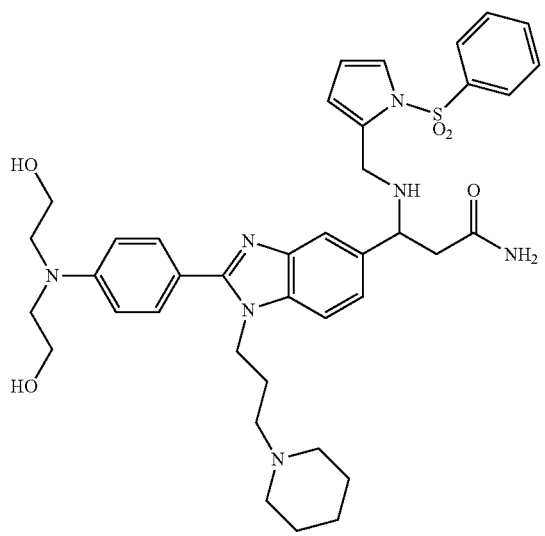 [SMILES: NC(=O)CC(NCc1cccn1S(=O)(=O)c1ccccc1)c1ccc2c(c1)nc(-c1ccc(N(CCO)CCO)cc1)n2CCCN1CCCCC1]

3-(2-(4-(bis(2-hydroxyethyl)amino)phenyl)-1-(3-(piperidin-1-yl)propyl)-1H-benzo[d]imidazol-5-yl)-3-(((1-(phenylsulfonyl)-1H-pyrrol-2-yl)methyl)amino)propanamide was prepared using the procedure detailed above with Method C. MALDI-TOF MS: m+H=728.42.

Example 51. LLS52Ac. ((4-(5-(3-amino-3-oxo-1-(((1-(phenylsulfonyl)-1H-pyrrol-2-yl)methyl)amino)propyl)-1-(3-(piperidin-1-yl)propyl)-1H-benzo[d]imidazol-2-yl)phenyl)azanediyl)bis(ethane-2,1-diyl) Diacetate

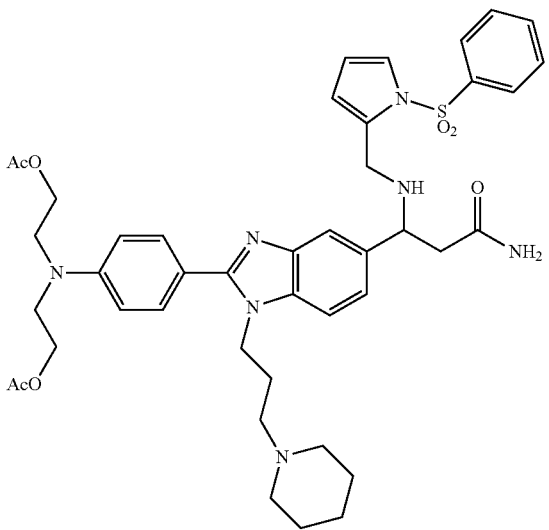 [SMILES: CC(=O)OCCN(CCOC(C)=O)c1ccc(-c2nc3cc(C(CC(N)=O)NCc4cccn4S(=O)(=O)c4ccccc4)ccc3n2CCCN2CCCCC2)cc1]

LLS52Ac. ((4-(5-(3-amino-3-oxo-1-(((1-(phenylsulfonyl)-1H-pyrrol-2-yl)methyl)amino)propyl)-1-(3-(piperidin-1-yl)propyl)-1H-benzo[d]imidazol-2-yl)phenyl)azanediyl)bis(ethane-2,1-diyl) diacetate was prepared using the procedure detailed above with Method C. MALDI-TOF MS: m+H=812.25.

Example 52. LLS53. 3-(((1H-indazol-5-yl)methyl)amino)-3-(2-(4-(bis(2-hydroxyethyl)amino)phenyl)-1-(4-methoxyphenethyl)-1H-benzo[d]imidazol-5-yl)propanamide

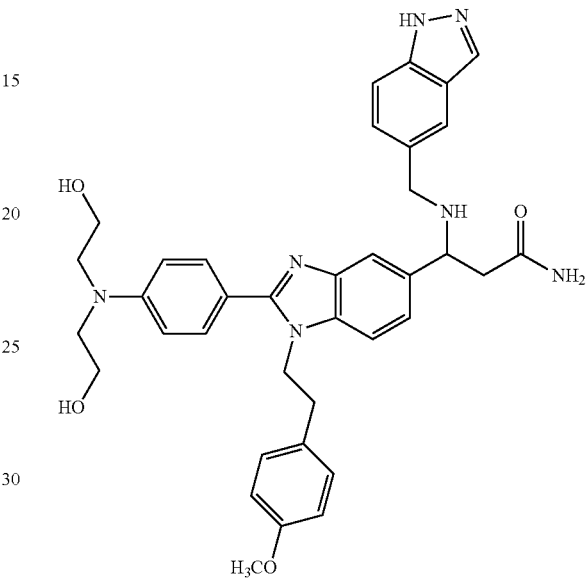

3-(((1H-indazol-5-yl)methyl)amino)-3-(2-(4-(bis(2-hydroxyethyl)amino)phenyl)-1-(4-methoxyphenethyl)-1H-benzo[d]imidazol-5-yl)propanamide was prepared using the procedure detailed above with Method C. MALDI-TOF MS: m+H=648.32.

Example 53. LLS53Ac. ((4-(5-(1-(((1H-indazol-5-yl)methyl)amino)-3-amino-3-oxopropyl)-1-(4-methoxyphenethyl)-1H-benzo[d]imidazol-2-yl)phenyl)azanediyl)bis(ethane-2,1-diyl) Diacetate

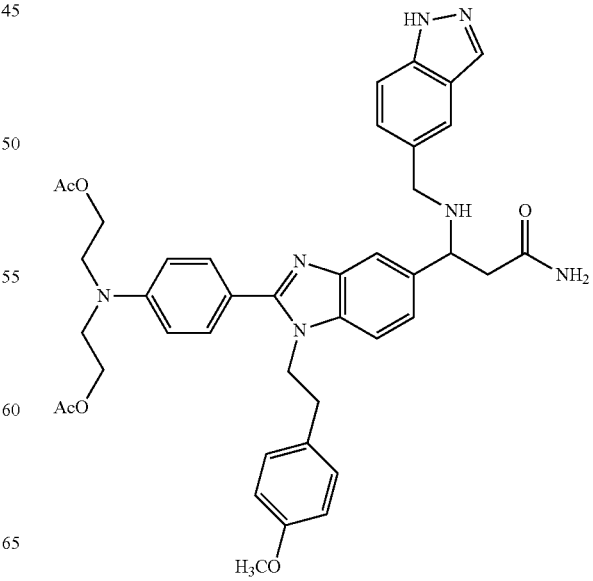

LLS53Ac. ((4-(5-(1-(((1H-indazol-5-yl)methyl)amino)-3-amino-3-oxopropyl)-1-(4-methoxyphenethyl)-1H-benzo[d]imidazol-2-yl)phenyl)azanediyl)bis(ethane-2,1-diyl) diacetate was prepared using the procedure detailed above with Method C. MALDI-TOF MS: m+H=732.39.

Example 54. LLS54. 3-(1-(3-aminopropyl)-2-(4-(bis(2-hydroxyethyl)amino)phenyl)-1H-benzo[d]imidazol-5-yl)-3-(((5-(4,5-dihydro-1H-pyrazol-5-yl)thiophen-2-yl)methyl)amino)propanamide

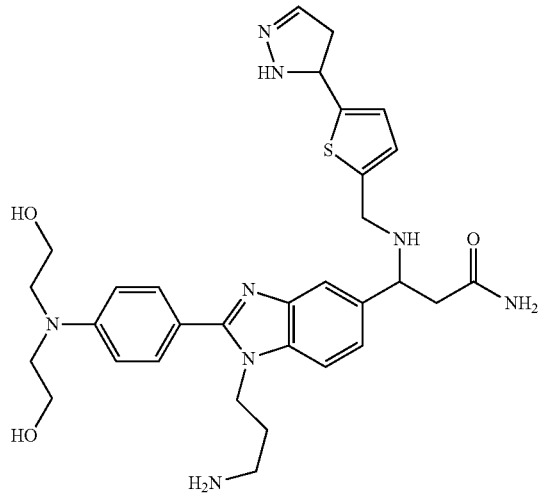 [SMILES: NCCCn1c(-c2ccc(N(CCO)CCO)cc2)nc2cc(C(CC(N)=O)NCc3ccc(C4CC=NN4)s3)ccc21]

3-(1-(3-aminopropyl)-2-(4-(bis(2-hydroxyethyl)amino)phenyl)-1H-benzo[d]imidazol-5-yl)-3-(((5-(4,5-dihydro-1H-pyrazol-5-yl)thiophen-2-yl)methyl)amino)propanamide was prepared using the procedure detailed above with Method C. MALDI-TOF MS: m+H=625.27.

Example 55. LLS55. 3-(((1H-indazol-5-yl)methyl)amino)-3-(2-(4-(bis(2-hydroxyethyl)amino)phenyl)-1-(4-(trifluoromethoxy)benzyl)-1H-benzo[d]imidazol-5-yl)propanamide

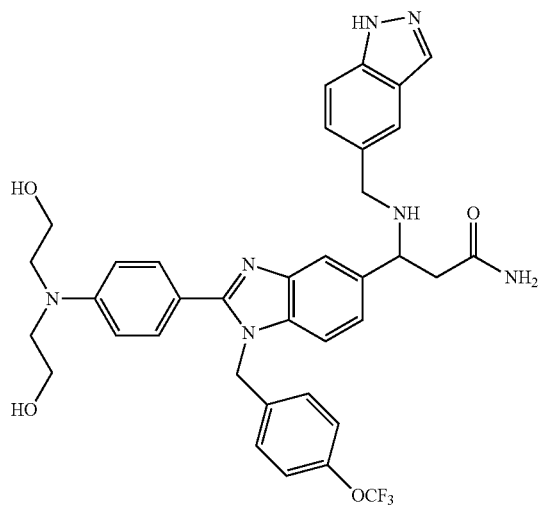

3-(((1H-indazol-5-yl)methyl)amino)-3-(2-(4-(bis(2-hydroxyethyl)amino)phenyl)-1-(4-(trifluoromethoxy)benzyl)-1H-benzo[d]imidazol-5-yl)propanamide was prepared using the procedure detailed above with Method C. MALDI-TOF MS: m+H=688.23.

Example 56. LLS56. (Z)-6-(2-(4-(bis(2-hydroxyethyl)amino)phenyl)-1-(4-methoxyphenethyl)-1H-imidazol-5-yl)-3-((cyclohexylmethyl)amino)hex-5-enamide

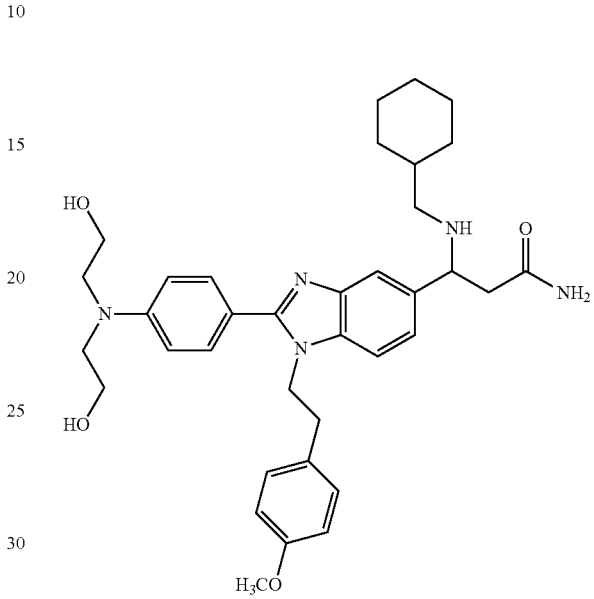

(Z)-6-(2-(4-(bis(2-hydroxyethyl)amino)phenyl)-1-(4-methoxyphenethyl)-1H-imidazol-5-yl)-3-((cyclohexylmethyl)amino)hex-5-enamide was prepared using the procedure detailed above with Method C. MALDI-TOF MS: m+H=614.41.

Example 57. LLS56Ac. ((4-(5-(3-amino-1-((cyclohexylmethyl)amino)-3-oxopropyl)-1-(4-methoxyphenethyl)-1H-benzo[d]imidazol-2-yl)phenyl)azanediyl)bis(ethane-2,1-diyl) Diacetate

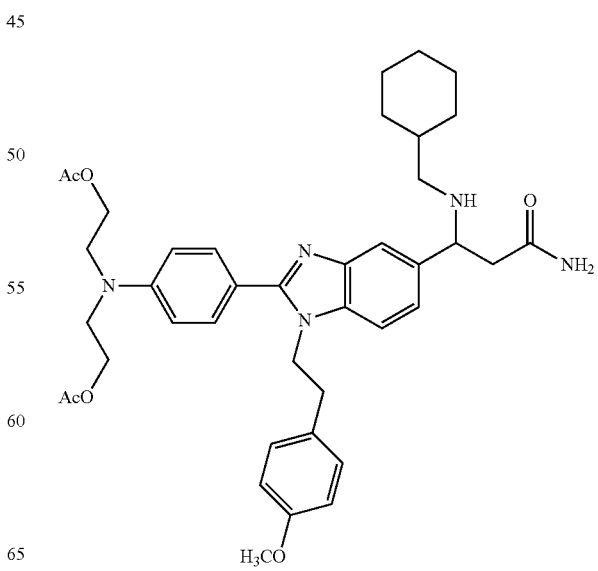

((4-(5-(3-amino-1-((cyclohexylmethyl)amino)-3-oxopropyl)-1-(4-methoxyphenethyl)-1H-benzo[d]imidazol-2-yl)phenyl)azanediyl)bis(ethane-2,1-diyl) diacetate was prepared using the procedure detailed above with Method C. MALDI-TOF MS: m+H=698.50.

Example 58. LLS58. 3-(1-(3-(1H-imidazol-1-yl)propyl)-2-(4-(bis(2-hydroxyethyl)amino)phenyl)-1H-benzo[d]imidazol-5-yl)-3-((4-(pyridin-4-yl)benzyl)amino)propanamide

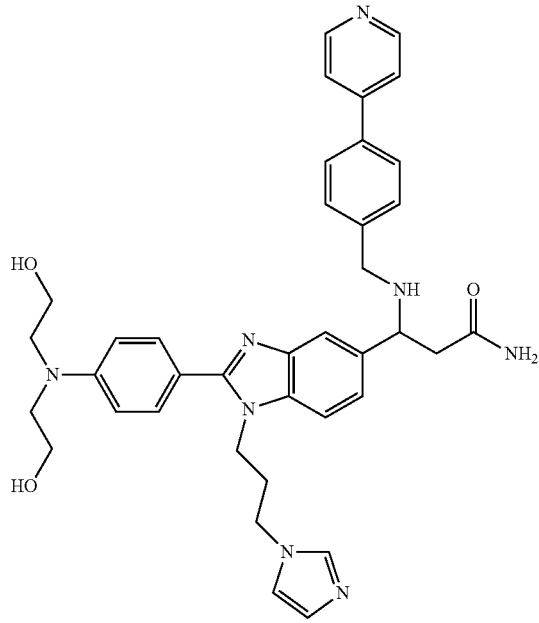 [SMILES: NC(=O)CC(NCc1ccc(-c2ccncc2)cc1)c1ccc2c(c1)nc(-c1ccc(N(CCO)CCO)cc1)n2CCCn1ccnc1]

3-(1-(3-(1H-imidazol-1-yl)propyl)-2-(4-(bis(2-hydroxyethyl)amino)phenyl)-1H-benzo[d]imidazol-5-yl)-3-((4-(pyridin-4-yl)benzyl)amino)propanamide was prepared using the procedure detailed above with Method C. MALDI-TOF MS: m+H=659.47.

Example 59. LLS58Ac. ((4-(1-(3-(1H-imidazol-1-yl)propyl)-5-(3-amino-3-oxo-1-((4-(pyridin-4-yl)benzyl)amino)propyl)-1H-benzo[d]imidazol-2-yl)phenyl)azanediyl)bis(ethane-2,1-diyl) Diacetate

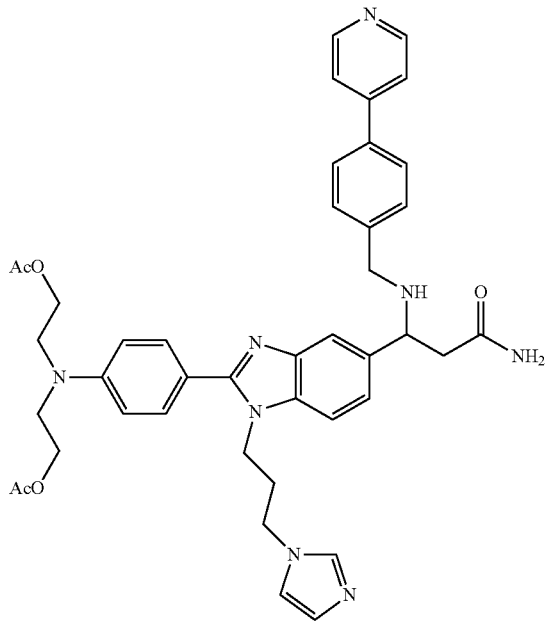 [SMILES: CC(=O)OCCN(CCOC(C)=O)c1ccc(-c2nc3cc(C(CC(N)=O)NCc4ccc(-c5ccncc5)cc4)ccc3n2CCCn2ccnc2)cc1]

LLS58Ac. ((4-(1-(3-(1H-imidazol-1-yl)propyl)-5-(3-amino-3-oxo-1-((4-(pyridin-4-yl)benzyl)amino)propyl)-1H-benzo[d]imidazol-2-yl)phenyl)azanediyl)bis(ethane-2,1-diyl) diacetate was prepared using the procedure detailed above with Method C. MALDI-TOF MS: m+H=743.54.

Example 60. LLS59. 3-(((1H-indazol-5-yl)methyl)amino)-3-(2-(4-(bis(2-hydroxyethyl)amino)phenyl)-1-(3-methoxybenzyl)-1H-benzo[d]imidazol-5-yl)propanamide

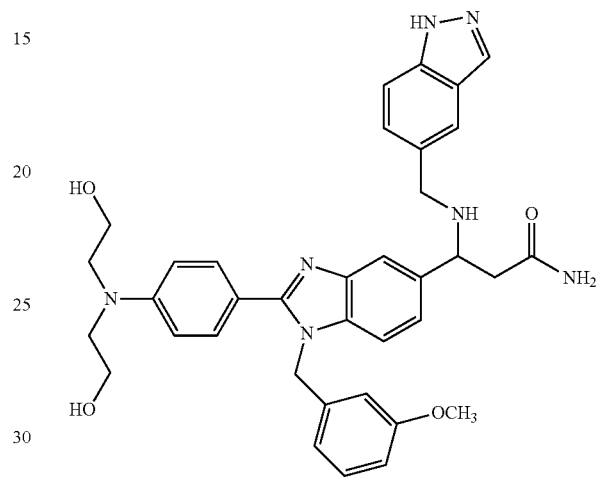

3-(((1H-indazol-5-yl)methyl)amino)-3-(2-(4-(bis(2-hydroxyethyl)amino)phenyl)-1-(3-methoxybenzyl)-1H-benzo[d]imidazol-5-yl)propanamide was prepared using the procedure detailed above with Method C. MALDI-TOF MS: m+H=634.49.

Example 61. LLS63. 3-(2-(4-(bis(2-hydroxyethyl)amino)phenyl)-1-(4-(trifluoromethoxy)benzyl)-1H-benzo[d]imidazol-5-yl)-3-((naphthalen-1-ylmethyl)amino)propanamide

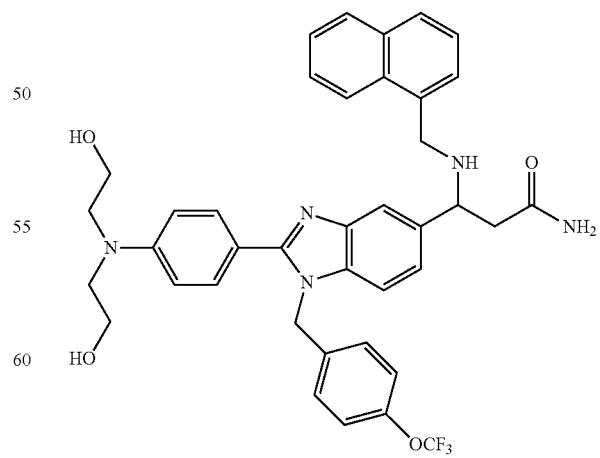

3-(2-(4-(bis(2-hydroxyethyl)amino)phenyl)-1-(4-(trifluoromethoxy)benzyl)-1H-benzo[d]imidazol-5-yl)-3-((naphthalen-1-ylmethyl)amino)propanamide was prepared using the procedure detailed above with Method C. MALDI-TOF MS: m+H=698.32.

Example 62. LLS64. 3-((3,4-dichlorobenzyl) amino)-3-(2-(4-(4-methylpiperazin-1-yl)phenyl)-1-(4-(trifluoromethyl)benzyl)-1H-benzo[d]imidazol-5-yl)propanamide

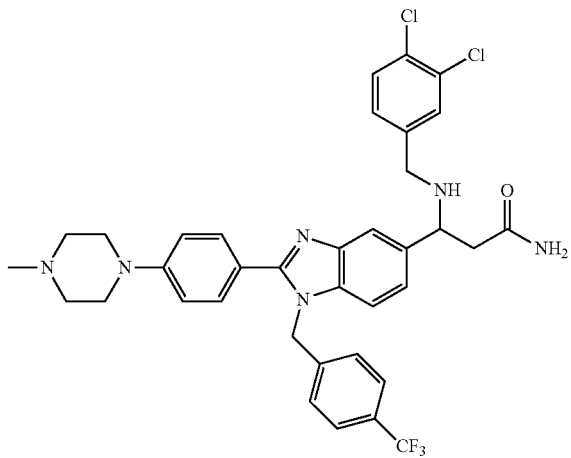 [SMILES: CN1CCN(c2ccc(-c3nc4cc(C(CC(N)=O)NCc5ccc(Cl)c(Cl)c5)ccc4n3Cc3ccc(C(F)(F)F)cc3)cc2)CC1]

3-((3,4-dichlorobenzyl)amino)-3-(2-(4-(4-methylpiperazin-1-yl)phenyl)-1-(4-(trifluoromethyl)benzyl)-1H-benzo[d]imidazol-5-yl)propanamide was prepared using the procedure detailed above with Method C. MALDI-TOF MS: m+H=695.81.

Example 63. LLS65. 3-((3,4-dichlorobenzyl) amino)-3-(2-(4-morpholinophenyl)-1-(3-(piperidin-1-yl)propyl)-1H-benzo[d]imidazol-5-yl)propanamide

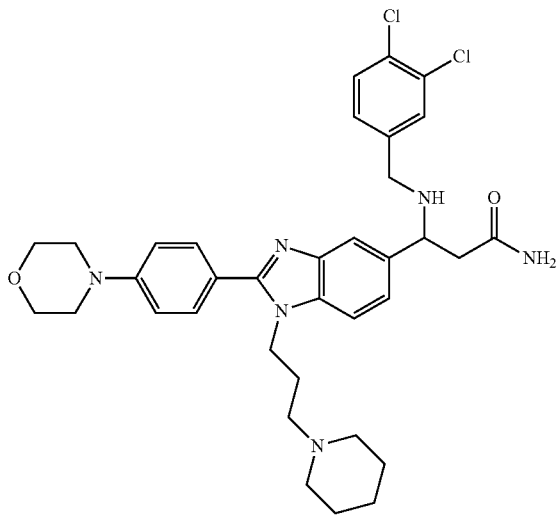 [SMILES: NC(=O)CC(NCc1ccc(Cl)c(Cl)c1)c1ccc2c(c1)nc(-c1ccc(N3CCOCC3)cc1)n2CCCN1CCCCC1]

3-((3,4-dichlorobenzyl)amino)-3-(2-(4-morpholinophenyl)-1-(3-(piperidin-1-yl)propyl)-1H-benzo[d]imidazol-5-yl)propanamide was prepared using the procedure detailed above with Method C. MALDI-TOF MS: m+H=649.35.

Example 64. LLS66. 2-((4-(5-(1-(((5-(1H-pyrazol-5-yl)thiophen-2-yl)methyl)amino)-3-amino-3-oxopropyl)-1-(3-(dimethylamino)propyl)-1H-benzo[d]imidazol-2-yl)phenyl)(2-hydroxyethyl)amino)ethyl Acetate

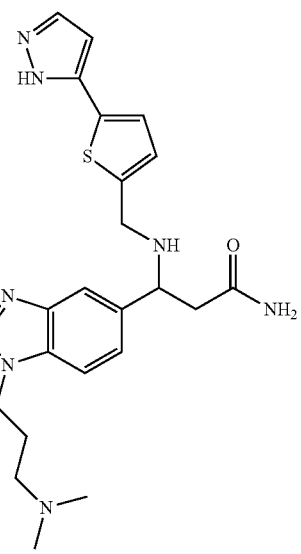

2-((4-(5-(1-(((5-(1H-pyrazol-5-yl)thiophen-2-yl)methyl) amino)-3-amino-3-oxopropyl)-1-(3-(dimethylamino)propyl)-1H-benzo[d]imidazol-2-yl)phenyl)(2-hydroxyethyl) amino)ethyl acetate was prepared using the procedure detailed above with Method C. MALDI-TOF MS: m+H=673.41.

Example 65. LLS67. 2-((4-(1-(3-(1H-imidazol-1-yl) propyl)-5-(3-amino-3-oxo-1-((4-(pyridin-4-yl)benzyl)amino)propyl)-1H-benzo[d]imidazol-2-yl)phenyl)(2-hydroxyethyl)amino)ethyl Acetate

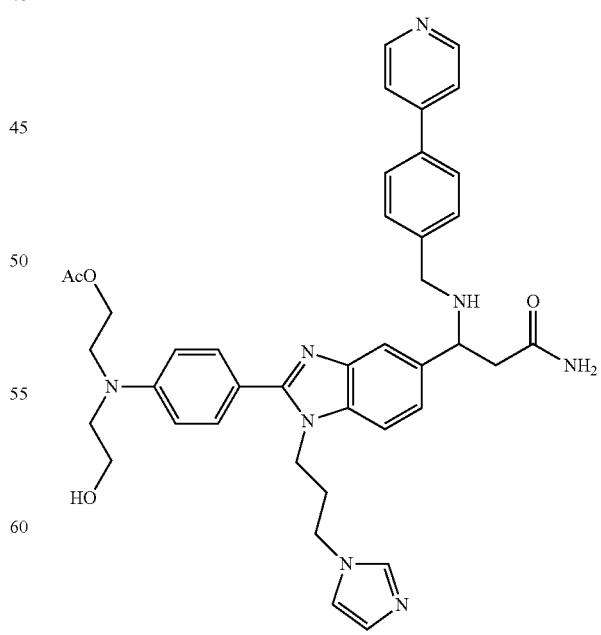

2-((4-(1-(3-(1H-imidazol-1-yl)propyl)-5-(3-amino-3-oxo-1-((4-(pyridin-4-yl)benzyl)amino)propyl)-1H-benzo[d]

imidazol-2-yl)phenyl)(2-hydroxyethyl)amino)ethyl acetate was prepared using the procedure detailed above with Method C. MALDI-TOF MS: m+H=701.48.

Example 66. LLS69Ac. ((4-(5-(1-(((1H-indol-5-yl)methyl)amino)-3-amino-3-oxopropyl)-1-(4-methoxyphenethyl)-1H-benzo[d]imidazol-2-yl)phenyl)azanediyl)bis(ethane-2,1-diyl) Diacetate

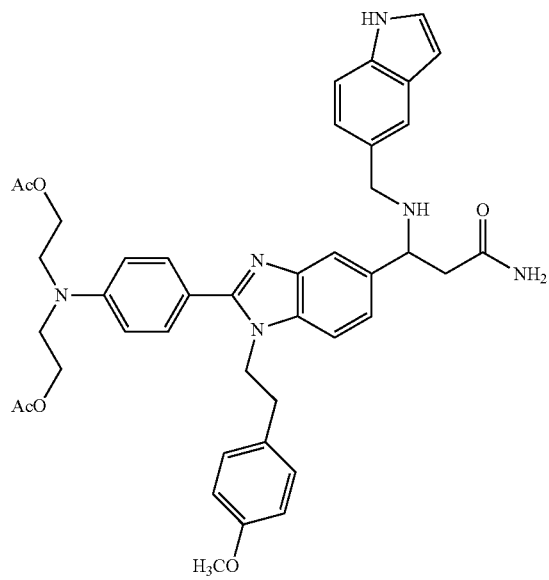 [SMILES: COc1ccc(CCn2c(-c3ccc(N(CCOC(C)=O)CCOC(C)=O)cc3)nc3cc(C(CC(N)=O)NCc4ccc5[nH]ccc5c4)ccc32)cc1]

((4-(5-(1-(((1H-indol-5-yl)methyl)amino)-3-amino-3-oxopropyl)-1-(4-methoxyphenethyl)-1H-benzo[d]imidazol-2-yl)phenyl)azanediyl)bis(ethane-2,1-diyl) diacetate was prepared using the procedure detailed above with Method C. MALDI-TOF MS: m+H=731.25.

Example 67. LLS71. 3-(2-(4-(bis(2-hydroxyethyl)amino)phenyl)-1-(4-(trifluoromethyl)benzyl)-1H-benzo[d]imidazol-5-yl)-3-((cyclohexylmethyl)amino)propanamide

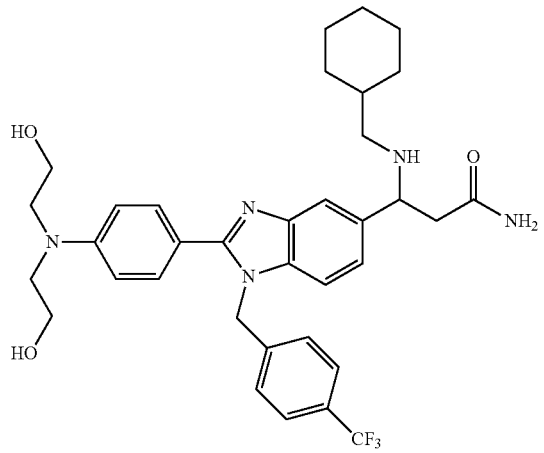 [SMILES: NC(=O)CC(NCC1CCCCC1)c1ccc2c(c1)nc(-c1ccc(N(CCO)CCO)cc1)n2Cc1ccc(C(F)(F)F)cc1]

3-(2-(4-(bis(2-hydroxyethyl)amino)phenyl)-1-(4-(trifluoromethyl)benzyl)-1H-benzo[d]imidazol-5-yl)-3-((cyclohex-ylmethyl)amino)propanamide was prepared using the procedure detailed above with Method C. MALDI-TOF MS: m+H=638.17.

Example 68. LLS73. 3-(2-(4-(bis(2-hydroxyethyl)amino)phenyl)-1-(4-(trifluoromethyl)benzyl)-1H-benzo[d]imidazol-5-yl)-3-((naphthalen-1-ylmethyl)amino)propanamide

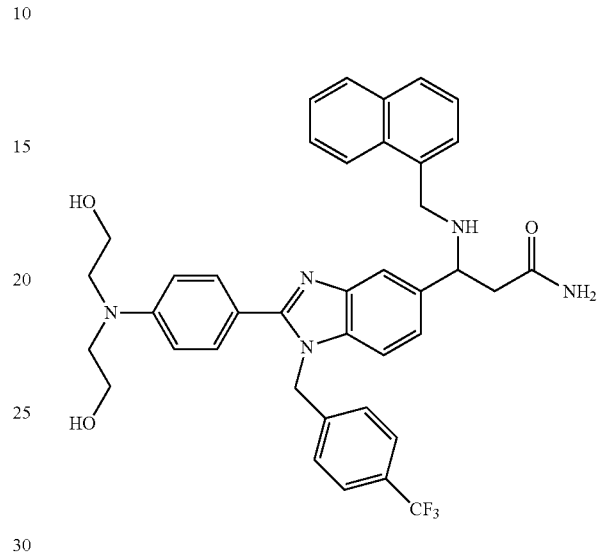

3-(2-(4-(bis(2-hydroxyethyl)amino)phenyl)-1-(4-(trifluoromethyl)benzyl)-1H-benzo[d]imidazol-5-yl)-3-((naphthalen-1-ylmethyl)amino)propanamide was prepared using the procedure detailed above with Method C. MALDI-TOF MS: m+H=682.67.

Example 69. LLS76. ((4-(5-(1,3-diamino-3-oxopropyl)-1-(4-methoxyphenethyl)-1H-benzo[d]imidazol-2-yl)phenyl)azanediyl)bis(ethane-2,1-diyl) Diacetate

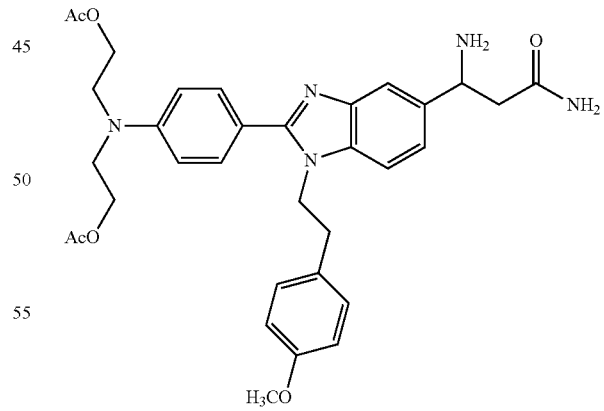

((4-(5-(1,3-diamino-3-oxopropyl)-1-(4-methoxyphenethyl)-1H-benzo[d]imidazol-2-yl)phenyl)azanediyl)bis(ethane-2,1-diyl) diacetate was prepared using the procedure detailed above synthesized without coupling of R³ and with cleavage off the beads after Alloc-deprotection by a mixture of 95% TFA, 2.5% TIS, and 2.5% water. MALDI-TOF MS: m+H=624.33.

Example 70. LLS77. 3-(((1H-indazol-5-yl)methyl) amino)-3-(2-(4-(bis(2-hydroxyethyl)amino)phenyl)-1-(4-(trifluoromethyl)benzyl)-1H-benzo[d]imidazol-5-yl)propanamide

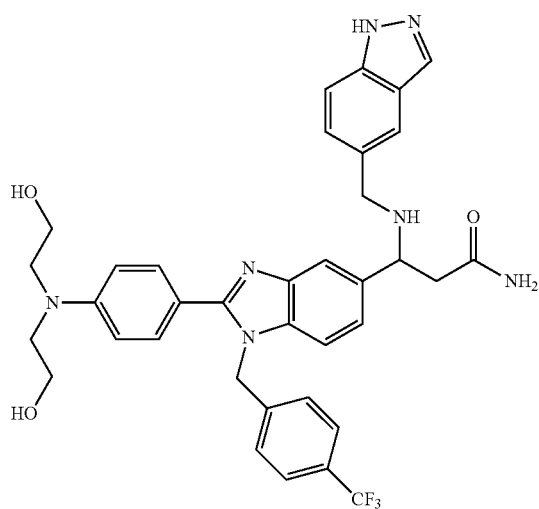 [SMILES: NC(=O)CC(NCc1ccc2[nH]ncc2c1)c1ccc2c(c1)nc(-c1ccc(N(CCO)CCO)cc1)n2Cc1ccc(C(F)(F)F)cc1]

3-(((1H-indazol-5-yl)methyl)amino)-3-(2-(4-(bis(2-hydroxyethyl)amino)phenyl)-1-(4-(trifluoromethyl)benzyl)-1H-benzo[d]imidazol-5-yl)propanamide was prepared using the procedure detailed above with Method C. MALDI-TOF MS: m+H=672.34.

Example 71. LLS78. ((4-(5-(1-(((5-(1H-pyrazol-5-yl)thiophen-2-yl)methyl)amino)-3-amino-3-oxopropyl)-1-(3-(dimethylamino)propyl)-1H-benzo[d]imidazol-2-yl)phenyl)azanediyl)bis(ethane-2,1-diyl) Diacetate

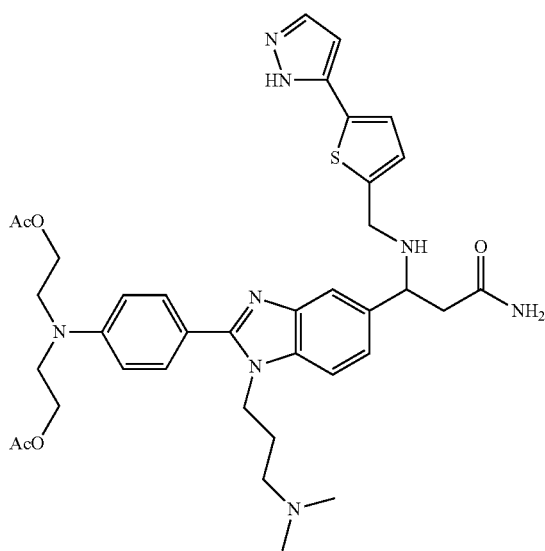 [SMILES: CC(=O)OCCN(CCOC(C)=O)c1ccc(-c2nc3cc(C(CC(N)=O)NCc4ccc(-c5ccn[nH]5)s4)ccc3n2CCCN(C)C)cc1]

((4-(5-(1-(((5-(1H-pyrazol-5-yl)thiophen-2-yl)methyl)amino)-3-amino-3-oxopropyl)-1-(3-(dimethylamino)propyl)-1H-benzo[d]imidazol-2-yl)phenyl)azanediyl)bis(ethane-2,1-diyl) diacetate was prepared using the procedure detailed above with Method C. MALDI-TOF MS: m+H=715.44.

Example 72. LLS80. 3-((cyclohexylmethyl)amino)-3-(2-(4-morpholinophenyl)-1-(4-(trifluoromethoxy)benzyl)-1H-benzo[d]imidazol-5-yl)propanamide

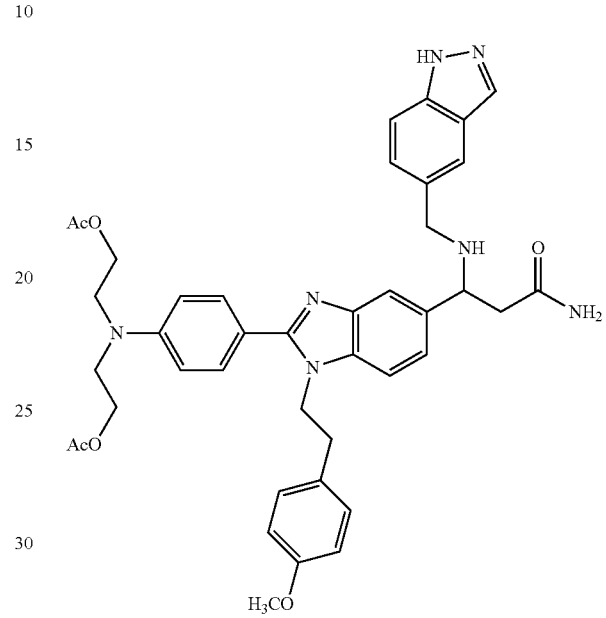

3-((cyclohexylmethyl)amino)-3-(2-(4-morpholinophenyl)-1-(4-(trifluoromethoxy)benzyl)-1H-benzo[d]imidazol-5-yl)propanamide was prepared using the procedure detailed above with Method C. MALDI-TOF MS: m+H=636.35.

Example 73. LLS82. 3-((cyclohexylmethyl)amino)-3-(2-(4-morpholinophenyl)-1-(4-(trifluoromethoxy)phenethyl)-1H-benzo[d]imidazol-5-yl)propanamide

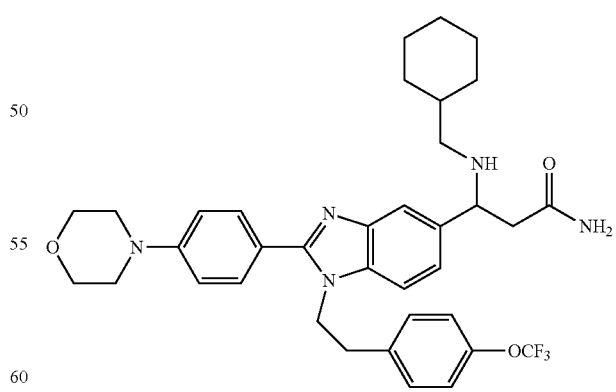

3-((cyclohexylmethyl)amino)-3-(2-(4-morpholinophenyl)-1-(4-(trifluoromethoxy)phenethyl)-1H-benzo[d]imidazol-5-yl)propanamide was prepared using the procedure detailed above with Method C. MALDI-TOF MS: m+H=650.36

Examples 74-100. Compounds LLS82A to LLS109

| Ex. | Structure | Chemical name | Preparation Method | Formula and MALDI-TOF MS |
|---|---|---|---|---|
| 74 LLS83 | 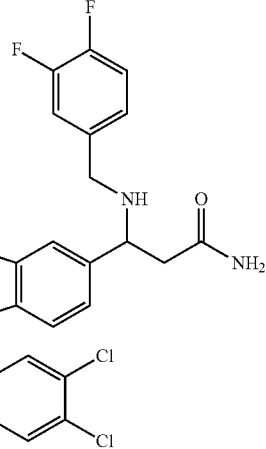 | 3-(2-(4-(bis(2-hydroxyethyl)amino)phenyl)-1-(3,4-dichlorobenzyl)-1H-benzo[d]imidazol-5-yl)-3-((3,4-difluorobenzyl)amino)propanamide | C | Chemical Formula: C34H33Cl2F2N5O3 Exact Mass: 667.19 MALDI-TOF MS: m + H = 668.36 |
| 75 LLS84 | 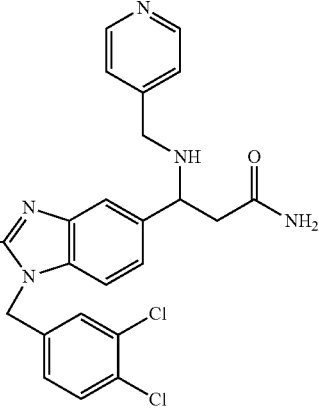 | 3-(2-(4-(bis(2-hydroxyethyl)amino)phenyl)-1-(3,4-dichlorobenzyl)-1H-benzo[d]imidazol-5-yl)-3-((pyridin-4-ylmethyl)amino)propanamide | C | Chemical Formula: C33H34Cl2N6O3 Exact Mass: 632.21 MALDI-TOF MS: m + H = 633.33 |
| 76 LLS85 | 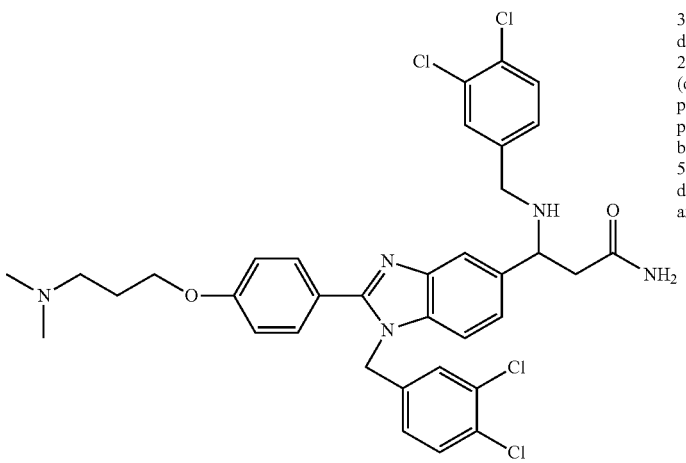 | 3-(1-(3,4-dichlorobenzyl)-2-(4-(3-(dimethylamino)propoxy)phenyl)-1H-benzo[d]imidazol-5-yl)-3-((3,4-dichlorobenzyl)amino)propanamide | C | Chemical Formula: C35H35Cl4N5O2 Exact Mass: 697.15 MALDI-TOF MS: m + H = 698.28 |

-continued

| Ex. | Structure | Chemical name | Preparation Method | Formula and MALDI-TOF MS |
|---|---|---|---|---|
| 77 LLS86 | 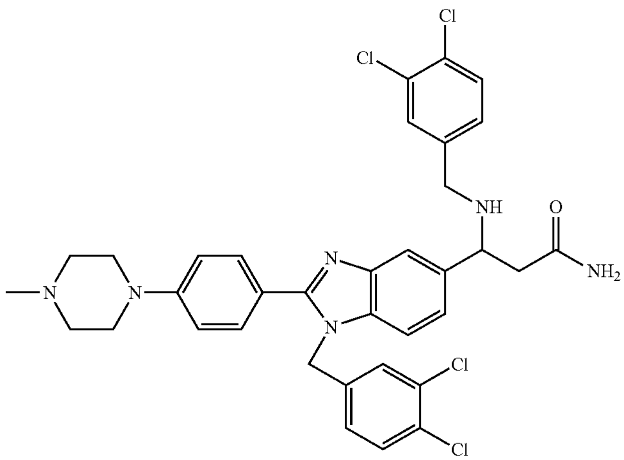 [SMILES: CN1CCN(c2ccc(-c3nc4cc(C(CC(N)=O)NCc5ccc(Cl)c(Cl)c5)ccc4n3Cc3ccc(Cl)c(Cl)c3)cc2)CC1] | 3-(1-(3,4-dichlorobenzyl)-2-(4-(4-methylpiperazin-1-yl)phenyl)-1H-benzo[d]imidazol-5-yl)-3-((3,4-dichlorobenzyl)amino)propanamide | C | Chemical Formula: C35H34Cl4N6O Exact Mass: 694.15 MALDI-TOF MS: m + H = 695.36 |
| 78 LLS87 | 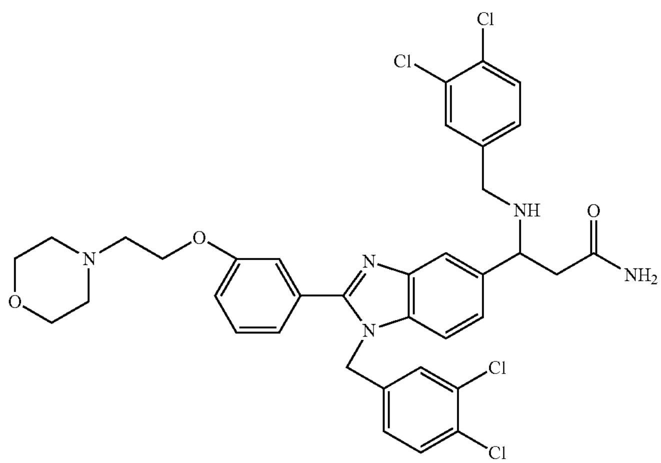 [SMILES: NC(=O)CC(NCc1ccc(Cl)c(Cl)c1)c1ccc2c(c1)nc(-c1cccc(OCCN3CCOCC3)c1)n2Cc1ccc(Cl)c(Cl)c1] | 3-(1-(3,4-dichlorobenzyl)-2-(3-(2-morpholinoethoxy)phenyl)-1H-benzo[d]imidazol-5-yl)-3-((3,4-dichlorobenzyl)amino)propanamide | C | Chemical Formula: C36H35Cl4N5O3 Exact Mass: 725.15 MALDI-TOF MS: m + H = 726.28 |
| 79 LLS88 | 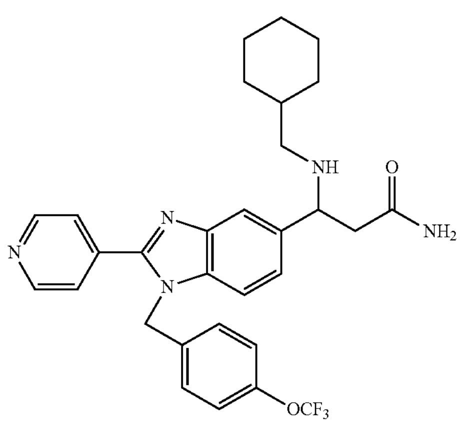 [SMILES: NC(=O)CC(NCC1CCCCC1)c1ccc2c(c1)nc(-c1ccncc1)n2Cc1ccc(OC(F)(F)F)cc1] | 3-((cyclohexylmethyl)amino)-3-(2-(pyridin-4-yl)-1-(4-(trifluoromethoxy)benzyl)-1H-benzo[d]imidazol-5-yl)propanamide | C | Chemical Formula: C30H32F3N5O2 Exact Mass: 551.25 MALDI-TOF MS: m + H = 552.32 |

-continued

| Ex. | Structure | Chemical name | Preparation Method | Formula and MALDI-TOF MS |
|---|---|---|---|---|
| 80 LLS89 | 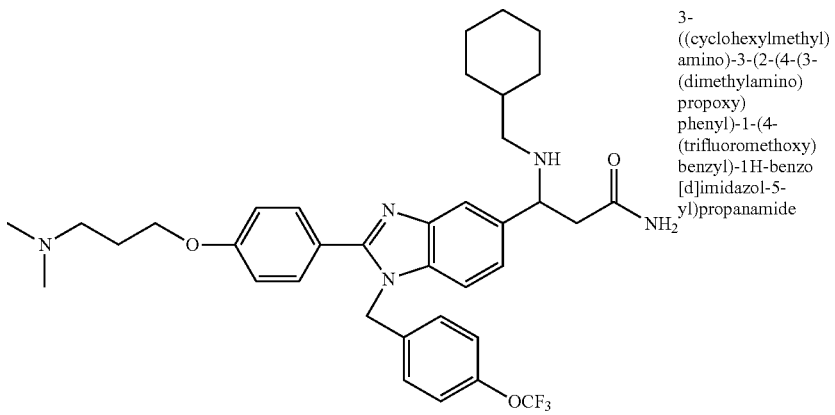 | 3-((cyclohexylmethyl)amino)-3-(2-(4-(3-(dimethylamino)propoxy)phenyl)-1-(4-(trifluoromethoxy)benzyl)-1H-benzo[d]imidazol-5-yl)propanamide | C | Chemical Formula: C36H44F3N5O3 Exact Mass: 651.34 MALDI-TOF MS: m + H = 652.44 |
| 81 LLS90 | 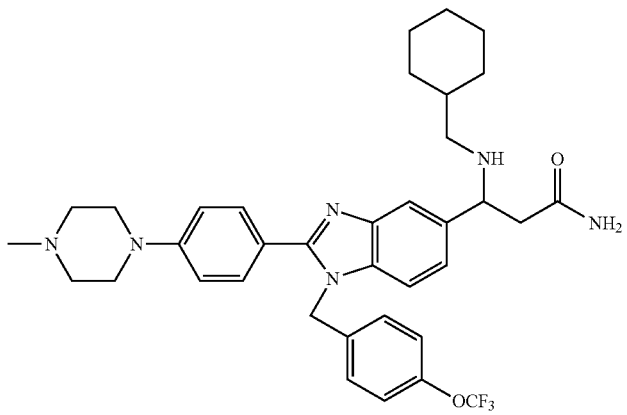 [SMILES: CN1CCN(c2ccc(-c3nc4cc(C(CC(N)=O)NCC5CCCCC5)ccc4n3Cc3ccc(OC(F)(F)F)cc3)cc2)CC1] | 3-((cyclohexylmethyl)amino)-3-(2-(4-(4-methylpiperazin-1-yl)phenyl)-1-(4-(trifluoromethoxy)benzyl)-1H-benzo[d]imidazol-5-yl)propanamide | C | Chemical Formula: C36H43F3N6O2 Exact Mass: 648.34 MALDI-TOF MS: m + H = 649.48 |
| 82 LLS91 | 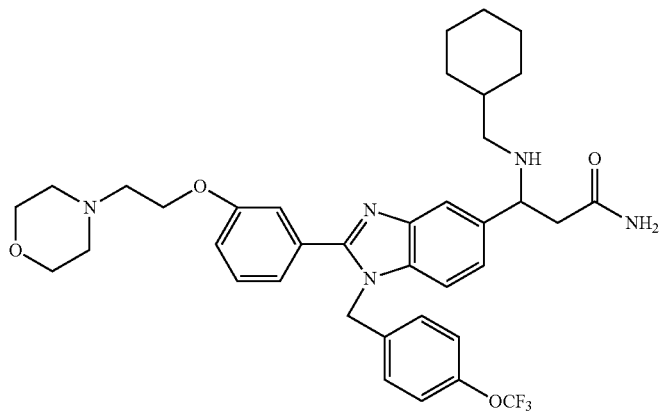 [SMILES: NC(=O)CC(NCC1CCCCC1)c1ccc2c(c1)nc(-c1cccc(OCCN3CCOCC3)c1)n2Cc1ccc(OC(F)(F)F)cc1] | 3-((cyclohexylmethyl)amino)-3-(2-(3-(2-morpholinoethoxy)phenyl)-1-(4-(trifluoromethoxy)benzyl)-1H-benzo[d]imidazol-5-yl)propanamide | C | Chemical Formula: C37H44F3N5O4 Exact Mass: 679.33 MALDI-TOF MS: m + H = 680.52 |

-continued

| Ex. | Structure | Chemical name | Preparation Method | Formula and MALDI-TOF MS |
|---|---|---|---|---|
| 83 LLS92 | 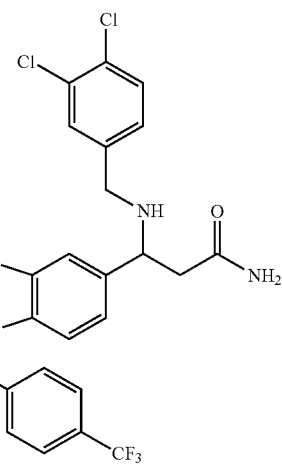 | 3-(2-(4-(bis(2-hydroxyethyl)amino)phenyl)-1-(4-(trifluoromethyl)benzyl)-1H-benzo[d]imidazol-5-yl)-3-((3,4-dichlorobenzyl)amino)propanamide | C | Chemical Formula: C35H34Cl2F3N5O3 Exact Mass: 699.20 MALDI-TOF MS: m + H = 700.34 |
| 84 LLS93 | 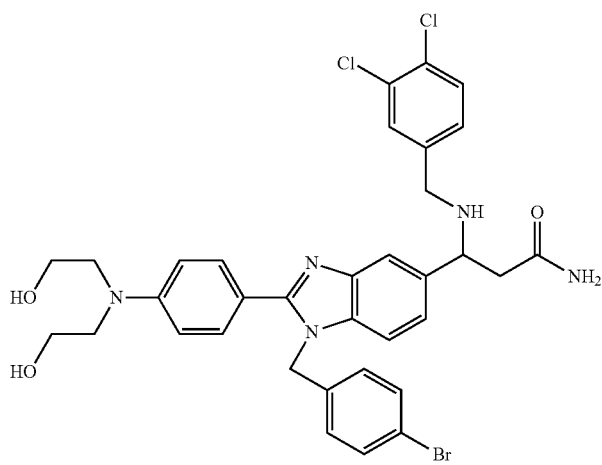 [SMILES: NC(=O)CC(NCc1ccc(Cl)c(Cl)c1)c1ccc2c(c1)nc(-c1ccc(N(CCO)CCO)cc1)n2Cc1ccc(Br)cc1] | 3-(2-(4-(bis(2-hydroxyethyl)amino)phenyl)-1-(4-bromobenzyl)-1H-benzo[d]imidazol-5-yl)-3-((3,4-dichlorobenzyl)amino)propanamide | C | Chemical Formula: C34H34BrCl2N5O3 Exact Mass: 709.12 MALDI-TOF MS: m + H = 710.38, 712.38 |
| 85 LLS94 | 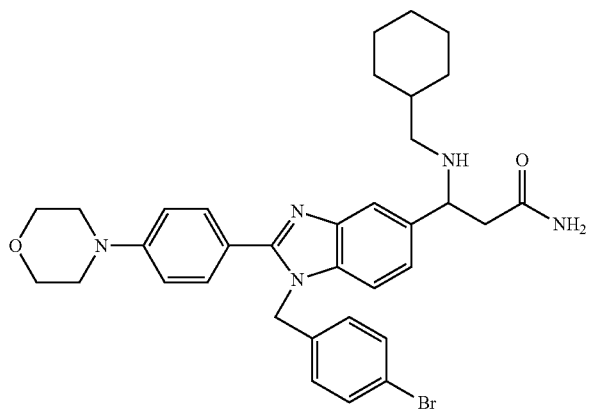 [SMILES: NC(=O)CC(NCC1CCCCC1)c1ccc2c(c1)nc(-c1ccc(N3CCOCC3)cc1)n2Cc1ccc(Br)cc1] | 3-(1-(4-bromobenzyl)-2-(4-morpholinophenyl)-1H-benzo[d]imidazol-5-yl)-3-((cyclohexylmethyl)amino)propanamide | C | Chemical Formula: C34H40BrN5O2 Exact Mass: 629.24 MALDI-TOF MS: m + H = 630.38, 632.38 |

-continued

| Ex. | Structure | Chemical name | Preparation Method | Formula and MALDI-TOF MS |
|---|---|---|---|---|
| 86 LLS95 | 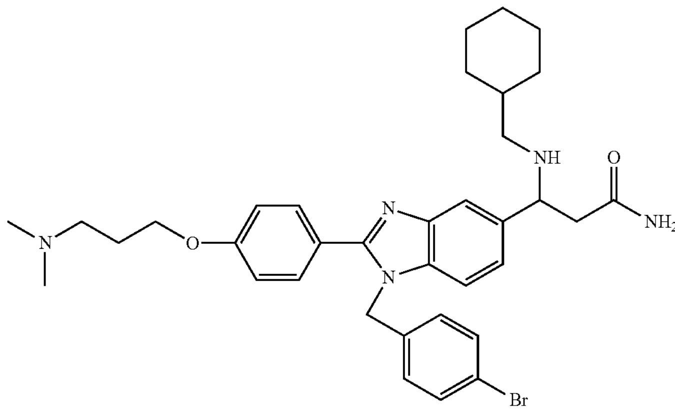 [SMILES: CN(C)CCCOc1ccc(-c2nc3cc(C(CC(N)=O)NCC4CCCCC4)ccc3n2Cc2ccc(Br)cc2)cc1] | 3-(1-(4-bromobenzyl)-2-(4-(3-(dimethylamino)propoxy)phenyl)-1H-benzo[d]imidazol-5-yl)-3-((cyclohexylmethyl)amino)propanamide | C | Chemical Formula: C35H44BrN5O2 Exact Mass: 645.27 MALDI-TOF MS: m + H = 646.41, 648.41 |
| 87 LLS96 | 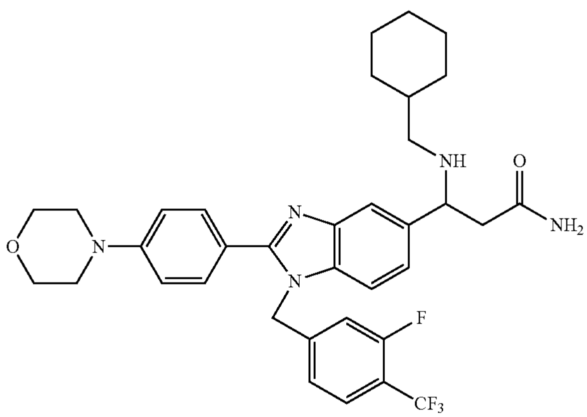 [SMILES: NC(=O)CC(NCC1CCCCC1)c1ccc2c(c1)nc(-c1ccc(N3CCOCC3)cc1)n2Cc1ccc(C(F)(F)F)c(F)c1] | 3-((cyclohexylmethyl)amino)-3-(1-(3-fluoro-4-(trifluoromethyl)benzyl)-2-(4-morpholinophenyl)-1H-benzo[d]imidazol-5-yl)propanamide | C | Chemical Formula: C35H39F4N5O2 Exact Mass: 637.30 MALDI-TOF MS: m + H = 638.50 |
| 88 LLS97 | 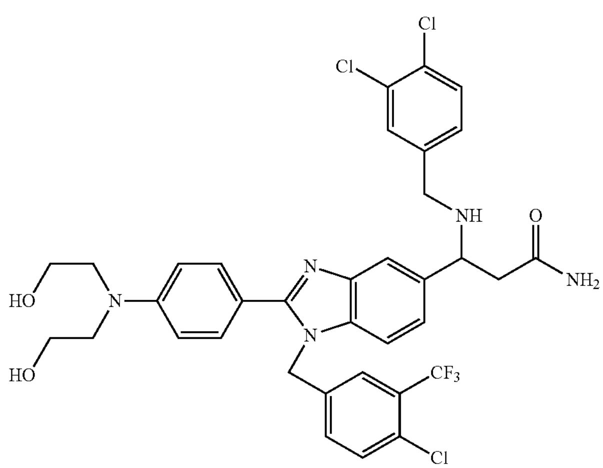 [SMILES: NC(=O)CC(NCc1ccc(Cl)c(Cl)c1)c1ccc2c(c1)nc(-c1ccc(N(CCO)CCO)cc1)n2Cc1ccc(Cl)c(C(F)(F)F)c1] | 3-(2-(4-(bis(2-hydroxyethyl)amino)phenyl)-1-(4-chloro-3-(trifluoromethyl)benzyl)-1H-benzo[d]imidazol-5-yl)-3-((3,4-dichlorobenzyl)amino)propanamide | C | Chemical Formula: C35H33Cl3F3N5O3 Exact Mass: 733.16 MALDI-TOF MS: m + H = 734.30 |

-continued

| Ex. | Structure | Chemical name | Preparation Method | Formula and MALDI-TOF MS |
|---|---|---|---|---|
| 89 LLS98 | 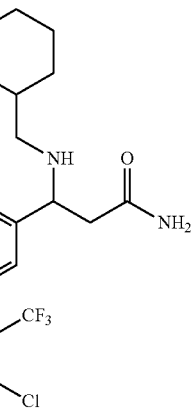 | 3-(1-(4-chloro-3-(trifluoromethyl)benzyl)-2-(4-morpholinophenyl)-1H-benzo[d]imidazol-5-yl)-3-((cyclohexylmethyl)amino)propanamide | C | Chemical Formula: C35H39ClF3N5O2 Exact Mass: 653.27 MALDI-TOF MS: m + H = 654.45 |
| 90 LLS99 | 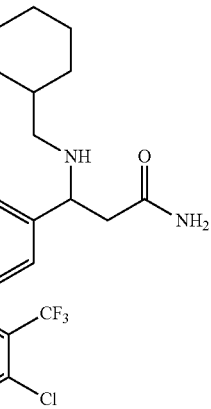 | 3-(1-(4-chloro-3-(trifluoromethyl)benzyl)-2-(4-(4-methylpiperazin-1-yl)phenyl)-1H-benzo[d]imidazol-5-yl)-3-((cyclohexylmethyl)amino)propanamide | C | Chemical Formula: C36H42ClF3N6O Exact Mass: 666.31 MALDI-TOF MS: m + H = 667.50 |
| 91 LLS100 | 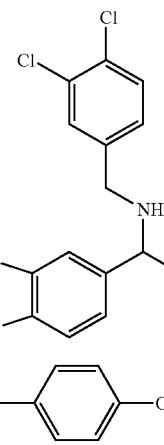 | 3-(2-(4-(bis(2-hydroxyethyl)amino)phenyl)-1-(4-(trifluoromethoxy)phenethyl)-1H-benzo[d]imidazol-5-dichlorobenzyl)amino)propanamide | C | Chemical Formula: C36H36Cl2F3N5O4 Exact Mass: 729.21 MALDI-TOF MS: m + H = 730.43 |

| Ex. | Structure | Chemical name | Preparation Method | Formula and MALDI-TOF MS |
|---|---|---|---|---|
| 92 LLS101 | 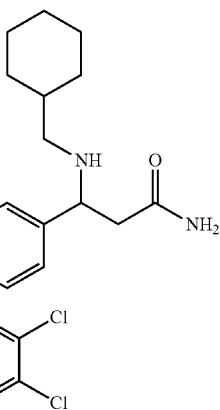 | 3-(2-(4-(bis(2-hydroxyethyl)amino)phenyl)-1-(3,4-dichlorobenzyl)-1H-benzo[d]imidazol-5-yl)-3-((cyclohexylmethyl)amino)propanamide | C | Chemical Formula: C34H41Cl2N5O3 Exact Mass: 637.26 MALDI-TOF MS: m + H = 638.45 |
| 93 LLS102 | 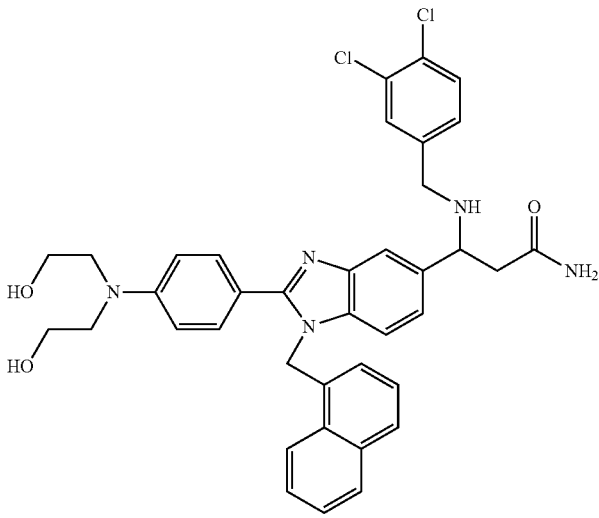 [SMILES: NC(=O)CC(NCc1ccc(Cl)c(Cl)c1)c1ccc2c(c1)nc(-c1ccc(N(CCO)CCO)cc1)n2Cc1cccc2ccccc12] | 3-(2-(4-(bis(2-hydroxyethyl)amino)phenyl)-1-(naphthalen-1-ylmethyl)-1H-benzo[d]imidazol-5-yl)-3-((3,4-dichlorobenzyl)amino)propanamide | C | Chemical Formula: C38H37Cl2N5O3 Exact Mass: 681.23 MALDI-TOF MS: m + H = 682.36 |
| 94 LLS103 | 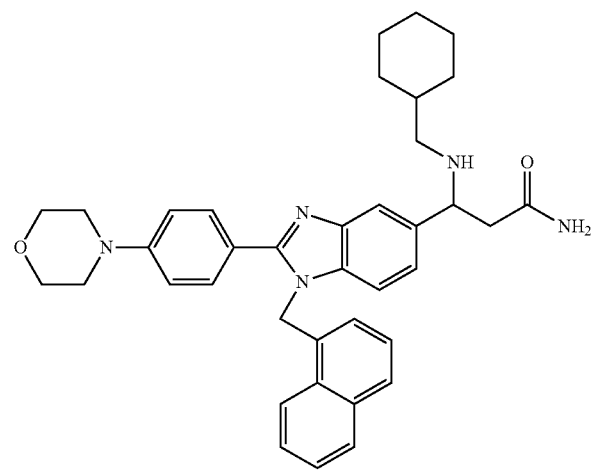 [SMILES: NC(=O)CC(NCC1CCCCC1)c1ccc2c(c1)nc(-c1ccc(N3CCOCC3)cc1)n2Cc1cccc2ccccc12] | 3-((cyclohexylmethyl)amino)-3-(2-(4-morpholinophenyl)-1-(naphthalen-1-ylmethyl)-1H-benzo[d]imidazol-5-yl)propanamide | C | Chemical Formula: C38H43N5O2 Exact Mass: 601.34 MALDI-TOF MS: m + H = 602.55 |

-continued

| Ex. | Structure | Chemical name | Preparation Method | Formula and MALDI-TOF MS |
|---|---|---|---|---|
| 95 LLS104 | 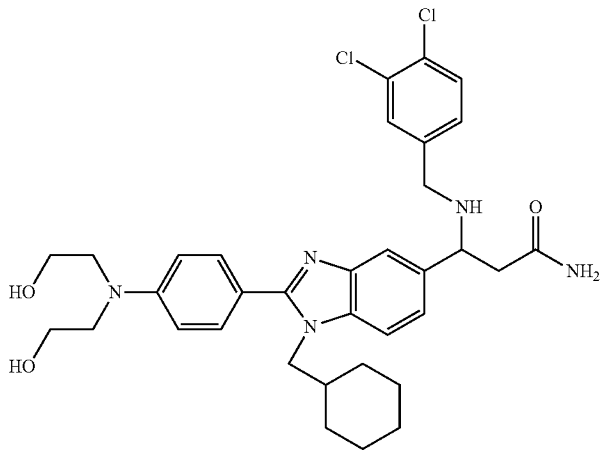 [SMILES: NC(=O)CC(NCc1ccc(Cl)c(Cl)c1)c1ccc2c(c1)nc(-c1ccc(N(CCO)CCO)cc1)n2CC1CCCCC1] | 3-(2-(4-(bis(2-hydroxyethyl)amino)phenyl)-1-(cyclohexylmethyl)-1H-benzo[d]imidazol-5-yl)-3-((3,4-dichlorobenzyl)amino)propanamide | C | Chemical Formula: C34H41Cl2N5O3<br>Exact Mass: 637.26<br>MALDI-TOF MS: m + H = 638.38 |
| 96 LLS105 | 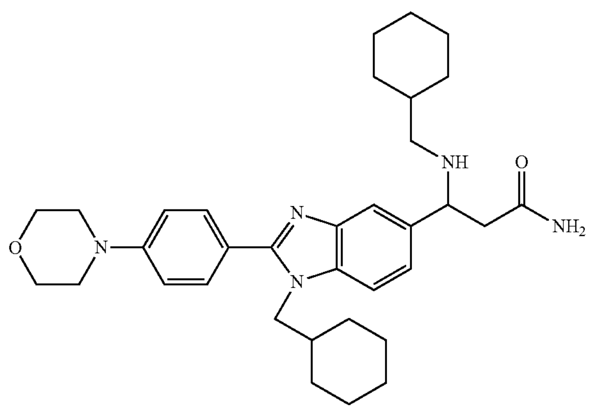 [SMILES: NC(=O)CC(NCC1CCCCC1)c1ccc2c(c1)nc(-c1ccc(N3CCOCC3)cc1)n2CC1CCCCC1] | 3-(1-(cyclohexylmethyl)-2-(4-morpholinophenyl)-1H-benzo[d]imidazol-5-yl)-3-((cyclohexylmethyl)amino)propanamide | C | Chemical Formula: C34H47N5O2<br>Exact Mass: 557.37<br>MALDI-TOF MS: m + H = 558.79 |
| 97 LLS106 | 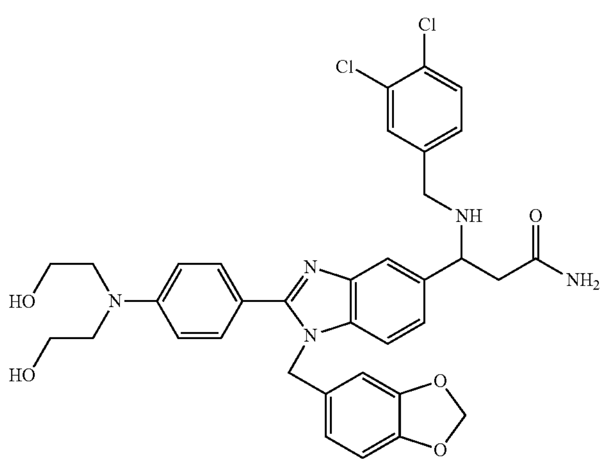 [SMILES: NC(=O)CC(NCc1ccc(Cl)c(Cl)c1)c1ccc2c(c1)nc(-c1ccc(N(CCO)CCO)cc1)n2Cc1ccc2c(c1)OCO2] | 3-(1-(benzo[d][1,3]dioxol-5-ylmethyl)-2-(4-(bis(2-hydroxyethyl)amino)phenyl)-1H-benzo[d]imidazol-5-yl)-3-((3,4-dichlorobenzyl)amino)propanamide | C | Chemical Formula: C35H35Cl2N5O5<br>Exact Mass: 675.20<br>MALDI-TOF MS: m + H = 676.30 |

-continued

| Ex. | Structure | Chemical name | Preparation Method | Formula and MALDI-TOF MS |
|---|---|---|---|---|
| 98 LLS107 | 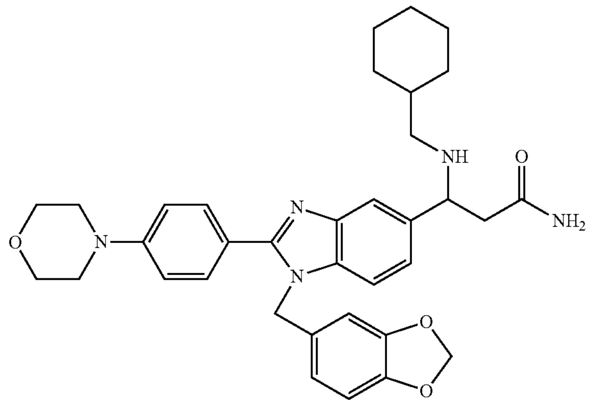 [SMILES: NC(=O)CC(NCC1CCCCC1)c1ccc2c(c1)nc(-c1ccc(N3CCOCC3)cc1)n2Cc1ccc2c(c1)OCO2] | 3-(1-(benzo[d][1,3] dioxol-5-ylmethyl)-2-(4-morpholinophenyl)-1H-benzo[d]imidazol-5-yl)-3-((cyclohexylmethyl)amino)propanamide | C | Chemical Formula: C35H41N5O4 Exact Mass: 595.32 MALDI-TOF MS: m + H = 596.39 |
| 99 LLS108 | 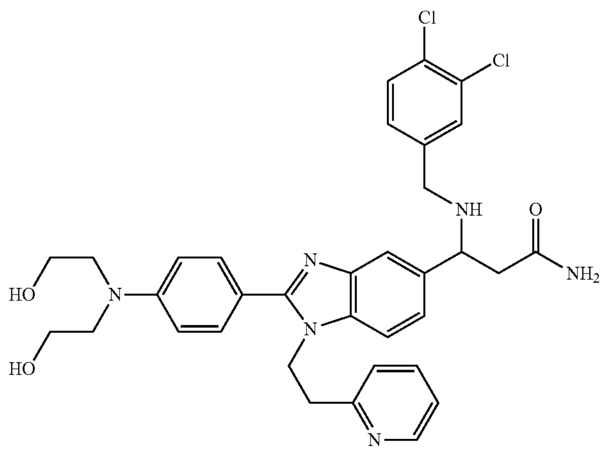 [SMILES: NC(=O)CC(NCc1ccc(Cl)c(Cl)c1)c1ccc2c(c1)nc(-c1ccc(N(CCO)CCO)cc1)n2CCc1ccccn1] | 3-(2-(4-(bis(2-hydroxyethyl)amino)phenyl)-1-(2-(pyridin-2-yl)ethyl)-1H-benzo[d]imidazol-5-yl)-3-((3,4-dichlorobenzyl)amino)propanamide | C | Chemical Formula: C34H36Cl2N6O3 Exact Mass: 646.22 MALDI-TOF MS: m + H = 647.33 |
| 100 LLS109 | 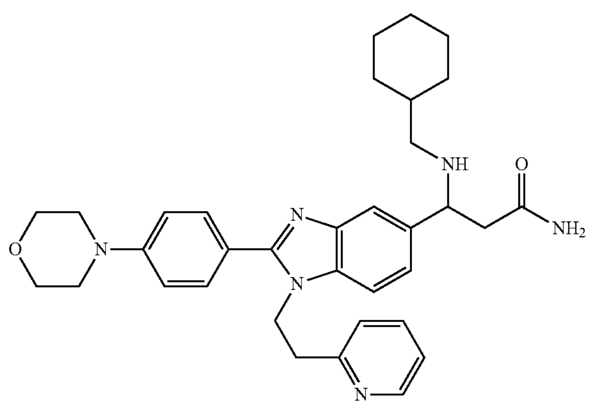 [SMILES: NC(=O)CC(NCC1CCCCC1)c1ccc2c(c1)nc(-c1ccc(N3CCOCC3)cc1)n2CCc1ccccn1] | 3-((cyclohexylmethyl)amino)-3-(2-(4-morpholinophenyl)-1-(2-(pyridin-2-yl)ethyl)-1H-benzo[d]imidazol-5-yl)propanamide | C | Chemical Formula: C34H42N6O2 Exact Mass: 566.34 MALDI-TOF MS: m + H = 567.44 |

Example 101. High-Throughput Screening of Compounds Using Immunocytochemistry

Figure 2:
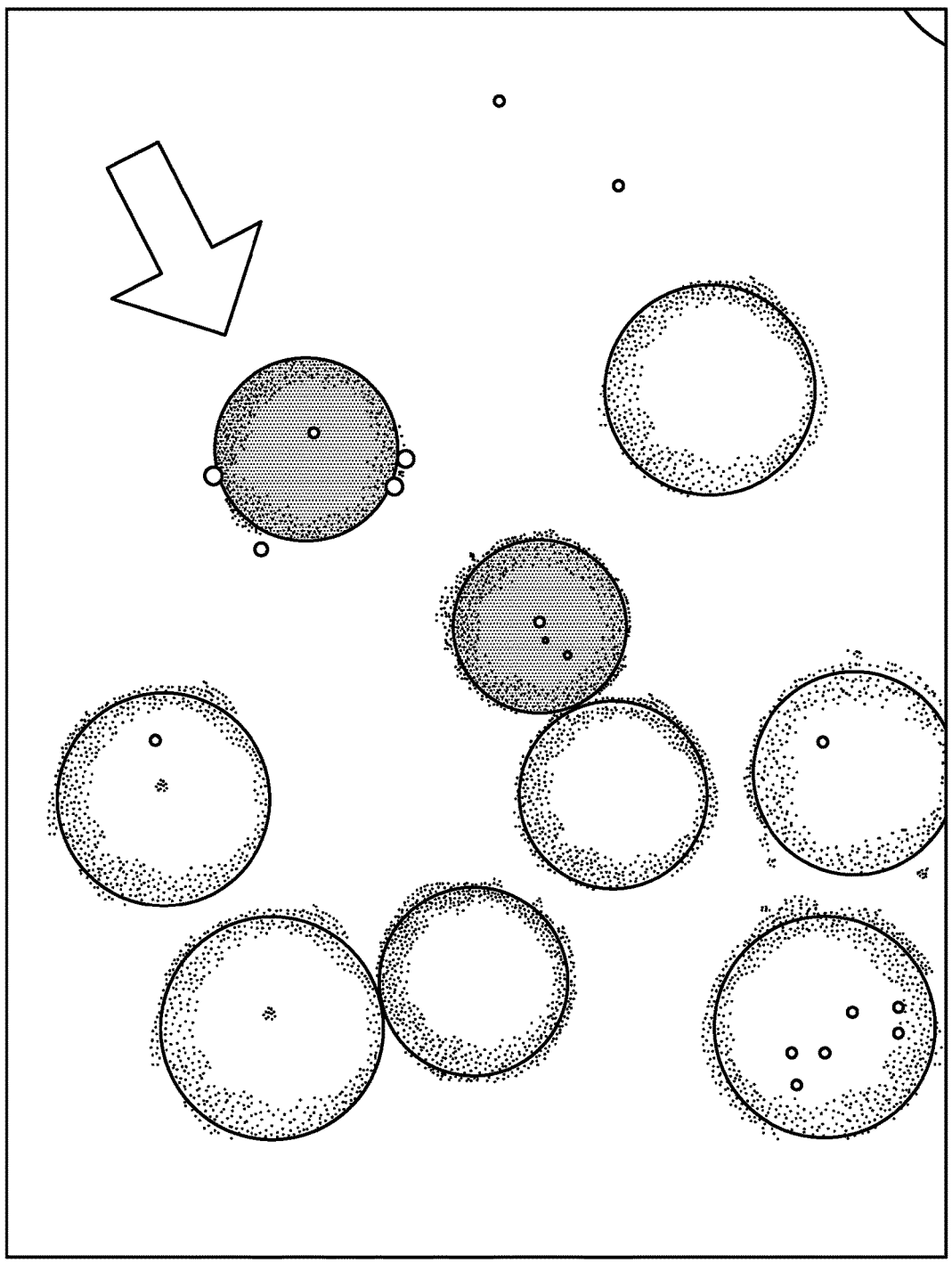
FIG. 2 shows photomicrograph results of a screening experiment using immunocytochemistry (anti-cleaved caspase 3 antibody) to stain bead-bound SVOV3 ovarian cancer cells.
Figure 3:
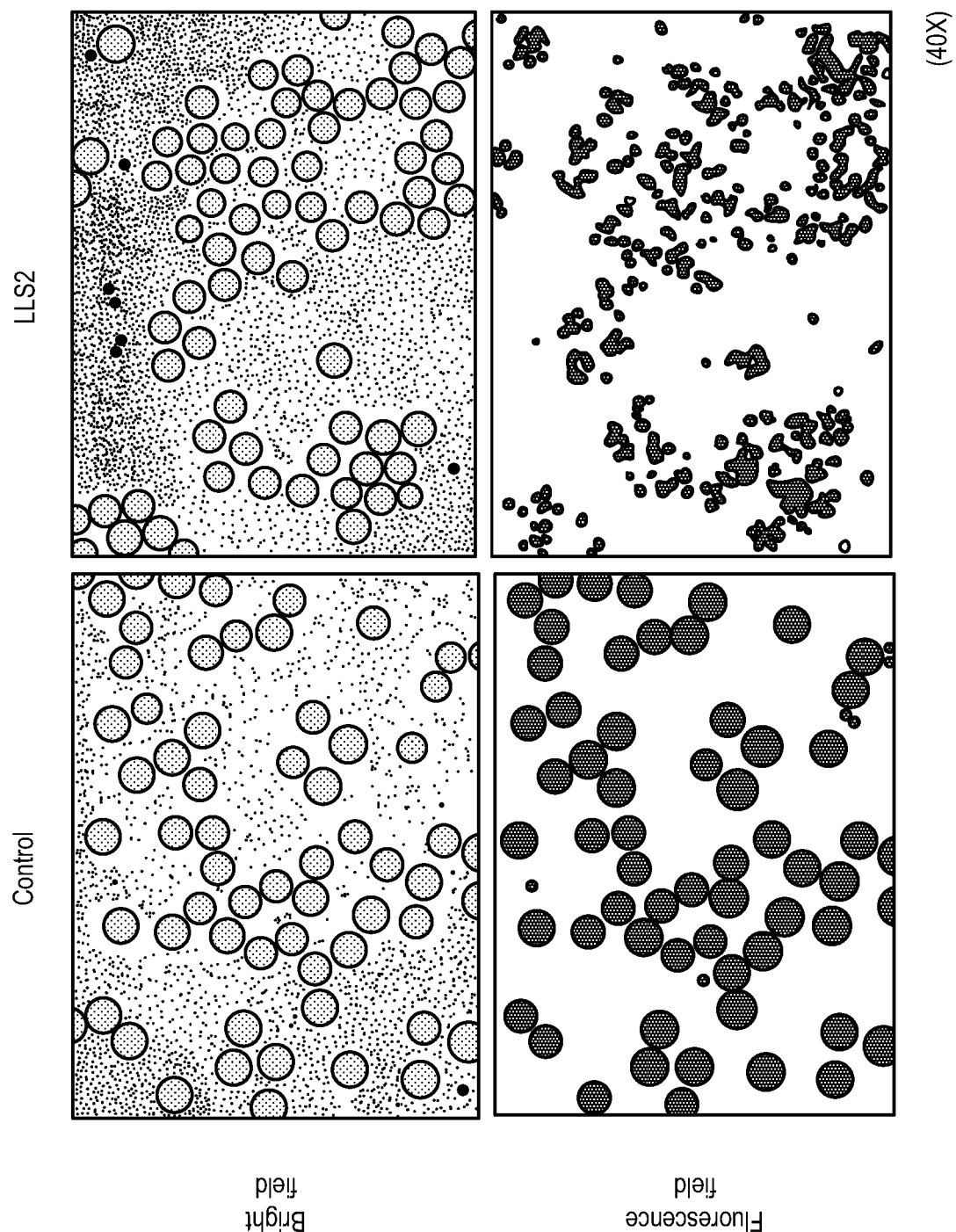
FIG. 3 shows propidium iodide staining of cells killed through treatment with LLS2.

A library of beads was created in which each bead displayed on its surface the cell-capturing molecule LXY30 and a benzimidazole compound. The LXY30 molecule is an alpha-3-beta-1 integrin binding ligand. Anti-cleaved caspase 3 antibody was used to perform immunocytochemistry staining of cells bound on library beads. An example of a positive result is shown in FIG. 2. Positive beads were physically isolated by hand-held micropipette and their chemical identity was determined by chemical decoding of a bead-associated peptide tag with automatic Edman microsequencing. Cell death was validated by the staining of late-apoptotic cells with propidium iodide as shown in FIG. 3.

Example 102. Confirmation of LLS2-Induced Cell Death

Figure 4:
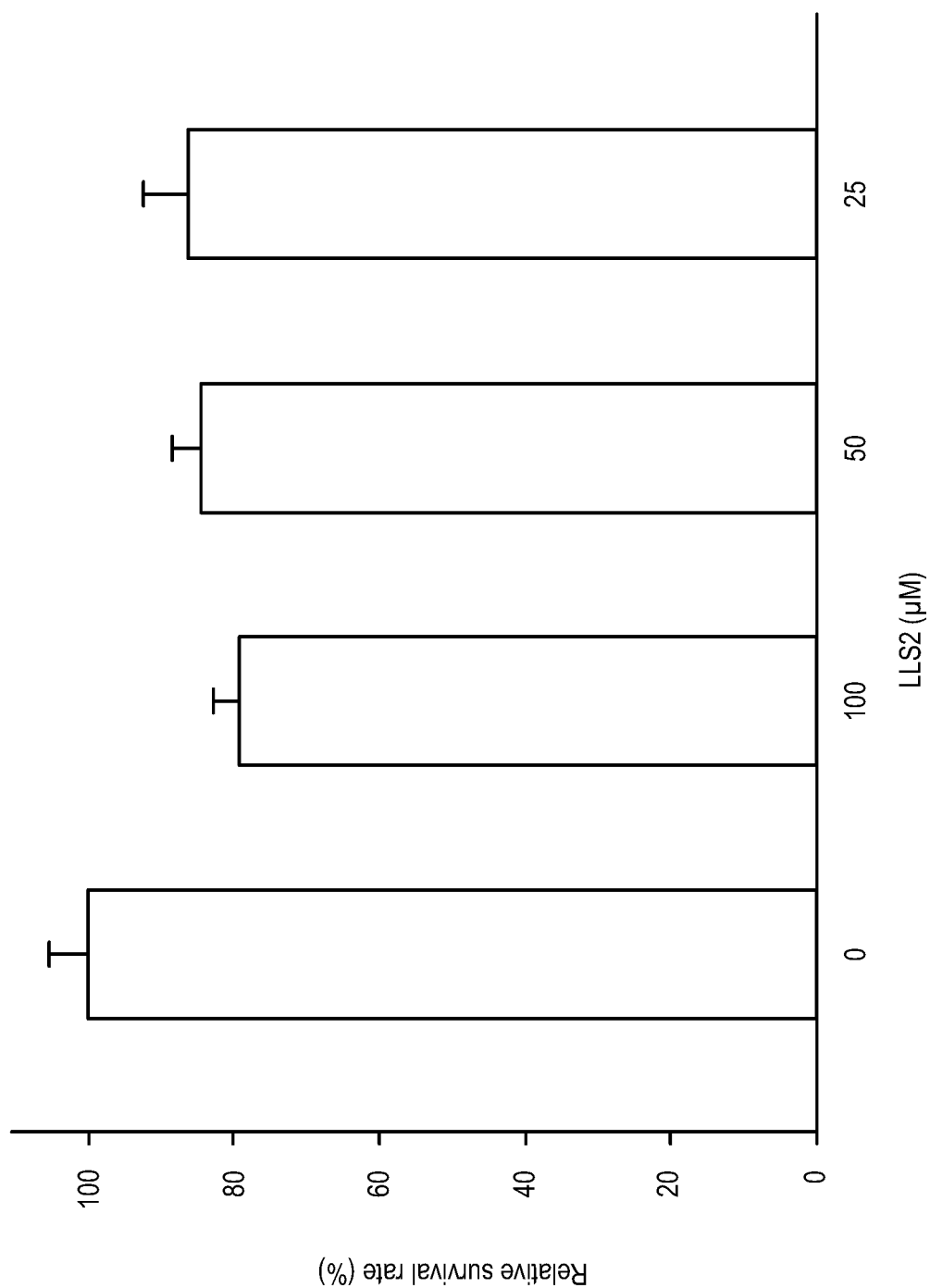
FIG. 4 shows cell viability assays for SKOV3 cells treated with various concentration of biotinylated LLS2 for 72 hours.
Figure 5:
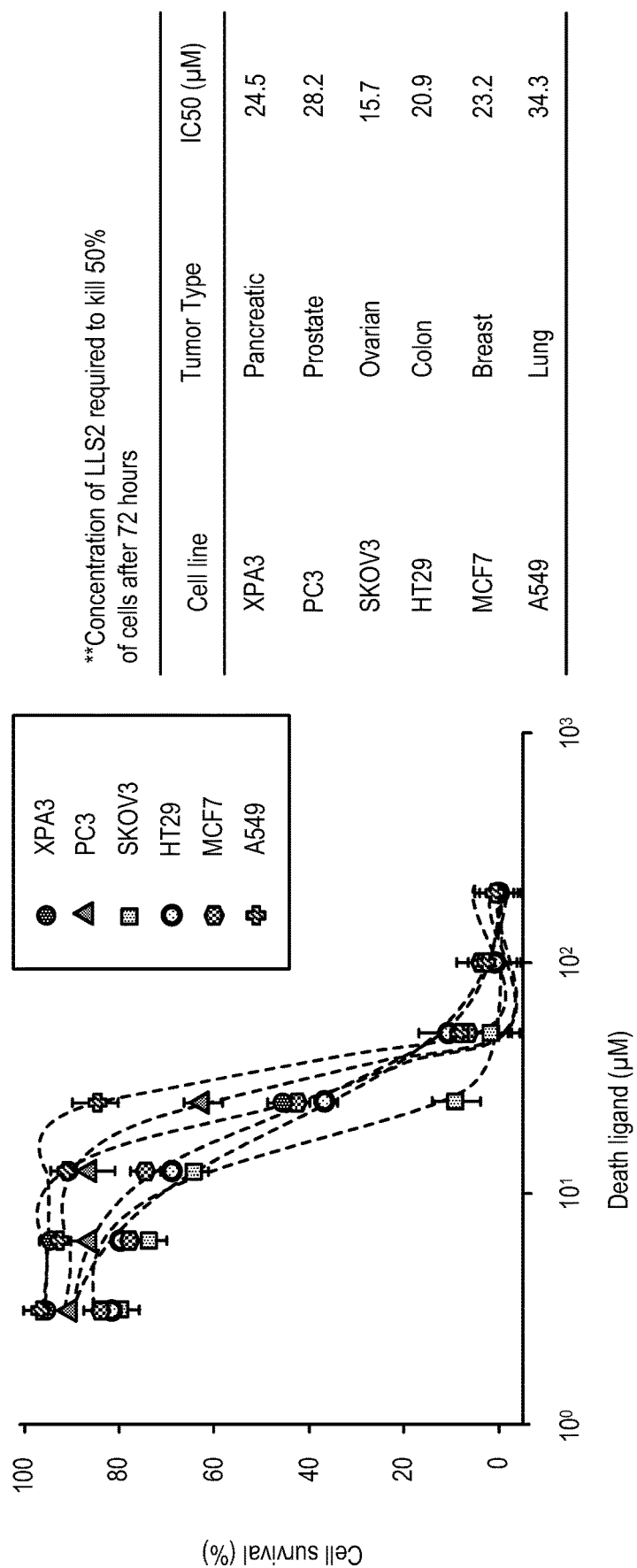
FIG. 5 shows the ability of soluble LLS2 to kill cells from different cancer cell lines.

Biotinylated LLS2 was synthesized in solution and loaded it onto a streptavidin-coated plate. The biotinylated LLS2 immobilized on the plate killed approximately 21% of SKOV3 ovarian cancer cells at 100 µM loading, 16% at 50 µM and 14% at 25 µM (FIG. 4). The killing effect of the LLS2 compound was also tested in solution. LLS2 was found to kill SKOV3 cells with an IC50 value of 15.7 µM (FIG. 5). In addition, LLS2 can kill pancreatic cancer cell line XPA3, prostate cancer cell line PC3, colon cancer cell line HT29, breast cancer cell line MCF7 and lung cancer cell line A549 (FIG. 4).

Example 103. Potentiation of Paclitaxel Anti-Tumor Activity on Cancer Cells

The synergistic effects of LLS2 with current chemotherapeutic drugs including docetaxel, paclitaxel, 5-Fu, oxaliplatin, carboplatin, doxorubicin and gemcitabine were examined in vitro. Among these chemodrugs, paclitaxel was of particular interest, since it has synergistic effect with LLS2 on many cancer cell lines. Paclitaxel was observed to exhibit moderate cytotoxicity against prostate cancer PC3 cancer cells, but had little effect on SKOV3 cells at particular concentrations. After combined treatment with LLS2, much stronger anti-proliferation effects were achieved (FIG. 6a). This synergistic effect was confirmed by measuring the combination index (CI) (FIG. 6b) and it was further determined at various concentrations of LLS2 and paclitaxel in SKOV3 (FIG. 6c). Increased apoptosis was observed after combined LLS2/paclitaxel treatment for 24 hours (FIG. 6d).

Figure 7A:
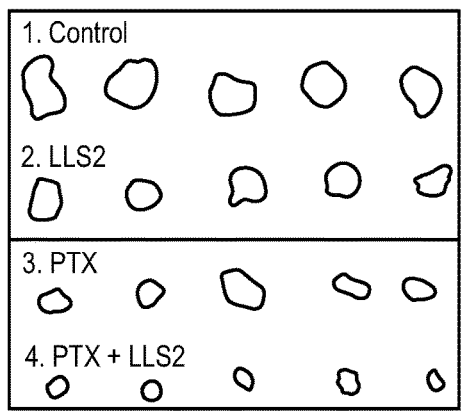
FIG. 7 shows (a) xenograft tumors. (b) tumor growth curves, (c) tumor weights of the xenografts in inoculated nude mice, and (d) body weights of nude mice. Briefly, 2.5×10$^6$ SKOV3 cells were subcutaneously injected to the right side of the dorsal flank of the female congenital athymic BALB/c nude mice. The tumors were allowed to grow to about 100 mm$^3$.
Figure 7B:
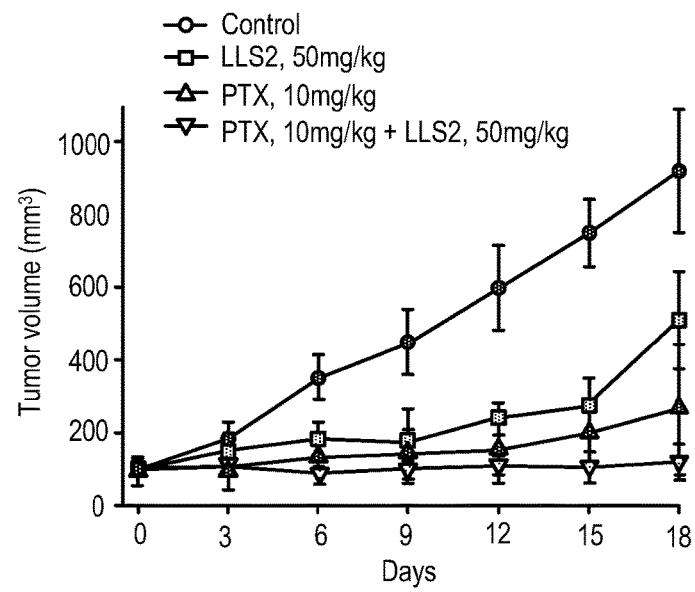
Figure 7C:
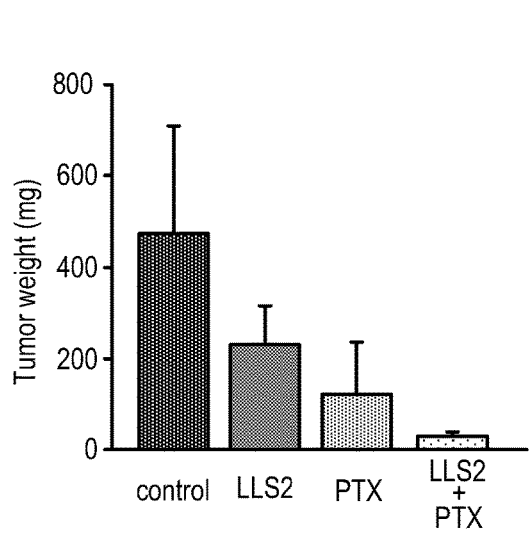
Figure 7D:
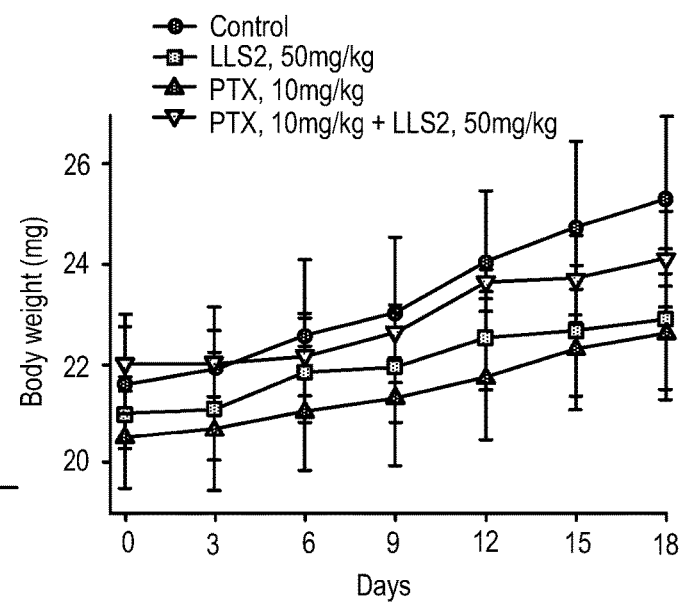

Example 104. In Vivo Anti-Tumor Activity of LLS2 Alone or in Combination with Paclitaxel SKOV3 ovarian cancer cells were subcutaneously injected on the dorsal flanks of mice. Results of LLS2 treatment showed smaller tumor size (FIG. 7a and FIG. 7b) and weight (FIG. 7c) in LLS2-treated mice. Notably, significant suppression of tumor growth was observed in a group treated with combination LLS2/paclitaxel, compared to groups treated with either LLS2 alone or paclitaxel alone (FIG. 7a-FIG. 7c). Furthermore, increasing body weight indicated that the LLS2/paclitaxel combination regimen is tolerable and without significant side effects (FIG. 7d). These results reveal a new efficacious combination regimen for paclitaxel, a very important anti-cancer drug currently used extensively in the clinic.

Example 105. Identification of Galectin-1 as the Target Protein of LLS2

Figure 8A:
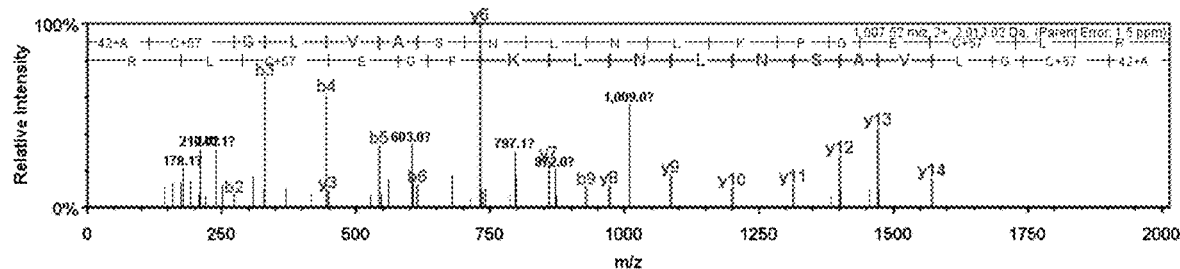
Figure 8B:
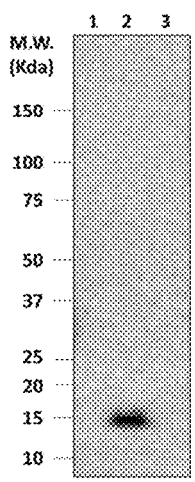
Figure 8C:
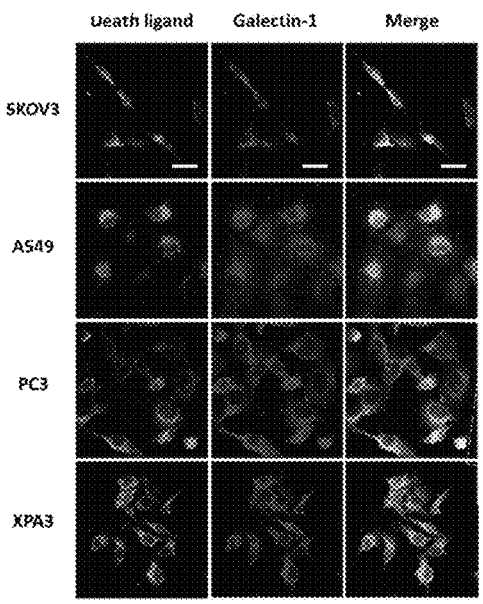

LLS2 was biotinylated, incubated with a cell membrane protein preparation, and bound proteins were pulled down with immobilized streptavidin resin. The bound proteins were eluted and subjected to identification by LC MS/MS. The MS result identified galectin-1 as the putative target protein of LLS2 (FIG. 8a). The identity of galectin-1 as the target protein of LLS2 was confirmed by immunoblot analysis of proteins eluted from (i) blank streptavidin-beads, (ii) biotin-LLS2/streptavidin beads, and (iii) biotinylated unrelated small molecule/streptavidin beads, using anti-galectin-1 antibody as the western blot probe (FIG. 8b). As shown in FIG. 8b, a 14 kd protein corresponding to galectin-1 was identified in lane 2 and lane 2 only, in which LLS2 was used as the affinity ligand, indicating that the target protein of LLS2 was indeed galectin-1. Fixed and permeated SKOV3 cells were then stained with (i) biotin-LLS2 followed by streptavidin-fluorophore, and (ii) anti-galectin-1 antibody, and it was demonstrated that fluorescent signals elicited by LLS2 and galectin-1 co-localized (FIG. 8c).

Figure 8D:
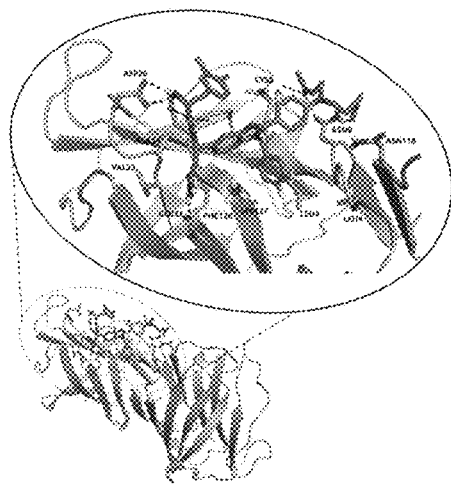

The putative binding site of LLS2 to dimeric galectin-1 as predicted by computer modeling is shown in FIG. 8d. Multiple computational docking simulations were performed to understand the binding of LLS2 to galectin-1 monomer and dimer structures. Blind docking studies were first performed to rapidly scan the protein surface and identify putative binding surfaces. These initial studies were followed by the more accurate and fine-grained docking simulations across the previously identified binding interfaces. These docking studies of LLS2 with galectin-1 dimer suggest stable binding interactions that span both components of the homodimeric complex (FIG. 8d). LLS2 shows good shape complementarity with the dimer-binding pocket. The "$R^2$" group of LLS2 forms hydrogen bond networks with the galectin-1 dimer, while the aromatic groups of LLS2 pack nicely against the hydrophobic core of the binding pocket.

Example 106. Effect of LLS2 on H-RAS (G12V) and K-RAS (G12V) Localization and MAPK/ERK Expression Galectin-1 is known to cooperate in H-Ras signaling and cell transformation as shown in FIG. 9a. Real time confocal images revealed that EGF-stimulated GFP-H-Ras(12V) mislocalizes to intracellular compartments after treatment with LLS2 (25 µM) for 30 min (FIG. 9b). Quantification of membrane-associated H-Ras showed significant down-expression of H-Ras in LLS2-treated MDCK cells compared to expression in non-treated MDCK cells (FIG. 9c). LLS2 treatment also miscolocalizes the EGF-stimulated K-Ras (G12V), whereas the localization of EGF-stimulated N-Ras (Q61D) is not changed (FIG. 9d). Ras activity assays show that LLS2 treatment decreases the EGF-stimulated levels of K-Ras-GTP (FIG. 9d, FIG. 9e). FIG. 9f shows that the expression level of phospho-MEK and phospho-ERK also are down-regulated after treatment with LLS2 for 2 hours. Without being bound to any particular theory, this implies that LLS2 induces cell death through suppression of the RAS-ERK pathway.

Example 107. Suppression of Angiogenesis by LLS2 Treatment

Human umbilical vascular endothelial cells (HUVECs) we used for tube-formation assays on Matrigel-coated plates as shown in FIG. 10. The expression level of secreted gal-1 in 6 different cancer cell lines was determined using ELISA assay. Results showed that (i) PC3 androgen-independent prostate cancer cells secreted the highest level of gal-1 into the culture medium, followed by SKOV3 cells, (ii) PC3 conditioned medium stimulated tube formation of cultured HUVECs, and (iii) tube-formation activity of PC3 conditioned medium was neutralized with addition of LLS2 (10 µM). The angiogenic effect of added gal-1 was also inhibited by LLS2. Together, this data indicates that gal-1 can stimulate tube formation and that tube formation can be suppressed by LLS2.

Example 108. Synergistic Ant-Tumor Activity of LLS30 and PTX

LLS30 was found to be about 2-fold more potent than LLS2 in in vitro cell proliferation assays, having an $IC_{50}$ of 9.2 µM and 10.2 µM against PC3 and SKOV3 cells, respectively. An in vivo efficacy study (i.v. q3dx4) showed that LLS30 at 10 mg/kg dose significantly suppressed the growth of PC3 tumor, and combination of LLS30 with PTX caused tumor regression (FIG. 11). Also, after 4 courses of treatment, CBC, platelets, liver function tests and renal panel results all remained within normal limits. Histological analysis of the resected tumor revealed that many necrotic cells were present after the animal was treated with LLS30. In addition, Ki-67 was down-regulated and more cleaved caspase-3 positive cells were observed with LLS30-treated tumor.

Example 109. Therapeutic Efficacy of LLS30 Against Neurofibromatosis Cells

Figure 12B:
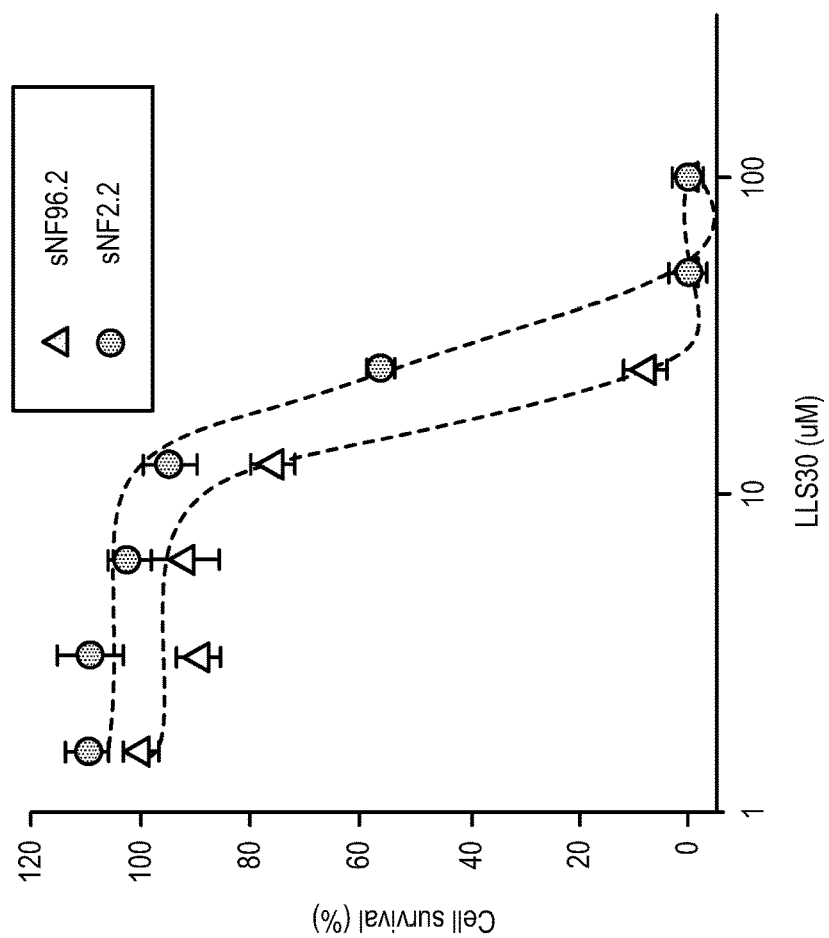
Figure 12A:
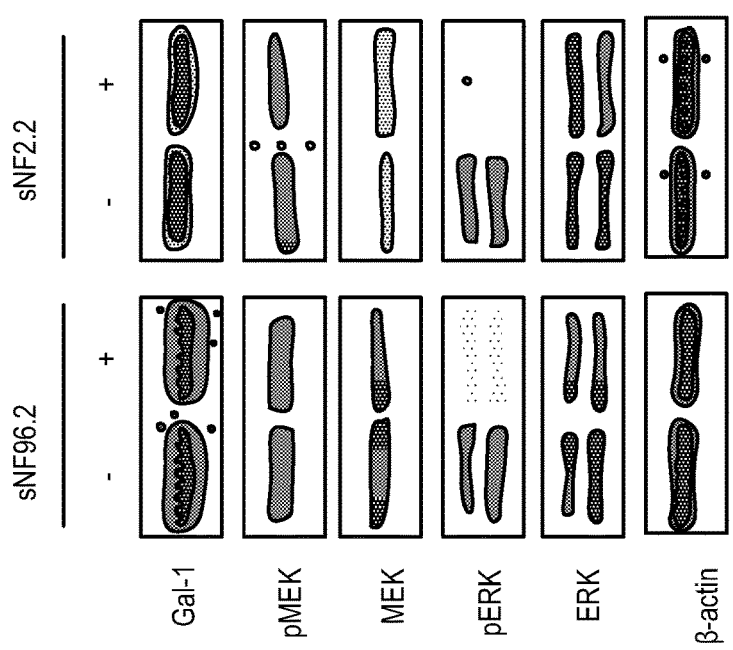

The biochemical and biological effects of LLS30 on sNF96.2 and sNF2.2 malignant peripheral nerve sheath tumor (MPNST) cells were evaluated. Phosphorylation of ERK was totally suppressed after 24 hrs treatment with 25 µM LLS30 (FIG. 12a). LLS30 was cytotoxic against sNF96.2 and sNF2.2 MPNST cells, with an $IC_{50}$ value of 16 µM and 26. µM, respectively (FIG. 12b). Combination studies showed that LLS30 displays strong synergistic effects with PTX, particularly on sNF2.2 MPNST cells, with a C.I. of 0.1.

Example 110. Anti-Cancer Activities of LLS1-LLS41

Anti-cancer activities of compounds LLS1-LLS41 against ovarian cancer cells SKOV3 are shown in Table 1 below:

TABLE 1

Anti-cancer activities of LLS1-LLS41

| Compound | $IC_{50}$ (µM) against SKOV3 |
|---|---|
| LLS1 | 29.5 |
| LLS2 | 18.7 |
| LLS3 | 37.6 |
| LLS4 | >50 |
| LLS5 | 18.7 |
| LLS6 | 7.8 |
| LLS7 | >50 |
| LLS8 | 16.7 |
| LLS9 | 17.6 |
| LLS10 | 36.4 |
| LLS11 | >50 |
| LLS12 | >50 |
| LLS13 | >50 |
| LLS14 | 29.2 |
| LLS15 | >50 |
| LLS16 | 35.1 |
| LLS17 | 10.6 |
| LLS18 | >50 |
| LLS19 | 16.8 |
| LLS20 | 7.5 |
| LLS21 | 8.9 |
| LLS22 | >50 |
| LLS23 | 8.4 |
| LLS24 | 40.1 |
| LLS25 | 20.7 |
| LLS26 | 10.5 |
| LLS27 | >50 |
| LLS28 | 16.1 |
| LLS29 | 25.5 |
| LLS30 | 10.2 (9.2 µM for PC3 cells) |
| LLS31 | 16.4 |
| LLS32 | 10.4 |
| LLS33 | 10.0 |
| LLS34 | 8.9 |
| LLS35 | 10.8 |
| LLS36 | >50 |
| LLS37 | >50 |
| LLS38 | >50 |
| LLS39 | ND |
| LLS40 | ND |
| LLS41 | ND |

Example 111. Effect of LLS Compound Treatment on Prostate Cancer Cell Viability Effects of compounds LLS42-LLS80 on the viability of PC3 prostate cancer cells after 72 hours of treatment are shown in Table 2 below:

TABLE 2

Cell viability % of prostate cancer PC3 cells after 72 hours treatment

| | 20 µM | 10 µM | 5 µM | 2.5 µM |
|---|---|---|---|---|
| LLS42 | 0 | 49 | 92 | 95 |
| LLS43 | 105 | 101 | 102 | 105 |
| LLS43Ac | 97 | 103 | 102 | 97 |
| LLS44 | 113 | 113 | 115 | 107 |
| LLS45 | 117 | 118 | 102 | 92 |
| LLS45Ac | 91 | 98 | 98 | 98 |
| LLS46 | 94 | 92 | 97 | 86 |
| LLS51 | 105 | 99 | 79 | 83 |
| LLS52 | 84 | 87 | 96 | 97 |
| LLS52Ac | 91 | 94 | 96 | 91 |
| LLS53 | 105 | 98 | 91 | 93 |
| LLS53Ac | 101 | 99 | 94 | 97 |
| LLS54 | 87 | 105 | 86 | 90 |
| LLS55 | 92 | 102 | 100 | 91 |
| LLS56 | 93 | 98 | 105 | 104 |
| LLS56Ac | 55 | 92 | 93 | 85 |
| LLS58 | 74 | 81 | 84 | 92 |
| LLS58Ac | 83 | 91 | 98 | 100 |
| LLS59 | 91 | 90 | 97 | 83 |
| LLS63 | 0 | 29 | 86 | 80 |
| LLS64 | 3 | 60 | 83 | 94 |
| LLS65 | 34 | 74 | 94 | 95 |
| LLS66 | 79 | 89 | 91 | 98 |
| LLS67 | 93 | 99 | 94 | 93 |
| LLS69Ac | 2 | 73 | 95 | 101 |
| LLS71 | 3 | 59 | 83 | 91 |
| LLS73 | 8 | 69 | 92 | 94 |
| LLS76 | 85 | 86 | 86 | 92 |
| LLS77 | 103 | 101 | 100 | 99 |
| LLS78 | 100 | 101 | 93 | 97 |
| LLS80 | 0 | 6 | 25 | 86 |
| LLS30 | 10 | 73 | 95 | 100 |
| LLS82 | ND | ND | ND | ND |

Effects of compounds on the viability of 22RV1 prostate cancer cells after 72 hours of treatment are shown in Table 3 below:

TABLE 3

Cell viability % of prostate cancer 22RV1 cells after 72 hours treatment

| | 10 µM | 5 µM | 2.5 µM |
|---|---|---|---|
| LLS30 | 0 | 3 | 47 |
| LLS83 | 0 | 1 | 20 |
| LLS84 | 138 | 109 | 119 |
| LLS85 | 0 | 1 | 65 |
| LLS86 | 0 | 0 | 45 |
| LLS87 | 0 | 56 | 76 |

TABLE 3-continued

Cell viability % of prostate cancer 22RV1 cells after 72 hours treatment

|  | 10 μM | 5 μM | 2.5 μM |
|---|---|---|---|
| LLS88 | 0 | 4 | 75 |
| LLS89 | 0 | 0 | 1 |
| LLS90 | 0 | 0 | 1 |
| LLS91 | 0 | 7 | 33 |
| LLS92 | 1 | 15 | 74 |
| LLS93 | 0 | 2 | 22 |
| LLS94 | 0 | 0 | 3 |
| LLS95 | 0 | 1 | 22 |
| LLS96 | 0 | 0 | 45 |
| LLS97 | 0 | 0 | 23 |
| LLS98 | 0 | 0 | 40 |
| LLS99 | 0 | 0 | 1 |
| LLS100 | 0 | 28 | 99 |
| LLS101 | 0 | 1 | 20 |
| LLS102 | 0 | 0 | 23 |
| LLS103 | 0 | 0 | 1 |
| LLS104 | 1 | 31 | 82 |
| LLS105 | ND | ND | ND |
| LLS106 | 0 | 2 | 30 |
| LLS107 | 0 | 4 | 67 |
| LLS108 | 101 | 100 | 89 |
| LLS109 | 88 | 88 | 98 |

Example 112. Design and Synthesis of Benzimidazole-Based One-Bead Two-Compound (OB2C) Small Molecule Library A bead-bound library was synthesized on topologically segregated tri-functional bi-layer beads as shown in FIG. 14. In the library, a random small molecule co-displays with biotin on the bead surface (each with 10% of total loading of single bead) and a tri-peptide coding tag (80% of total loading) comprised of 42 sequenceable α-amino acids (shown in FIG. 15) resides inside the beads. The biotin molecule displayed on bead surface was used to link cell-capturing ligand LXY30 through (ligand-biotin)-neutravidin-(biotin-bead) linkages. The chemical coding tag decoding can be readily achieved with an automated protein microsequencer with Edman microsequencing (Liu, Lam, 2001, *Anal. Biochem,* 2001, 295: 9-16). The library has three diversities from 42 primary amines ($R_1NH_2$ of FIG. 14), 42 aldehydes ($R_2CHO$ of FIG. 14) and 42 amino acids ($X_3$ of FIG. 14) containing both L- and D-amino acids, natural and unnatural amino acids, respectively. The permutation of the OB2C library is then 42×42×42=74,088.

TentaGel S $NH_2$ resin (Rapp Polymere, Tubingen, Germany) was used as solid support for synthesis of the library using the synthetic approach of FIG. 14. The tri-functional bi-layer beads 2 were prepared using a bi-phasic solvent approach (Liu, Marik, Lam, J Am Chem Soc, 2002, 124: 7678-7680). The derivatizing reagents were a mixture of Fmoc-OSu and Alloc-OSu (1:1, total 20% of bead loading). TentaGel S—$NH_2$ resin beads (6.0 g, 1.44 mmol, loading 0.24 mmol/g) were swollen in water for 24 h. Water was removed by filtration, and the solution of Fmoc-OSu (48.6 mg, 0.144 mmol) and Alloc-OSu (28.7 mg, 0.144 mmol) in DCM/diethyl ether (300 ml, 55/45) mixture was added to the wet beads, followed by addition of DIEA (201 μL, 1.152 mmol). The mixture was shaken vigorously at room temperature for 45 min. After removal of the liquid by filtration, the beads were washed with DMF (5×300 mL) to remove water from inside the beads, followed by MeOH (3×300 mL) and DMF (3×300 mL). A solution of $(Boc)_2O$ (1.006 g, 4.61 mmol) and DIEA (1.606 mL, 9.22 mmol) in DCM (45 mL) was added to the beads. The slurry beads were shaken at room temperature for 1 h. The Fmoc was removed followed by washing, then a mixture of D-Biotin (175.9 mg, 0.72 mmol), HBTU (273 mg, 0.72 mmol) and DIEA (251 μL, 1.44 mmol) in NMP (45 mL) was added to the beads. The column was rotated until a Kaiser test was negative. The resin beads 3 were washed and subjected to Alloc deprotection with $Pd(PPh_3)_4$ (66.5 mg, 0.0576 mmol) and $PhSiH_3$ (355 μL, 2.88 mmol) in DCM (45 mL), for 45 min twice. Following de-protection, the beads were washed sequentially with DCM (6×45 mL), DMF (3×45 mL), 0.5% DIEA in DMF (3×45 mL), 0.5% sodium diethyldithiocarbamate in DMF (3×45 mL), 50% DCM in DMF (3×45 mL), MeOH (3×45 mL) and DMF (3×45 mL). A solution of scaffold (224.8 mg, 0.72 mmol), 6-Cl-HOBt (122 mg, 0.72 mmol) and DIC (111.5 μL, 072 mmol) in DMF (35 mL) was added to the beads. The coupling was carried out at room temperature for 2 h to generate beads 4. Then the beads were treated with 50% TFA in DCM (12 mL) for 30 min to remove Boc inside the beads. The beads were neutralized with 2% DIEA in DMF (2×12 mL) and washed with DMF (3×12 mL), MeOH (3×12 mL) and DMF (3×12 mL) before split-mix coupling of 42 amino acids. The beads were split into 42 equal portions in 42 disposable polypropylene columns with a polyethylene frit (5 mL).

Forty-two different Fmoc-amino acids shown in FIG. 15 (4 eq. to bead total substitution) were separately dissolved in a solution of 6-Cl-HOBt (4 eq.) and DIC (4 eq.) in DMF (2 mL), and added to 42 columns, each column receiving one amino acid. The coupling was carried out at room temperature until the Kaiser test was negative to give beads 5. Forty-two primary amines (FIG. 16, 4 eq. to beads loading) were added to the beads (each column received one amines) in presence of 8 eq. of DIEA and rotated overnight to give beads 6. The beads were pooled to a column, drained, washed and $NO_2$ was reduced with 2M $SnCl_2.2H_2O$ for 3 days to yield beads 7. After washing, the beads were split into 42 columns and coupled with 42 aldehydes (FIG. 17), each column received one aldehyde) and rotated overnight to give beads 8. Then, Fmoc was deprotected in each separate column and the beads were coupled with one the 42 Fmoc-amino acids as described above to give beads 9. All beads were combined in one column and washed. The Fmoc and Alloc were deprotected sequentially as described above. The beads were again split into 42 columns, and each portion of beads was coupled with one of 42 Fmoc-amino acids. After a last cycle of coupling, the beads were combined, and Fmoc was deprotected. The beads were washed with DMF (3×12 mL), MeOH (3×12 mL), and DCM (3×12 mL), respectively, three times. The beads were then dried under vacuum. Side-chain deprotection was achieved using a TFA cocktail (a mixture of 82.5% TFA: 5% phenol: 5% thioanisole: 5% water: 2.5% TIS, v/v) for 4 h. After neutralization with 5% DIEA/DMF (2×12 mL), the beads were washed sequentially with DMF (3×12 mL), MeOH (3×12 mL), DCM (3×12 mL), DMF (3×12 mL), 50% DMF/water (3×12 mL), water (3×12 mL) and 70% ethanol/water (3×12 mL), respectively. The bead library was stored in 70% ethanol/water and was ready for screening.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the formula:

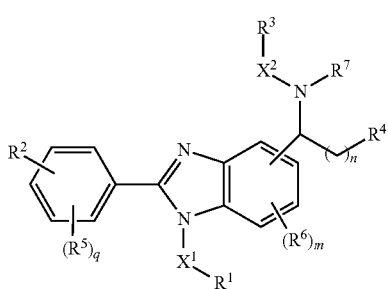

(I)

wherein
R$^1$ is selected from the group consisting of C$_{1-6}$ alkyl, —NR$^{1a}$R$^{1b}$, C$_{3-10}$ cycloalkyl, C$_{3-8}$ heterocycloalkyl, C$_{6-12}$ aryl, and C$_{5-12}$ heteroaryl, wherein the aryl is optionally substituted with 1-4 R$^{1c}$ groups;
R$^{1a}$ and R$^{1b}$ are each independently selected from the group consisting of hydrogen and C$_{1-6}$ alkyl;
R$^2$ is selected from the group consisting of, —NR$^{2a}$R$^{2b}$, C$_{5-12}$ heteroaryl and C$_{1-6}$ alkyl-C$_{5-12}$ heteroaryl, wherein the heteroaryl is optionally substituted with C$_{1-6}$ hydroxyalkyl;
R$^{2a}$ and R$^{2b}$ are each independently selected from the group consisting of C$_{1-6}$ alkyl, C$_{1-6}$ hydroxyalkyl, and C$_{1-6}$ alkyl-OC(O)CH$_3$, or are combined with the nitrogen to which they are attached to form a C$_{3-8}$ heterocycloalkyl having 0 to 2 additional heteroatoms selected from the group consisting of N, O, and S, wherein the C$_{3-8}$ heterocycloalkyl is optionally substituted with 1 to 4 R$^{2c}$ groups;
each R$^{1c}$ and R$^{2c}$ is independently selected from the group consisting of C$_{1-6}$ alkyl, halogen, C$_{1-6}$ haloalkyl, hydroxy, C$_{1-6}$ alkoxy, C$_{1-6}$ haloalkoxy, and C$_{6-12}$ aryl;
R$^3$ is selected from the group consisting of hydrogen, C$_{1-6}$ alkyl, C$_{3-8}$ cycloalkyl, C$_{3-8}$ heterocycloalkyl, C$_{6-12}$ aryl, and C$_{5-12}$ heteroaryl, wherein the heterocycloalkyl, aryl, and heteroaryl are optionally substituted with 0 to 4 R$^{3a}$ groups
each R$^{3a}$ is independently selected from the group consisting of C$_{1-6}$ alkyl, halogen, C$_{1-6}$ haloalkyl, hydroxy, C$_{1-6}$ alkoxy, C$_{1-6}$ haloalkoxy, C$_{3-8}$ cycloalkyl, C$_{3-8}$ heterocycloalkyl, C$_{6-12}$ aryl, C$_{5-12}$ heteroaryl, and —SO$_2$—C$_{6-12}$ aryl;
R$^4$ is selected from the group consisting of —C(O)R$^{4a}$, —C(O)OR$^{4a}$ and —C(O)NR$_{4a}$R$^{4b}$;
each R$^{4a}$ and R$^{4b}$ is independently selected from the group consisting of hydrogen and C$_{1-6}$ alkyl;
each R$^5$ and R$^6$ is independently selected from the group consisting of hydrogen and C$_{1-6}$ alkyl;
R$^7$ is selected from the group consisting of hydrogen and C$_{1-6}$ alkyl-C$_{6-12}$ aryl, optionally substituted with 1-4 R$^{7a}$ groups, each R$^{7a}$ is independently selected from the group consisting of C$_{1-6}$ alkyl, halogen, C$_{1-6}$ haloalkyl, C$_{1-6}$ alkoxy, and C$_{1-6}$ haloalkoxy;
X$^1$ is C$_{1-6}$ alkylene;
X$^2$ is absent or selected from the groups consisting of C$_{1-6}$ alkylene, —C(O)CH(NH$_2$)CH$_2$— and —C(O)CH(NH$_2$)CH(OH)—;

the subscripts n and m are each independently integers from 0 to 3; and
the subscript q is an integer from 0 to 4;
or pharmaceutically acceptable salts thereof.

2. The compound of claim 1, wherein
R$^1$ selected from the group consisting of C$_{1-6}$ alkyl, —NH$_2$, C$_{3-10}$ cycloalkyl, C$_{3-8}$ heterocycloalkyl, C$_{6-12}$ aryl, and C$_{5-12}$ heteroaryl, wherein the aryl is optionally substituted with 1-4 R$^{1c}$ groups; and
each R$^{1c}$ is independently selected from the group consisting of halogen, C$_{1-6}$ haloalkyl, C$_{1-6}$ alkoxy, and C$_{1-6}$ haloalkoxy.

3. The compound of claim 1, wherein R$^{2a}$ and R$^{2b}$ are each independently selected from the group consisting of —CH$_2$CH$_2$OH and —CH$_2$CH$_2$OC(O)CH$_3$.

4. The compound of claim 1, wherein
R$^{2a}$ and R$^{2b}$ are combined with the nitrogen to which they are attached to form a C$_{3-8}$ heterocycloalkyl having from 0 to 2 additional heteroatoms selected from the group consisting of N, O, and S, wherein the heterocycloalkyl is optionally substituted with 1 to 4 R$^{2c}$ groups; and
each R$^{2c}$ is independently C$_{1-6}$ alkyl.

5. The compound of claim 1, wherein
R$^3$ is selected from the group consisting of hydrogen, C$_{3-8}$ cycloalkyl, C$_{6-12}$ aryl, and C$_{5-12}$ heteroaryl, wherein the aryl and heteroaryl are optionally substituted with 1 to 4 R$^{3a}$ groups; and
each R$^{3a}$ is independently selected from the group consisting of halogen, C$_{1-6}$ haloalkyl, C$_{1-6}$ alkoxy, C$_{5-12}$ heteroaryl, and —SO$_2$—C$_{6-12}$ aryl.

6. The compound of claim 1, having the formula:

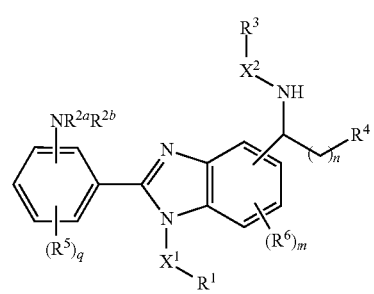

(Ia)

wherein q is an integer from 0 to 4.

7. The compound of claim 1, having the formula:

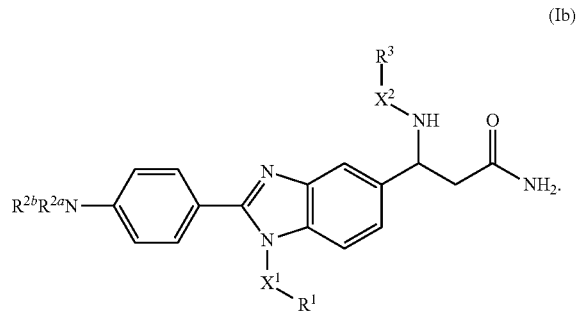

(Ib)

8. The compound of claim 1, wherein
R$^1$ is selected from the group consisting of C$_{1-6}$ alkyl, —NH$_2$, C$_{3-8}$ heterocycloalkyl, C$_{6-12}$ aryl, and C$_{5-12}$ heteroaryl, wherein the aryl is optionally substituted with 1-4 R$^{1c}$ groups; and each $R^{1c}$ is independently selected from the group consisting of halogen, $C_{1-6}$ haloalkyl, $C_{1-6}$ alkoxy, and $C_{1-6}$ haloalkoxy.

9. The compound of claim 1, wherein $R^{2a}$ and $R^{2b}$ are each independently selected from the group consisting of —$CH_2CH_2OH$ and —$CH_2CH_2OC(O)CH_3$, or are combined with the nitrogen to which they are attached to form a $C_{3-8}$ heterocycloalkyl having from 0 to 2 additional heteroatoms selected from the group consisting of N, O, and S, wherein the heterocycloalkyl is optionally substituted with 1 to 4 $R^{2c}$ groups;

each $R^{2c}$ is independently $C_{1-6}$ alkyl;

$R^3$ is selected from the group consisting of hydrogen, $C_{3-8}$ cycloalkyl, $C_{6-12}$ aryl, and $C_{5-12}$ heteroaryl, wherein the aryl and heteroaryl are optionally substituted with 1 to 4 $R^{3a}$ groups;

each $R^{3a}$ is independently selected from the group consisting of halogen, $C_{1-6}$ haloalkyl, $C_{1-6}$ alkoxy, $C_{5-12}$ heteroaryl, and —$SO_2$—$C_{6-12}$ aryl;

$X^1$ is $C_{1-6}$ alkylene; and $X^2$ is absent or selected from the groups consisting of $C_{1-6}$ alkylene, and —$C(O)CH(NH_2)CH_2$—;

or pharmaceutically acceptable salts thereof.

10. The compound of claim 1, wherein the compound is selected from the group consisting of:

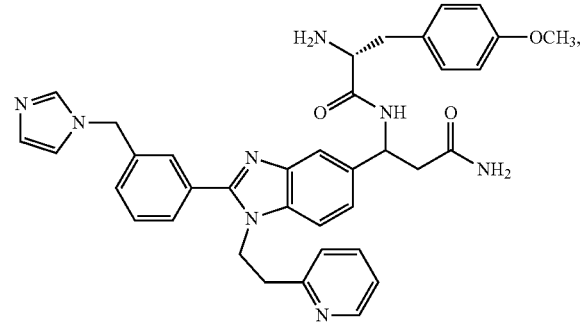

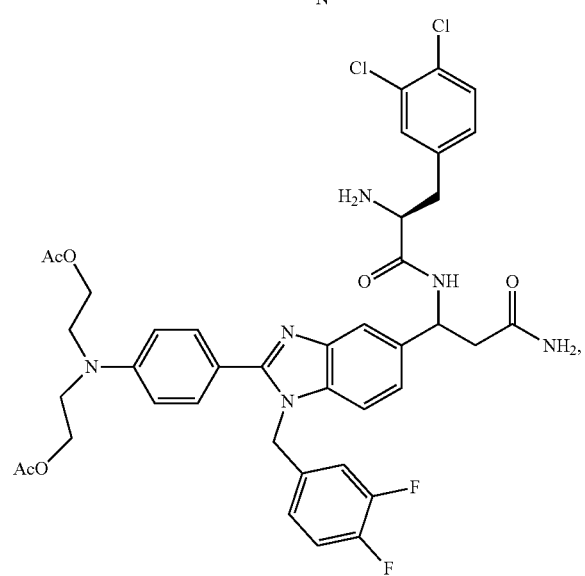

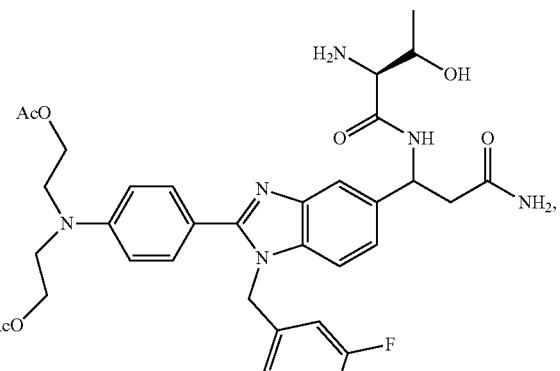

-continued

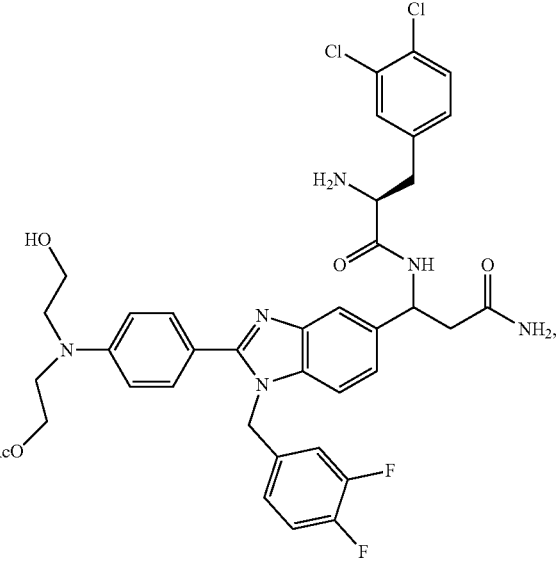

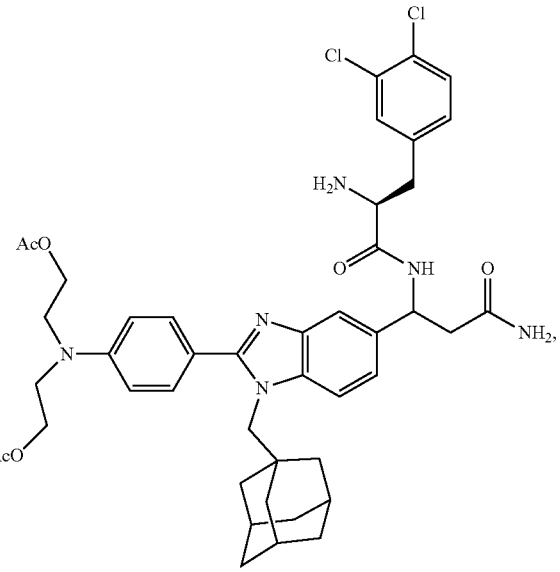

125
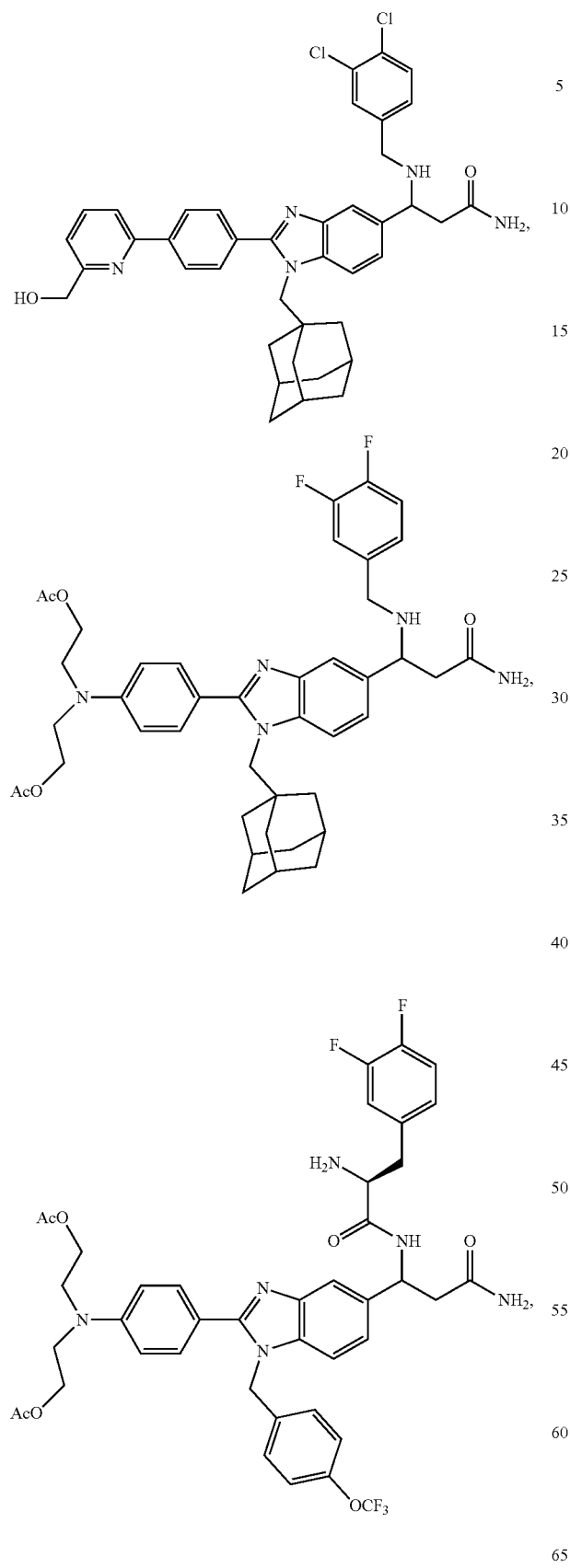
126
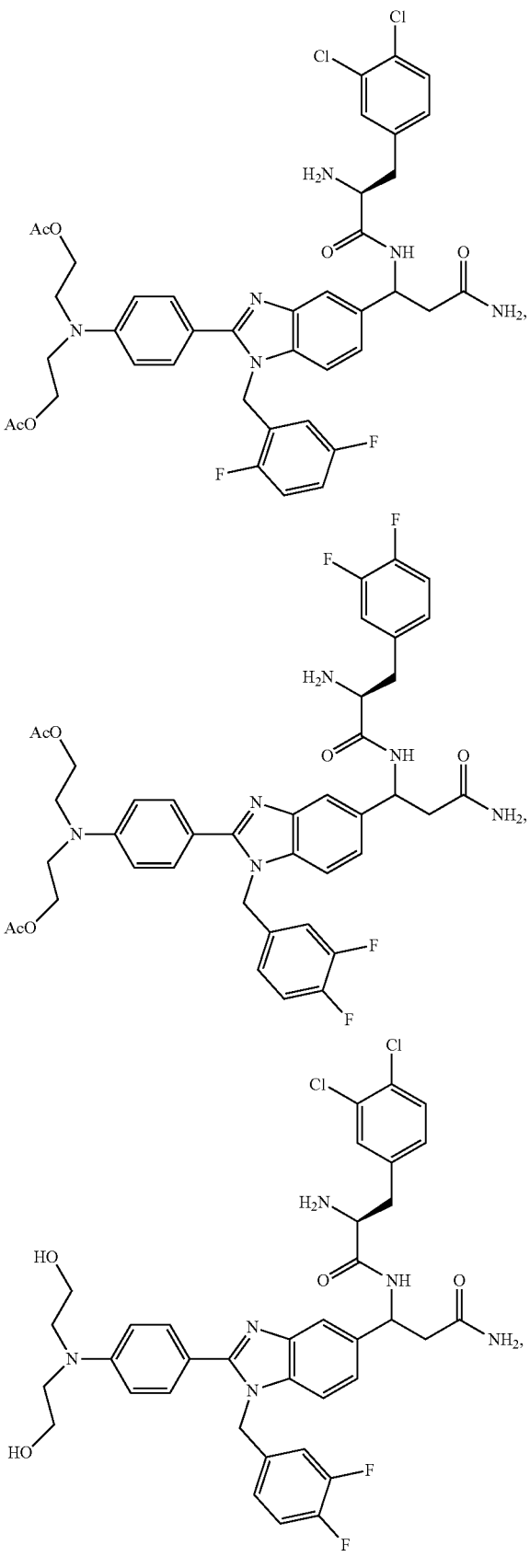

127
-continued
128
-continued
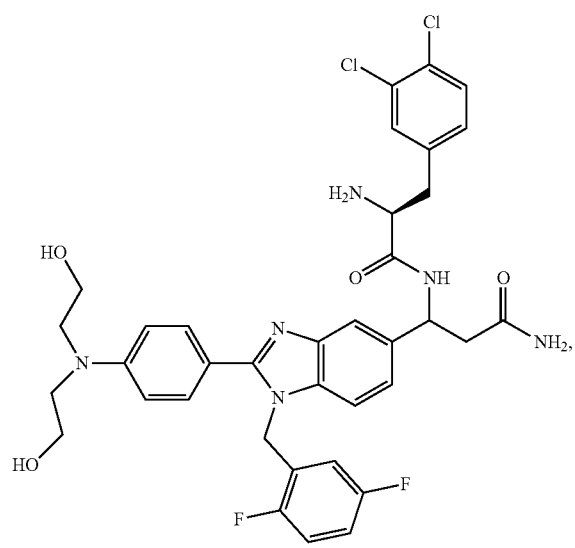
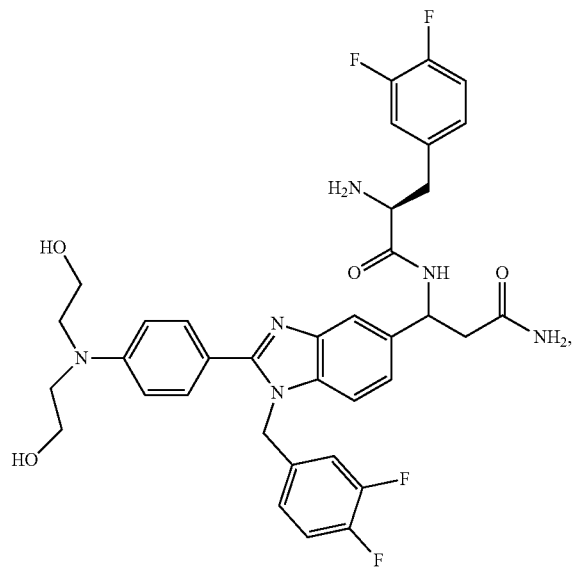

129
-continued
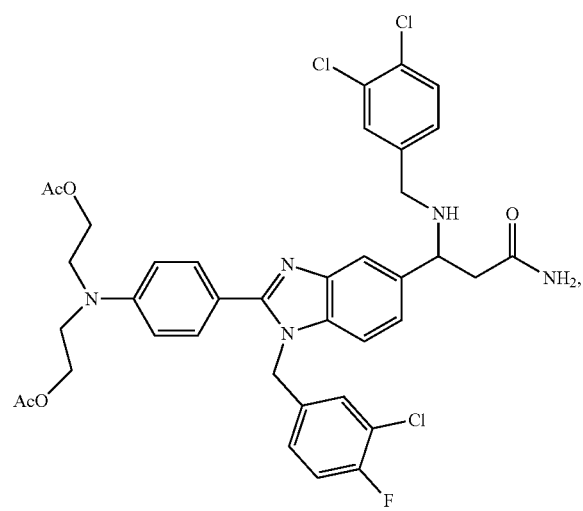
130
-continued
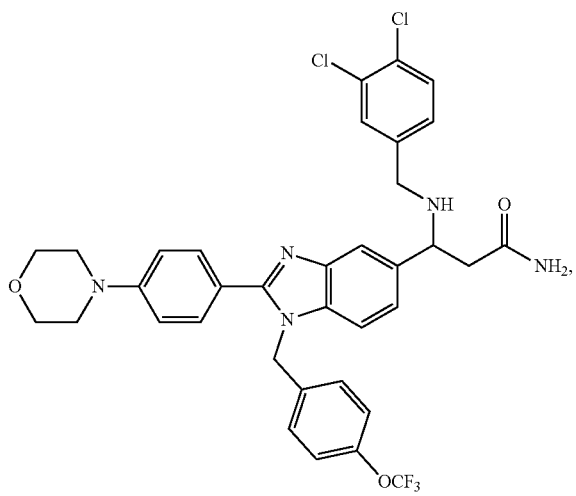
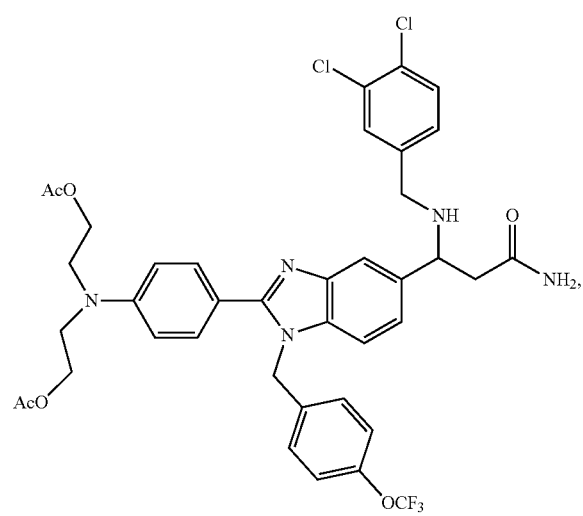
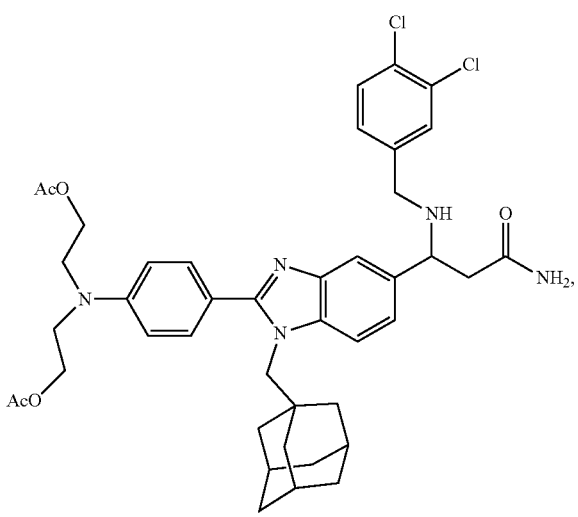

131
-continued
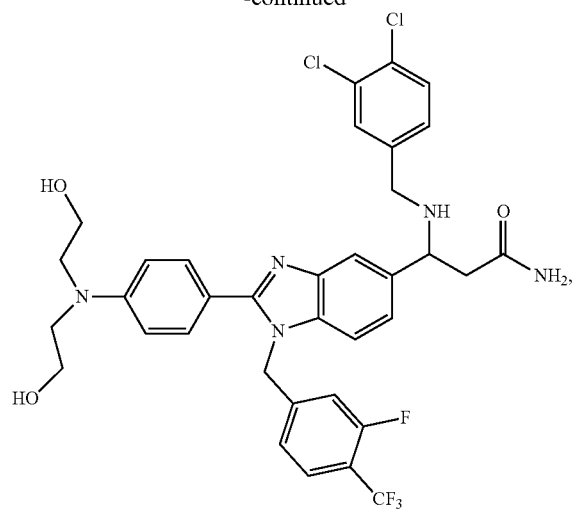
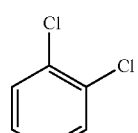
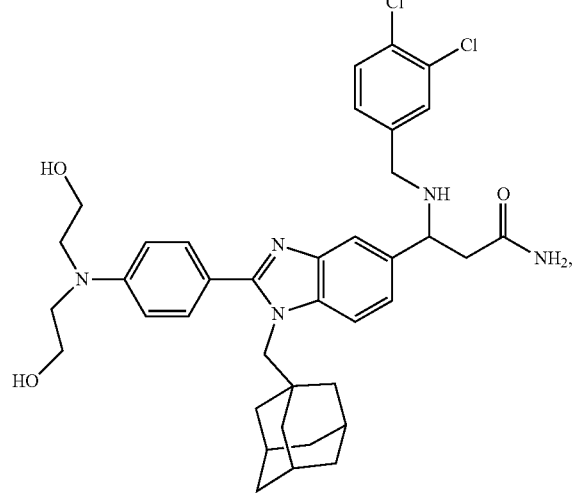
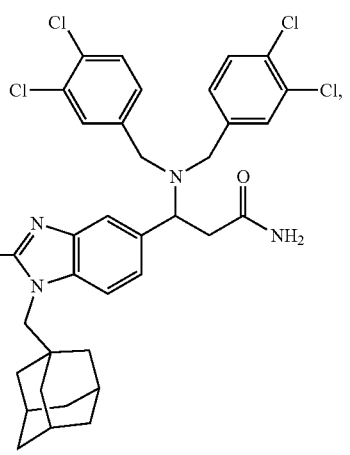
132
-continued
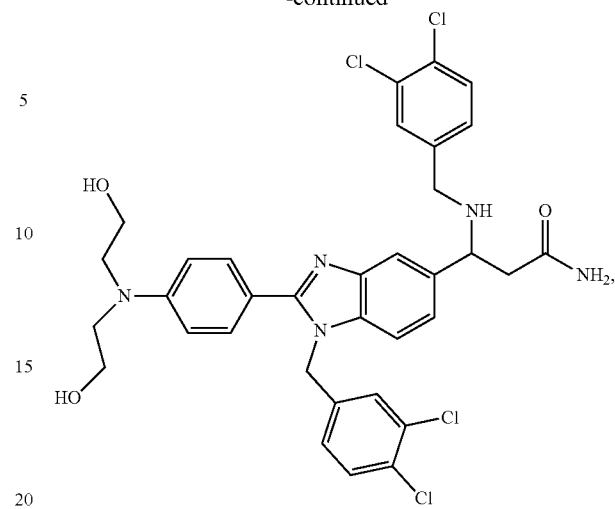
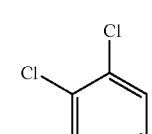
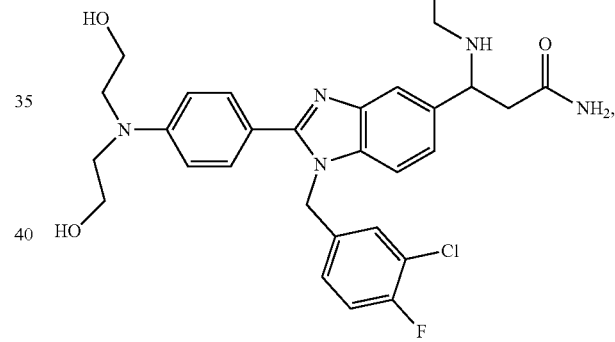
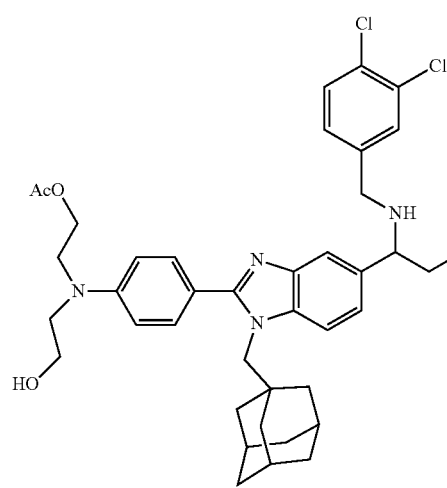

133
-continued
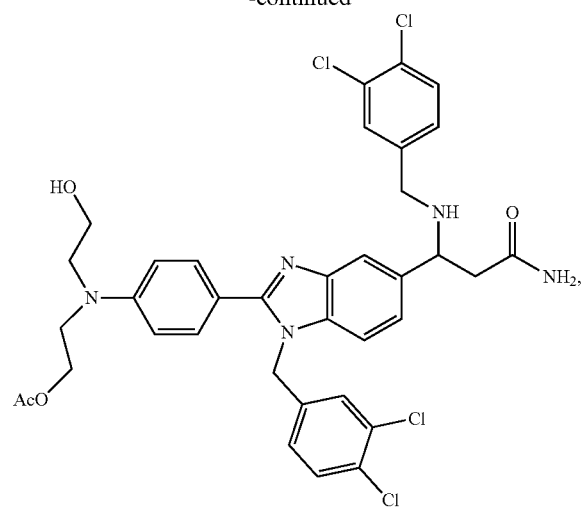
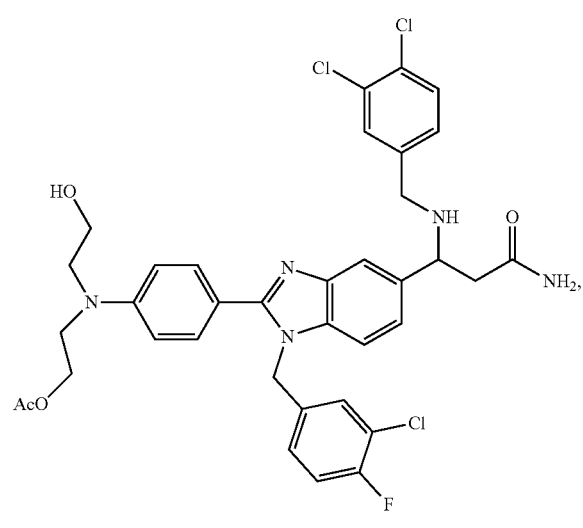
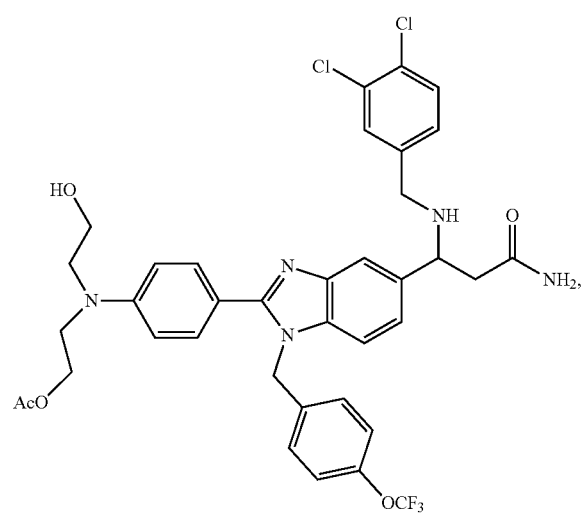
134
-continued
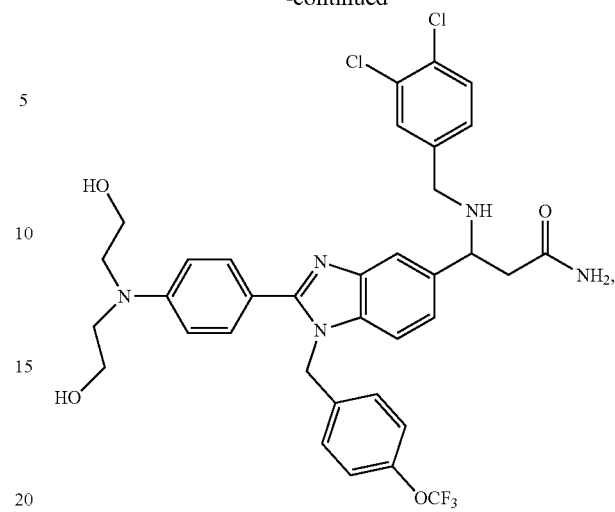
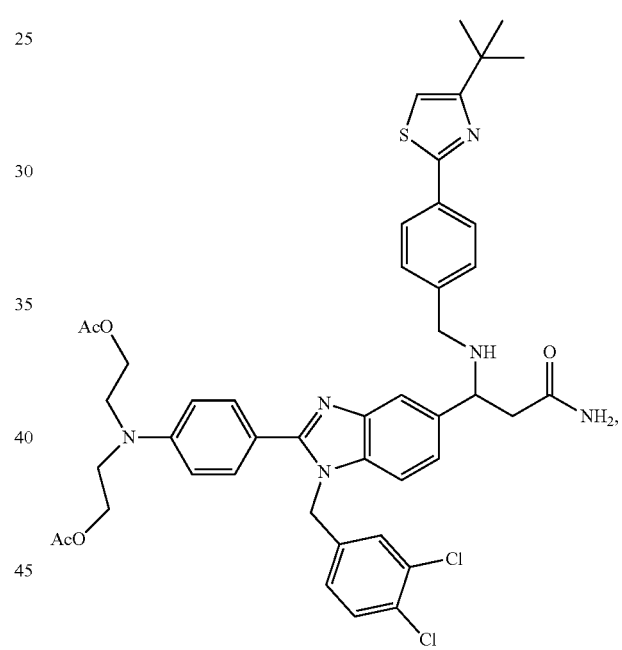
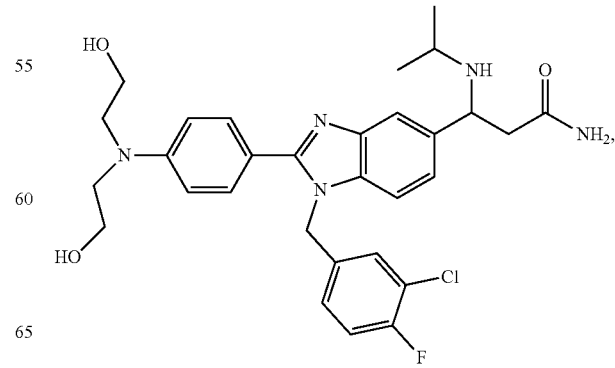

135
-continued
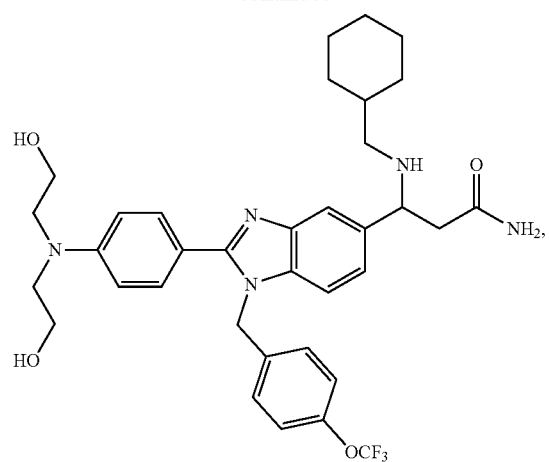
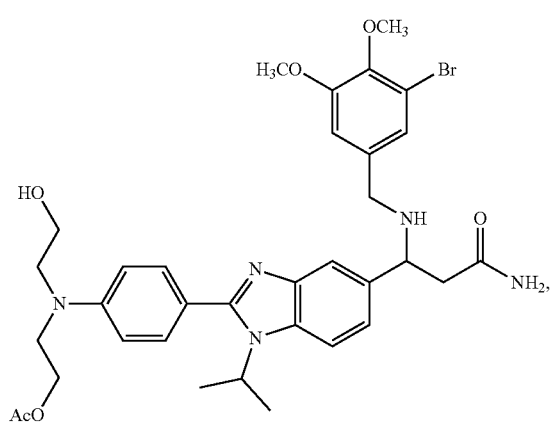
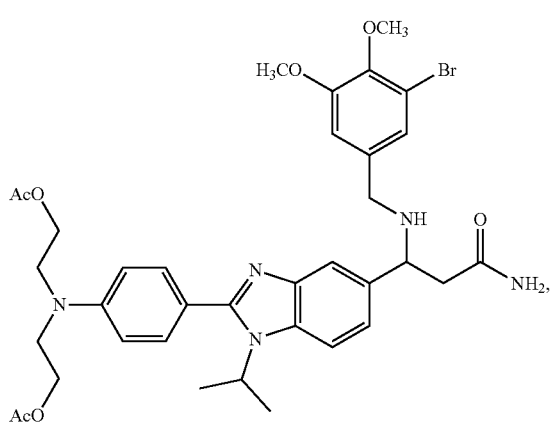
136
-continued
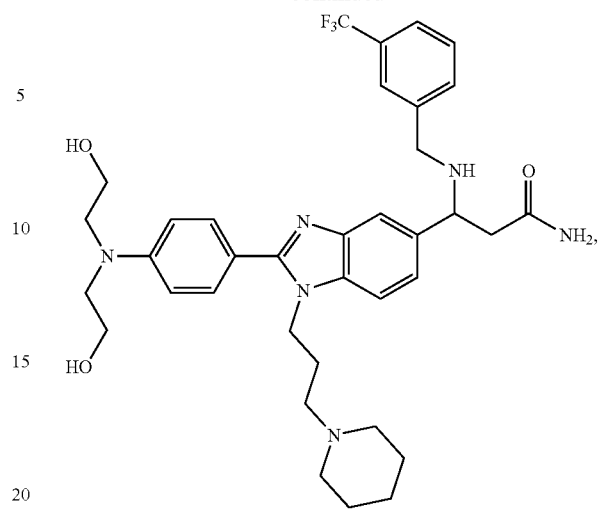
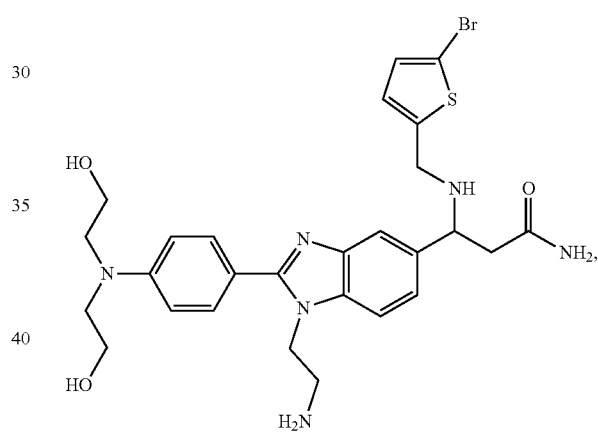
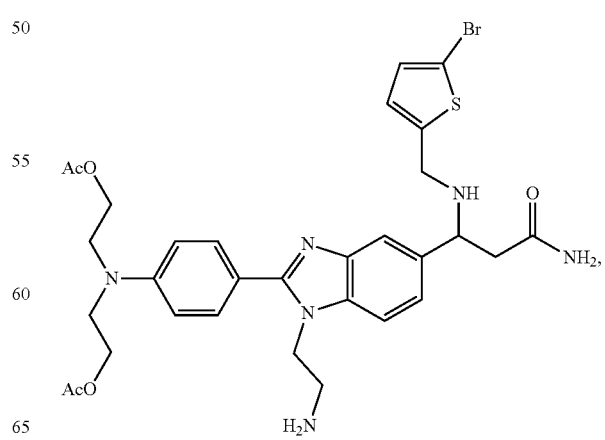

137
-continued
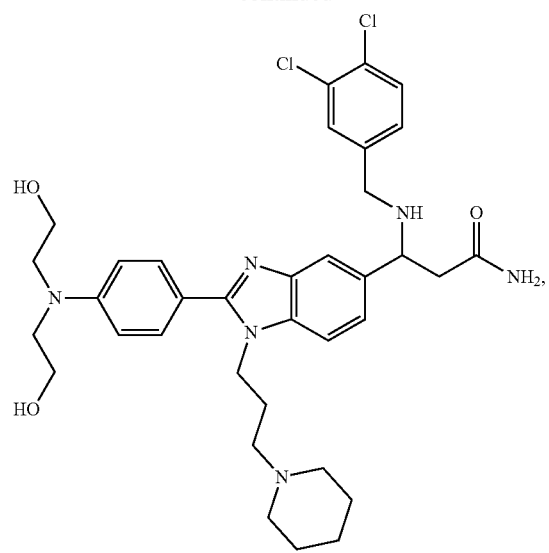
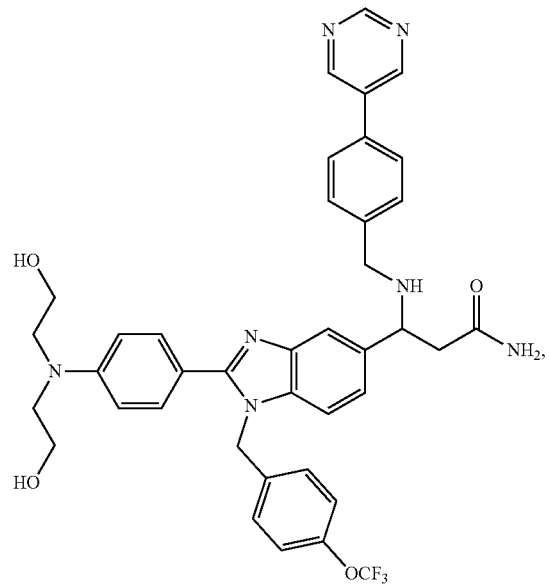
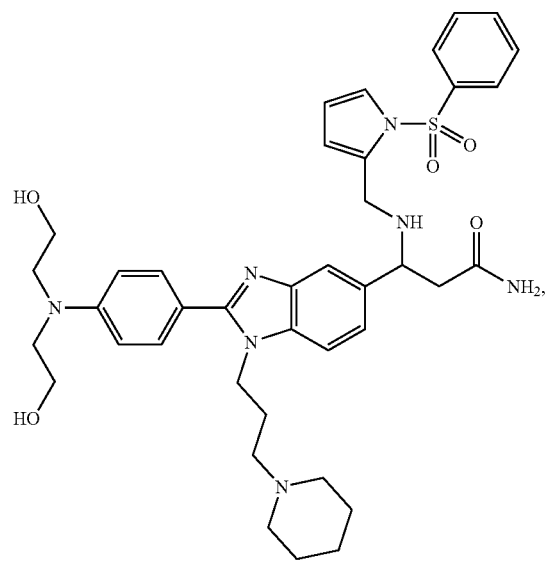
138
-continued
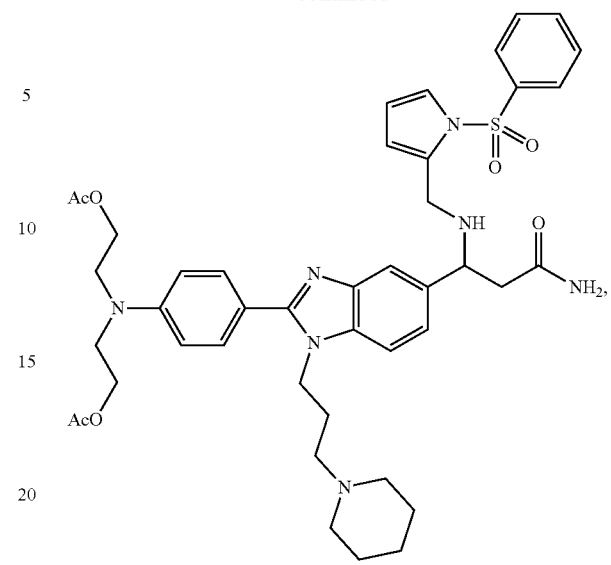
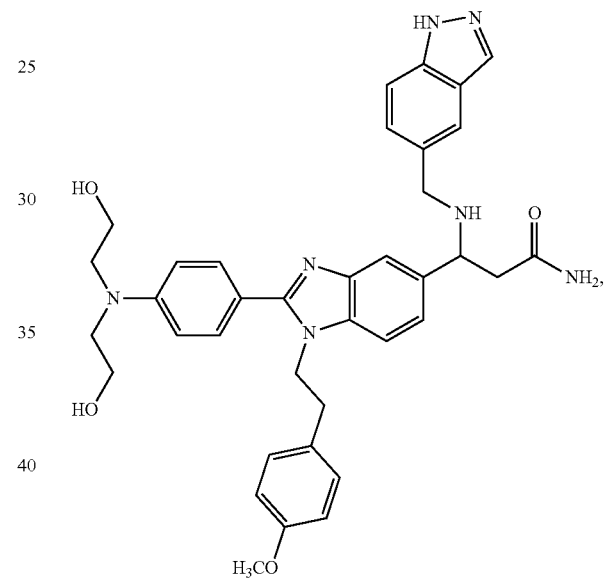
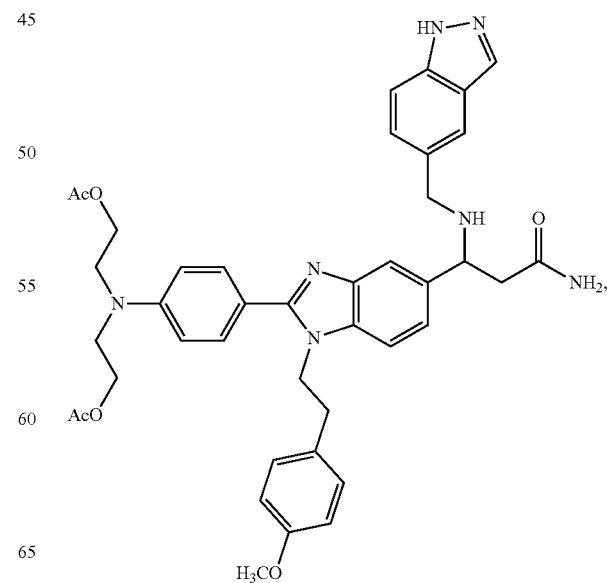

139
-continued
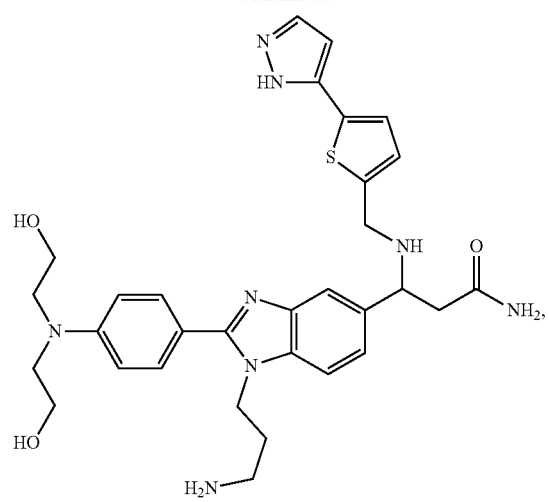
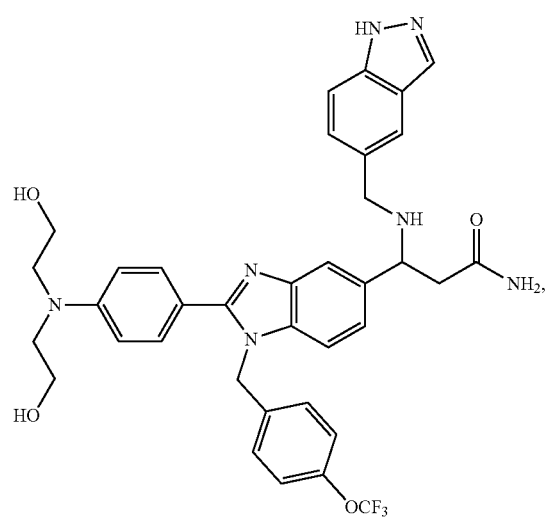
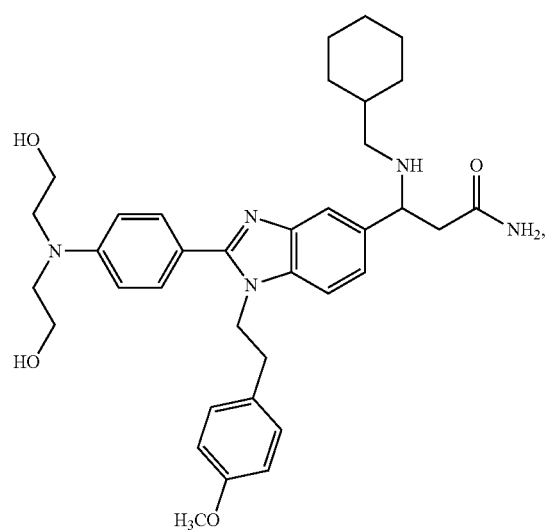
140
-continued
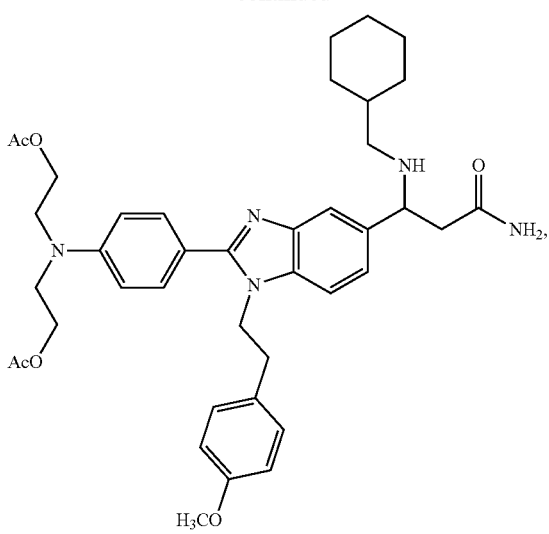
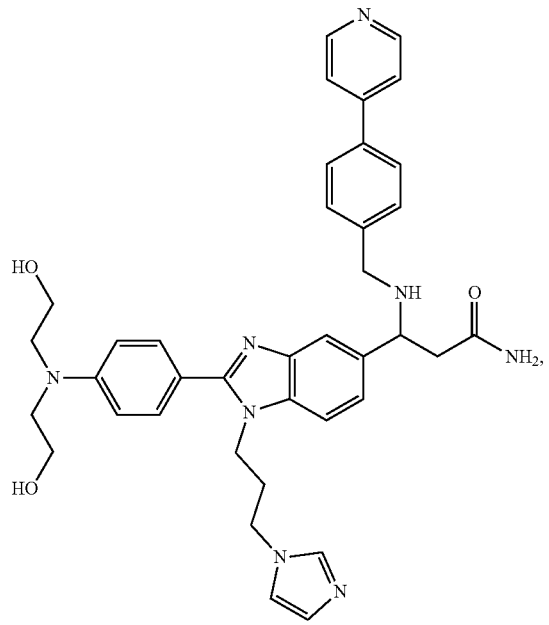

141
-continued
142
-continued
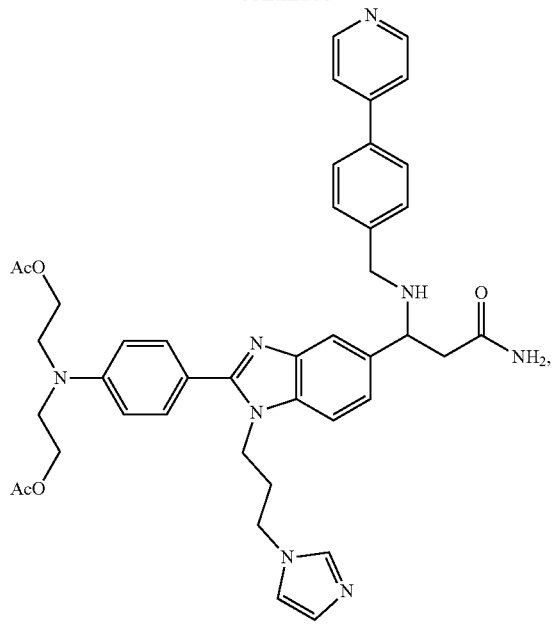
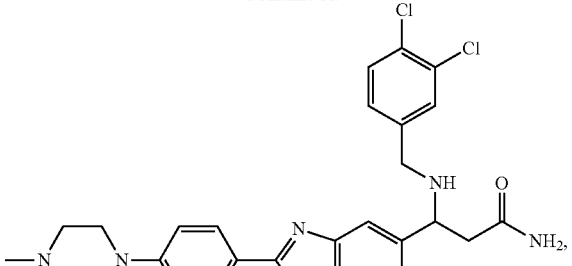
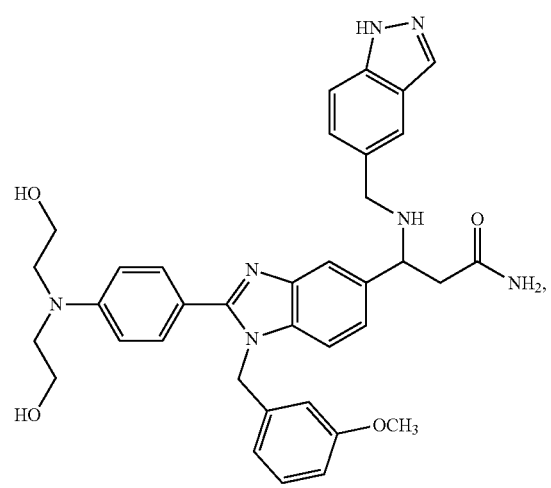
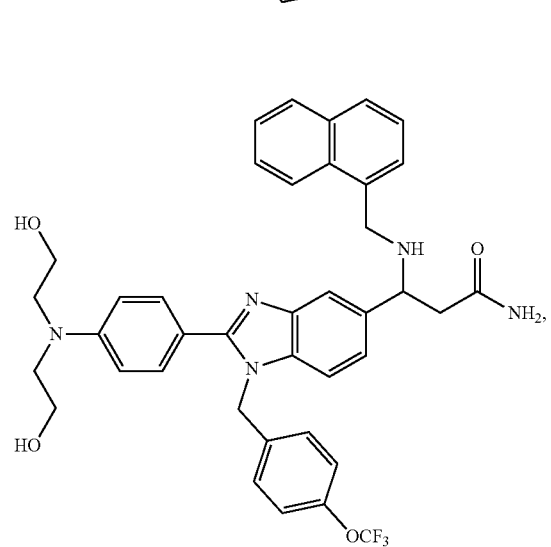
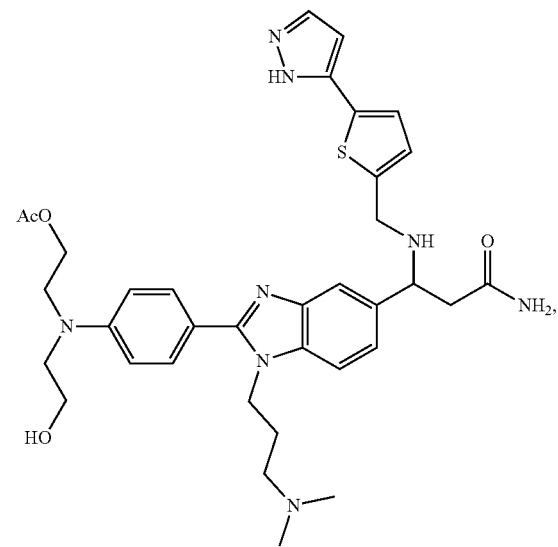

143
-continued
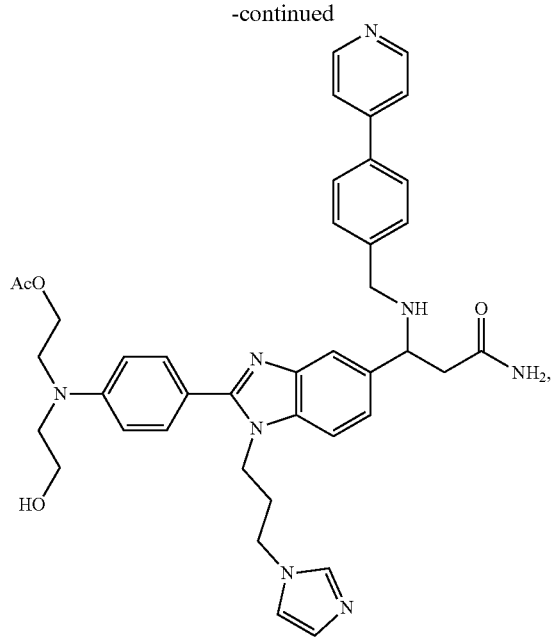
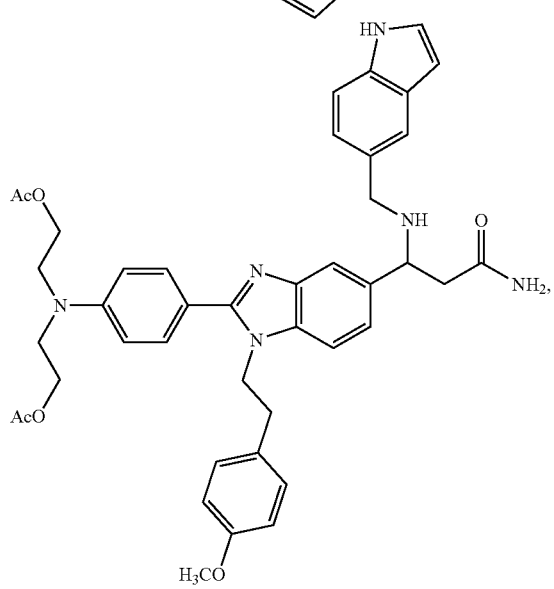
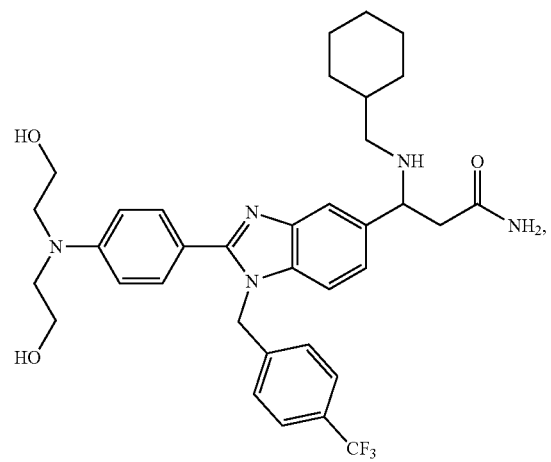
144
-continued
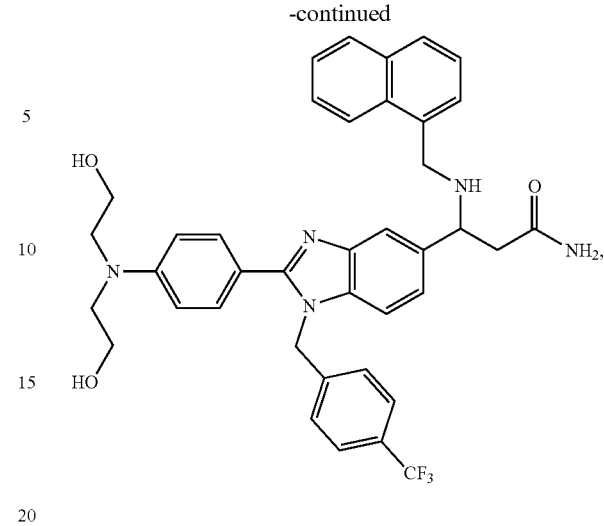
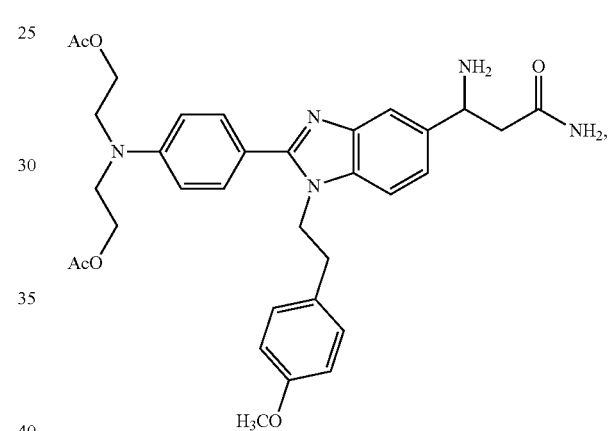
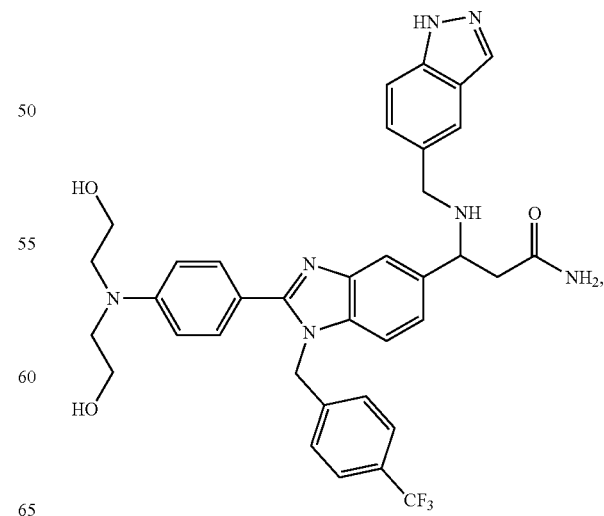

-continued
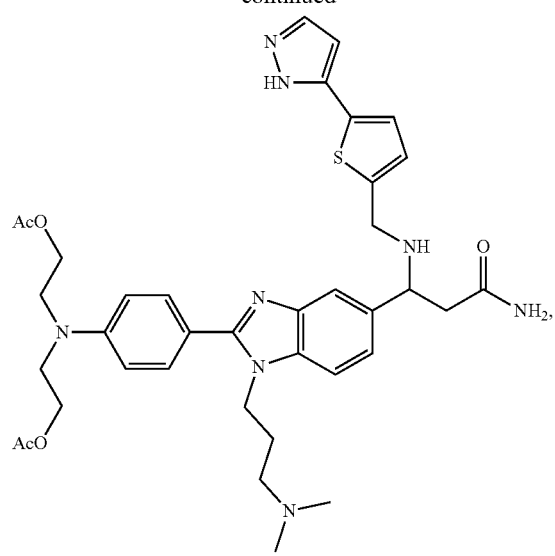
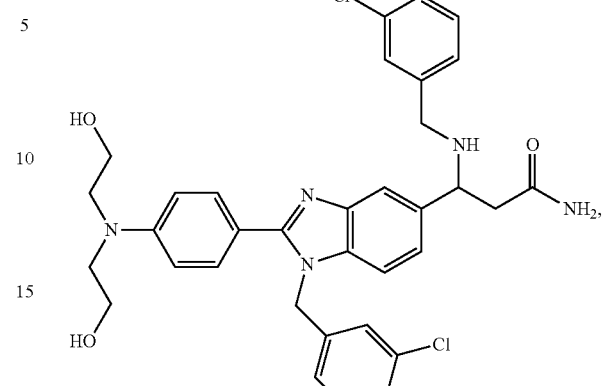
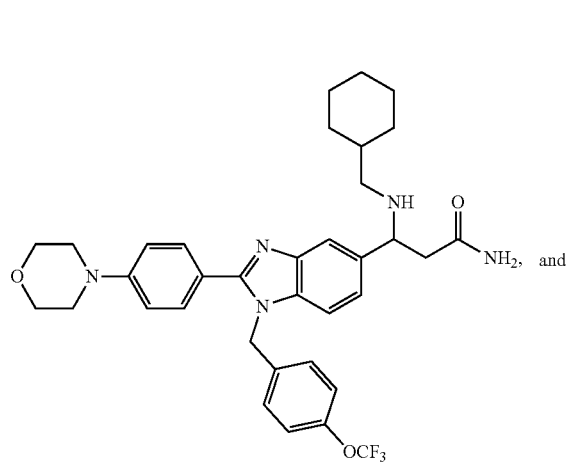
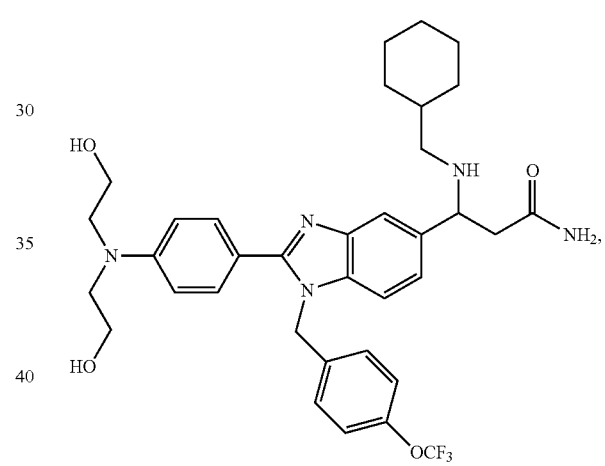
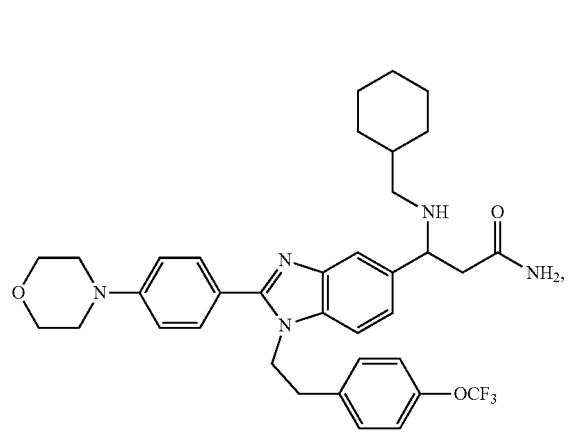
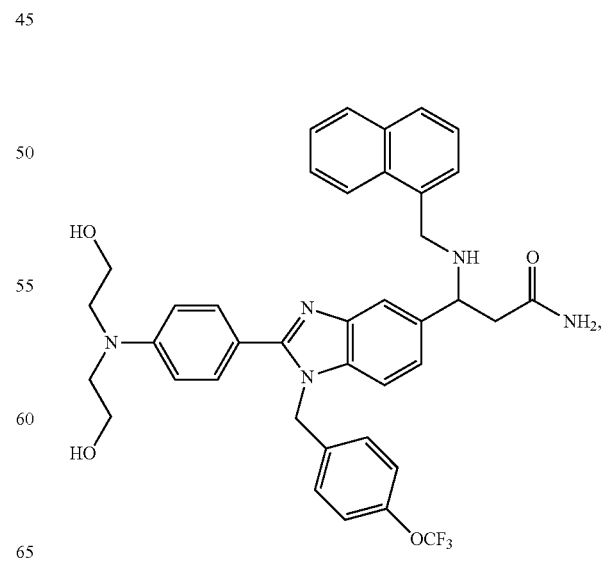
or pharmaceutically acceptable salts thereof.
11. The compound claim 1, selected from the group consisting of:

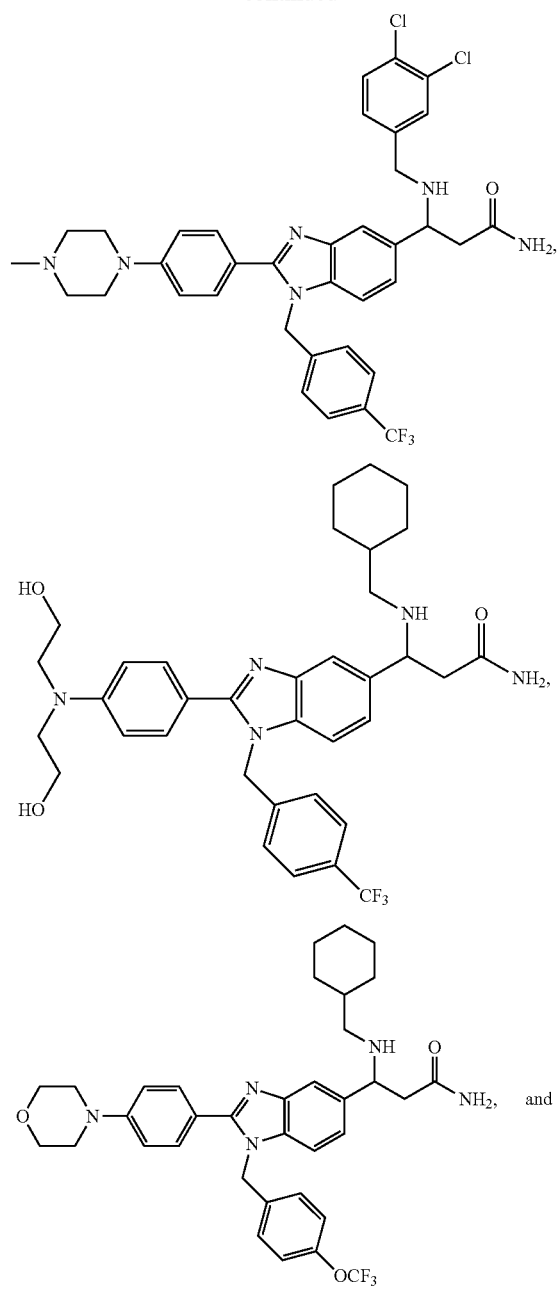
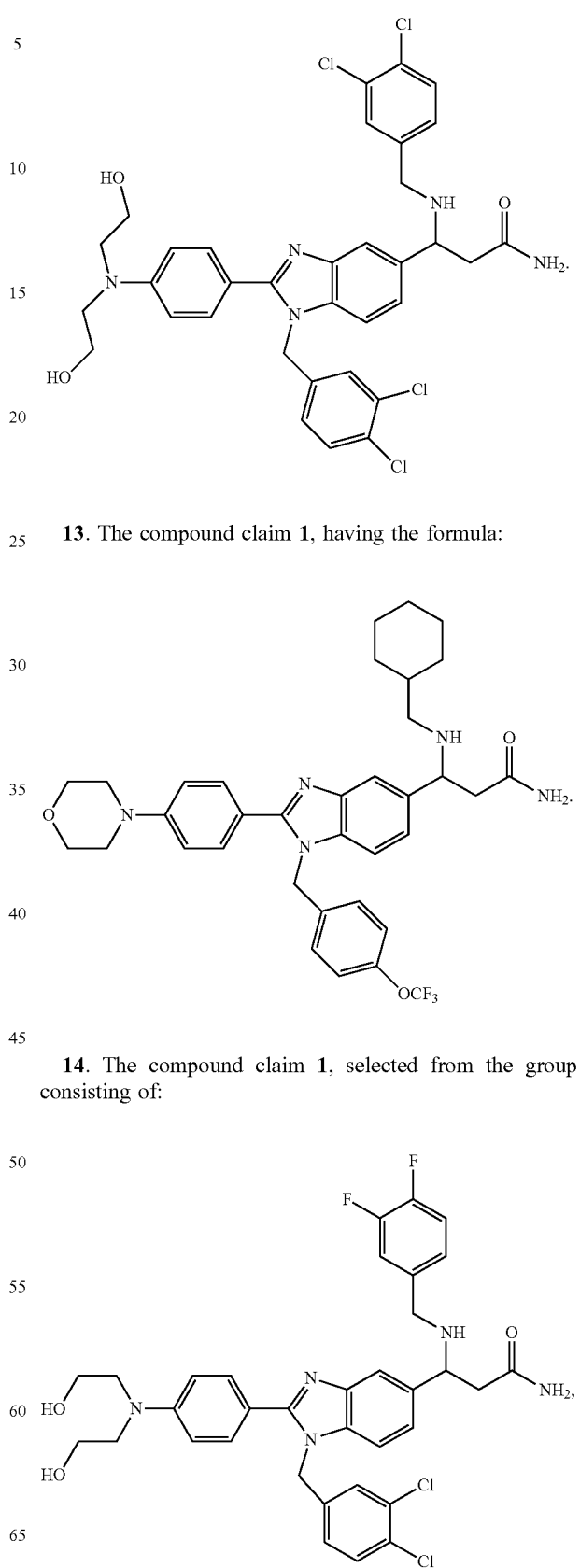
12. The compound claim 1, having the formula:
13. The compound claim 1, having the formula:
14. The compound claim 1, selected from the group consisting of:

149
-continued
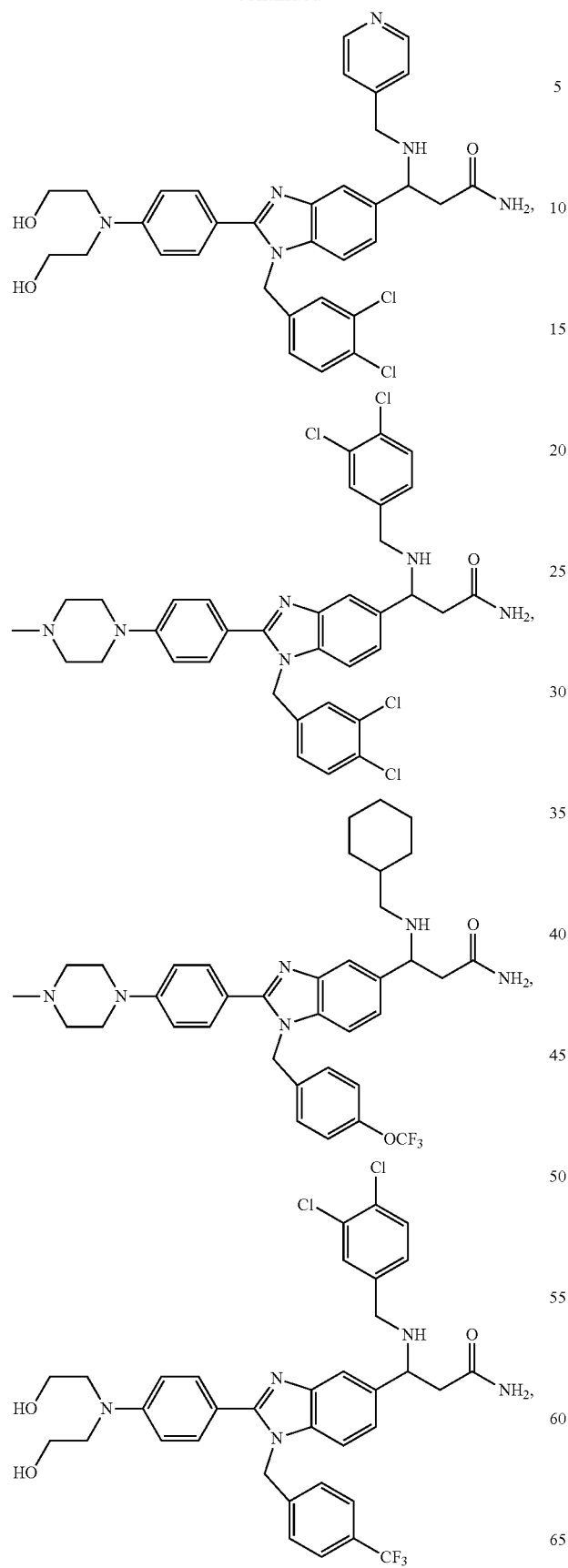
150
-continued
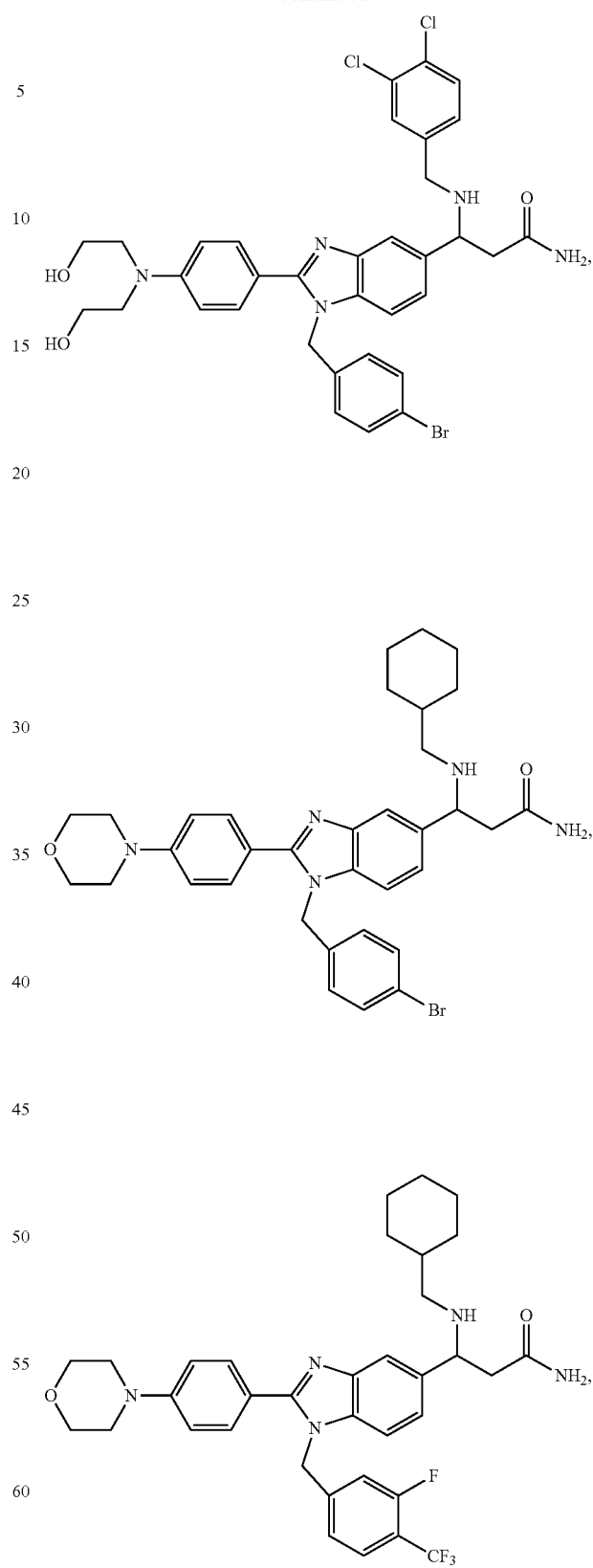

151
-continued
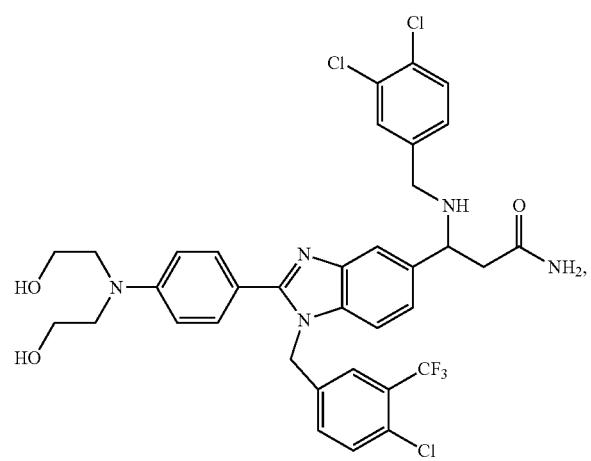
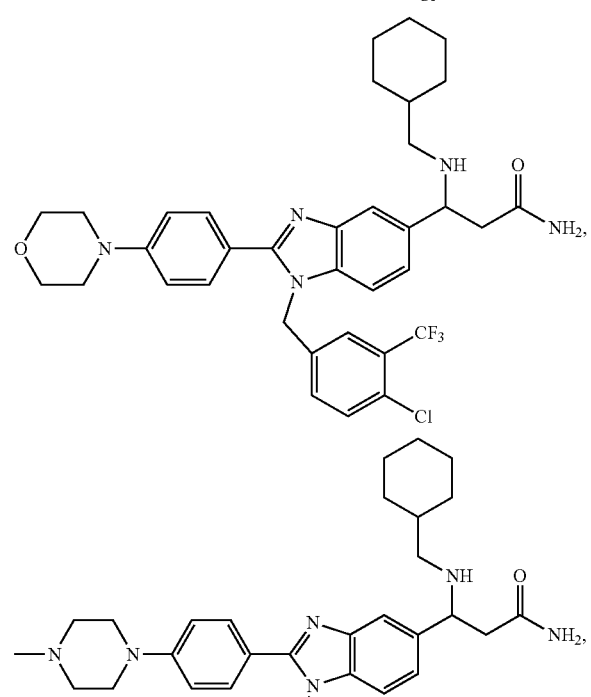
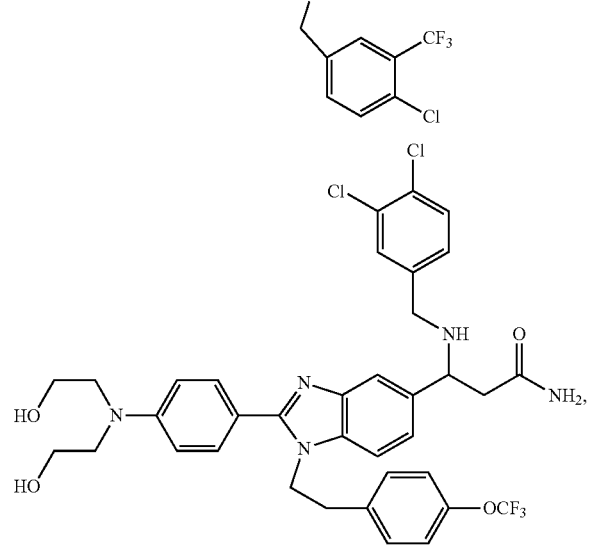
152
-continued
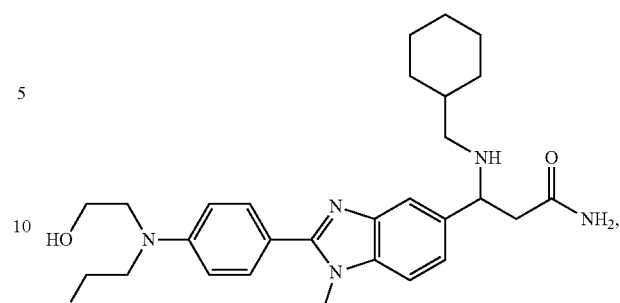
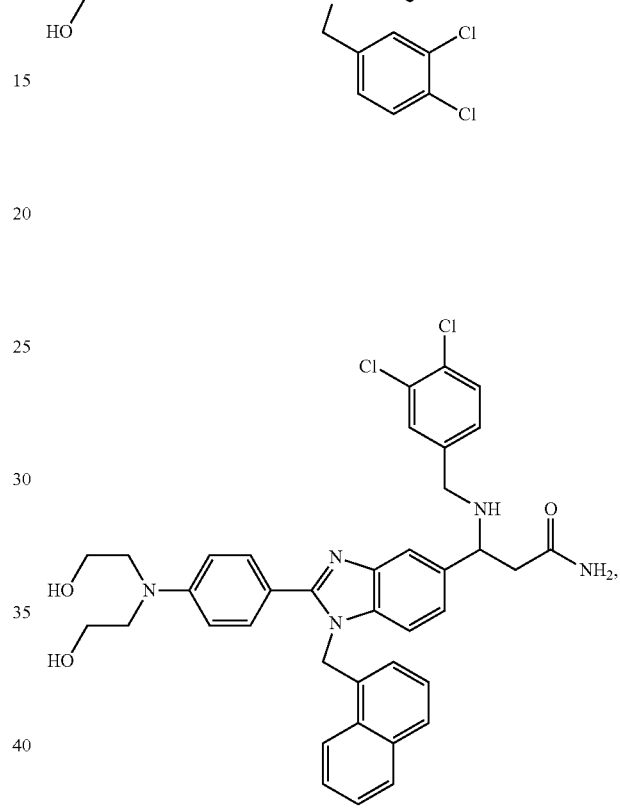
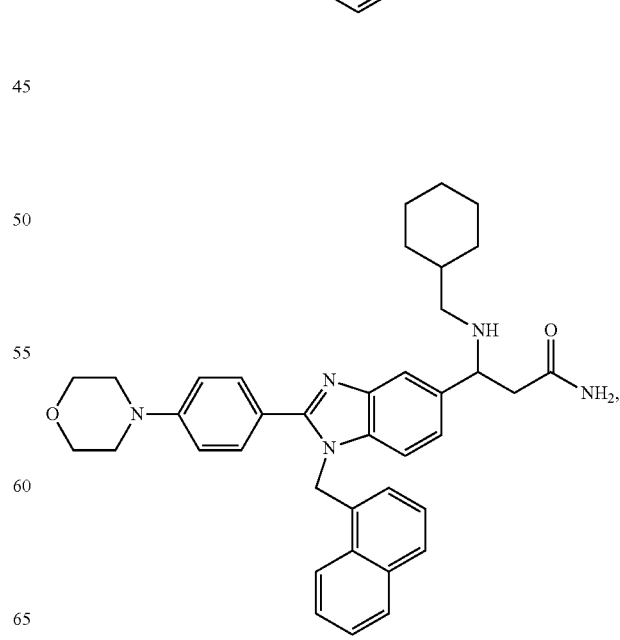

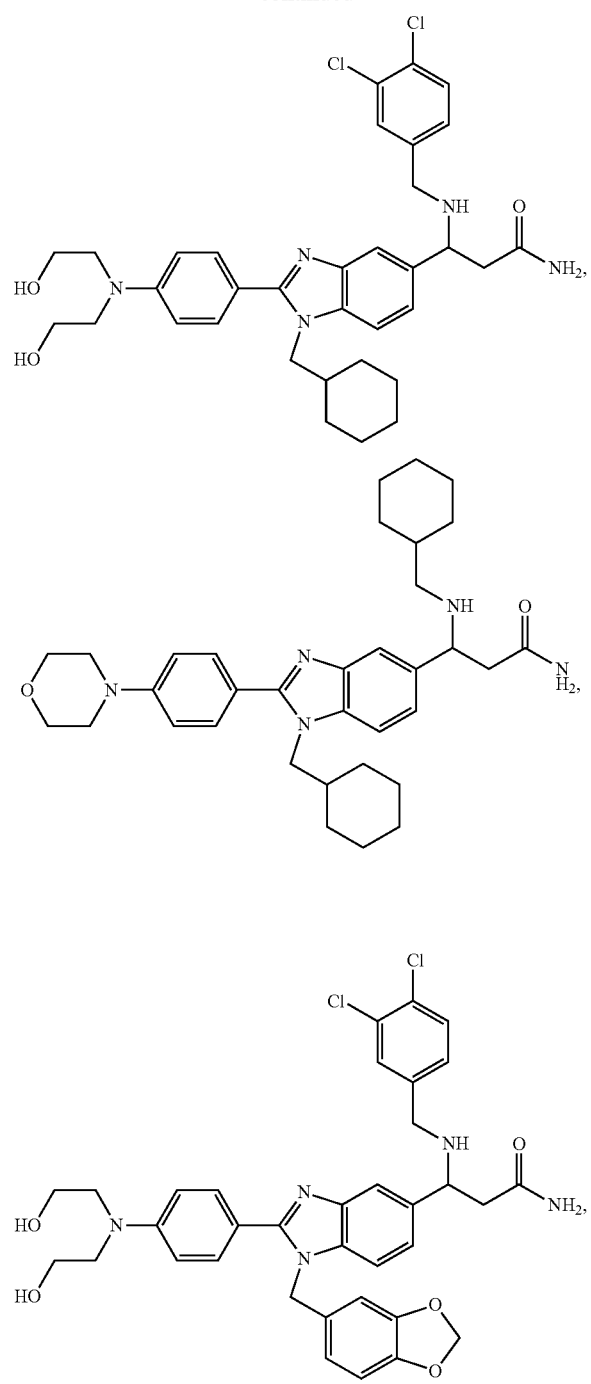

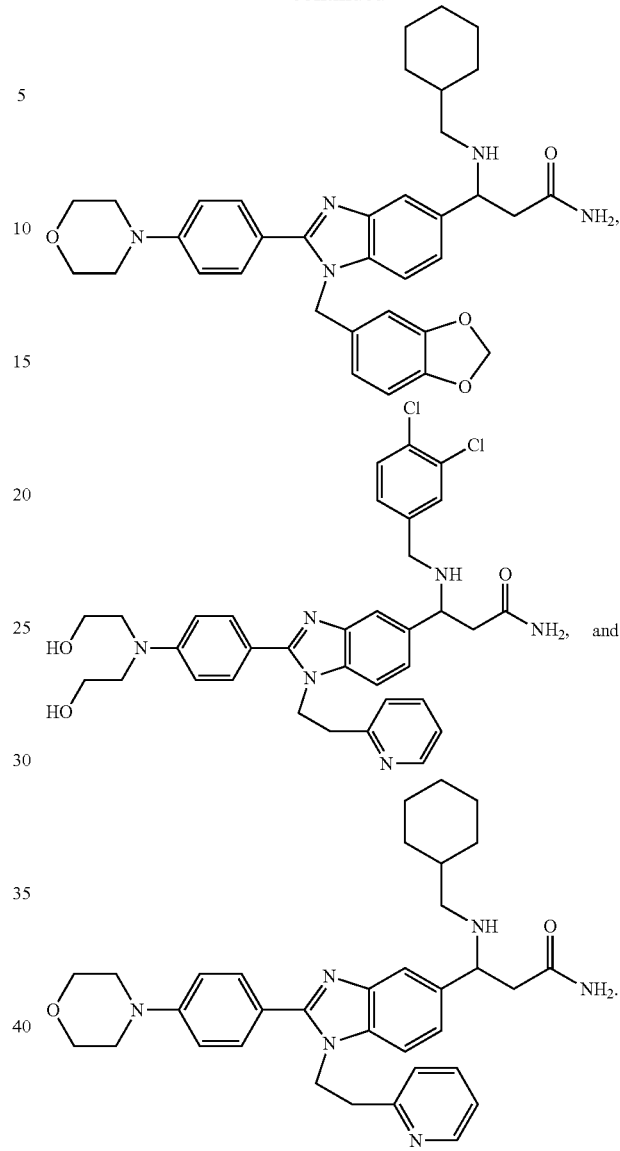

15. A pharmaceutical composition comprising a compound of claim 1 and a pharmaceutically acceptable excipient.

16. A method of treating a cancer, the method comprising administering to a subject in need thereof, a therapeutically effective amount of a compound of claim 1, wherein the cancer is selected from the group consisting of ovarian cancer, prostate cancer, pancreatic cancer, breast cancer, colon cancer, non-small cell lung cancer, and neurofibromatosis.

* * * * *